(12) United States Patent  (10) Patent No.: US 7,687,491 B2
Nishi et al.  (45) Date of Patent: Mar. 30, 2010

(54) HETEROCYCLIC COMPOUND

(75) Inventors: Takahide Nishi, Tokyo (JP); Tsuyoshi Nakamura, Tokyo (JP); Yukiko Sekiguchi, Tokyo (JP); Yumiko Mizuno, Tokyo (JP); Takaichi Shimozato, Kanagawa (JP); Futoshi Nara, Chiba (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 109 days.

(21) Appl. No.: 11/975,664

(22) Filed: Oct. 19, 2007

(65) Prior Publication Data

US 2008/0113961 A1 May 15, 2008

Related U.S. Application Data

(63) Continuation-in-part of application No. PCT/JP2006/308387, filed on Apr. 21, 2006.

(30) Foreign Application Priority Data

Apr. 22, 2005 (JP) .............................. 2005-124353

(51) Int. Cl.
 *A61K 31/397* (2006.01)
 *A61K 31/42* (2006.01)
 *A61K 31/381* (2006.01)
 *A61K 31/4427* (2006.01)
 *A61K 31/443* (2006.01)
 *C07D 271/06* (2006.01)
 *C07D 409/14* (2006.01)
 *C07D 205/04* (2006.01)
 *C07D 413/14* (2006.01)

(52) U.S. Cl. .............................. 514/210.18; 514/210.2; 514/341; 514/364; 514/444; 546/269.4; 548/131; 548/953; 549/59

(58) Field of Classification Search ................. 514/210; 548/131
See application file for complete search history.

(56) References Cited

U.S. PATENT DOCUMENTS

| 6,458,830 | B1 | 10/2002 | Owen et al. |
| 2002/0035132 | A1 | 3/2002 | Castro Pineiro et al. |
| 2004/0063974 | A1 | 4/2004 | Pineiro et al. |
| 2005/0014724 | A1 | 1/2005 | Marsilje et al. |
| 2005/0014725 | A1 | 1/2005 | Mi et al. |
| 2005/0014728 | A1 | 1/2005 | Pan et al. |
| 2005/0033055 | A1 | 2/2005 | Bugianesi et al. |
| 2005/0245575 | A1 | 11/2005 | Chen et al. |
| 2006/0161005 | A1 | 7/2006 | Doherty et al. |

FOREIGN PATENT DOCUMENTS

| WO | WO 00/56727 A1 | 9/2000 |
| WO | WO 00/56728 A1 | 9/2000 |

OTHER PUBLICATIONS

Wu and Farrelly, Toxicology 236:1-6, 2007.*

* cited by examiner

*Primary Examiner*—Yong Chu
(74) *Attorney, Agent, or Firm*—Frishauf, Holtz, Goodman & Chick, P.C.

(57) ABSTRACT

A compound having immunosuppressive activity with low toxicity or a pharmacological salt thereof. The compound has a general formula (I) shown below or a pharmacologically acceptable salt thereof, or a pharmacologically acceptable prodrug thereof

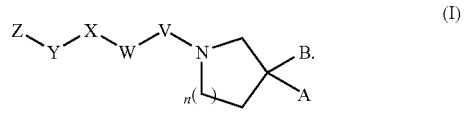

32 Claims, No Drawings

HETEROCYCLIC COMPOUND

This is a continuation-in-part of International Application PCT/JP2006/308387 filed Apr. 21, 2006 (incorporated herein by this reference).

TECHNICAL FIELD

The present invention relates to a heterocyclic compound which exhibits an excellent immunosuppressive activity, a pharmacologically acceptable salt thereof, or a pharmacologically acceptable prodrug thereof.

BACKGROUND OF THE INVENTION

Antiinflammatory drugs such as steroids have been conventionally used as symptomatic therapy in the treatment of autoimmune diseases and the like, but better radical therapy for these diseases is needed. In addition, abnormal changes in the immune system have been reported in relation to the incidence of diabetes mellitus and nephritis (for example, refer to Non-patent Literature 1 and Non-patent Literature 2). However, no drug that ameliorates abnormal changes in the immune system has been developed to date.

On the other hand, it is important to develop a method to suppress immune responses not only for preventing rejection symptoms in organ transplants and cell transplants but also for preventing as well as treating various autoimmune diseases. However, since previously known immunosuppressants such as cyclosporin A (CsA), tacrolimus (TRL), and the like are known to exhibit liver and kidney toxicity, concomitant use of a steroid or the like has widely been used to suppress such side effects. On the other hand, a significant immunosuppressive effect without side effects has not yet been obtained.

Based on this background, many attempts have been made to discover an agent that exerts excellent immunosuppressive activity with low toxicity. The following reports describing the background of the present invention are disclosed. present invention are disclosed.

For example, the following compounds shown below are disclosed in Patent Literature 1.

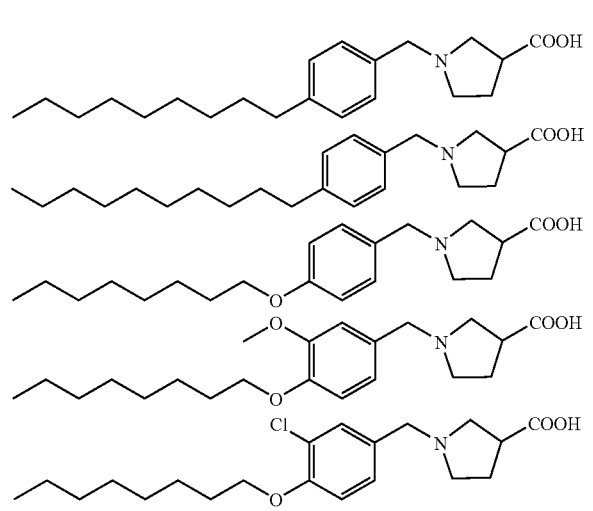

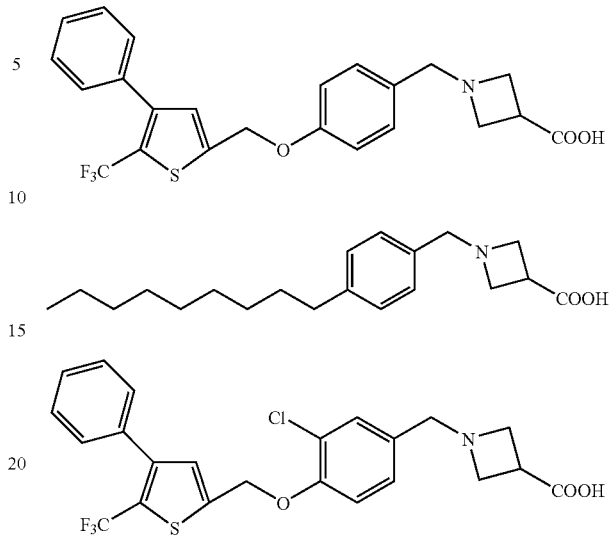

For example, the following compounds shown below are disclosed in Patent Literature 2.

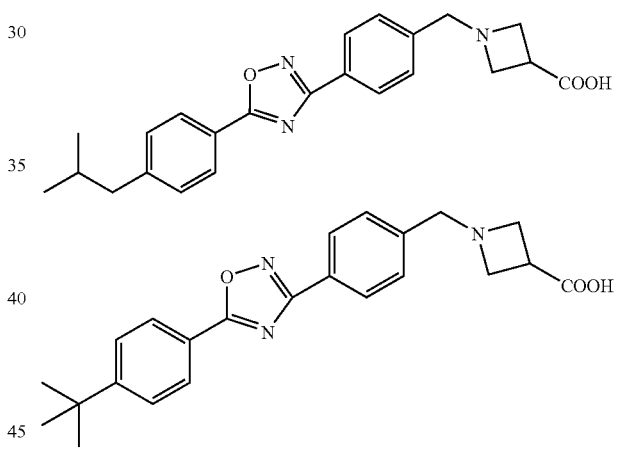

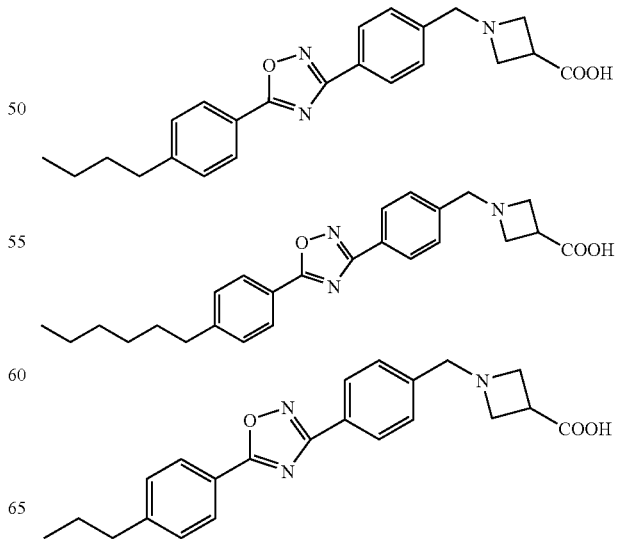

-continued
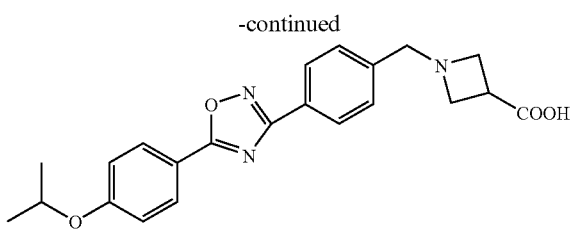
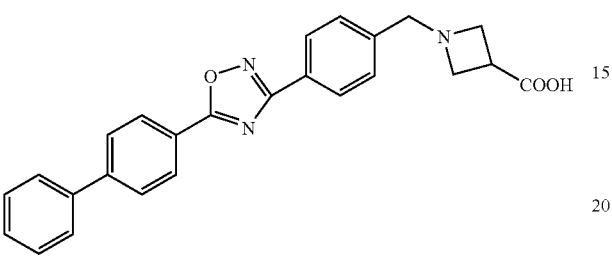
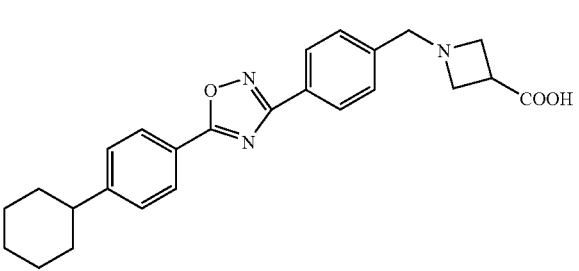
For example, the following compounds shown below are disclosed in Patent Literature 3.
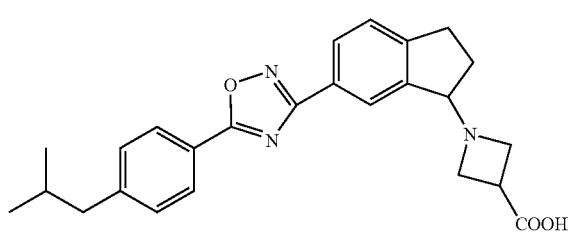
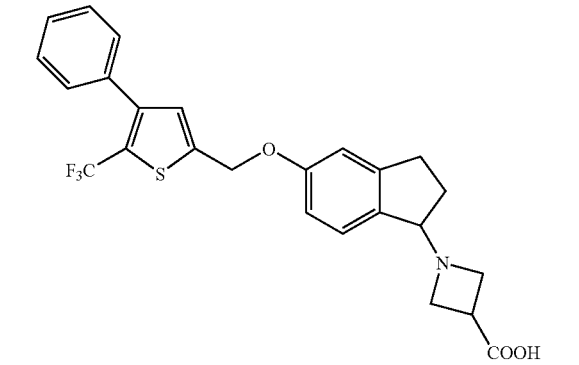
-continued
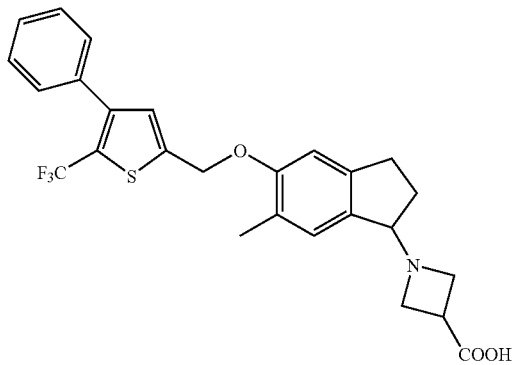
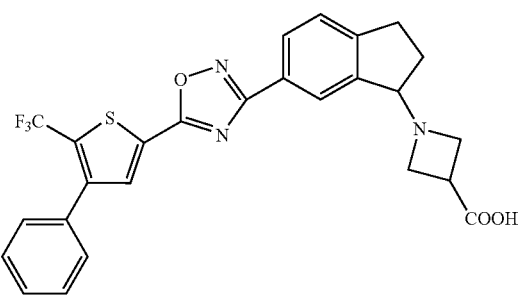
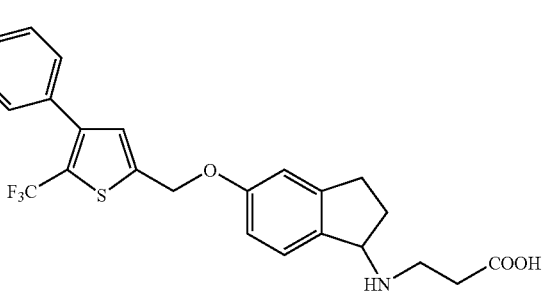
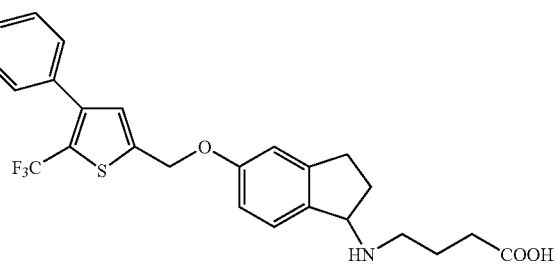
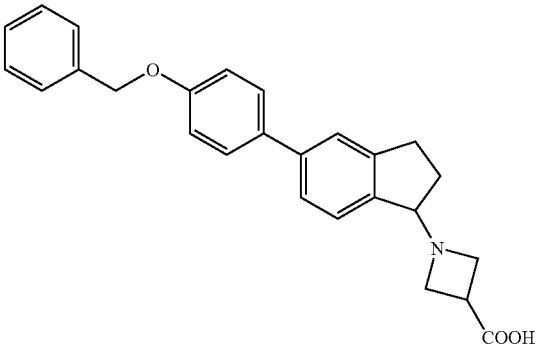

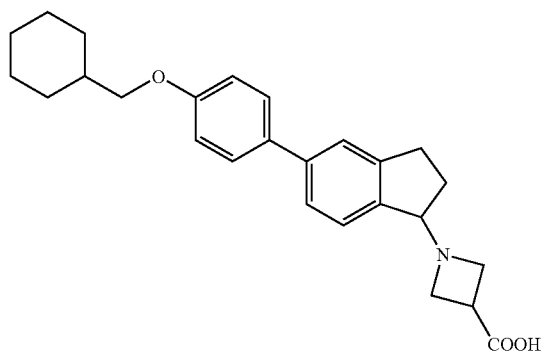
For example, the following compounds shown below are disclosed in Patent Literature 4.
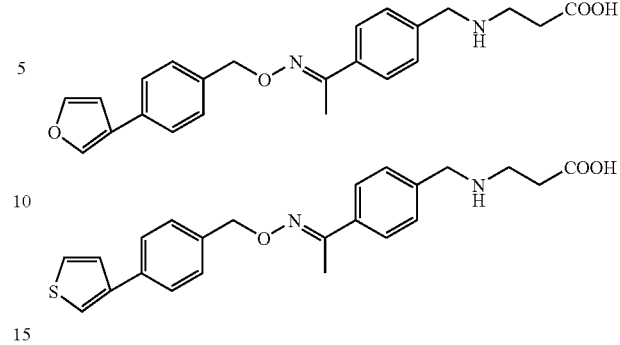
For example, the following compounds shown below are disclosed in Patent Literature 5.
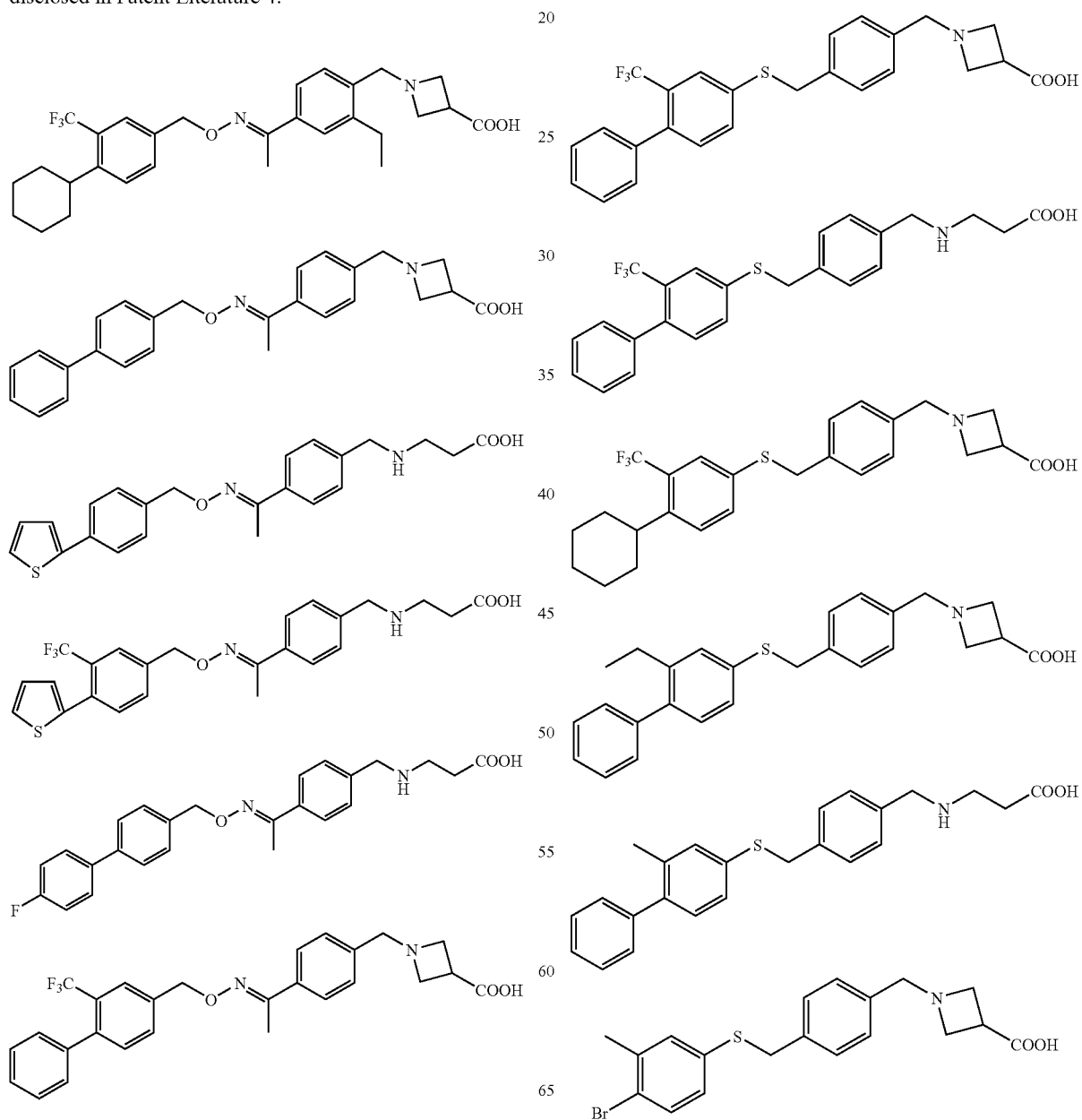

-continued

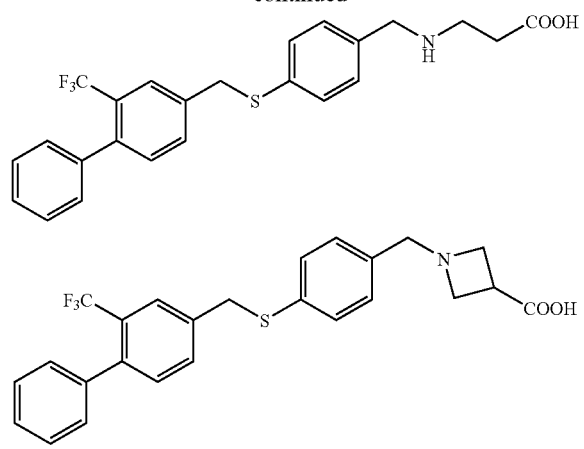

For example, the following compounds shown below are disclosed in Patent Literature 6.

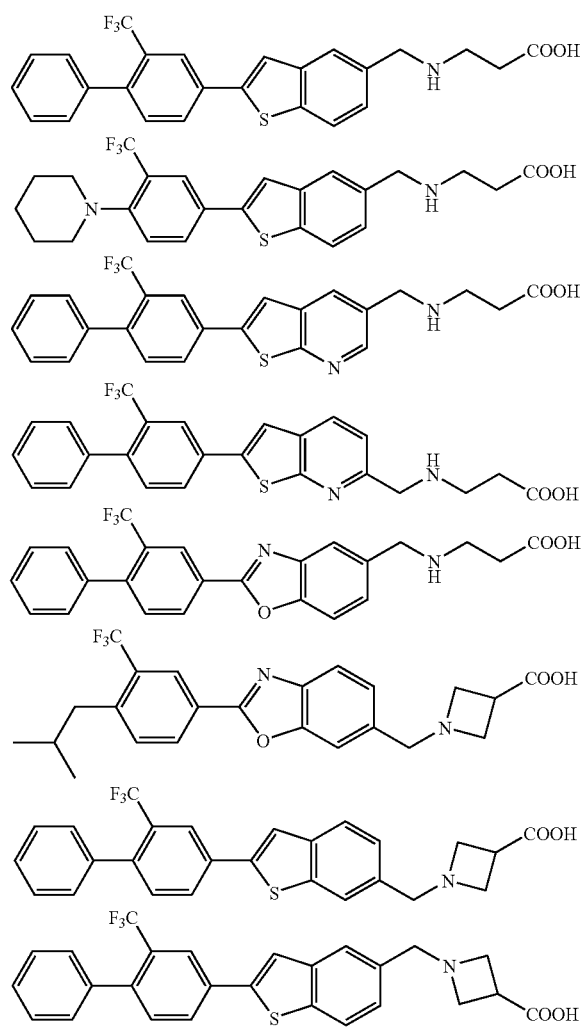

However, the chemical structures of the compounds disclosed in the literatures from Patent Literature 1 to Patent Literature 6 described above differ from those of the compounds of the present invention.

[Patent Literature 1] International publication number WO 03/062252 (US2005/0033055)
[Patent Literature 2] International publication number WO 03/105771 (US2005/0245575)
[Patent Literature 3] International publication number WO 2004/058149 (US2006/0161005)
[Patent Literature 4] International publication number WO 2004/103306 (US2005/0014728)
[Patent Literature 5] International publication number WO 2004/103309 (US2005/0014724)
[Patent Literature 6] International publication number WO 2005/000833 (US2005/0014725)
[Non-patent Literature 1] Kidney International, Vol. 51, 94 (1997)
[Non-patent Literature 2] Journal of Immunology, Vol. 157, 4691 (1996)

DISCLOSURE OF THE INVENTION

Object of the Invention

The inventors of the present invention have over a long time diligently investigated various novel compounds that might exert excellent immunosuppressive activity with low toxicity. As a result, the present inventors discovered novel compounds that are useful against rejection symptoms in transplantation of various organs or in skin tissue grafting, and against autoimmune diseases such as systematic lupus erythematosus, chronic rheumatic arthritis, polymyositis, fibrositis, skeletal muscle myositis, arthritis, osteoarthritis, dermatomyositis, scleroderma, Behcet's syndrome, Crohn's disease, ulcerative colitis, autoimmune hepatitis, aplastic anemia, idiopathic thrombocytopenic purpura, autoimmune hemolytic anemia, multiple sclerosis, autoimmune bullous dermatosis, psoriasis, vasculitis syndrome, Wegener's granulomatosis, uveitis, Sjögren's syndrome, idiopathic interstitial pneumonia, Goodpasture's syndrome, sarcoidosis, allergic granulomatous angiitis, bronchial asthma, myocarditis, cardiomyopathy, aortitis syndrome, postmyocardial infarction syndrome, primary pulmonary hypertension, minimal change nephrotic syndrome, membranous nephropathy, membranoproliferative glomerulonephritis, focal glomerular sclerosis, crescentic glomerulonephritis, myasthenia gravis, inflammatory neuropathy, atopic dermatitis, chronic actinic dermatitis, photosensitivity, pressure ulcer, Sydenham's chorea, sclerosis, adult-onset type diabetes mellitus, insulin dependent diabetes mellitus, juvenile diabetes mellitus, atherosclerosis, glomerular nephritis, IgA nephropathy, tubulointerstitial nephritis, primary biliary cirrhosis, primary sclerosing cholangitis, fulminant hepatitis, viral hepatitis, GVHD, contact dermatitis, sepsis, and the like, or other immune-related diseases, and in addition, for infection disease caused by fungus, mycoplasma, virus, and protozoa, for cardiovascular diseases such as cardiac failure, cardiac hypertrophy, arrhythmia, angina, cardiac ischemia, arterial embolus, aneurysm, varix, and disturbance of blood circulation, for central nervous system diseases such as Alzheimer's disease, dementia, Parkinson's disease, stroke, cerebral infarction, cerebral ischemia, depression, depression and mania, schizophrenia, Huntington's chorea, epilepsy, convulsion, attention deficit hyperactivity disorder (ADHD), encephalitis, meningitis, anorexia, and hyperphagia, and for various other diseases such as lymphomatosis, leukemia, polyuria, frequent urination, diabetic retinopathy, and the like (particularly useful against rejection symptoms in transplantation of various organs or in skin tissue grafting, and against autoimmune diseases such as systematic lupus erythematosus, chronic rheumatoid arthritis, multiple sclerosis, atopic dermatitis, and the like) and consequently the inventors completed the present invention.

Therefore, the object of the present invention is to provide novel compounds having excellent immunosuppressive activity with low toxicity, pharmacologically acceptable salts thereof, and pharmacologically acceptable prodrugs thereof.

Means to Achieve the Object

The present inventors have diligently explored compounds having immunosuppressive activity and discovered that compounds having the general formula (I) of the present invention, pharmacologically acceptable salts thereof, or pharmacologically acceptable prodrugs thereof (hereinafter expressed as "a compound of the present invention" in some cases) have excellent immunosuppressive activity with low toxicity and are useful for prophylaxis or treatment of the diseases described above, and thus the present inventors completed the present invention.

Thus the present invention is described in detail hereinafter.

The present invention relates to (1) a compound having the general formula (I) shown below,

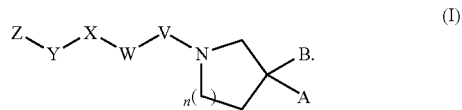

[wherein
A represents a carboxyl group, a phospho group, a sulfo group, or a 1H-tetrazol-5-yl group, B represents a hydrogen atom or a group selected from Substituent group A, n represents an integer of from 0 to 2, V represents a methylene group which may optionally be substituted with substituent(s) selected from Substituent group A or a single bond, W represents a 5- to 7-membered heterocyclic group which may optionally be substituted with from 1 to 3 substituents selected from Substituent group A, in the case that V represents a methylene group which may optionally be substituted with substituent(s) selected from Substituent group A, while in the case that V represents a single bond, W represents a fused ring heterocyclic group which may optionally be substituted with from 1 to 3 substituents selected from Substituent group A, X represents a $C_1$-$C_8$ alkylene group which may optionally be substituted with from 1 to 5 substituents selected from Substituent group A, a $C_1$-$C_8$ alkylene group containing an oxygen atom or a sulfur atom in the carbon chain which may optionally be substituted with from 1 to 5 substituents selected from Substituent group A, a $C_6$-$C_{10}$ arylene group which may optionally be substituted with from 1 to 3 substituents selected from Substituent group A, a 5- to 7-membered heterocyclic group which may optionally be substituted with from 1 to 3 substituents selected from Substituent group A, or a fused ring heterocyclic group which may optionally be substituted with from 1 to 3 substituents selected from Substituent group A, Y represents a $C_6$-$C_{10}$ arylene group which may optionally be substituted with from 1 to 3 substituents selected from Substituent group A, a 5- to 7-membered heterocyclic group which may optionally be substituted with from 1 to 3 substituents selected from Substituent group A, or a fused ring heterocyclic group which may optionally be substituted with from 1 to 3 substituents selected from Substituent group A, Z represents a group selected from Substituent group A, a $C_1$-$C_8$ alkyl group which may optionally be substituted with from 1 to 5 substituents selected from Substituent group A, a $C_1$-$C_8$ alkyl group containing an oxygen atom or a sulfur atom in the carbon chain which may optionally be substituted with from 1 to 5 substituents selected from Substituent group A, a $C_3$-$C_7$ cycloalkyl group which may optionally be substituted with from 1 to 5 substituents selected from Substituent group A, a $C_6$-$C_{10}$ aryl group which may optionally be substituted with from 1 to 5 substituents selected from Substituent group A, a $C_6$-$C_{10}$ aryloxy group which may optionally be substituted with from 1 to 5 substituents selected from Substituent group A, a $C_6$-$C_{10}$ arylthio group which may optionally be substituted with from 1 to 5 substituents selected from Substituent group A, a $C_6$-$C_{12}$ aralkyl group which may optionally be substituted with from 1 to 5 substituents selected from Substituent group A, or a $C_6$-$C_{10}$ arylcarbonyl group which may optionally be substituted with from 1 to 5 substituents selected from Substituent group A, Substituent group A represents the group consisting of a halogen atom, a $C_1$-$C_6$ alkyl group, a $C_3$-$C_7$ cycloalkyl group, a $C_6$-$C_{10}$ aryl group, a $C_6$-$C_{10}$ aryloxy group, a $C_6$-$C_{12}$ aralkyl group, a halogeno $C_1$-$C_6$ alkyl group, a $C_1$-$C_6$ alkoxy group, a halogeno $C_1$-$C_6$ alkoxy group, a $C_1$-$C_6$ alkylthio group, a carboxyl group, a $C_1$-$C_6$ alkylcarboxy group, a hydroxyl group, a $C_1$-$C_6$ aliphatic acyl group, an amino group, a mono-$C_1$-$C_6$ alkylamino group, a di-$C_1$-$C_6$ alkylamino group, a $C_1$-$C_6$ aliphatic acylamino group, a cyano group, and a nitro group], a pharmacologically acceptable salt thereof, or a pharmacologically acceptable prodrug thereof, and preferably, (2) a compound as described in (1) wherein B is a hydrogen atom, or a pharmacologically acceptable salt thereof, (3) a compound as described in (1) or (2) wherein A is a carboxyl group, or a pharmacologically acceptable salt thereof, (4) a compound as described in any one selected from (1) to (3) wherein n represents an integer of 0, or a pharmacologically acceptable salt thereof, (5) a compound as described in any one selected from (1) to (4) wherein V represents a methylene group and W represents a 5- to 7-membered heterocyclic group which may optionally be substituted with from 1 to 3 substituents selected from Substituent group A, or a pharmacologically acceptable salt thereof, (6) a compound as described in (5) wherein the 5- to 7-membered heterocyclic group represents a thienylene, furylene, pyrrolene or pyridylene group, or a pharmacologically acceptable salt thereof, (7) a compound as described in (5) wherein W represents a thienylene or a pyridylene group which may optionally be substituted with 1 to 2 substituents selected from Substituent group A, or a pharmacologically acceptable salt thereof, (8) a compound as described in (6) wherein the thienylene or pyridylene group represents a group shown below, respectively, or a pharmacologically acceptable salt thereof,

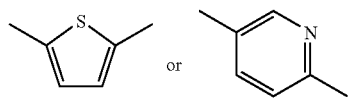 or (9) a compound as described in any one selected from (1) to (4) wherein V represents a single bond and W is a fused ring heterocyclic group which may optionally be substituted with from 1 to 3 substituents selected from Substituent group A, or a pharmacologically acceptable salt thereof,
(10) a compound as described in (9) wherein W represents a fused ring heterocyclic group or a pharmacologically acceptable salt thereof,
(11) a compound as described in (10) wherein the fused ring heterocyclic group is a tetrahydrobenzofuranylene, tetrahydrobenzothienylene or N-methyltetrahydroindolylene group, or a pharmacologically acceptable salt thereof,
(12) a compound as described in (11) wherein the fused ring heterocyclic group has its two positions available for bonding at the 2- and 4-position, or a pharmacologically acceptable salt thereof,
(13) a compound as described in (12) wherein the substituent at the 2-position represents the group of formula Z—Y—X—, or a pharmacologically acceptable salt thereof,
(14) a compound as described in any one selected from (1) to (13) wherein X represents a $C_1$-$C_8$ alkylene group, a $C_1$-$C_8$ alkylene group containing an oxygen atom or a sulfur atom in the carbon chain, a $C_6$-$C_{10}$ arylene group, a 5- to 7-membered heterocyclic group or a fused ring heterocyclic group, or a pharmacologically acceptable salt thereof,
(15) a compound as described in any one selected from (1) to (13) wherein X represents a 5- to 7-membered heterocyclic group, or a pharmacologically acceptable salt thereof,
(16) a compound as described in any one selected from (1) to (15) wherein Y represents any one group selected from the group consisting of a phenylene group, a 5- to 7-membered heterocyclic group which may optionally be substituted with from 1 to 3 substituents selected from Substituent group A, and a fused ring heterocyclic group which may optionally be substituted with from 1 to 3 substituents selected from Substituent group A, or a pharmacologically acceptable salt thereof,
(17) a compound as described in any one selected from (1) to (15) wherein Y represents a phenylene group, or a thienylene, pyridylene, or indolylene group which may optionally be substituted with from 1 to 3 substituents selected from Substituent group A, or a pharmacologically acceptable salt thereof,
(18) a compound as described in any one selected from (1) to (15) wherein Y represents a phenylene or pyridylene group, or a pharmacologically acceptable salt thereof,
(19) a compound as described in any one selected from (1) to (18) wherein Z represents a $C_6$-$C_{10}$ aryloxy group which may optionally be substituted with from 1 to 5 substituents selected from Substituent group A, or a pharmacologically acceptable salt thereof, and
(20) a compound as described in any one selected from (1) to (18) wherein Z represents a phenoxy group, or a pharmacologically acceptable salt thereof,
(21) a compound as described in (1) wherein the general formula (I) is the general formula (I') shown below:

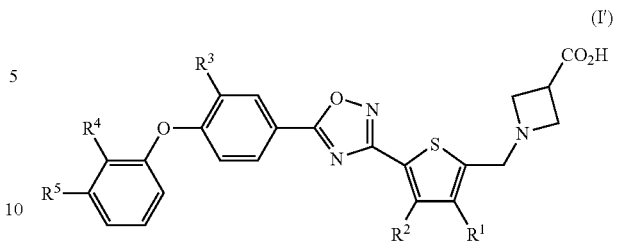

(I')

[wherein
 $R^1$ represents a hydrogen atom or a $C_1$-$C_6$ alkyl group,
 $R^2$ represents a hydrogen atom or a $C_1$-$C_6$ alkyl group,
 $R^3$ represents a hydrogen atom, a halogen atom, or a $C_1$-$C_6$ alkyl group,
 $R^4$ represents a hydrogen atom, a halogen atom, a cyano group, a $C_1$-$C_6$ alkyl group, or a $C_1$-$C_6$ alkoxy group, and
 $R^5$ represents a hydrogen atom or a halogen atom], or a pharmacologically acceptable salt thereof,
(22) a compound as described in (21) wherein $R^1$ represents a hydrogen atom, or a pharmacologically acceptable salt thereof,
(23) a compound as described in (21) or (22) wherein $R^2$ represents a hydrogen atom, a methyl group, or an ethyl group, or a pharmacologically acceptable salt thereof,
(24) a compound as described in any one selected from (21) to (23) wherein $R^3$ represents a hydrogen atom, a fluorine atom, a chlorine atom, or a methyl group, or a pharmacologically acceptable salt thereof,
(25) a compound as described in any one selected from (21) to (24) wherein $R^4$ represents a hydrogen atom, a fluorine atom, a chlorine atom, a cyano group, a methyl group, or a methoxy group, or a pharmacologically acceptable salt thereof,
(26) a compound as described in any one selected from (21) to (25) wherein $R^5$ represents a hydrogen atom or a fluorine atom, or a pharmacologically acceptable salt thereof,
(27) a compound as described in (1) wherein the general formula (I) is the general formula (I'') shown below:

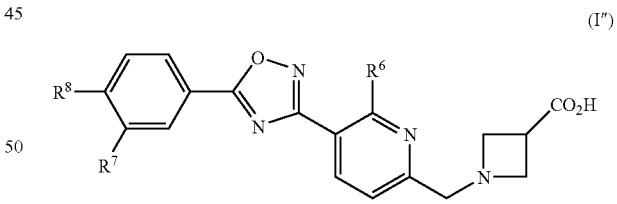

(I'')

[wherein
 $R^6$ represents a hydrogen atom or a $C_1$-$C_6$ alkyl group,
 $R^7$ represents a hydrogen atom, a halogen atom, or a $C_1$-$C_6$ alkyl group, and
 $R^8$ represents a $C_1$-$C_6$ alkyl group or a $C_1$-$C_6$ alkoxy group], or a pharmacologically acceptable salt thereof,
(28) a compound as described in (27) wherein $R^6$ represents a hydrogen atom, a methyl group, or an ethyl group, or a pharmacologically acceptable salt thereof,
(29) a compound as described in any one selected from (27) or (28) wherein $R^7$ represents a hydrogen atom, a fluorine atom, a chlorine atom, or a methyl group, or a pharmacologically acceptable salt thereof,

(30) a compound as described in any one selected from (27) to (29) wherein R⁸ represents a n-propyl group, a n-butyl group or an isobutyl group, or a pharmacologically acceptable salt thereof.

(31) a compound as described in (1) wherein said compound is any one selected from the following compounds, or a pharmacologically acceptable salt thereof:

1-[(4-{5-[4-Phenyl-5-(trifluoromethyl)-2-thienyl]-1,2,4-oxadiazol-3-yl}-2-furyl)methyl]azetidine-3-carboxylic acid, 1-({5-[5-(4-Isobutylphenyl)-1,2,4-oxadiazol-3-yl]-2-furyl}methyl)azetidine-3-carboxylic acid, 1-({5-[5-(4-Cyclohexylphenyl)-1,2,4-oxadiazol-3-yl]-2-furyl}methyl)azetidine-3-carboxylic acid, 1-(2-{5-[4-Phenyl-5-(trifluoromethyl)-2-thienyl]-1,2,4-oxadiazol-3-yl}-4,5,6,7-tetrahydro-1-benzofuran-4-yl)azetidine-3-carboxylic acid, 1-({5-[5-(4-Phenoxyphenyl)-1,2,4-oxadiazol-3-yl]-2-thienyl}methyl)azetidine-3-carboxylic acid, 1-({4-[5-(4-Benzoylphenyl)-1,2,4-oxadiazol-3-yl]-2-thienyl}methyl)azetidine-3-carboxylic acid, 1-({4-[5-(4-Benzylphenyl)-1,2,4-oxadiazol-3-yl]-2-thienyl}methyl)azetidine-3-carboxylic acid, 1-({4-[5-(1-Isobutyl-1H-indol-5-yl)-1,2,4-oxadiazol-3-yl]-2-thienyl}methyl)azetidine-3-carboxylic acid, 1-({6-[5-(4-Isobutylphenyl)-1,2,4-oxadiazol-3-yl]pyridin-3-yl}methyl)azetidine-3-carboxylic acid, and 1-({5-[5-(4-Isobutylphenyl)-1,2,4-oxadiazol-3-yl]pyridin-2-yl}methyl)azetidine-3-carboxylic acid,

(32) a compound as described in (1) wherein said compound is any one selected from the following compounds, or a pharmacologically acceptable salt thereof:

1-({5-[5-(4-Phenoxyphenyl)-1,2,4-oxadiazol-3-yl]-2-thienyl}methyl)azetidine-3-carboxylic acid, 1-({4-Methyl-5-[5-(4-phenoxyphenyl)-1,2,4-oxadiazol-3-yl]-2-thienyl}methyl)azetidine-3-carboxylic acid, 1-({5-[5-(3-Fluoro-4-phenoxyphenyl)-1,2,4-oxadiazol-3-yl]-4-methyl-2-thienyl}methyl)azetidine-3-carboxylic acid, 1-({4-Ethyl-5-[5-(4-phenoxyphenyl)-1,2,4-oxadiazol-3-yl]-2-thienyl}methyl)azetidine-3-carboxylic acid, 1-[(4-Ethyl-5-{5-[4-(3-fluorophenoxy)phenyl]-1,2,4-oxadiazol-3-yl}-2-thienyl)methyl]azetidine-3-carboxylic acid, 1-({4-Ethyl-5-[5-(3-fluoro-4-phenoxyphenyl)-1,2,4-oxadiazol-3-yl]-2-thienyl}methyl)azetidine-3-carboxylic acid, 1-[(4-Ethyl-5-{5-[3-fluoro-4-(3-fluorophenoxy)phenyl]-1,2,4-oxadiazol-3-yl}-2-thienyl)methyl]azetidine-3-carboxylic acid, 1-[(4-Ethyl-5-{5-[4-(2-methoxyphenoxy)phenyl]-1,2,4-oxadiazol-3-yl}-2-thienyl)methyl]azetidine-3-carboxylic acid, 1-[(5-{5-[3-Chloro-4-(3-fluorophenoxy)phenyl]-1,2,4-oxadiazol-3-yl}-4-ethyl-2-thienyl)methyl]azetidine-3-carboxylic acid, 1-[(4-Ethyl-5-{5-[4-(2-methoxyphenoxy)phenyl]-1,2,4-oxadiazol-3-yl}-2-thienyl)methyl]azetidine-3-carboxylic acid, 1-[(4-Ethyl-5-{5-[4-(2-fluorophenoxy)phenyl]-1,2,4-oxadiazol-3-yl}-2-thienyl)methyl]azetidine-3-carboxylic acid, 1-[(5-{5-[4-(2,3-Difluorophenoxy)phenyl]-1,2,4-oxadiazol-3-yl}-4-ethyl-2-thienyl)methyl]azetidine-3-carboxylic acid, 1-[(4-Ethyl-5-{5-[3-fluoro-4-(2-fluorophenoxy)phenyl]-1,2,4-oxadiazol-3-yl}-2-thienyl)methyl]azetidine-3-carboxylic acid, 1-[(5-(5-[4-(2,3-Difluorophenoxy)-3-fluorophenyl]-1,2,4-oxadiazol-3-yl)-4-ethyl-2-thienyl)methyl]azetidine-3-carboxylic acid, 1-[(5-{5-[3-Chloro-4-(2-fluorophenoxy)phenyl]-1,2,4-oxadiazol-3-yl}-4-ethyl-2-thienyl)methyl]azetidine-3-carboxylic acid, 1-[(5-{5-[3-Chloro-4-(2,3-difluorophenoxy)phenyl]-1,2,4-oxadiazol-3-yl}-4-ethyl-2-thienyl)methyl]azetidine-3-carboxylic acid, 1-[(5-{5-[4-(2-Chlorophenoxy)phenyl]-1,2,4-oxadiazol-3-yl}-4-ethyl-2-thienyl)methyl]azetidine-3-carboxylic acid, 1-[(5-{5-[4-(2-Chlorophenoxy)-3-fluorophenyl]-1,2,4-oxadiazol-3-yl}-4-ethyl-2-thienyl)methyl]azetidine-3-carboxylic acid, 1-({3-Methyl-5-[5-(4-phenoxyphenyl)-1,2,4-oxadiazol-3-yl]-2-thienyl}methyl)azetidine-3-carboxylic acid and 1-({3-Ethyl-5-[5-(4-phenoxyphenyl)-1,2,4-oxadiazol-3-yl]-2-thienyl}methyl)azetidine-3-carboxylic acid, and

(33) a compound as described in (1) wherein said compound is any one selected from the following compounds, or a pharmacologically acceptable salt thereof:

1-({5-[5-(4-Isobutyl-3-methylphenyl)-1,2,4-oxadiazol-3-yl]pyridin-2-yl}methyl)azetidine-3-carboxylic acid, 1-({5-[5-(3-Fluoro-4-isobutylphenyl)-1,2,4-oxadiazol-3-yl]pyridin-2-yl}methyl)azetidine-3-carboxylic acid, 1-({5-[5-(3-Chloro-4-isobutylphenyl)-1,2,4-oxadiazol-3-yl]pyridin-2-yl}methyl)azetidine-3-carboxylic acid, 1-({5-[5-(4-Isobutyl-3-methylphenyl)-1,2,4-oxadiazol-3-yl]-6-methylpyridin-2-yl}methyl)azetidine-3-carboxylic acid, 1-({5-[5-(3-Fluoro-4-propylphenyl)-1,2,4-oxadiazol-3-yl]-6-methylpyridin-2-yl}methyl)azetidine-3-carboxylic acid, 1-({5-[5-(4-Butyl-3-fluorophenyl)-1,2,4-oxadiazol-3-yl]-6-methylpyridin-2-yl}methyl)azetidine-3-carboxylic acid, 1-({5-[5-(3-Fluoro-4-isobutylphenyl)-1,2,4-oxadiazol-3-yl]-6-methylpyridin-2-yl}methyl)azetidine-3-carboxylic acid, 1-({5-[5-(3-Chloro-4-isobutylphenyl)-1,2,4-oxadiazol-3-yl]-6-methylpyridin-2-yl}methyl)azetidine-3-carboxylic acid, 1-({6-Ethyl-5-[5-(4-isobutyl-3-methylphenyl)-1,2,4-oxadiazol-3-yl]pyridin-2-yl}methyl)azetidine-3-carboxylic acid, 1-({6-Ethyl-5-[5-(3-fluoro-4-propylphenyl)-1,2,4-oxadiazol-3-yl]pyridin-2-yl}methyl)azetidine-3-carboxylic acid, 1-({5-[5-(4-Butyl-3-fluorophenyl)-1,2,4-oxadiazol-3-yl]-6-ethylpyridin-2-yl}methyl)azetidine-3-carboxylic acid, 1-({6-Ethyl-5-[5-(3-fluoro-4-isobutylphenyl)-1,2,4-oxadiazol-3-yl]pyridin-2-yl}methyl)azetidine-3-carboxylic acid, and 1-({5-[5-(3-Chloro-4-isobutylphenyl)-1,2,4-oxadiazol-3-yl]-6-ethylpyridin-2-yl}methyl)azetidine-3-carboxylic acid. Furthermore, the present invention provides

(34) a medicinal composition comprising one or two or more compounds as described in any one selected from (1) to (33) as an active ingredient, or a pharmacologically acceptable salt thereof,

(35) a medicinal composition as stated in (34) which can be used for suppressing immunological rejection symptoms occurring after skin tissue grafting or transplantation of various organs,

(36) a medicinal composition as stated in (34) which can be used for prophylaxis or therapy of autoimmune diseases,

(37) a medicinal composition as stated in (36) wherein said autoimmune disease is one or two or more condition(s)

selected from the group consisting of rheumatoid arthritis, psoriasis, atopic dermatitis, multiple sclerosis, ulcerative colitis, and Crohn's disease,

(38) a method for suppressing immunological rejection symptoms occurring after skin tissue grafting or transplantation of various organs which is characterized by administering an effective dose of a pharmaceutical composition as stated in (34) to a mammal,

(39) a method for prophylaxis or therapy of autoimmune diseases which is characterized by administering an effective dose of a pharmaceutical composition as stated in (34) to a mammal, and

(40) a method for prophylaxis or therapy as stated in (39) wherein said autoimmune disease is one, or two, or more condition(s) selected from the group consisting of rheumatoid arthritis, psoriasis, atopic dermatitis, multiple sclerosis, ulcerative colitis, and Crohn's disease.

Substituent group A described above is preferably a group consisting of a halogen atom, a $C_1$-$C_6$ alkyl group, a $C_3$-$C_7$ cycloalkyl group, a $C_6$-$C_{10}$ aryl group, a $C_6$-$C_{10}$ aryloxy group, a $C_6$-$C_{12}$ aralkyl group, a halogeno $C_1$-$C_6$ alkyl group, a $C_1$-$C_6$ alkoxy group, a halogeno $C_1$-$C_6$ alkoxy group, and a $C_1$-$C_6$ alkylthio group.

The "5- to 7-membered heterocyclic group" in the definitions of W, X, and Y in the above formula is, for example, a 5- or 7-membered aromatic heterocyclic group containing one or more (for example, from 1 to 3) heteroatoms selected from a nitrogen atom, a sulfur atom, and an oxygen atom in addition to carbon atoms, which has two positions available for bonding, and can be concretely a thienylene, furylene, pyrrolylene, imidazolylene, pyrazolylene, thiazolylene, isothiazolylene, oxazolylene, isoxazolylene, pyridylene, pyrazinylene, pyrimidinylene, pyridazinylene, oxadiazolylene, thiadiazolylene, or furazanylene group, W is preferably a furylene, thienylene, pyrrolylene, or pyridylene group, X is preferably an isoxazolylene or oxadiazolylene group, and Y is preferably a phenylene, pyridylene, or thienylene group.

The "fused ring heterocyclic group" in the definitions of W, X, and Y in the above formula represents a substituent in which the "5- to 7-membered heterocyclic group" described above is fused with other cyclic group(s), and concretely, a 9- to 14-membered (preferably, a 9- or 10-membered) fused multi-ring aromatic heterocyclic group containing one or more heteroatoms (for example, from 1 to 3 heteroatoms) selected from a nitrogen atom, a sulfur atom and an oxygen atom in addition to carbon atoms, which has two positions available for bonding, and is preferably a bicyclic, tricyclic, or tetracyclic group and more preferably a bicyclic group, and can be, for example, a benzothienylene, benzofuranylene, benzimidazolylene, benzoxazolylene, benzothiazolylene, benzisothiazolylene, naphtho[2,3-b]thiophenylene, isoquinolylene, quinolylene, indolylene, quinoxalinylene, phenanthridinylene, phenothiazinylene, phenoxazinylene, phthalazinylene, naphthyridinylene, quinazolinylene, cinnolinylene, carbazolylene, β-carbolinylene, acridinylene, phenazinylene, phthalimidoylene, (thioxanthenyl)tetrahydroquinolylene, tetrahydroisoquinolylene, tetrahydroindolylene, tetrahydrobenzofuranylene, tetrahydrobenzothienylene, 5,6-dihydro-4H-cyclopenta[b]furanylene, 5,6-dihydro-4H-cyclopenta[b]thienylene, or 1,4,5,6-tetrahydrocyclopenta[b]pyrrolylene group, W is preferably a tetrahydrobenzofuranylene, tetrahydrobenzothienylene, tetrahydroindolylene, 5,6-dihydro-4H-cyclopenta[b]furanylene, 5,6-dihydro-4H-cyclopenta[b]thienylene, or 1,4,5,6-tetrahydrocyclopenta[b]pyrrolylene group, or the like and Y is preferably an indolylene group.

The "$C_1$-$C_8$ alkylene group" in the definition of X in the above formula represents a straight or branched $C_1$-$C_8$ alkylene group, and can be, for example, a methylene, ethylene, propylene, butylene, pentylene, hexylene, heptylene, octylene, isopropylene, s-butylene, t-butylene, 3,3-dimethylpropylene, or 4,4-dimethylbutylene group, or the like, and is preferably a methylene, ethylene, or propylene group.

The "$C_1$-$C_8$ alkylene group containing an oxygen atom or a sulfur atom in the carbon chain" in the definition of X in the above formula represents, for example, a —$(CH_2)_{m1}$O$(CH_2)_{m2}$—, —$(CH_2)_{m1}$S$(CH_2)_{m2}$—, —$(CH_2)_{m1}$CO$(CH_2)_{m2}$—, —$(CH_2)_{m1}$SO$(CH_2)_{m2}$—, —$(CH_2)_{m1}$SO$_2$$(CH_2)_{m2}$— or the like (wherein m1 and m2 are the same or different and each represents an integer of from 0 to 7, but the sum of m1 and m2 represents an integer of from 0 to 7), and is preferably a —$CH_2OCH_2$—, —$CH_2SCH_2$—, —$OCH_2$—, —$SCH_2$—, —$CH_2O$—, or —$CH_2S$— group.

The "$C_1$-$C_8$ alkyl group" in the definition of Z in the above formula is a straight or branched $C_1$-$C_8$ alkyl group, and can be, for example, a methyl, ethyl, propyl, butyl, pentyl, hexyl, heptyl, octyl, isopropyl, s-butyl, t-butyl, 3,3-dimethylpropyl, or 4,4-dimethylbutyl group, or the like, and is preferably a methylene, ethylene, or propylene group.

The "$C_1$-$C_8$ alkyl group containing an oxygen atom or a sulfur atom in the carbon chain" in the definition of Z in the above formula represents, for example, a H$(CH_2)_{m1}$O$(CH_2)_{m2}$—, H$(CH_2)_{m1}$S$(CH_2)_{m2}$—, H$(CH_2)_{m1}$CO$(CH_2)_{m2}$—, H$(CH_2)_{m1}$SO$(CH_2)_{m2}$—, or H$(CH_2)_{m1}$SO$_2$$(CH_2)_{m2}$— (wherein m1 and m2 are the same or different and each represents an integer of from 0 to 7, and furthermore the sum of m1 and m2 represents an integer of from 0 to 7), and is preferably a methoxymethyl, methylthiomethyl, methoxy, or methylthio group.

The "$C_3$-$C_7$ cycloalkyl group" in the definitions of Z and Substituent group A in the above formula represents a cyclopropyl group, a cyclobutyl group, a cyclopentyl group, a cyclohexyl group, or a cycloheptyl group.

The "$C_6$-$C_{10}$ arylene group" in the definitions of X and Y in the above formula can be, for example, a phenylene group, an indenylene group, or a naphthylene group, and is preferably a phenylene group.

The "$C_6$-$C_{10}$ aryl group" in the definitions of Z and Substituent group A in the above formula can be, for example, a phenyl group, an indenyl group, or a naphthyl group, and is preferably a phenyl group.

The "$C_6$-$C_{10}$ aryloxy group" in the definitions of Z and Substituent group A in the above formula can be, for example, a phenyloxy group, an indenyloxy group, or a naphthyloxy group, and is preferably a phenyloxy group.

The "$C_6$-$C_{10}$ arylthio group" in the definition of Z in the above formula can be, for example, a phenylthio group, an indenylthio group, or a naphthylthio group, and is preferably a phenylthio group.

The "$C_6$-$C_{10}$ aralkyl group" in the definition of Z in the above formula can be, for example, a benzyl group, an indenylmethyl group, or a naphthylmethyl group, and is preferably a benzyl group.

The "$C_6$-$C_{10}$ arylcarbonyl group" in the definition of Z in the above formula can be, for example, a benzoyl group, an indenylcarbonyl group, or a naphthylcarbonyl group, and is preferably a benzoyl group.

The "halogen atom" in the definition of Substituent group A in the above formula is a fluorine atom, a chlorine atom, a bromine atom, or an iodine atom.

The "$C_1$-$C_6$ alkyl" group in the definition of Substituent group A in the above formula can be, for example, a methyl group, an ethyl group, a propyl group, an isopropyl group, a butyl group, an isobutyl group, a s-butyl group, a t-butyl group, a pentyl group, an isopentyl group, or a hexyl group, and is preferably a methyl group, an ethyl group, a propyl group, an isopropyl group, or an isobutyl group.

The "halogeno $C_1$-$C_6$ alkyl group" in the definition of Substituent group A in the above formula represents a group wherein a $C_1$-$C_6$ alkyl group described above is substituted as much as possible with a halogen atom, and can be, for example, a fluoromethyl group, a difluoromethyl group, a trifluoromethyl group, a fluoroethyl group, a difluoroethyl group, a trifluoroethyl group, a fluoropropyl group, a difluoropropyl group, a trifluoropropyl group, a fluorobutyl group, a difluorobutyl group, a trifluorobutyl group, a fluoropentyl group, a difluoropentyl group, a trifluoropentyl group, a fluorohexyl group, a difluorohexyl group, a trifluorohexyl group, a pentafluoroethyl group, a hexafluoropropyl group, a nonafluorobutyl group, a chloromethyl group, a dichloromethyl group, a trichloromethyl group, a chloroethyl group, a dichloroethyl group, a trichloroethyl group, a chloropropyl group, a dichloropropyl group, a trichloropropyl group, a chlorobutyl group, a dichlorobutyl group, a trichlorobutyl group, a chloropentyl group, a dichloropentyl group, a trichloropentyl group, a chlorohexyl group, a dichlorohexyl group, a trichlorohexyl group, pentachloroethyl group, a hexachloropropyl group, or a nonachlorobutyl group, and is preferably a fluoromethyl group, a difluoromethyl group, a trifluoromethyl group, a fluoroethyl group, a difluoroethyl group, a trifluoroethyl group, a fluoropropyl group, a difluoropropyl group or a trifluoropropyl group, and more preferably a fluoromethyl group, a difluoromethyl group, a trifluoromethyl group, a fluoroethyl group, a difluoroethyl group, or a trifluoroethyl group.

The "$C_1$-$C_6$ alkoxy group" in the definition of Substituent group A in the above formula represents a group wherein an oxygen atom is bonded to the $C_1$-$C_6$ alkyl group described above, and is preferably a methoxy group, an ethoxy group, a propoxy group, an isopropoxy group, or a butoxy group, and more preferably a methoxy group or an ethoxy group.

The "$C_1$-$C_6$ alkylthio group" in the definition of Substituent group A in the above formula represents a group wherein a sulfur atom is bonded to the $C_1$-$C_6$ alkyl group described above, and is preferably a methylthio group, an ethylthio group, a propylthio group, an isopropylthio group, or a butylthio group, and more preferably a methylthio group or an ethylthio group.

The "$C_1$-$C_6$ alkylcarboxy group" in the definition of Substituent group A in the above formula represents a group wherein a carboxyl group is bonded to the $C_1$-$C_6$ alkyl group described above, and is preferably a methylcarboxyl group, an ethylcarboxyl group, a propylcarboxyl group, an isopropylcarboxyl group, or a butylcarboxyl group, and more preferably a methyl carboxyl group or an ethylcarboxyl group.

The "$C_1$-$C_6$ aliphatic acyl group" in the definition of Substituent group A in the above formula represents a group wherein a carbonyl group is bonded to the $C_1$-$C_6$ alkyl group described above, and can be, for example, an acetyl group, an ethylcarbonyl group, a propylcarbonyl group, a butylcarbonyl group, a pentylcarbonyl group, or a hexylcarbonyl group, and is preferably an acetyl group, an ethylcarbonyl group, or a propylcarbonyl group.

The "mono-$C_1$-$C_6$ alkylamino group" in the definition of Substituent group A in the above formula represents a group wherein an amino group is bonded to the $C_1$-$C_6$ alkyl group described above, and is preferably a methylamino group, an ethylamino group, a propylamino group, an isopropylamino group, or a butylamino group and more preferably a methylamino group or an ethylamino group.

The "di-$C_1$-$C_6$ alkylamino group" in the definition of Substituent group A in the above formula represents a group wherein two $C_1$-$C_6$ alkyl groups described above are bonded to one amino group, and is, for example, preferably a dimethylamino group, a diethylamino group, a dipropylamino group, a diisopropylamino group, or a dibutylamino group, and more preferably a dimethylamino group or a diethylamino group.

The "$C_1$-$C_6$ aliphatic acylamino group" in the definition of Substituent group A in the above formula represents a group wherein a carbonyl group is bonded to the $C_1$-$C_6$ alkyl group and additionally, to such carbonyl group is bonded an amino group, and can be, for example, an acetylamino group, an ethylcarbonylamino group, a propylcarbonylamino group, a butylcarbonylamino group, a pentylcarbonylamino group, or a hexylcarbonylamino group, and is preferably an acetylamino group, an ethylcarbonylamino group, or a propylcarbonylamino group.

A compound having the general formula (I) of the present invention is preferably a compound having the general formula (I') or a compound having the general formula (I").

In the compound having the general formula (I) of the present invention, A is preferably a carboxyl group.

B is preferably a hydrogen atom.

n is preferably 0.

V is preferably a methylene group

W is preferably a 5- to 7-membered heterocyclic group which may optionally be substituted with from 1 to 3 substituents selected from Substituent group A, more preferably a thienylene, furylene, pyrrolene or pyridylene group which may optionally be substituted with from 1 to 3 substituents selected from Substituent group A, and still more preferably a thienylene or pyridylene group which may optionally be substituted with one or two substituents selected from Substituent group A.

X is preferably a $C_1$-$C_8$ alkylene group, a $C_1$-$C_8$ alkylene group containing an oxygen atom or a sulfur atom in the carbon chain, a $C_6$-$C_{10}$ arylene group, a 5- to 7-membered heterocyclic group or a fused ring heterocyclic group, and more preferably a 5- to 7-membered heterocyclic group.

Y is preferably any one group selected from the group consisting of a phenylene group, a 5- to 7-membered heterocyclic group which may optionally be substituted with from 1 to 3 substituents selected from Substituent group A, and a fused ring heterocyclic group which may optionally be substituted with from 1 to 3 substituents selected from Substituent group A, more preferably a phenylene group, or a thienylene, pyridylene or indolylene group which may optionally be substituted with from 1 to 3 substituents selected from Substituent group A, and still more preferably a phenylene or pyridylene group.

Z is preferably a $C_6$-$C_{10}$ aryloxy group which may optionally be substituted with from 1 to 5 substituents selected from Substituent group A, and more preferably a phenoxy group.

In a compound having the general formula (I') of the present invention, $R^1$ is preferably a hydrogen atom.

$R^2$ is preferably a hydrogen atom, a methyl group, or an ethyl group.

$R^3$ is preferably a hydrogen atom, a fluorine atom, a chlorine atom, or a methyl group.

$R^4$ is preferably a hydrogen atom, a fluorine atom, a chlorine atom, a cyano group, a methyl group, or a methoxy group.

$R^5$ is preferably a hydrogen atom or a fluorine atom.

In a compound having the general formula (I") of the present invention, $R^6$ is preferably a hydrogen atom, a methyl group or an ethyl group.

$R^7$ is preferably a hydrogen atom, a fluorine atom, a chlorine atom or a methyl group.

$R^8$ is preferably a n-propyl group, a n-butyl group or an isobutyl group.

The "pharmacologically acceptable salt thereof" described hereinbefore means a salt which can be prepared by reacting a compound having the general formula (I) of the present invention having an acidic group or a basic group, and can be prepared as a base salt or an acid salt by reacting with a base or an acid, respectively. Such salt is described hereinafter.

The pharmacologically acceptable "basic salt" of a compound having the general formula (I) of the present invention is preferably an alkali metal salt such as sodium salt, potassium salt, or lithium salt; an alkaline earth metal salt such as magnesium salt or calcium salt; an organic base salt such as N-methylmorpholine salt, triethylamine salt, tributylamine salt, diisopropylethylamine salt, dicyclohexylamine salt, N-methylpiperidine salt, pyridine salt, 4-pyrrolidinopyridine salt, or picoline salt, or an amino acid salt such as glycine salt, lysine salt, arginine salt, ornithine salt, glutamic acid salt, or aspartic acid salt. The salt is preferably an alkali metal salt.

The pharmacologically acceptable "acid salt" of a compound having the general formula (I) of the present invention is preferably an inorganic acid salt, for example, a hydrohalide such as hydrofluoride, hydrochloride, hydrobromide, or hydroiodide, a nitrate, a perchlorate, a sulfate, a phosphate, or the like; an organic acid salt, for example, a lower alkanesulfonate such as methanesulfonate, trifluoromethanesulfonate, or ethanesulfonate, an arylsulfonate such as benzenesulfonate or p-toluenesulfonate, an acetate, a malate, a fumarate, a succinate, a citrate, an ascorbate, a tartrate, an oxalate, a maleate, or the like; or an amino acid salt such as glycine salt, lysine salt, arginine salt, ornithine salt, glutamic acid salt, or aspartic acid salt, and most preferably a hydrohalide.

The "pharmacologically acceptable prodrug thereof" described above is a compound which is converted into the compound (I) through the reaction of enzymes, gastric acid, or the like under the physiological conditions in vivo, that is, a compound that is converted to the compound (I) by enzymatic oxidation, reduction, hydrolysis or the like, or a compound that is converted to the compound (I) by gastric acid-induced hydrolysis.

The prodrug described above is a compound which, when the compounds (I) have a carboxyl group, can be derived by esterification or amidation of such carboxyl group (for example, compounds derived by ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification, or methylamidation of the carboxyl group of a compound (I)) or the like.

These compounds can be prepared from the compound (I) by known methods.

Furthermore, as the prodrug of the compounds (I) of the present invention, various derivatives which are described in the literature ("Development of medicine" Vol. 7, Molecular design, pp 163-198, published in 1990 by Hirokawa Shoten) and cleaved into the compounds (I) under physiological conditions are also included.

When the compounds of the present invention are allowed to stand in contact with the atmosphere or to recrystallize, they may absorb water or water may attach to them to form a hydrate. The present invention encompasses such hydrates.

The compounds of the present invention also include the corresponding compounds which are labeled with isotopes (for example, $^3H$, $^{14}C$, $^{35}S$, etc.).

When the compounds of the present invention have asymmetric carbon atom(s) in their structures, these compounds can exist as optical isomers due to such asymmetric carbon atom(s). In the present invention, a single optical isomer and mixtures of optical isomers are represented as a single chemical formula. The present invention encompasses both individual optical isomers and mixtures thereof in any ratio.

Preferred examples of the compounds having the general formula (I) of the present invention are, for example, the compounds having the general formula (I-1), (I-2), (I'-1), or (I"-1) shown in the following Tables 1, 2, 3 and 4, but the scope of the present invention should not be limited to these compounds.

The meaning of the abbreviations in the following Tables is shown below. The dotted line (---) represents a single bond or a double bond, and which bond to adopt is logically determined depending on the nature of atoms substituted.

| | |
|---|---|
| N | straight chain |
| I | iso |
| C | cyclo |
| Me | methyl group |
| MeO | methoxy group |
| Et | ethyl group |
| Bn | benzyl group |
| Bu | butyl group |
| Hex | hexyl group |
| Ph | phenyl group |

TABLE 1

(I-1)

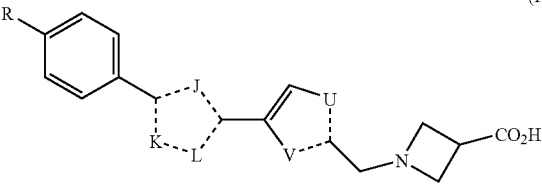

| Compound No. | R | J | K | L | U | V |
|---|---|---|---|---|---|---|
| 1-1 | n-Bu | N | N | O | S | CH |
| 1-2 | i-Bu | N | N | O | S | CH |
| 1-3 | c-Hex | N | N | O | S | CH |
| 1-4 | PhO | N | N | O | S | CH |
| 1-5 | Bn | N | N | O | S | CH |
| 1-6 | n-Bu | N | N | O | O | CH |
| 1-7 | i-Bu | N | N | O | O | CH |
| 1-8 | c-Hex | N | N | O | O | CH |
| 1-9 | PhO | N | N | O | O | CH |
| 1-10 | Bn | N | N | O | O | CH |
| 1-11 | n-Bu | N | N | O | NMe | CH |
| 1-12 | i-Bu | N | N | O | NMe | CH |
| 1-13 | c-Hex | N | N | O | NMe | CH |
| 1-14 | PhO | N | N | O | NMe | CH |
| 1-15 | Bn | N | N | O | NMe | CH |
| 1-16 | n-Bu | N | N | O | N | —CH=CH— |
| 1-17 | i-Bu | N | N | O | N | —CH=CH— |
| 1-18 | c-Hex | N | N | O | N | —CH=CH— |
| 1-19 | PhO | N | N | O | N | —CH=CH— |
| 1-20 | Bn | N | N | O | N | —CH=CH— |
| 1-21 | n-Bu | N | N | O | CH | —N=CH— |
| 1-22 | i-Bu | N | N | O | CH | —N=CH— |

TABLE 1-continued

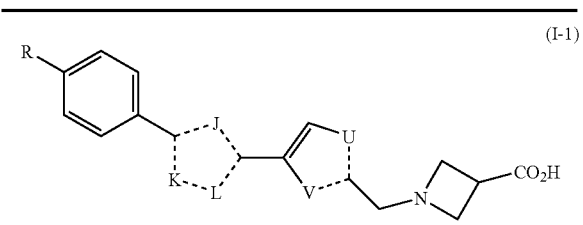

(I-1)

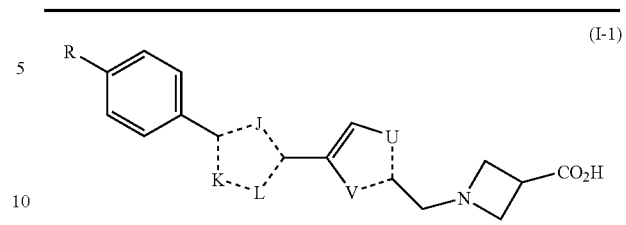

(I-1)

| Compound No. | R | J | K | L | U | V |
|---|---|---|---|---|---|---|
| 1-23 | c-Hex | N | N | O | CH | —N=CH— |
| 1-24 | PhO | N | N | O | CH | —N=CH— |
| 1-25 | Bn | N | N | O | CH | —N=CH— |
| 1-26 | n-Bu | N | N | O | CH | S |
| 1-27 | i-Bu | N | N | O | CH | S |
| 1-28 | c-Hex | N | N | O | CH | S |
| 1-29 | PhO | N | N | O | CH | S |
| 1-30 | Bn | N | N | O | CH | S |
| 1-31 | n-Bu | N | N | O | CH | O |
| 1-32 | i-Bu | N | N | O | CH | O |
| 1-33 | c-Hex | N | N | O | CH | O |
| 1-34 | PhO | N | N | O | CH | O |
| 1-35 | Bn | N | N | O | CH | O |
| 1-36 | n-Bu | N | N | O | CH | NMe |
| 1-37 | i-Bu | N | N | O | CH | NMe |
| 1-38 | c-Hex | N | N | O | CH | NMe |
| 1-39 | PhO | N | N | O | CH | NMe |
| 1-40 | Bn | N | N | O | CH | NMe |
| 1-41 | n-Bu | CH | N | O | S | CH |
| 1-42 | i-Bu | CH | N | O | S | CH |
| 1-43 | c-Hex | CH | N | O | S | CH |
| 1-44 | PhO | CH | N | O | S | CH |
| 1-45 | Bn | CH | N | O | S | CH |
| 1-46 | n-Bu | CH | N | O | O | CH |
| 1-47 | i-Bu | CH | N | O | O | CH |
| 1-48 | c-Hex | CH | N | O | O | CH |
| 1-49 | PhO | CH | N | O | O | CH |
| 1-50 | Bn | CH | N | O | O | CH |
| 1-51 | n-Bu | CH | N | O | NMe | CH |
| 1-52 | i-Bu | CH | N | O | NMe | CH |
| 1-53 | c-Hex | CH | N | O | NMe | CH |
| 1-54 | PhO | CH | N | O | NMe | CH |
| 1-55 | Bn | CH | N | O | NMe | CH |
| 1-56 | n-Bu | CH | N | O | N | —CH=CH— |
| 1-57 | i-Bu | CH | N | O | N | —CH=CH— |
| 1-58 | c-Hex | CH | N | O | N | —CH=CH— |
| 1-59 | PhO | CH | N | O | N | —CH=CH— |
| 1-60 | Bn | CH | N | O | N | —CH=CH— |
| 1-61 | n-Bu | CH | N | O | CH | —N=CH— |
| 1-62 | i-Bu | CH | N | O | CH | —N=CH— |
| 1-63 | c-Hex | CH | N | O | CH | —N=CH— |
| 1-64 | PhO | CH | N | O | CH | —N=CH— |
| 1-65 | Bn | CH | N | O | CH | —N=CH— |
| 1-66 | n-Bu | CH | N | O | CH | S |
| 1-67 | i-Bu | CH | N | O | CH | S |
| 1-68 | c-Hex | CH | N | O | CH | S |
| 1-69 | PhO | CH | N | O | CH | S |
| 1-70 | Bn | CH | N | O | CH | S |
| 1-71 | n-Bu | CH | N | O | CH | O |
| 1-72 | i-Bu | CH | N | O | CH | O |
| 1-73 | c-Hex | CH | N | O | CH | O |
| 1-74 | PhO | CH | N | O | CH | O |
| 1-75 | Bn | CH | N | O | CH | O |
| 1-76 | n-Bu | CH | N | O | CH | NMe |
| 1-77 | i-Bu | CH | N | O | CH | NMe |
| 1-78 | c-Hex | CH | N | O | CH | NMe |
| 1-79 | PhO | CH | N | O | CH | NMe |
| 1-80 | Bn | CH | N | O | CH | NMe |
| 1-81 | n-Bu | N | O | N | S | CH |
| 1-82 | i-Bu | N | O | N | S | CH |
| 1-83 | c-Hex | N | O | N | S | CH |
| 1-84 | PhO | N | O | N | S | CH |
| 1-85 | Bn | N | O | N | S | CH |
| 1-86 | n-Bu | N | O | N | O | CH |
| 1-87 | i-Bu | N | O | N | O | CH |
| 1-88 | c-Hex | N | O | N | O | CH |
| 1-89 | PhO | N | O | N | O | CH |
| 1-90 | Bn | N | O | N | O | CH |
| 1-91 | n-Bu | N | O | N | NMe | CH |
| 1-92 | i-Bu | N | O | N | NMe | CH |
| 1-93 | c-Hex | N | O | N | NMe | CH |
| 1-94 | PhO | N | O | N | NMe | CH |
| 1-95 | Bn | N | O | N | NMe | CH |
| 1-96 | n-Bu | N | O | N | N | —CH=CH— |
| 1-97 | i-Bu | N | O | N | N | —CH=CH— |
| 1-98 | c-Hex | N | O | N | N | —CH=CH— |
| 1-99 | PhO | N | O | N | N | —CH=CH— |
| 1-100 | Bn | N | O | N | N | —CH=CH— |
| 1-101 | n-Bu | N | O | N | CH | —N=CH— |
| 1-102 | i-Bu | N | O | N | CH | —N=CH— |
| 1-103 | c-Hex | N | O | N | CH | —N=CH— |
| 1-104 | PhO | N | O | N | CH | —N=CH— |
| 1-105 | Bn | N | O | N | CH | —N=CH— |
| 1-106 | n-Bu | N | O | N | CH | S |
| 1-107 | i-Bu | N | O | N | CH | S |
| 1-108 | c-Hex | N | O | N | CH | S |
| 1-109 | PhO | N | O | N | CH | S |
| 1-110 | Bn | N | O | N | CH | S |
| 1-111 | n-Bu | N | O | N | CH | O |
| 1-112 | i-Bu | N | O | N | CH | O |
| 1-113 | c-Hex | N | O | N | CH | O |
| 1-114 | PhO | N | O | N | CH | O |
| 1-115 | Bn | N | O | N | CH | O |
| 1-116 | n-Bu | N | O | N | CH | NMe |
| 1-117 | i-Bu | N | O | N | CH | NMe |
| 1-118 | c-Hex | N | O | N | CH | NMe |
| 1-119 | PhO | N | O | N | CH | NMe |
| 1-120 | Bn | N | O | N | CH | NMe |
| 1-121 | n-Bu | CH | O | N | S | CH |
| 1-122 | i-Bu | CH | O | N | S | CH |
| 1-123 | c-Hex | CH | O | N | S | CH |
| 1-124 | PhO | CH | O | N | S | CH |
| 1-125 | Bn | CH | O | N | S | CH |
| 1-126 | n-Bu | CH | O | N | O | CH |
| 1-127 | i-Bu | CH | O | N | O | CH |
| 1-128 | c-Hex | CH | O | N | O | CH |
| 1-129 | PhO | CH | O | N | O | CH |
| 1-130 | Bn | CH | O | N | O | CH |
| 1-131 | n-Bu | CH | O | N | NMe | CH |
| 1-132 | i-Bu | CH | O | N | NMe | CH |
| 1-133 | c-Hex | CH | O | N | NMe | CH |
| 1-134 | PhO | CH | O | N | NMe | CH |
| 1-135 | Bn | CH | O | N | NMe | CH |
| 1-136 | n-Bu | CH | O | N | N | —CH=CH— |
| 1-137 | i-Bu | CH | O | N | N | —CH=CH— |
| 1-138 | c-Hex | CH | O | N | N | —CH=CH— |
| 1-139 | PhO | CH | O | N | N | —CH=CH— |
| 1-140 | Bn | CH | O | N | N | —CH=CH— |
| 1-141 | n-Bu | CH | O | N | CH | —N=CH— |
| 1-142 | i-Bu | CH | O | N | CH | —N=CH— |
| 1-143 | c-Hex | CH | O | N | CH | —N=CH— |
| 1-144 | PhO | CH | O | N | CH | —N=CH— |
| 1-145 | Bn | CH | O | N | CH | —N=CH— |
| 1-146 | n-Bu | CH | O | N | CH | S |
| 1-147 | i-Bu | CH | O | N | CH | S |
| 1-148 | c-Hex | CH | O | N | CH | S |
| 1-149 | PhO | CH | O | N | CH | S |
| 1-150 | Bn | CH | O | N | CH | S |
| 1-151 | n-Bu | CH | O | N | CH | O |
| 1-152 | i-Bu | CH | O | N | CH | O |

TABLE 1-continued (I-1)

R–[phenyl]–[ring with J,K,L,U,V]–CH2–N(azetidine)–CO2H

| Compound No. | R | J | K | L | U | V |
|---|---|---|---|---|---|---|
| 1-153 | c-Hex | CH | O | N | CH | O |
| 1-154 | PhO | CH | O | N | CH | O |
| 1-155 | Bn | CH | O | N | CH | O |
| 1-156 | n-Bu | CH | O | N | CH | NMe |
| 1-157 | i-Bu | CH | O | N | CH | NMe |
| 1-158 | c-Hex | CH | O | N | CH | NMe |
| 1-159 | PhO | CH | O | N | CH | NMe |
| 1-160 | Bn | CH | O | N | CH | NMe |

In Table 1 described above, the preferred compounds (I-1) of the present invention include Exemplification Compound Number 1-3:
1-({4-[3-(4-Cyclohexylphenyl)-1,2,4-oxadiazol-5-yl]-2-thienyl}methyl)azetidine-3-carboxylic acid Exemplification Compound Number 1-8:
1-({4-[3-(4-Cyclohexylphenyl)-1,2,4-oxadiazol-5-yl]-2-furyl}methyl)azetidine-3-carboxylic acid Exemplification Compound Number 1-17:
1-({5-[3-(4-Isobutylphenyl)-1,2,4-oxadiazol-5-yl]pyridin-2-yl}methyl)azetidine-3-carboxylic acid Exemplification Compound Number 1-22:
1-({6-[3-(4-Isobutylphenyl)-1,2,4-oxadiazol-5-yl]pyridin-3-yl}methyl)azetidine-3-carboxylic acid Exemplification Compound Number 1-28:
1-({5-[3-(4-Cyclohexylphenyl)-1,2,4-oxadiazol-5-yl]-2-thienyl}methyl)azetidine-3-carboxylic acid Exemplification Compound Number 1-33:
1-({5-[3-(4-Cyclohexylphenyl)-1,2,4-oxadiazol-5-yl]-2-furyl}methyl)azetidine-3-carboxylic acid Exemplification Compound Number 1-43:
1-({4-[3-(4-Cyclohexylphenyl)isooxazol-5-yl]-2-thienyl}methyl)azetidine-3-carboxylic acid Exemplification Compound Number 1-48:
1-({4-[3-(4-Cyclohexylphenyl)isooxazol-5-yl]-2-furyl}methyl)azetidine-3-carboxylic acid, Exemplification Compound Number 1-57:
1-({5-[3-(4-Isobutylphenyl)isooxazol-5-yl]pyridin-2-yl}methyl)azetidine-3-carboxylic acid, Exemplification Compound Number 1-62:
1-({6-[3-(4-Isobutylphenyl)isooxazol-5-yl]pyridin-2-yl}methyl)azetidine-3-carboxylic acid, Exemplification Compound Number 1-68:
1-({5-[3-(4-Cyclohexylphenyl)isooxazol-5-yl]-2-thienyl}methyl)azetidine-3-carboxylic acid, Exemplification Compound Number 1-73:
1-({5-[3-(4-Cyclohexylphenyl)isooxazol-5-yl]-2-furyl}methyl)azetidine-3-carboxylic acid, Exemplification Compound Number 1-82:
1-({4-[5-(4-Isobutylphenyl)-1,2,4-oxadiazol-3-yl]-2-thienyl}methyl)azetidine-3-carboxylic acid, Exemplification Compound Number 1-83:
1-({4-[5-(4-Cyclohexylphenyl)-1,2,4-oxadiazol-3-yl]-2-thienyl}methyl)azetidine-3-carboxylic acid, Exemplification Compound Number 1-84:
1-({4-[5-(4-Cyclohexylphenyl)-1,2,4-oxadiazol-3-yl]-2-thienyl}methyl)azetidine-3-carboxylic acid, Exemplification Compound Number 1-88:
1-({4-[5-(4-Cyclohexylphenyl)-1,2,4-oxadiazol-3-yl]-2-furyl}methyl)azetidine-3-carboxylic acid, Exemplification Compound Number 1-97:
1-({5-[5-(4-Isobutylphenyl)-1,2,4-oxadiazol-3-yl]pyridin-2-yl}methyl)azetidine-3-carboxylic acid, Exemplification Compound Number 1-102:
1-({6-[5-(4-Isobutylphenyl)-1,2,4-oxadiazol-3-yl]pyridin-2-yl}methyl)azetidine-3-carboxylic acid, Exemplification Compound Number 1-107:
1-({5-[5-(4-Isobutylphenyl)-1,2,4-oxadiazol-3-yl]-2-thienyl}methyl)azetidine-3-carboxylic acid, Exemplification Compound Number 1-108:
1-({5-[5-(4-Cyclohexylphenyl)-1,2,4-oxadiazol-3-yl]-2-thienyl}methyl)azetidine-3-carboxylic acid, Exemplification Compound Number 1-109:
1-({5-[5-(4-Phenoxyphenyl)-1,2,4-oxadiazol-3-yl]-2-thienyl}methyl)azetidine-3-carboxylic acid, Exemplification Compound Number 1-113:
1-({5-[5-(4-Cyclohexylphenyl)-1,2,4-oxadiazol-3-yl]-2-furyl}methyl)azetidine-3-carboxylic acid, Exemplification Compound Number 1-122:
1-({4-[5-(4-Isobutylphenyl)isoxazol-3-yl]-2-thienyl}methyl)azetidine-3-carboxylic acid, Exemplification Compound Number 1-123:
1-({4-[5-(4-Cyclohexylphenyl)isoxazol-3-yl]-2-thienyl}methyl)azetidine-3-carboxylic acid, Exemplification Compound Number 1-124:
1-({4-[5-(4-Phenoxyphenyl)isoxazol-3-yl]-2-thienyl}methyl)azetidine-3-carboxylic acid, Exemplification Compound Number 1-128:
1-({4-[5-(4-Cyclohexylphenyl)isoxazol-3-yl]-2-furyl}-methyl)azetidine-3-carboxylic acid, Exemplification Compound Number 1-137:
1-({5-[5-(4-Isobutylphenyl)isoxazol-3-yl]pyridin-2-yl}methyl)azetidine-3-carboxylic acid, Exemplification Compound Number 1-142:
1-({6-[5-(4-Isobutylphenyl)isoxazol-3-yl]pyridin-3-yl}methyl)azetidine-3-carboxylic acid, Exemplification Compound Number 1-147:
1-({5-[5-(4-Isobutylphenyl)isoxazol-3-yl]-2-thienyl}methyl)azetidine-3-carboxylic acid, Exemplification Compound Number 1-148:
1-({5-[5-(4-Cyclohexylphenyl)isoxazol-3-yl]-2-thienyl}methyl)azetidine-3-carboxylic acid, Exemplification Compound Number 1-149:
1-({5-[5-(4-Phenoxyphenyl)isoxazol-3-yl]-2-thienyl}methyl)azetidine-3-carboxylic acid, and Exemplification Compound Number 1-153:
1-({5-[5-(4-Cyclohexylphenyl)isoxazol-3-yl]-2-furyl}methyl)azetidine-3-carboxylic acid, more preferred compounds are the compounds of Exemplification Compound Nos. 1-83, 1-84, 1-88, 1-97, 1-102, 1-108, 1-109, 1-113, 1-123, 1-124, 1-137, 1-142, and 1-148.

TABLE 2

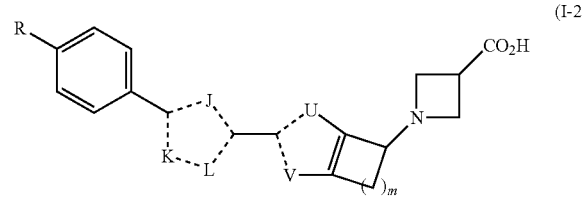

(I-2)

| Compound No. | R | J | K | L | U | V | m |
|---|---|---|---|---|---|---|---|
| 2-1 | n-Bu | N | N | O | S | CH | 2 |
| 2-2 | i-Bu | N | N | O | S | CH | 2 |
| 2-3 | c-Hex | N | N | O | S | CH | 2 |
| 2-4 | PhO | N | N | O | S | CH | 2 |
| 2-5 | Bn | N | N | O | S | CH | 2 |
| 2-6 | n-Bu | N | N | O | S | CH | 3 |
| 2-7 | i-Bu | N | N | O | S | CH | 3 |
| 2-8 | c-Hex | N | N | O | S | CH | 3 |
| 2-9 | PhO | N | N | O | S | CH | 3 |
| 2-10 | Bn | N | N | O | S | CH | 3 |
| 2-11 | n-Bu | N | N | O | O | CH | 2 |
| 2-12 | i-Bu | N | N | O | O | CH | 2 |
| 2-13 | c-Hex | N | N | O | O | CH | 2 |
| 2-14 | PhO | N | N | O | O | CH | 2 |
| 2-15 | Bn | N | N | O | O | CH | 2 |
| 2-16 | n-Bu | N | N | O | O | CH | 3 |
| 2-17 | i-Bu | N | N | O | O | CH | 3 |
| 2-18 | c-Hex | N | N | O | O | CH | 3 |
| 2-19 | PhO | N | N | O | O | CH | 3 |
| 2-20 | Bn | N | N | O | O | CH | 3 |
| 2-21 | n-Bu | N | N | O | NMe | CH | 2 |
| 2-22 | i-Bu | N | N | O | NMe | CH | 2 |
| 2-23 | c-Hex | N | N | O | NMe | CH | 2 |
| 2-24 | PhO | N | N | O | NMe | CH | 2 |
| 2-25 | Bn | N | N | O | NMe | CH | 2 |
| 2-26 | n-Bu | N | N | O | NMe | CH | 3 |
| 2-27 | i-Bu | N | N | O | NMe | CH | 3 |
| 2-28 | c-Hex | N | N | O | NMe | CH | 3 |
| 2-29 | PhO | N | N | O | NMe | CH | 3 |
| 2-30 | Bn | N | N | O | NMe | CH | 3 |
| 2-31 | n-Bu | N | N | O | CH | S | 2 |
| 2-32 | i-Bu | N | N | O | CH | S | 2 |
| 2-33 | c-Hex | N | N | O | CH | S | 2 |
| 2-34 | PhO | N | N | O | CH | S | 2 |
| 2-35 | Bn | N | N | O | CH | S | 2 |
| 2-36 | n-Bu | N | N | O | CH | S | 3 |
| 2-37 | i-Bu | N | N | O | CH | S | 3 |
| 2-38 | c-Hex | N | N | O | CH | S | 3 |
| 2-39 | PhO | N | N | O | CH | S | 3 |
| 2-40 | Bn | N | N | O | CH | S | 3 |
| 2-41 | n-Bu | N | N | O | CH | O | 2 |
| 2-42 | i-Bu | N | N | O | CH | O | 2 |
| 2-43 | c-Hex | N | N | O | CH | O | 2 |
| 2-44 | PhO | N | N | O | CH | O | 2 |
| 2-45 | Bn | N | N | O | CH | O | 2 |
| 2-46 | n-Bu | N | N | O | CH | O | 3 |
| 2-47 | i-Bu | N | N | O | CH | O | 3 |
| 2-48 | c-Hex | N | N | O | CH | O | 3 |
| 2-49 | PhO | N | N | O | CH | O | 3 |
| 2-50 | Bn | N | N | O | CH | O | 3 |
| 2-51 | n-Bu | N | N | O | CH | NMe | 2 |
| 2-52 | i-Bu | N | N | O | CH | NMe | 2 |
| 2-53 | c-Hex | N | N | O | CH | NMe | 2 |
| 2-54 | PhO | N | N | O | CH | NMe | 2 |
| 2-55 | Bn | N | N | O | CH | NMe | 2 |
| 2-56 | n-Bu | N | N | O | CH | NMe | 3 |
| 2-57 | i-Bu | N | N | O | CH | NMe | 3 |
| 2-58 | c-Hex | N | N | O | CH | NMe | 3 |
| 2-59 | PhO | N | N | O | CH | NMe | 3 |
| 2-60 | Bn | N | N | O | CH | NMe | 3 |
| 2-61 | n-Bu | CH | N | O | S | CH | 2 |
| 2-62 | i-Bu | CH | N | O | S | CH | 2 |
| 2-63 | c-Hex | CH | N | O | S | CH | 2 |
| 2-64 | PhO | CH | N | O | S | CH | 2 |
| 2-65 | Bn | CH | N | O | S | CH | 2 |
| 2-66 | n-Bu | CH | N | O | S | CH | 3 |
| 2-67 | i-Bu | CH | N | O | S | CH | 3 |
| 2-68 | c-Hex | CH | N | O | S | CH | 3 |
| 2-69 | PhO | CH | N | O | S | CH | 3 |
| 2-70 | Bn | CH | N | O | S | CH | 3 |
| 2-71 | n-Bu | CH | N | O | O | CH | 2 |
| 2-72 | i-Bu | CH | N | O | O | CH | 2 |
| 2-73 | c-Hex | CH | N | O | O | CH | 2 |
| 2-74 | PhO | CH | N | O | O | CH | 2 |
| 2-75 | Bn | CH | N | O | O | CH | 2 |
| 2-76 | n-Bu | CH | N | O | O | CH | 3 |
| 2-77 | i-Bu | CH | N | O | O | CH | 3 |
| 2-78 | c-Hex | CH | N | O | O | CH | 3 |
| 2-79 | PhO | CH | N | O | O | CH | 3 |
| 2-80 | Bn | CH | N | O | O | CH | 3 |
| 2-81 | n-Bu | CH | N | O | NMe | CH | 2 |
| 2-82 | i-Bu | CH | N | O | NMe | CH | 2 |
| 2-83 | c-Hex | CH | N | O | NMe | CH | 2 |
| 2-84 | PhO | CH | N | O | NMe | CH | 2 |
| 2-85 | Bn | CH | N | O | NMe | CH | 2 |
| 2-86 | n-Bu | CH | N | O | NMe | CH | 3 |
| 2-87 | i-Bu | CH | N | O | NMe | CH | 3 |
| 2-88 | c-Hex | CH | N | O | NMe | CH | 3 |
| 2-89 | PhO | CH | N | O | NMe | CH | 3 |
| 2-90 | Bn | CH | N | O | NMe | CH | 3 |
| 2-91 | n-Bu | CH | N | O | CH | S | 2 |
| 2-92 | i-Bu | CH | N | O | CH | S | 2 |
| 2-93 | c-Hex | CH | N | O | CH | S | 2 |
| 2-94 | PhO | CH | N | O | CH | S | 2 |
| 2-95 | Bn | CH | N | O | CH | S | 2 |
| 2-96 | n-Bu | CH | N | O | CH | S | 3 |
| 2-97 | i-Bu | CH | N | O | CH | S | 3 |
| 2-98 | c-Hex | CH | N | O | CH | S | 3 |
| 2-99 | PhO | CH | N | O | CH | S | 3 |
| 2-100 | Bn | CH | N | O | CH | S | 3 |
| 2-101 | n-Bu | CH | N | O | CH | O | 2 |
| 2-102 | i-Bu | CH | N | O | CH | O | 2 |
| 2-103 | c-Hex | CH | N | O | CH | O | 2 |
| 2-104 | PhO | CH | N | O | CH | O | 2 |
| 2-105 | Bn | CH | N | O | CH | O | 2 |
| 2-106 | n-Bu | CH | N | O | CH | O | 3 |
| 2-107 | i-Bu | CH | N | O | CH | O | 3 |
| 2-108 | c-Hex | CH | N | O | CH | O | 3 |
| 2-109 | PhO | CH | N | O | CH | O | 3 |
| 2-110 | Bn | CH | N | O | CH | O | 3 |
| 2-111 | n-Bu | CH | N | O | CH | NMe | 2 |
| 2-112 | i-Bu | CH | N | O | CH | NMe | 2 |
| 2-113 | c-Hex | CH | N | O | CH | NMe | 2 |
| 2-114 | PhO | CH | N | O | CH | NMe | 2 |
| 2-115 | Bn | CH | N | O | CH | NMe | 2 |
| 2-116 | n-Bu | CH | N | O | CH | NMe | 3 |
| 2-117 | i-Bu | CH | N | O | CH | NMe | 3 |
| 2-118 | c-Hex | CH | N | O | CH | NMe | 3 |
| 2-119 | PhO | CH | N | O | CH | NMe | 3 |
| 2-120 | Bn | CH | N | O | CH | NMe | 3 |
| 2-121 | n-Bu | N | O | N | S | CH | 2 |
| 2-122 | i-Bu | N | O | N | S | CH | 2 |

TABLE 2-continued (I-2)

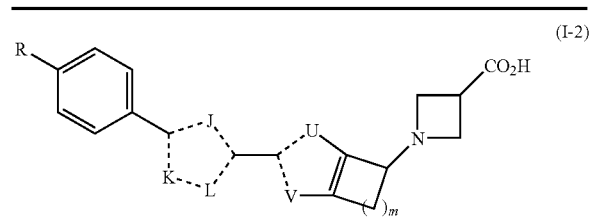

| Compound No. | R | J | K | L | U | V | m |
|---|---|---|---|---|---|---|---|
| 2-123 | c-Hex | N | O | N | S | CH | 2 |
| 2-124 | PhO | N | O | N | S | CH | 2 |
| 2-125 | Bn | N | O | N | S | CH | 2 |
| 2-126 | n-Bu | N | O | N | S | CH | 3 |
| 2-127 | i-Bu | N | O | N | S | CH | 3 |
| 2-128 | c-Hex | N | O | N | S | CH | 3 |
| 2-129 | PhO | N | O | N | S | CH | 3 |
| 2-130 | Bn | N | O | N | S | CH | 3 |
| 2-131 | n-Bu | N | O | N | O | CH | 2 |
| 2-132 | i-Bu | N | O | N | O | CH | 2 |
| 2-133 | c-Hex | N | O | N | O | CH | 2 |
| 2-134 | PhO | N | O | N | O | CH | 2 |
| 2-135 | Bn | N | O | N | O | CH | 2 |
| 2-136 | n-Bu | N | O | N | O | CH | 3 |
| 2-137 | i-Bu | N | O | N | O | CH | 3 |
| 2-138 | c-Hex | N | O | N | O | CH | 3 |
| 2-139 | PhO | N | O | N | O | CH | 3 |
| 2-140 | Bn | N | O | N | O | CH | 3 |
| 2-141 | n-Bu | N | O | N | NMe | CH | 2 |
| 2-142 | i-Bu | N | O | N | NMe | CH | 2 |
| 2-143 | c-Hex | N | O | N | NMe | CH | 2 |
| 2-144 | PhO | N | O | N | NMe | CH | 2 |
| 2-145 | Bn | N | O | N | NMe | CH | 2 |
| 2-146 | n-Bu | N | O | N | NMe | CH | 3 |
| 2-147 | i-Bu | N | O | N | NMe | CH | 3 |
| 2-148 | c-Hex | N | O | N | NMe | CH | 3 |
| 2-149 | PhO | N | O | N | NMe | CH | 3 |
| 2-150 | Bn | N | O | N | NMe | CH | 3 |
| 2-151 | n-Bu | N | O | N | CH | S | 2 |
| 2-152 | i-Bu | N | O | N | CH | S | 2 |
| 2-153 | c-Hex | N | O | N | CH | S | 2 |
| 2-154 | PhO | N | O | N | CH | S | 2 |
| 2-155 | Bn | N | O | N | CH | S | 2 |
| 2-156 | n-Bu | N | O | N | CH | S | 3 |
| 2-157 | i-Bu | N | O | N | CH | S | 3 |
| 2-158 | c-Hex | N | O | N | CH | S | 3 |
| 2-159 | PhO | N | O | N | CH | S | 3 |
| 2-160 | Bn | N | O | N | CH | S | 3 |
| 2-161 | n-Bu | N | O | N | CH | O | 2 |
| 2-162 | i-Bu | N | O | N | CH | O | 2 |
| 2-163 | c-Hex | N | O | N | CH | O | 2 |
| 2-164 | PhO | N | O | N | CH | O | 2 |
| 2-165 | Bn | N | O | N | CH | O | 2 |
| 2-166 | n-Bu | N | O | N | CH | O | 3 |
| 2-167 | i-Bu | N | O | N | CH | O | 3 |
| 2-168 | c-Hex | N | O | N | CH | O | 3 |
| 2-169 | PhO | N | O | N | CH | O | 3 |
| 2-170 | Bn | N | O | N | CH | O | 3 |
| 2-171 | n-Bu | N | O | N | CH | NMe | 2 |
| 2-172 | i-Bu | N | O | N | CH | NMe | 2 |
| 2-173 | c-Hex | N | O | N | CH | NMe | 2 |
| 2-174 | PhO | N | O | N | CH | NMe | 2 |
| 2-175 | Bn | N | O | N | CH | NMe | 2 |
| 2-176 | n-Bu | N | O | N | CH | NMe | 3 |
| 2-177 | i-Bu | N | O | N | CH | NMe | 3 |
| 2-178 | c-Hex | N | O | N | CH | NMe | 3 |
| 2-179 | PhO | N | O | N | CH | NMe | 3 |
| 2-180 | Bn | N | O | N | CH | NMe | 3 |
| 2-181 | n-Bu | CH | O | N | S | CH | 2 |
| 2-182 | i-Bu | CH | O | N | S | CH | 2 |
| 2-183 | c-Hex | CH | O | N | S | CH | 2 |
| 2-184 | PhO | CH | O | N | S | CH | 2 |
| 2-185 | Bn | CH | O | N | S | CH | 2 |
| 2-186 | n-Bu | CH | O | N | S | CH | 3 |
| 2-187 | i-Bu | CH | O | N | S | CH | 3 |

TABLE 2-continued (I-2)

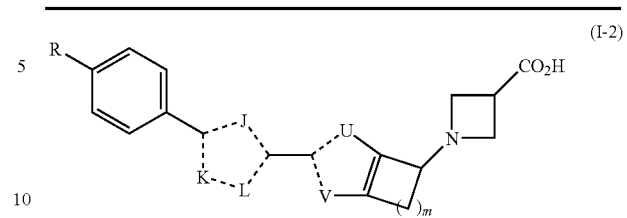

| Compound No. | R | J | K | L | U | V | m |
|---|---|---|---|---|---|---|---|
| 2-188 | c-Hex | CH | O | N | S | CH | 3 |
| 2-189 | PhO | CH | O | N | S | CH | 3 |
| 2-190 | Bn | CH | O | N | S | CH | 3 |
| 2-191 | n-Bu | CH | O | N | O | CH | 2 |
| 2-192 | i-Bu | CH | O | N | O | CH | 2 |
| 2-193 | c-Hex | CH | O | N | O | CH | 2 |
| 2-194 | PhO | CH | O | N | O | CH | 2 |
| 2-195 | Bn | CH | O | N | O | CH | 2 |
| 2-196 | n-Bu | CH | O | N | O | CH | 3 |
| 2-197 | i-Bu | CH | O | N | O | CH | 3 |
| 2-198 | c-Hex | CH | O | N | O | CH | 3 |
| 2-199 | PhO | CH | O | N | O | CH | 3 |
| 2-200 | Bn | CH | O | N | O | CH | 3 |
| 2-201 | n-Bu | CH | O | N | NMe | CH | 2 |
| 2-202 | i-Bu | CH | O | N | NMe | CH | 2 |
| 2-203 | c-Hex | CH | O | N | NMe | CH | 2 |
| 2-204 | PhO | CH | O | N | NMe | CH | 2 |
| 2-205 | Bn | CH | O | N | NMe | CH | 2 |
| 2-206 | n-Bu | CH | O | N | NMe | CH | 3 |
| 2-207 | i-Bu | CH | O | N | NMe | CH | 3 |
| 2-208 | c-Hex | CH | O | N | NMe | CH | 3 |
| 2-209 | PhO | CH | O | N | NMe | CH | 3 |
| 2-210 | Bn | CH | O | N | NMe | CH | 3 |
| 2-211 | n-Bu | CH | O | N | CH | S | 2 |
| 2-212 | i-Bu | CH | O | N | CH | S | 2 |
| 2-213 | c-Hex | CH | O | N | CH | S | 2 |
| 2-214 | PhO | CH | O | N | CH | S | 2 |
| 2-215 | Bn | CH | O | N | CH | S | 2 |
| 2-216 | n-Bu | CH | O | N | CH | S | 3 |
| 2-217 | i-Bu | CH | O | N | CH | S | 3 |
| 2-218 | c-Hex | CH | O | N | CH | S | 3 |
| 2-219 | PhO | CH | O | N | CH | S | 3 |
| 2-220 | Bn | CH | O | N | CH | S | 3 |
| 2-221 | n-Bu | CH | O | N | CH | O | 2 |
| 2-222 | i-Bu | CH | O | N | CH | O | 2 |
| 2-223 | c-Hex | CH | O | N | CH | O | 2 |
| 2-224 | PhO | CH | O | N | CH | O | 2 |
| 2-225 | Bn | CH | O | N | CH | O | 2 |
| 2-226 | n-Bu | CH | O | N | CH | O | 3 |
| 2-227 | i-Bu | CH | O | N | CH | O | 3 |
| 2-228 | c-Hex | CH | O | N | CH | O | 3 |
| 2-229 | PhO | CH | O | N | CH | O | 3 |
| 2-230 | Bn | CH | O | N | CH | O | 3 |
| 2-231 | n-Bu | CH | O | N | CH | NMe | 2 |
| 2-232 | i-Bu | CH | O | N | CH | NMe | 2 |
| 2-233 | c-Hex | CH | O | N | CH | NMe | 2 |
| 2-234 | PhO | CH | O | N | CH | NMe | 2 |
| 2-235 | Bn | CH | O | N | CH | NMe | 2 |
| 2-236 | n-Bu | CH | O | N | CH | NMe | 3 |
| 2-237 | i-Bu | CH | O | N | CH | NMe | 3 |
| 2-238 | c-Hex | CH | O | N | CH | NMe | 3 |
| 2-239 | PhO | CH | O | N | CH | NMe | 3 |
| 2-240 | Bn | CH | O | N | CH | NMe | 3 |

In Table 2 described above, the preferred compounds (I-2) of the present invention include Exemplification Compound Number 2-33:
1-{2-[3-(4-Cyclohexylphenyl)-1,2,4-oxadiazol-5-yl]-5,6-dihydro-4H-cyclopenta[b]thien-4-yl}azetidine-3-carboxylic acid, Exemplification Compound Number 2-38:
1-{2-[3-(4-Cyclohexylphenyl)-1,2,4-oxadiazol-5-yl]-4,5,6,7-tetrahydro-1-benzothien-4-yl}azetidine-3-carboxylic acid, Exemplification Compound Number 2-43:
1-{2-[3-(4-Cyclohexylphenyl)-1,2,4-oxadiazol-5-yl]-5,6-dihydro-4H-cyclopenta[b]furan-4-yl}azetidine-3-carboxylic acid, Exemplification Compound Number 2-48:
1-{2-[3-(4-Cyclohexylphenyl)-1,2,4-oxadiazol-5-yl]-4,5,6,7-tetrahydro-1-benzofuran-4-yl}azetidine-3-carboxylic acid, Exemplification Compound Number 2-93:
1-(2-[3-(4-Cyclohexylphenyl)isoxazol-5-yl]-5,6-dihydro-4H-cyclopenta[b]thien-4-yl)azetidine-3-carboxylic acid, Exemplification Compound Number 2-98:
1-{2-[3-(4-Cyclohexylphenyl)isoxazol-5-yl]-4,5,6,7-tetrahydro-1-benzothien-4-yl}azetidine-3-carboxylic acid, Exemplification Compound Number 2-103:
1-{2-[3-(4-Cyclohexylphenyl)isoxazol-5-yl]-5,6-dihydro-4H-cyclopenta[b]thien-4-yl}azetidine-3-carboxylic acid, Exemplification Compound Number 2-108:
1-{2-[3-(4-Cyclohexylphenyl)isoxazol-5-yl]-4,5,6,7-tetrahydro-1-benzofuran-4-yl}azetidine-3-carboxylic acid, Exemplification Compound Number 2-153:
1-{2-[5-(4-Cyclohexylphenyl)1,2,4-oxadiazol-3-yl]-5,6-dihydro-4H-cyclopenta[b]thien-4-yl}azetidine-3-carboxylic acid, Exemplification Compound Number 2-158:
1-{2-[5-(4-Cyclohexylphenyl)1,2,4-oxadiazol-3-yl]-4,5,6,7-tetrahydro-1-benzothien-4-yl}azetidine-3-carboxylic acid, Exemplification Compound Number 2-163:
1-{2-[5-(4-Cyclohexylphenyl)1,2,4-oxadiazol-3-yl]-5,6-dihydro-4H-cyclopenta[b]furan-4-yl}azetidine-3-carboxylic acid, Exemplification Compound Number 2-168:
1-{2-[5-(4-Cyclohexylphenyl)1,2,4-oxadiazol-3-yl]-4,5,6,7-tetrahydro-1-benzofuran-4-yl}azetidine-3-carboxylic acid, Exemplification Compound Number 2-213:
1-{2-[5-(4-Cyclohexylphenyl)isoxazol-3-yl]-5,6-dihydro-4H-cyclopenta[b]thien-4-yl}azetidine-3-carboxylic acid, Exemplification Compound Number 2-218:
1-{2-[5-(4-Cyclohexylphenyl)isoxazol-3-yl]-4,5,6,7-tetrahydro-1-benzothien-4-yl}azetidine-3-carboxylic acid, Exemplification Compound Number 2-223:
1-{2-[5-(4-Cyclohexylphenyl)isoxazol-3-yl]-5,6-dihydro-4H-cyclopenta[b]furan-4-yl}azetidine-3-carboxylic acid, and Exemplification Compound Number 2-228:
1-{2-[5-(4-Cyclohexylphenyl)isoxazol-3-yl]-4,5,6,7-tetrahydro-1-benzofuran-4-yl}azetidine-3-carboxylic acid,
more preferred compounds are the compounds of Exemplification Compound Nos. 2-43, 2-48, 2-103, 2-108, 2-163, 2-168, 2-223, and 2-228.

TABLE 3

| Compound No. | $R^1$ | $R^2$ | $R^3$ | $R^4$ | $R^5$ |
|---|---|---|---|---|---|
| 3-1 | H | H | H | H | H |
| 3-2 | H | H | H | H | F |
| 3-3 | H | H | F | H | H |
| 3-4 | H | H | F | H | F |
| 3-5 | H | H | Cl | H | H |
| 3-6 | H | H | Cl | H | F |
| 3-7 | H | H | H | MeO | H |
| 3-8 | H | H | H | MeO | F |
| 3-9 | H | H | F | MeO | H |
| 3-10 | H | H | F | MeO | F |
| 3-11 | H | H | Cl | MeO | H |
| 3-12 | H | H | Cl | MeO | F |
| 3-13 | H | H | H | F | H |
| 3-14 | H | H | H | F | F |
| 3-15 | H | H | F | F | H |
| 3-16 | H | H | F | F | F |
| 3-17 | H | H | Cl | F | H |
| 3-18 | H | H | Cl | F | F |
| 3-19 | H | H | H | Cl | H |
| 3-20 | H | H | H | Cl | F |
| 3-21 | H | H | F | Cl | H |
| 3-22 | H | H | F | Cl | F |
| 3-23 | H | H | Cl | Cl | H |
| 3-24 | H | H | Cl | Cl | F |
| 3-25 | H | Me | H | H | H |
| 3-26 | H | Me | H | H | F |
| 3-27 | H | Me | F | H | H |
| 3-28 | H | Me | F | H | F |
| 3-29 | H | Me | Cl | H | H |
| 3-30 | H | Me | Cl | H | F |
| 3-31 | H | Me | H | MeO | H |
| 3-32 | H | Me | H | MeO | F |
| 3-33 | H | Me | F | MeO | H |
| 3-34 | H | Me | F | MeO | F |
| 3-35 | H | Me | Cl | MeO | H |
| 3-36 | H | Me | Cl | MeO | F |
| 3-37 | H | Me | H | F | H |
| 3-38 | H | Me | H | F | F |
| 3-39 | H | Me | F | F | H |
| 3-40 | H | Me | F | F | F |
| 3-41 | H | Me | Cl | F | H |
| 3-42 | H | Me | Cl | F | F |
| 3-43 | H | Me | H | Cl | H |
| 3-44 | H | Me | H | Cl | F |
| 3-45 | H | Me | F | Cl | H |
| 3-46 | H | Me | F | Cl | F |
| 3-47 | H | Me | Cl | Cl | H |
| 3-48 | H | Me | Cl | Cl | F |
| 3-49 | H | Et | H | H | H |
| 3-50 | H | Et | H | H | F |
| 3-51 | H | Et | F | H | H |
| 3-52 | H | Et | F | H | F |
| 3-53 | H | Et | Cl | H | H |
| 3-54 | H | Et | Cl | H | F |
| 3-55 | H | Et | H | MeO | H |
| 3-56 | H | Et | H | MeO | F |
| 3-57 | H | Et | F | MeO | H |
| 3-58 | H | Et | F | MeO | F |
| 3-59 | H | Et | Cl | MeO | H |
| 3-60 | H | Et | Cl | MeO | F |
| 3-61 | H | Et | H | F | H |
| 3-62 | H | Et | H | F | F |
| 3-63 | H | Et | F | F | H |
| 3-64 | H | Et | F | F | F |

TABLE 3-continued (I'-1)

| Compound No. | R¹ | R² | R³ | R⁴ | R⁵ |
|---|---|---|---|---|---|
| 3-65 | H | Et | Cl | F | H |
| 3-66 | H | Et | Cl | F | F |
| 3-67 | H | Et | H | Cl | H |
| 3-68 | H | Et | H | Cl | F |
| 3-69 | H | Et | F | Cl | H |
| 3-70 | H | Et | F | Cl | F |
| 3-71 | H | Et | Cl | Cl | H |
| 3-72 | H | Et | Cl | Cl | F |
| 3-73 | Me | H | H | H | H |
| 3-74 | Me | H | H | H | F |
| 3-75 | Me | H | F | H | H |
| 3-76 | Me | H | F | H | F |
| 3-77 | Me | H | Cl | H | H |
| 3-78 | Me | H | Cl | H | F |
| 3-79 | Me | H | H | MeO | H |
| 3-80 | Me | H | H | MeO | F |
| 3-81 | Me | H | F | MeO | H |
| 3-82 | Me | H | F | MeO | F |
| 3-83 | Me | H | Cl | MeO | H |
| 3-84 | Me | H | Cl | MeO | F |
| 3-85 | Me | H | H | F | H |
| 3-86 | Me | H | H | F | F |
| 3-87 | Me | H | F | F | H |
| 3-88 | Me | H | F | F | F |
| 3-89 | Me | H | Cl | F | H |
| 3-90 | Me | H | Cl | F | F |
| 3-91 | Me | H | H | Cl | H |
| 3-92 | Me | H | H | Cl | F |
| 3-93 | Me | H | F | Cl | H |
| 3-94 | Me | H | F | Cl | F |
| 3-95 | Me | H | Cl | Cl | H |
| 3-96 | Me | H | Cl | Cl | F |
| 3-97 | Et | H | H | H | H |
| 3-98 | Et | H | H | H | F |
| 3-99 | Et | H | F | H | H |
| 3-100 | Et | H | F | H | F |
| 3-101 | Et | H | Cl | H | H |
| 3-102 | Et | H | Cl | H | F |
| 3-103 | Et | H | H | MeO | H |
| 3-104 | Et | H | H | MeO | F |
| 3-105 | Et | H | F | MeO | H |
| 3-106 | Et | H | F | MeO | F |
| 3-107 | Et | H | Cl | MeO | H |
| 3-108 | Et | H | Cl | MeO | F |
| 3-109 | Et | H | H | F | H |
| 3-110 | Et | H | H | F | F |
| 3-111 | Et | H | F | F | H |
| 3-112 | Et | H | F | F | F |
| 3-113 | Et | H | Cl | F | H |
| 3-114 | Et | H | Cl | F | F |
| 3-115 | Et | H | H | Cl | H |
| 3-116 | Et | H | H | Cl | F |
| 3-117 | Et | H | F | Cl | H |
| 3-118 | Et | H | F | Cl | F |
| 3-119 | Et | H | Cl | Cl | H |
| 3-120 | Et | H | Cl | Cl | F |

In Table 3 described above, the preferred compounds (I'-1) of the present invention include Exemplification Compound Number 3-1:
1-({5-[5-(4-Phenoxyphenyl)-1,2,4-oxadiazol-3-yl]-2-thienyl}methyl)azetidine-3-carboxylic acid (Example 5), Exemplification Compound Number 3-25:
1-({4-Methyl-5-[5-(4-phenoxyphenyl)-1,2,4-oxadiazol-3-yl]-2-thienyl}methyl)azetidine-3-carboxylic acid (Example 12), Exemplification Compound Number 3-27:
1-({5-[5-(3-Fluoro-4-phenoxyphenyl)-1,2,4-oxadiazol-3-yl]-4-methyl-2-thienyl}methyl)azetidine-3-carboxylic acid (Example 11), Exemplification Compound Number 3-49:
1-({4-Ethyl-5-[5-(4-phenoxyphenyl)-1,2,4-oxadiazol-3-yl]-2-thienyl}methyl)azetidine-3-carboxylic acid (Example 13), Exemplification Compound Number 3-50:
1-[(4-Ethyl-5-{5-[4-(3-fluorophenoxy)phenyl]-1,2,4-oxadiazol-3-yl}-2-thienyl)methyl]azetidine-3-carboxylic acid (Example 17), Exemplification Compound Number 3-51:
1-({4-Ethyl-5-[5-(3-fluoro-4-phenoxyphenyl)-1,2,4-oxadiazol-3-yl]-2-thienyl}methyl)azetidine-3-carboxylic acid (Example 14), Exemplification Compound Number 3-52:
1-[(4-Ethyl-5-{5-[3-fluoro-4-(3-fluorophenoxy)phenyl]-1,2,4-oxadiazol-3-yl}-2-thienyl)methyl]azetidine-3-carboxylic acid (Example 20), Exemplification Compound Number 3-53:
1-[(4-Ethyl-5-{5-[4-(2-methoxyphenoxy)phenyl]-1,2,4-oxadiazol-3-yl}-2-thienyl)methyl]azetidine-3-carboxylic acid (Example 15), Exemplification Compound Number 3-54:
1-[(5-{5-[3-Chloro-4-(3-fluorophenoxy)phenyl]-1,2,4-oxadiazol-3-yl}-4-ethyl-2-thienyl)methyl]azetidine-3-carboxylic acid (Example 16), Exemplification Compound Number 3-55:
1-[(4-Ethyl-5-{5-[4-(2-methoxyphenoxy)phenyl]-1,2,4-oxadiazol-3-yl}-2-thienyl)methyl]azetidine-3-carboxylic acid (Example 21), Exemplification Compound Number 3-61:
1-[(4-Ethyl-5-{5-[4-(2-fluorophenoxy)phenyl]-1,2,4-oxadiazol-3-yl}-2-thienyl)methyl]azetidine-3-carboxylic acid (Example 10), Exemplification Compound Number 3-62:
1-[(5-{5-[4-(2,3-Difluorophenoxy)phenyl]-1,2,4-oxadiazol-3-yl}-4-ethyl-2-thienyl)methyl]azetidine-3-carboxylic acid (Example 18), Exemplification Compound Number 3-63:
1-[(4-Ethyl-5-{5-[3-fluoro-4-(2-difluorophenoxy)phenyl]-1,2,4-oxadiazol-3-yl}-2-thienyl)methyl]azetidine-3-carboxylic acid, Exemplification Compound Number 3-64:
1-[(5-{5-[4-(2,3-Difluorophenoxy)-3-fluorophenyl]-1,2,4-oxadiazol-3-yl}-4-ethyl-2-thienyl)methyl]azetidine-3-carboxylic acid, Exemplification Compound Number 3-65:
1-[(5-{5-[3-Chloro-4-(2-fluorophenoxy)phenyl]-1,2,4-oxadiazol-3-yl}-4-ethyl-2-thienyl)methyl]azetidine-3-carboxylic acid, Exemplification Compound Number 3-66:
1-[(5-{5-[3-Chloro-4-(2,3-difluorophenoxy)phenyl]-1,2,4-oxadiazol-3-yl}-4-ethyl-2-thienyl)methyl]azetidine-3-carboxylic acid, Exemplification Compound Number 3-67:
1-[(5-{5-[4-(2-Chlorophenoxy)phenyl]-1,2,4-oxadiazol-3-yl}-4-ethyl-2-thienyl)methyl]azetidine-3-carboxylic acid (Example 19), Exemplification Compound Number 3-69:
1-[(5-{5-[4-(2-Chlorophenoxy)-3-fluorophenyl]-1,2,4-oxadiazol-3-yl}-4-ethyl-2-thienyl)methyl]azetidine-3-carboxylic acid, Exemplification Compound Number 3-73:
1-({3-Methyl-5-[5-(4-phenoxyphenyl)-1,2,4-oxadiazol-3-yl]-2-thienyl}methyl)azetidine-3-carboxylic acid, and Exemplification Compound Number 3-97:
1-({3-Ethyl-5-[5-(4-phenoxyphenyl)-1,2,4-oxadiazol-3-yl]-2-thienyl}methyl)azetidine-3-carboxylic acid (Example 22), more preferred compounds are the compounds of Exemplification Compound Nos. 3-25, 3-27, 3-49, 3-50, 3-51, 3-52, 3-53, 3-54, 3-55, 3-61, and 3-67.

TABLE 4

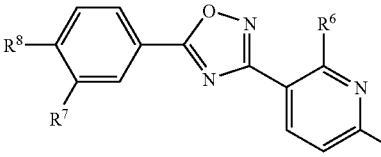

(I''-1)

| Compound No. | $R^6$ | $R^7$ | $R^8$ |
|---|---|---|---|
| 4-1 | H | H | Pr |
| 4-2 | H | H | Bu |
| 4-3 | H | H | iBu |
| 4-4 | H | Me | Pr |
| 4-5 | H | Me | Bu |
| 4-6 | H | Me | iBu |
| 4-7 | H | F | Pr |
| 4-8 | H | F | Bu |
| 4-9 | H | F | iBu |
| 4-10 | H | Cl | Pr |
| 4-11 | H | Cl | Bu |
| 4-12 | H | Cl | iBu |
| 4-13 | H | $CF_3$ | Pr |
| 4-14 | H | $CF_3$ | Bu |
| 4-15 | H | $CF_3$ | iBu |
| 4-16 | Me | H | Pr |
| 4-17 | Me | H | Bu |
| 4-18 | Me | H | iBu |
| 4-19 | Me | Me | Pr |
| 4-20 | Me | Me | Bu |
| 4-21 | Me | Me | iBu |
| 4-22 | Me | F | Pr |
| 4-23 | Me | F | Bu |
| 4-24 | Me | F | iBu |
| 4-25 | Me | Cl | Pr |
| 4-26 | Me | Cl | Bu |
| 4-27 | Me | Cl | iBu |
| 4-28 | Me | $CF_3$ | Pr |
| 4-29 | Me | $CF_3$ | Bu |
| 4-30 | Me | $CF_3$ | iBu |
| 4-31 | Et | H | Pr |
| 4-32 | Et | H | Bu |
| 4-33 | Et | H | iBu |
| 4-34 | Et | Me | Pr |
| 4-35 | Et | Me | Bu |
| 4-36 | Et | Me | iBu |
| 4-37 | Et | F | Pr |
| 4-38 | Et | F | Bu |
| 4-39 | Et | F | iBu |
| 4-40 | Et | Cl | Pr |
| 4-41 | Et | Cl | Bu |
| 4-42 | Et | Cl | iBu |

TABLE 4-continued (I''-1)

| Compound No. | $R^6$ | $R^7$ | $R^8$ |
|---|---|---|---|
| 4-43 | Et | $CF_3$ | Pr |
| 4-44 | Et | $CF_3$ | Bu |
| 4-45 | Et | $CF_3$ | iBu |

In Table 4 described above, the preferred compounds (I''-1) of the present invention include Exemplification Compound Number 4-6:
1-({5-[5-(4-Isobutyl-3-methylphenyl)-1,2,4-oxadiazol-3-yl]pyridin-2-yl}methyl)azetidine-3-carboxylic acid (Example 28), Exemplification Compound Number 4-9:
1-({5-[5-(3-Fluoro-4-isobutylphenyl)-1,2,4-oxadiazol-3-yl]pyridin-2-yl}methyl)azetidine-3-carboxylic acid (Example 23), Exemplification Compound Number 4-12:
1-({5-[5-(3-Chloro-4-isobutylphenyl)-1,2,4-oxadiazol-3-yl]pyridin-2-yl}methyl)azetidine-3-carboxylic acid (Example 26), Exemplification Compound Number 4-21:
1-({5-[5-(4-Isobutyl-3-methylphenyl)-1,2,4-oxadiazol-3-yl]-6-methylpyridin-2-yl}methyl)azetidine-3-carboxylic acid (Example 27), Exemplification Compound Number 4-22:
1-({5-[5-(3-Fluoro-4-propylphenyl)-1,2,4-oxadiazol-3-yl]-6-methylpyridin-2-yl}methyl)azetidine-3-carboxylic acid, Exemplification Compound Number 4-23:
1-({5-[5-(4-Butyl-3-fluorophenyl)-1,2,4-oxadiazol-3-yl]-6-methylpyridin-2-yl}methyl)azetidine-3-carboxylic acid, Exemplification Compound Number 4-24:
1-({5-[5-(3-Fluoro-4-isobutylphenyl)-1,2,4-oxadiazol-3-yl]-6-methylpyridin-2-yl}methyl)azetidine-3-carboxylic acid, Exemplification Compound Number 4-27:
1-({5-[5-(3-Chloro-4-isobutylphenyl)-1,2,4-oxadiazol-3-yl]-6-methylpyridin-2-yl}methyl)azetidine-3-carboxylic acid (Example 24), Exemplification Compound Number 4-36:
1-({6-Ethyl-5-[5-(4-isobutyl-3-methylphenyl)-1,2,4-oxadiazol-3-yl]pyridin-2-yl}methyl)azetidine-3-carboxylic acid (Example 29), Exemplification Compound Number 4-37:
1-({6-Ethyl-5-[5-(3-fluoro-4-propylphenyl)-1,2,4-oxadiazol-3-yl]pyridin-2-yl}methyl)azetidine-3-carboxylic acid, Exemplification Compound Number 4-38:
1-({5-[5-(4-Butyl-3-fluorophenyl)-1,2,4-oxadiazol-3-yl]-6-ethylpyridin-2-yl}methyl)azetidine-3-carboxylic acid, Exemplification Compound Number 4-39:
1-({6-Ethyl-5-[5-(3-fluoro-4-isobutylphenyl)-1,2,4-oxadiazol-3-yl]pyridin-2-yl}methyl)azetidine-3-carboxylic acid (Example 30), and Exemplification Compound Number 4-42:
1-({5-[5-(3-Chloro-4-isobutylphenyl)-1,2,4-oxadiazol-3-yl]-6-ethylpyridin-2-yl}methyl)azetidine-3-carboxylic acid (Example 25), more preferred compounds are the compounds of Exemplification Compound Nos. 4-6, 4-9, 4-12, 4-21, 4-27, 4-36, and 4-42.

The present invention includes that a medicinal composition which contains compounds having the general formula (I) or pharmacologically acceptable salts thereof which has augment the pharmacological immunosuppressive activity and lower its side effect and toxicity. Thus the medicinal composition of the present invention is useful as a prophylactic or therapeutic agent for autoimmune diseases such as systemic lupus erythematosus, rheumatoid arthritis, polymyositis, dermatomyositis, scleroderma, Behcet's syndrome, Crohn's disease, ulcerative colitis, autoimmune hepatitis, aplastic anemia, idiopathic thrombocytopenic purpura, autoimmune hemolytic anemia, multiple sclerosis, autoimmune bullosis, psoriasis vulgaris, vasculitis syndrome, Wegener's granuloma, uveitis, idiopathic interstitial pneumonia, Goodpasture's syndrome, sarcoidosis, allergic granulomatous angitis, bronchial asthma, myocarditis, cardiomyopathy, aortitis syndrome, postmyocardial infarction syndrome, primary pulmonary hypertension, minimal change nephrotic syndrome, membranous nephropathy, membranoproliferative glomerulonephritis, focal glomerular sclerosis, crescentic glomerulonephritis, myasthenia gravis, inflammatory neuropathy, atopic dermatitis, chronic actinic dermatitis, acute polyarthritis, Sydenham's chorea, systemic sclerosis, adult-onset type diabetes mellitus, insulin dependent diabetes mellitus, juvenile diabetes mellitus, atherosclerosis, glomerular nephritis, tubulointerstitial nephritis, primary biliary cirrhosis, primary sclerosing cholangitis, fulminant hepatitis, viral hepatitis, GVHD, reject reactions caused by transplantation of various organs, contact dermatitis, and sepsis, or other immunology-related diseases.

In the case that the medicinal composition of the present invention is used as a prophylactic or therapeutic agent for diseases described above, the medicinal composition of the present invention can be administered in a suitable dosage form by mixing with a suitable pharmacologically acceptable excipient and/or diluent, for example, as tablets, capsules, granules, powders, or syrups for oral administration, or injections or suppositories for parenteral administration.

The medicinal compositions are prepared, according to well known techniques, using additives such as excipients (for example, organic excipients including sugar derivatives such as lactose, sucrose, glucose, mannitol, and sorbitol; starch derivatives such as corn starch, potato starch, a-starch, and dextrin; cellulose derivatives such as crystalline cellulose; gum arabic; dextran; pullulan; and inorganic excipients including silicate derivatives such as light anhydrous silicic acid, synthetic aluminum silicate, calcium silicate, and magnesium aluminometasilicate; phosphates such as calcium hydrogenphosphate; carbonates such as calcium carbonate; and sulfates such as calcium sulfate can be listed), lubricants (for example, stearic acid and metal salts of stearic acid such as calcium stearate and magnesium stearate; talc; colloidal silica; waxes such as veegum and spermaceti; boric acid; adipic acid; sulfates such as sodium sulfate; glycol; fumaric acid; sodium benzoate; DL-leucine; sodium fatty acid; lauryl sulfates such as sodium lauryl sulfate and magnesium lauryl sulfate; silicates such as silicic anhydride and silicic hydrate; and the starch derivatives described above can be listed), binders (for example, hydroxypropylcellulose, hydroxypropylmethylcellulose, polyvinylpyrrolidone, Macrogol, and similar excipients to those described above can be listed), disintegrants (for example, cellulose derivatives such as low-substituted hydroxypropylcellulose, carboxymethylcellulose, calcium carboxymethylcellulose, and internally crosslinked sodium carboxymethylcellulose; and chemically modified starch/cellulose derivatives such as carboxymethylstarch, sodium carboxymethylstarch, and crosslinked polyvinylpyrrolidone can be listed), stabilizers (for example, paraoxybenzoates such as methylparaben and propylparaben; alcohols such as chlorobutanol, benzyl alcohol, and phenylethyl alcohol; benzalkonium chloride; phenols such as phenol and cresol; thimerosal; dehydroacetic acid; and sorbic acid can be listed), flavourings (for example, conventionally employed sweeteners, acidifiers, and flavourings can be listed), diluents, and the like.

The dose may vary depending on a variety of factors such as the symptoms and age of the patient. For example, in the case of oral administration, the dose is between 0.01 mg and 200 mg per one time for a human adult (body weight: about 60 kg), and is preferably between 0.1 mg and 50 mg. In the case of intravenous administration, the dose is between 0.005 mg and 100 mg per one time for a human adult (body weight: about 60 kg), and is preferably between 0.01 mg and 10 mg. The dosing frequency is from one to six times per day for a human adult (body weight: about 60 kg), and the defined daily dosage may be administered throughout the day at the same time or at certain intervals depending on the symptoms of the patient.

ADVANTAGES OF THE INVENTION

Since the compounds of the present invention exert excellent immunosuppressive activity with low toxicity, the compounds of the present invention are useful as a prophylactic agent or a therapeutic agent (particularly a therapeutic agent) for diseases related to suppression of the immune system in mammals (particularly in humans).

BEST MODE FOR CARRYING OUT THE INVENTION

The compound having the general formula (I) of the present invention can be prepared according to the procedures described hereinafter.

The preparation methods described below were generally established in accordance with known procedures. As known procedures, there are the procedures described, for example, in "Organic Functional Group Preparation", Second Edition, Academic Press, Inc., 1989, and "Comprehensive Organic Transformations", VCH Publishers Inc., 1989, and the like.

Method A is a method for the preparation of a compound having the general formula (I).

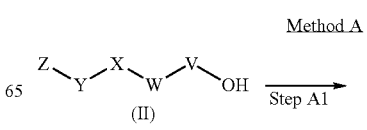

Method A

-continued $$\underset{(III)}{Z-Y-X-W-V-LG} + \underset{(IV)}{\overset{B}{\underset{HN}{\bigtriangleup}}\hspace{-2mm}{}_{n}^{AP}} \xrightarrow{\text{Step A2}}$$

$$\underset{(V)}{Z-Y-X-W-V-N\underset{n}{\bigtriangleup}\overset{B}{\hspace{-2mm}{}^{AP}}} \xrightarrow{\text{Step A3}}$$

$$\underset{(I)}{Z-Y-X-W-V-N\underset{n}{\bigtriangleup}\overset{B}{\hspace{-2mm}{}^{A}}}$$

In the above reaction scheme, A, B, V, W, X, Y, Z and n have the same meanings as those indicated hereinbefore.

LG represents a group which is known as a leaving group in the field of organic synthesis chemistry, and can be, for example, a halogen atom or a group of formula $-O-S(O)_2 R^c$ (wherein, $R^c$ is a methoxy group, a $C_1$-$C_6$ alkyl group which may optionally be substituted with from 1 to 3 halogen atoms, or a phenyl group which may optionally be substituted with from 1 to 3 substituents selected from the group consisting of a halogen atom and a methyl group), and is preferably a chlorine atom, a bromine atom, an iodine atom, a methanesulfonyloxy group or a p-toluenesulfonyloxy group.

AP represents a group in which a functional group indicated in the definition of A is protected by a protecting group as a form considered to be suitable in the organic synthesis chemistry, and such protecting group P can be, for example, a protecting group found in "Protective Groups in Organic Synthesis third edition" (ed. by Green, T. W. and Wuts, P. G. M., John Wiley and Sons, Inc., 1999).

In the case that A is a carboxyl group, such protecting group P is preferably a lower alkyl group such as a methyl group, an ethyl group, a propyl group, or the like, and particularly preferably an ethyl group.

In the case that A is a phospho group, such protecting group P is preferably a lower alkyl group such as a methyl group or an ethyl group; an allyl group or a 2,2,2-trichloroethyl group, and particularly preferably an allyl group.

In the case that A is a sulfo group, such protecting group P is preferably a phenyl group, a p-methoxyphenyl group or a p-nitrophenyl group, and particularly preferably a phenyl group.

In the case that A is a 1H-tetrazol-5-yl group, such protecting group P is preferably a triphenylmethyl group, a p-methoxyphenyldiphenylmethyl group or a di(p-methoxyphenyl) phenylmethyl group, and particularly preferably a triphenylmethyl group.

Step A1

Step A1 is a process for the preparation of a compound having the general formula (III) by converting a hydroxyl group of a compound having the general formula (II) to a leaving group.

This process is accomplished by reacting the compound having the general formula (II) with a halogenating agent or a sulfonylating agent, and is preferably carried out by reacting with a halogenating agent in a solvent.

The halogenating agent described above can be, for example, a phosphorus trihalide such as phosphorus trichloride or phosphorus tribromide; or a combination of a phosphine, which consists of a triarylphosphine including triphenylphosphine and a tri-lower alkylphosphine such as tributylphosphine, and either a molecular simple halogen such as bromine or iodine, or a halogen equivalent such as carbon tetrachloride, carbon tetrabromide or hexachloroacetone, and is preferably a combination of a triarylphosphine and a halogen equivalent, and particularly preferably a combination of triphenylphosphine and carbon tetrabromide.

The solvent employed in the above reaction is not particularly restricted provided that it has no adverse effect on the reaction, and can be, for example, a halogenated hydrocarbon such as dichloromethane, chloroform, 1,2-dichloroethane, or the like; or an ether such as tetrahydrofuran, 1,2-dimethoxyethane, or the like, and is preferably a halogenated hydrocarbon and particularly preferably dichloromethane.

The reaction temperature employed in the above reaction is generally between −23° C. and 60° C., and preferably between 0° C. and 30° C.

The reaction time employed in the above reaction is different depending on the reaction temperature, the starting material, the reagent used or the kind of solvent employed, but is generally from 15 minutes to 3 hours, and preferably from 30 minutes to 1 hour.

After the reaction is completed, the desired compound of this reaction can be isolated from the reaction mixture by conventional treatments. The desired compound can be obtained, for example, by neutralization of the reaction mixture, if necessary, or filtration of the reaction mixture when insoluble material is present in the reaction mixture, extraction of the neutralized solution or the filtrate with an organic solvent immiscible with water such as toluene, washing the resulting organic layer with water, separation of the organic layer containing the desired compound, and then evaporation of the organic solvent under reduced pressure.

The desired product thus obtained can, if necessary, be further isolated and purified by conventional treatments, for example, by recrystallization, reprecipitation, or by conventional procedures generally used in the isolation and purification of organic compounds (for example, absorption column chromatography using a carrier such as silica gel, alumina or Florisil consisting of magnesium and silica gel; partition column chromatography using Sephadex LH-20 (product of Pharmacia Co., Ltd.), Amberlite XAD-11 (product of Rohm & Hass Co., Ltd.) or Diaion HP-20 (product of Mitsubishi Chemicals Co., Ltd.); ion exchange chromatography; or normal phase or reversed phase column chromatography using silica gel or alkylated silica gel, and preferably by column chromatography using silica gel).

Step A2

Step A2 is a process for the preparation of a compound having the general formula (V) by substituting a leaving group LG of a compound having the general formula (III) with a compound having the general formula (IV).

This process is carried out in the presence of a base in a solvent.

The base employed in the above reaction can be, for example, a trialkylamine such as triethylamine, N,N-diisopropylethylamine, tributylamine, or the like; or a pyridine such as pyridine; lutidine, collidine, or the like; an alkali metal carbonate such as sodium hydrogencarbonate, potassium hydrogencarbonate, sodium carbonate or potassium carbonate, or the like, and is preferably a trialkylamine and particularly preferably N,N-diisopropylethylamine.

The solvent employed in the above reaction is not particularly restricted provided that it has no adverse effect on the reaction and can be, for example, a halogenated hydrocarbon such as dichloromethane, chloroform, 1,2-dichloroethane, or the like; or an ether such as diethyl ether, tetrahydrofuran, 1,2-dimethoxyethane, dioxane, or the like, and is preferably a halogenated hydrocarbon and particularly preferably dichloromethane.

The reaction temperature employed in the above reaction is generally between 0° C. and 100° C., and preferably between 0° C. and 30° C.

The reaction time employed in the above reaction is different depending on the reaction temperature, the starting material, the reagent used or the solvent employed, but is generally from 15 minutes to 3 hours, and preferably from 30 minutes to 2 hours.

After the reaction is completed, the desired compound of this reaction can, if necessary, be isolated from the reaction mixture and purified in the same manner as described in Step A1.

Step A3

Step A3 is a process for the preparation of a compound having the general formula (I) by carrying out the deprotection reaction on the substituent AP of a compound having the general formula (V).

The deprotection reaction conditions in this process are different depending on the protecting group employed for preparing the substituent AP, wherein the substituent A is maintained under the protected condition. Hereinafter, general preparation procedures are described, for example, for the case that the substituent A is a carboxyl group and the substituent AP is a lower alkyl ester group.

This process is carried out in the presence of a base in a solvent containing water.

The base employed in the above reaction can be, for example, an alkali metal hydroxide such as lithium hydroxide, sodium hydroxide, potassium hydroxide, or the like; an alkali metal carbonate such as lithium carbonate, sodium carbonate, potassium carbonate, or the like; or a metal alkoxide such as lithium methoxide, sodium methoxide or sodium ethoxide, and is preferably an alkali metal hydroxide and particularly preferably lithium hydroxide.

The solvent employed in the above reaction is not particularly restricted provided that it has no adverse effect on the reaction, and can be, for example, an ether such as diethyl ether, tetrahydrofuran, 1,2-dimethoxyethane or dioxane; an alcohol such as methanol, ethanol, isopropanol, t-butanol, or the like; water; or a mixture of water and solvent(s) described above, and is preferably a mixture of an ether, an alcohol and water, and particularly preferably a mixture of tetrahydrofuran, methanol and water.

The reaction temperature employed in the above reaction is generally between 0° C. and 100° C., and preferably between 0° C. and 40° C.

The reaction time employed in the above reaction is different depending on the reaction temperature, the starting material, the reagent used or the solvent employed, but is generally from 15 minutes to 3 hours, and preferably from 30 minutes to 2 hours.

Furthermore, even in case that a substituent is other than that indicated specifically in this process, this process can be carried out according to the procedures, for example, found in "Protective Groups in Organic Synthesis third edition" (ed. by Green, T. W. and Wuts, P. G. M., John Wiley and Sons, Inc., 1999), and the like.

After the reaction is completed, the desired compound of this reaction can, if necessary, be isolated from the reaction mixture and purified in the same manner as described in Step A1.

The preparation method of a compound having the general formula (II) employed in Method A is different depending on the nature of the substituent X. Hereinafter, a general preparation method is described, for example, for the case that the substituent X is an oxadiazole ring or an isoxazole ring.

Method B is a method for the preparation of a compound having the general formula (II-1), which is included in a compound having the general formula (II), wherein the substituent X is an oxadiazole ring.

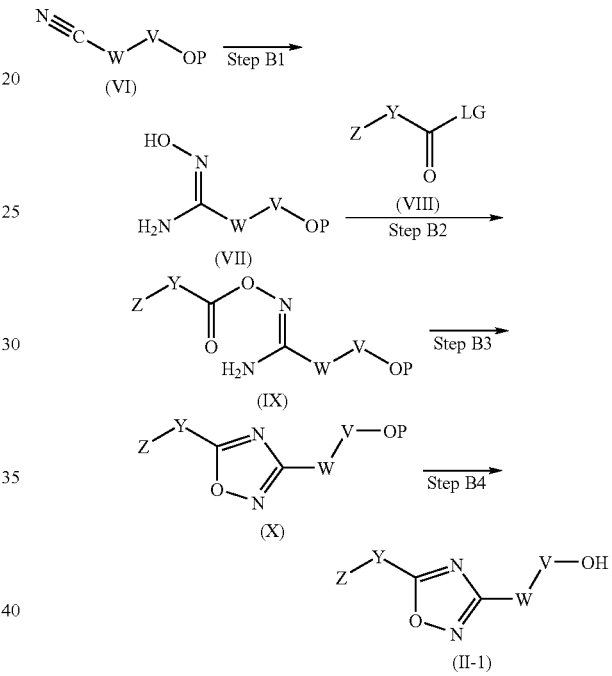

In the above reaction scheme, V, W, Y and Z have the same meanings as those indicated hereinbefore.

LG has the same meaning as that indicated hereinbefore or represents a hydroxyl group, P represents a protecting group for a hydroxyl group. Such protecting group for a hydroxyl group is, for example, a protecting group for a hydroxyl group found in "Protective Groups in Organic Synthesis third edition" (ed. by Green, T. W. and Wuts, P. G. M., John Wiley and Sons, Inc., 1999), and the like, and can be preferably a trialkylsilyl group such as a triethylsilyl group, a t-butyldimethylsilyl group or a t-butyldiphenylsilyl group; a substituted methyl ether group such as a methoxymethyl group, tetrahydropyranyl group or a 2-(trimethylsilyl)ethoxymethyl group; or an acyl group such as an acetyl group, a benzoyl group or a pivaloyl group. Such protecting group is preferably a trialkylsilyl group and particularly preferably a t-butyldimethylsilyl group.

Step B1

Step B1 is a process for the preparation of a compound having the general formula (VII) by carrying out an addition reaction of hydroxylamine on a compound having the general formula (VI).

This process can be accomplished by reacting a compound having the general formula (VI) with hydroxylamine or a hydroxylamine equivalent in a solvent.

The hydroxylamine equivalent can be a solution of hydroxylamine such as an aqueous solution of hydroxylamine, a mixed solution of hydroxylamine and methanol, a mixed solution of hydroxylamine and ethanol, or the like; or a combination of a hydroxylamine salt, such as hydroxylamine hydrochloride, hydroxylamine phosphate, hydroxylamine sulfate, or the like, and a tri-lower alkylamine, such as triethylamine, N,N-diisopropylethylamine or tributylamine, or an alkali metal carbonate, such as sodium hydrogencarbonate, potassium hydrogencarbonate, sodium carbonate, potassium carbonate, or the like, and is preferably a solution of hydroxylamine and particularly preferably an aqueous solution of hydroxylamine.

The solvent employed in the above reaction is not particularly restricted provided that it has no adverse effect on the reaction and can be, for example, a halogenated hydrocarbon such as dichloromethane, chloroform, 1,2-dichloroethane, or the like; or an ether such as tetrahydrofuran, 1,2-dimethoxyethane, or the like, or an alcohol such as methanol, ethanol, isopropanol, t-butanol, or the like, and is preferably an alcohol and particularly preferably ethanol.

The reaction temperature employed in the above reaction is generally between 0° C. and 80° C., and preferably between 30° C. and 60° C.

The reaction time employed in the above reaction is different depending on the reaction temperature, the starting material, the reagent used or the solvent employed, but is generally from 15 minutes to 5 hours, and preferably from 30 minutes to 2 hours.

After the reaction is completed, the desired compound of this reaction can, if necessary, be isolated from the reaction mixture and purified in the same manner as described in Step A1.

Step B2

Step B2 is a process for the preparation of a compound having the general formula (IX) by reacting a compound having the general formula (VII) with a compound having the general formula (VIII).

Hereinafter, preparation methods are described for the cases that (1) the substituent LG in a compound having the general formula (VIII) is a hydroxyl group, and (2) the substituent LG in a compound having the general formula (VIII) is a group other than a hydroxyl group.

(1) The case that the substituent LG in a compound having the general formula (VIII) is a hydroxyl group.

This process is accomplished by reacting a compound having the general formula (VII) with a compound having the general formula (VIII) in the presence of a condensing agent in a solvent.

The condensing agent employed in the above reaction can be, for example, a carbodiimide such as N,N'-dicyclohexylcarbodiimide, N,N'-diisopropylcarbodiimide, 1-ethyl-3-(3'-dimethylaminopropyl)carbodiimide (WSCI), or the like; or an O-benzotriazole such as BOP [benzotriazol-1-yloxytris(dimethylamino)phosphonium hexafluorophosphate], HATU [O-(7-azabenzotriazol-1-yl)-N,N,N',N'-tetramethyluronium hexafluorophosphate], HBTU [O-benzotriazol-1-yl-N,N,N',N'-tetramethyluronium hexafluorophosphate], and the like, and is preferably a carbodiimide and particularly preferably N,N'-dicyclohexylcarbodiimide.

The solvent employed in the above reaction is not particularly restricted provided that it has no adverse effect on the reaction and can be, for example, a halogenated hydrocarbon such as dichloromethane, chloroform, 1,2-dichloroethane, or the like; an ether such as tetrahydrofuran, 1,2-dimethoxyethane, or the like; or a benzene such as benzene, toluene or xylene, and is preferably a halogenated hydrocarbon and particularly preferably dichloromethane.

The reaction temperature employed in the above reaction is generally between −20° C. and 40° C., and preferably between 0° C. and 30° C.

The reaction time employed in the above reaction is different depending on the reaction temperature, the starting material, the reagent used or the solvent employed, but is generally from 15 minutes to 5 hours, and preferably from 30 minutes to 2 hours.

After the reaction is completed, the desired compound of this reaction can, if necessary, be isolated from the reaction mixture and purified in the same manner as described in Step A1.

(2) The case that the substituent LG in a compound having the general formula (VIII) is a group other than a hydroxyl group.

This process is accomplished by reacting a compound having the general formula (VII) with a compound having the general formula (VIII) in the presence of a base in an inert solvent.

The substituent LG is preferably a chlorine atom.

The base employed in the above reaction can be, for example, a trialkylamine such as triethylamine, N,N-diisopropylethylamine, tributylamine, or the like; or a pyridine such as pyridine, lutidine, collidine, or the like, and is preferably a trialkylamine and particularly preferably N,N-diisopropylethylamine.

The solvent employed in the above reaction is not particularly restricted provided that it has no adverse effect on the reaction and can be, for example, a halogenated hydrocarbon such as dichloromethane, chloroform, 1,2-dichloroethane, or the like; an ether such as diethyl ether, tetrahydrofuran, 1,2-dimethoxyethane, or the like; or a benzene such as benzene, toluene, xylene, or the like, and is preferably a halogenated hydrocarbon and particularly preferably dichloromethane.

The reaction temperature employed in the above reaction is generally between −20° C. and 40° C., and preferably between 0° C. and 30° C.

The reaction time employed in the above reaction is different depending on the reaction temperature, the starting material, the reagent used or the solvent employed, but is generally from 15 minutes to 5 hours, and preferably from 30 minutes to 2 hours.

After the reaction is completed, the desired compound of this reaction can, if necessary, be isolated from the reaction mixture and purified in the same manner as described in Step A1.

Step B3

Step B3 is a process for the preparation of a compound having the general formula (X) from a compound having the general formula (IX).

This process can be accomplished by reacting a compound having the general formula (IX) with a base in a solvent.

The base employed in the above reaction can be a tetra-lower alkylammonium fluoride such as tetrabutylammonium fluoride, benzyltrimethylammonium fluoride, benzyltriethylammonium fluoride, or the like; a tri-lower alkylamine such as triethylamine, N,N-diisopropylethylamine or tributylamine; a pyridine such as pyridine, lutidine, collidine, or the like; or an alkali metal hydride such as lithium hydride, sodium hydride, potassium hydride, or the like, and is preferably a tetra-lower alkylammonium fluoride and particularly preferably tetrabutylammonium fluoride.

The solvent employed in the above reaction is not particularly restricted provided that it has no adverse effect on the reaction and can be, for example, an ether such as diethyl ether, tetrahydrofuran, 1,2-dimethoxyethane, or the like; a halogenated hydrocarbon such as dichloromethane, chloroform, 1,2-dichloroethane, or the like; or an amide such as N,N-dimethylformamide, N,N-dimethylacetamide, or the like, and is preferably an ether and particularly preferably tetrahydrofuran.

The reaction temperature employed in the above reaction is generally between 0° C. and 80° C., and preferably between 30° C. and 60° C.

The reaction time employed in the above reaction is different depending on the reaction temperature, the starting material, the reagent used or the solvent employed, but is generally from 15 minutes to 5 hours, and preferably from 30 minutes to 2 hours.

After the reaction is completed, the desired compound of this reaction can, if necessary, be isolated from the reaction mixture and purified in the same manner as described in Step A1.

Step B4

Step B4 is a process for the preparation of a compound having the general formula (II-1) by removing the protecting group P of the hydroxyl group of a compound having the general formula (X).

The method for removing the protecting group P is different depending on a nature of the protecting group employed, but generally carried out according to the deprotection method for a hydroxyl group described in "Protective Groups in Organic Synthesis third edition" (ed. by Green, T. W. and Wuts, P. G. M., John Wiley and Sons, Inc., 1999), and the like.

Hereinafter, a general preparation method is described for the case that the protecting group is a trialkylsilyl group. This process is accomplished by reacting a compound having the general formula (X) with a fluorine anion equivalent in a solvent.

The fluorine anion equivalent employed in the above reaction can be, for example, a tetralkylammonium fluoride such as tetrabutylammonium fluoride or benzyltrimethyl ammonium fluoride; a hydrogen fluoride-amine complex such as hydrogen fluoride-triethylamine complex or hydrogen fluoride-pyridine complex, and is preferably a tetralkylammonium fluoride and particularly preferably tetrabutylammonium fluoride.

The solvent employed in the above reaction is not particularly restricted provided that it has no adverse effect on the reaction and can be, for example, an ether such as diethyl ether, tetrahydrofuran, 1,2-dimethoxyethane, or the like; a halogenated hydrocarbon such as dichloromethane, chloroform, 1,2-dichloroethane, or the like; or an amide such as N,N-dimethylformamide, N,N-dimethylacetamide, or the like, and is preferably an ether and particularly preferably tetrahydrofuran.

The reaction temperature employed in the above reaction is generally between 0° C. and 80° C., and preferably between 30° C. and 60° C.

The reaction time employed in the above reaction is different depending on the reaction temperature, the starting material, the reagent used or the solvent employed, but is generally from 15 minutes to 5 hours, and preferably from 30 minutes to 2 hours.

After the reaction is completed, the desired compound of this reaction can, if necessary, be isolated from the reaction mixture and purified in the same manner as described in Step A1.

Method C is a method for the preparation of a compound having the general formula (II-2), which is included in a compound having the general formula (II), wherein the substituent X is an isoxazole ring.

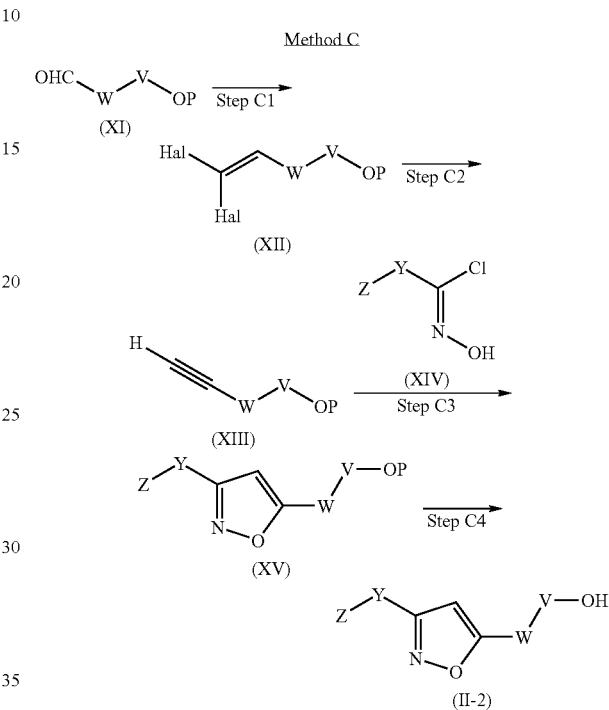

In the above reaction scheme, V, P, W, Y and Z have the same meanings as those indicated hereinbefore.

Hal represents a halogen atom.

Step C1

Step C1 is a process for the preparation of a compound having the general formula (XII) by converting a formyl group of a compound having the general formula (XI) into a dihalovinyl group.

This process is accomplished by reacting the compound having the general formula (XI) with a gem-dihalomethylenating agent in a solvent.

The gem-dihalomethylenating agent employed in this process can be a combination of a phosphine, consisting of a triarylphosphine including triphenylphosphine and a tri-lower alkylphosphine such as tributylphosphine, and a carbon tetrahalide, such as carbon tetrachloride, carbon tetrabromide or carbon tetraiodide; or a combination of a di-lower alkyl (trihalogenated methyl)phosphonate, such as diethyl(trichloromethyl)phosphonate, diethyl(tribromomethyl)phosphonate, dimethyl(trichloromethyl)phosphonate or dimethyl(tribromomethyl)phosphonate, and an alkyllithium, such as methyllithium, n-butyllithium, s-butyllithium or t-butyllithium, and is preferably a combination of a triarylphosphine and a carbon tetrahalide and particularly preferably a combination of triphenylphosphine and carbon tetrabromide.

The solvent employed in the above reaction is not particularly restricted provided that it has no adverse effect on the reaction and can be, for example, a halogenated hydrocarbon such as dichloromethane, chloroform, 1,2-dichloroethane, or the like; or an ether such as diethyl ether, tetrahydrofuran, 1,2-dimethoxyethane, dioxane, or the like, and is preferably an ether and particularly preferably tetrahydrofuran.

The reaction temperature employed in the above reaction is generally between −23° C. and 60° C., and preferably between 0° C. and 30° C.

The reaction time employed in the above reaction is different depending on the reaction temperature, the starting material, the reagent used or the solvent employed, but is generally from 15 minutes to 5 hours, and preferably from 30 minutes to 3 hours.

After the reaction is completed, the desired compound of this reaction can, if necessary, be isolated from the reaction mixture and purified in the same manner as described in Step A1.

Step C2

Step C2 is a process for the preparation of a compound having the general formula (XIII) by converting a dihalovinyl group of a compound having the general formula (XII) to an ethynyl group.

This process is accomplished by reacting the compound (XII) with an alkylmetal in a solvent.

The alkylmetal employed in the above reaction can be, for example, an alkyllithium such as methyllithium, n-butyllithium, s-butyllithium or t-butyllithium; or an alkylsodium such as methylsodium, butylsodium, s-butylsodium, or the like, and is preferably an alkyllithium and particularly preferably n-butyllithium.

The solvent employed in the above reaction is not particularly restricted provided that it has no adverse effect on the reaction and can be, for example, an ether such as diethyl ether, tetrahydrofuran, 1,2-dimethoxyethane, dioxane, or the like; or a benzene such as benzene, toluene, xylene, or the like, and is preferably an ether and particularly preferably tetrahydrofuran. The reaction temperature employed in the above reaction is generally between −100° C. and 0° C., and preferably between −78° C. and −45° C.

The reaction time employed in the above reaction is different depending on the reaction temperature, the starting material, the reagent used or the solvent employed, but is generally from 15 minutes to 2 hours, and preferably from 30 minutes to 1 hour.

After the reaction is completed, the desired compound of this reaction can, if necessary, be isolated from the reaction mixture and purified in the same manner as described in Step A1.

Step C3

Step C3 is a process for the preparation of a compound having the general formula (XV) by reacting a compound having the general formula (XIII) with a compound having the general formula (XIV)

This process can be accomplished by reacting both compounds with a base in a solvent. The general preparation method of the compounds having the general formula (XIV) is described in literatures, J. Org. Chem., 45, 3916 (1980) and Acta. Chemica, Scandinavica, 426 (1987), and these compounds can easily be synthesized from well-known compounds.

The base employed in the above reaction can be, for example, a trialkylamine such as triethylamine, N,N-diisopropylethylamine, tributylamine, or the like; or a pyridine such as pyridine, lutidine, collidine, or the like, and is preferably a trialkylamine and particularly preferably triethylamine.

The solvent employed in the above reaction is not particularly restricted provided that it has no adverse effect on the reaction and can be, for example, an ether such as diethyl ether, tetrahydrofuran, 1,2-dimethoxyethane, dioxane, or the like; an ester such as ethyl acetate, propyl acetate, butyl acetate, or the like; or a halogenated hydrocarbon such as dichloromethane, chloroform, 1,2-dichloroethane, or the like; and is preferably an ester and particularly preferably ethyl acetate.

The reaction temperature employed in the above reaction is generally between −20° C. and 80° C., and preferably between 0° C. and 40° C.

The reaction time employed in the above reaction is different depending on the reaction temperature, the starting material, the reagent used or the solvent employed, but is generally from 5 hours to 72 hours, and preferably from 24 hours to 48 hours.

After the reaction is completed, the desired compound of this reaction can, if necessary, be isolated from the reaction mixture and purified in the same manner as described in Step A1.

Step C4

Step C4 is a process for the preparation of a compound having the general formula (II-2) by removing the protecting group P of the hydroxyl group of a compound having the general formula (XV).

This process can be carried out in the same manner as described in Step B4 of Method B.

The preparation method of the compound having the general formula (VI) used in Method B is different depending on the nature of the substituent W. Hereinafter, the general preparation procedures are described, for example, as Method D for the case that the substituent W is a thiophene ring or a furan ring and as Method E for the case that the substituent W is a group having a fused structure such as a 4,5,6,7-tetrahydrobenzothiophene ring or a 4,5,6,7-tetrahydrobenzofuran ring, respectively.

Method D

Method D is a method for the preparation of a compound having the general formula (VI-1), which is included in a compound having the general formula (VI), wherein the substituent W is a thiophene ring or a furan ring.

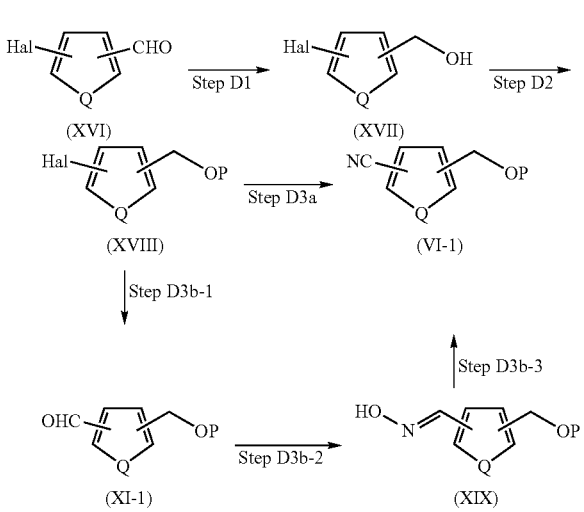

In the above reaction scheme, Hal represents a halogen atom as described above, and is preferably a bromine atom or an iodine atom, Q represents an oxygen atom or a sulfur atom, and P represents a protecting group for a hydroxyl group as described above.

Step D1

Step D1 is a process for the preparation of a compound having the general formula (XVII) by converting a formyl group of a compound having the general formula (XVI) to a hydroxymethyl group.

This process is accomplished by reacting the compound (XVI) with a reducing agent in a solvent. Additionally, many of the compounds having the general formula (XVI) employed as the starting compounds are commercially available, and can also easily be synthesized according to publicly known preparation methods.

The reducing agent employed in the above reaction can be, for example, an aluminum hydride such as lithium aluminum hydride, sodium aluminum hydride or diisobutylaluminum hydride; a borohydride such as lithium borohydride, sodium borohydride or borane, and is preferably a borohydride and particularly preferably sodium borohydride.

The solvent employed in the above reaction is not particularly restricted provided that it has no adverse effect on the reaction and can be, for example, an ether such as diethyl ether, tetrahydrofuran, 1,2-dimethoxyethane, dioxane, or the like; or an alcohol such as methanol, ethanol, isopropanol, or the like, and is preferably an alcohol and particularly preferably methanol.

The reaction temperature employed in the above reaction is generally between −23° C. and 50° C., and preferably between 0° C. and 30° C.

The reaction time employed in the above reaction is different depending on the reaction temperature, the starting material, the reagent used or the solvent employed, but is generally from 15 minutes to 2 hours, and preferably from 30 minutes to 1 hour.

After the reaction is completed, the desired compound of this reaction can, if necessary, be isolated from the reaction mixture and purified in the same manner as described in Step A1.

Step D2

Step D2 is a process for the preparation of a compound having the general formula (XVIII) by protecting a hydroxyl group of a compound having the general formula (XVII) with an appropriate protecting group for a hydroxyl group. The protecting group employed in this reaction is not particularly restricted provided that it has no adverse effect on the reaction in succeeding processes and additionally can easily be removed, and is preferably a trialkylsilane. The general preparation method for the case that a trialkylsilane is employed as the protecting group is described hereinafter.

This process can be carried out by reacting a compound having the general formula (XVII) with a silylating agent in the presence of a suitable base in a solvent.

The silylating agent employed in the above reaction can be, for example, a trialkylsilyl chloride such as triethylsilyl chloride, t-butyldimethylsilyl chloride, triisopropylsilyl chloride or t-butyldiphenylsilyl chloride; or a trialkylsilyl trifluoromethanesulfonate such as triethylsilyl trifluoromethanesulfonate, t-butyldimethylsilyl trifluoromethanesulfonate, triisopropylsilyl trifluoromethanesulfonate or t-butyldiphenylsilyl trifluoromethanesulfonate, and is preferably a trialkylsilyl chloride, and particularly preferably t-butyldimethylsilyl chloride.

The base employed in the above reaction can be, for example, a trialkylamine such as triethylamine, N,N-diisopropylethylamine, or the like; an imidazole such as imidazole, 2-methylimidazole, or the like; or a pyridine such as pyridine, lutidine, collidine, or the like, and is preferably an imidazole and particularly preferably imidazole.

The solvent employed in the above reaction is not particularly restricted provided that it has no adverse effect on the reaction and can be, for example, an ether such as diethyl ether, tetrahydrofuran, 1,2-dimethoxyethane, dioxane, or the like; a halogenated hydrocarbon such as dichloromethane, 1,2-dichloroethane, chloroform, or the like; or an amide such as N,N-dimethylformamide, N,N-dimethylacetamide, or the like, and is preferably an amide and particularly preferably N,N-dimethylformamide.

The reaction temperature employed in the above reaction is generally between −23° C. and 50° C., and preferably between 0° C. and 30° C.

The reaction time employed in the above reaction is different depending on the reaction temperature, the starting material, the reagent used or the solvent employed, but is generally from 30 minutes to 4 hours, and preferably from 1 hour to 3 hours.

After the reaction is completed, the desired compound of this reaction can, if necessary, be isolated from the reaction mixture and purified in the same manner as described in Step A1.

Step D3

Step D3 is a process for the preparation of a compound having the general formula (VI-1) by converting a halogen atom of a compound having the general formula (XVIII) into a nitrile group.

This process can be carried out according to two methods, one of which is a method by a direct conversion of a halogen atom of a compound having general formula (XVIII) into a nitrile group (Step D3a) and the other is a method by derivatization of a compound (XVIII) to a compound having a formyl group (XI-1), followed by conversion of the formyl group into a nitrile group through an oximation reaction and a dehydration reaction (Step D3b). Hereinafter, these processes are described individually.

Step D3a

Step D3a is a process for the preparation of a compound having the general formula (VI-1) by converting a halogen atom of a compound having the general formula (XVIII) into a nitrile group.

This process can be accomplished by reacting a compound having the general formula (XVIII) with an appropriate cyanating agent in a solvent.

The cyanating agent employed in this reaction can be, for example, a copper compound such as copper cyanide; or a combination of a palladium catalyst, such as tetrakis(triphenylphosphine)palladium, dichlorobis(triphenylphosphine) palladium, or the like, and a metal cyanide, such as zinc cyanide, trimethylsilyl cyanide, or tributyltin cyanide, and is preferably copper cyanide or a combination of tetrakis(triphenylphosphine)palladium and zinc cyanide and particularly preferably copper cyanide.

The solvent employed in the above reaction is not particularly restricted provided that it has no adverse effect on the reaction and can be, for example, an ether such as diethyl ether, tetrahydrofuran, 1,2-dimethoxyethane, dioxane, or the like; or an amide such as N,N-dimethylformamide, N,N-dimethylacetamide, or the like, and is preferably an amide and particularly preferably N,N-dimethylformamide.

The reaction temperature employed in the above reaction is generally between 20° C. and 180° C., and preferably between 100° C. and 140° C.

The reaction time employed in the above reaction is different depending on the reaction temperature, the starting material, the reagent used or the solvent employed, but is generally from 2 hours to 12 hours, and preferably from 3 hours to 10 hours.

After the reaction is completed, the desired compound of this reaction can, if necessary, be isolated from the reaction mixture and purified in the same manner as described in Step A1.

Step D3b

Step D3b-1

Step D3b-1 is a process for the preparation of a compound having the general formula (XI-1) by converting a halogen atom of a compound having the general formula (XVIII) into a formyl group.

This process can also be used as the general preparation procedure of a compound having the general formula (XI) that is used as the starting material in Method C described hereinbefore.

This process is accomplished by carrying out a halogen-metal exchange on a compound having the general formula (XVIII), followed by reacting the resulting product with a suitable formylating agent in a solvent.

The metalating agent employed in the above reaction can be, for example, a metal such as metallic lithium, metallic magnesium, metallic zinc, or the like; or an alkyllithium such as n-butyllithium, s-butyllithium, t-butyllithium, or the like; and is preferably an alkyllithium and particularly preferably n-butyllithium.

The formylating agent employed in this reaction can be a formamide such as N,N-dimethylformamide, N-methylformanilide, N-formylpiperidine, or the like; a formate such as methyl formate, ethyl formate, propyl formate, or the like, and is preferably a formamide and particularly preferably N,N-dimethylformamide.

The solvent employed in the above reaction is not particularly restricted provided that it has no adverse effect on the reaction and can be, for example, an ether such as diethyl ether, tetrahydrofuran, 1,2-dimethoxyethane, dioxane, or the like; or an aromatic hydrocarbon such as toluene, xylene, or the like, and is preferably an ether and particularly preferably tetrahydrofuran.

The reaction temperature employed in the above reaction is generally between $-100°$ C. and $0°$ C., and preferably between $-78°$ C. and $-45°$ C.

The reaction time employed in the above reaction is different depending on the reaction temperature, the starting material, the reagent used or the solvent employed, but is generally from 15 minutes to 2 hours, and preferably from 30 minutes to 1 hour.

After the reaction is completed, the desired compound of this reaction can, if necessary, be isolated from the reaction mixture and purified in the same manner as described in Step A1.

Step D3b-2

Step D3b-2 is a process for the preparation of a compound having the general formula (XIX) by converting a formyl group of a compound having the general formula (XI-1) into an oxime group.

This process can be accomplished by reacting a compound having the general formula (XI-1) with hydroxylamine or a hydroxylamine equivalent in a solvent.

The hydroxylamine equivalent can be a solution of hydroxylamine such as an aqueous solution of hydroxylamine, a mixed solution of hydroxylamine and methanol, a mixed solution of hydroxylamine and ethanol, or the like; or a combination of a hydroxylamine salt, such as hydroxylamine hydrochloride, hydroxylamine phosphate, hydroxylamine sulfate, or the like, and a tri-lower alkylamine, such as triethylamine, N,N-diisopropylethylamine or tributylamine, or an alkali metal carbonate, such as sodium hydrogencarbonate, potassium hydrogencarbonate, sodium carbonate, potassium carbonate, or the like, and is preferably a combination of a hydroxylamine salt and a tri-lower alkylamine and particularly preferably a combination of hydroxylamine hydrochloride and triethylamine.

The solvent employed in the above reaction is not particularly restricted provided that it has no adverse effect on the reaction and can be, for example, a halogenated hydrocarbon such as dichloromethane, chloroform, 1,2-dichloroethane, or the like; or an ether such as tetrahydrofuran, 1,2-dimethoxyethane, or the like, and is preferably a halogenated hydrocarbon and particularly preferably dichloromethane.

The reaction temperature employed in the above reaction is generally between $0°$ C. and $80°$ C., and preferably between $20°$ C. and $60°$ C.

The reaction time employed in the above reaction is different depending on the reaction temperature, the starting material, the reagent used or the solvent employed, but is generally from 30 minutes to 5 hours, and preferably from 1 hour to 3 hours.

After the reaction is completed, the desired compound of this reaction can, if necessary, be isolated from the reaction mixture and purified in the same manner as described in Step A1.

Step D3b-3

Step D3b-3 is a process for the preparation of a compound having the general formula (VI-1) by converting an oxime group of a compound having the general formula (XIX) into a nitrile group.

This process can be accomplished by reacting a compound having the general formula (XIX) with an appropriate dehydrating agent in a solvent.

The dehydrating agent employed in the above reaction can be a carbodiimide such as N,N'-dicyclohexylcarbodiimide, N,N'-diisopropylcarbodiimide, 1-ethyl-3-(3'-dimethylaminopropyl)carbodiimide (WSCI), or the like; a phosphorus compound such as diphosphorus pentaoxide or phosphorus oxychloride; or thionyl chloride or the like, and is preferably a carbodiimide and particularly preferably N,N'-dicyclohexylcarbodiimide.

The solvent employed in the above reaction is not particularly restricted provided that it has no adverse effect on the reaction and can be, for example, a halogenated hydrocarbon such as dichloromethane, chloroform, 1,2-dichloroethane, or the like; or an ether such as tetrahydrofuran, 1,2-dimethoxyethane, dioxane, or the like; or an aromatic hydrocarbon such as benzene, toluene, xylene, or the like, and is preferably an aromatic hydrocarbon and particularly preferably toluene.

The reaction temperature employed in the above reaction is generally between $20°$ C. and $150°$ C., and preferably between $60°$ C. and $110°$ C.

The reaction time employed in the above reaction is different depending on the reaction temperature, the starting material, the reagent used or the solvent employed, but is generally from 2 hours to 24 hours, and preferably from 6 hours to 12 hours.

After the reaction is completed, the desired compound of this reaction can, if necessary, be isolated from the reaction mixture and purified in the same manner as described in Step A1.

Method E

Method E is a method for the preparation of a compound having the general formula (VI-2), which is included in a compound having the general formula (VI), wherein the substituent W is a group having a fused structure such as a 4,5,6,7-tetrahydrobenzothiophene ring or a 4,5,6,7-tetrahydrobenzofuran ring.

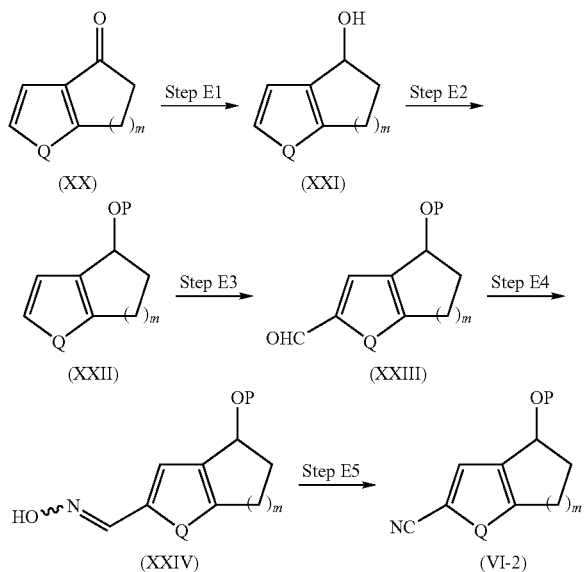

In the above reaction scheme, P and Q have the same meanings as those indicated hereinbefore, and m represents an integer of 1 or 2.

Step E1

Step E1 is a process for the preparation of a compound having the general formula (XXI) by converting a carbonyl group of a compound having the general formula (XX) into a hydroxyl group.

This process can be accomplished by reacting a compound having the general formula (XX) with an appropriate reducing agent in a solvent. Additionally, of the compounds having the general formula (XX) employed as the starting compounds, the compounds wherein m is 2 are commercially available and can be obtained easily. Furthermore, the compounds wherein m is 1 can also be synthesized according to the preparation method(s) described in a literature, J. Am. Chem. Soc., 127 (10), 3248-3249 (2005).

The reducing agent employed in the above reaction can be, for example, an aluminum hydride such as lithium aluminum hydride, sodium aluminum hydride or diisobutylaluminum hydride; a borohydride such as lithium borohydride, sodium borohydride, or borane, and is preferably a borohydride and particularly preferably sodium borohydride.

The solvent employed in the above reaction is not particularly restricted provided that it has no adverse effect on the reaction and can be, for example, an ether such as diethyl ether, tetrahydrofuran, 1,2-dimethoxyethane, dioxane, or the like; or an alcohol such as methanol, ethanol, isopropanol, or the like, and is preferably an alcohol and particularly preferably methanol.

The reaction temperature employed in the above reaction is generally between −23° C. and 50° C., and preferably between 0° C. and 30° C.

The reaction time employed in the above reaction is different depending on the reaction temperature, the starting material, the reagent used or the solvent employed, but is generally from 15 minutes to 2 hours, and preferably from 30 minutes to 1 hour.

After the reaction is completed, the desired compound of this reaction can, if necessary, be isolated from the reaction mixture and purified in the same manner as described in Step A1.

Step E2

Step E2 is a process for the preparation of a compound having the general formula (XXII) by protecting a hydroxyl group of a compound having the general formula (XXI) with an appropriate protecting group for a hydroxyl group. Such protecting group employed in this reaction is not particularly restricted provided that it has no adverse effect on the reaction in succeeding processes and additionally can easily be removed, and is preferably a trialkylsilane. The general preparation method for the case that a trialkylsilane is employed as the protecting group is described hereinafter.

This process can be carried out by reacting a compound having the general formula (XXI) with a silylating agent in the presence of a suitable base in a solvent.

The silylating agent employed in the above reaction can be, for example, a trialkylsilyl chloride such as triethylsilyl chloride, t-butyldimethylsilyl chloride, triisopropylsilyl chloride or t-butyldiphenylsilyl chloride; or a trialkylsilyl trifluoromethanesulfonate such as triethylsilyl trifluoromethanesulfonate, t-butyldimethylsilyl trifluoromethanesulfonate, triisopropylsilyl trifluoromethanesulfonate or t-butyldiphenylsilyl trifluoromethanesulfonate, and is preferably a trialkylsilyl chloride and particularly preferably t-butyldiphenylsilyl chloride.

The base employed in the above reaction can be, for example, a trialkylamine such as triethylamine, N,N-diisopropylethylamine, or the like; an imidazole such as imidazole, 2-methylimidazole, or the like; or a pyridine such as pyridine, lutidine, collidine, or the like and is preferably an imidazole and particularly preferably imidazole.

The solvent employed in the above reaction is not particularly restricted provided that it has no adverse effect on the reaction and can be, for example, an ether such as diethyl ether, tetrahydrofuran, 1,2-dimethoxyethane, dioxane, or the like; a halogenated hydrocarbon such as dichloromethane, 1,2-dichloroethane or chloroform; or an amide such as N,N-dimethylformamide, N,N-dimethylacetamide, or the like; and is preferably an amide and particularly preferably N,N-dimethylformamide.

The reaction temperature employed in the above reaction is generally between −23° C. and 100° C., and preferably between 0° C. and 60° C.

The reaction time employed in the above reaction is different depending on the reaction temperature, the starting material, the reagent used or the solvent employed, but is generally from 30 minutes to 4 hours, and preferably from 1 hour to 3 hours.

After the reaction is completed, the desired compound of this reaction can, if necessary, be isolated from the reaction mixture and purified in the same manner as described in Step A1.

Step E3

Step E3 is a process for the preparation of a compound having the general formula (XXIII) by introducing a formyl group into a compound having the general formula (XXII)

This process can be accomplished by reacting a compound having the general formula (XXII) with a strong base, followed by reacting the resulting product with an appropriate formylating agent in a solvent.

The strong base employed in the above reaction can be, for example, an alkyllithium such as n-butyllithium, s-butyllithium or t-butyllithium; or an alkali metal amide such as lithium diisopropylamide, lithium hexamethyldisilazide, sodium hexamethyldisilazide, potassium hexamethyldisilazide, or the like, and is preferably an alkyllithium and particularly preferably n-butyllithium.

The formylating agent employed in this reaction can be a formamide such as N,N-dimethylformamide, N-methylformanilide, N-formylpiperidine, or the like; a formate such as methyl formate, ethyl formate, propyl formate, or the like and is preferably a formamide and particularly preferably N,N-dimethylformamide.

The solvent employed in the above reaction is not particularly restricted provided that it has no adverse effect on the reaction and can be, for example, an ether such as diethyl ether, tetrahydrofuran, 1,2-dimethoxyethane, dioxane, or the like; or an aromatic hydrocarbon such as toluene, xylene, or the like, and is preferably an ether and particularly preferably tetrahydrofuran.

The reaction temperature employed in the above reaction is generally between −100° C. and 0° C., and preferably between −78° C. and 0° C.

The reaction time employed in the above reaction is different depending on the reaction temperature, the starting material, the reagent used or the solvent employed, but is generally from 15 minutes to 4 hours, and preferably from 1 hour to 3 hours.

After the reaction is completed, the desired compound of this reaction can, if necessary, be isolated from the reaction mixture and purified in the same manner as described in Step A1.

Step E4

Step E4 is a process for the preparation of a compound having the general formula (XXIV) by converting a formyl group of a compound having the general formula (XXIII) into an oxime group.

This process can be accomplished by reacting a compound having the general formula (XXIII) with hydroxylamine or a hydroxylamine equivalent in a solvent, and can be carried out in the same manner as described in Step D3b-2.

Step E5

Step E5 is a process for the preparation of a compound having the general formula (VI-2) by converting an oxime group of a compound having the general formula (XXIV) into a nitrile group.

This process can be accomplished by reacting a compound having the general formula (XXIV) with an appropriate dehydrating agent in a solvent, and can be carried out in the same manner as described in Step D3b-2.

Method F

Method F is a method for the preparation of a compound having the general formula (VI-3), which is included in a compound having the general formula (VI), wherein the substituent W is a thiophene ring or a furan ring and additionally, these rings are substituted with an alkyl group as a substituent R.

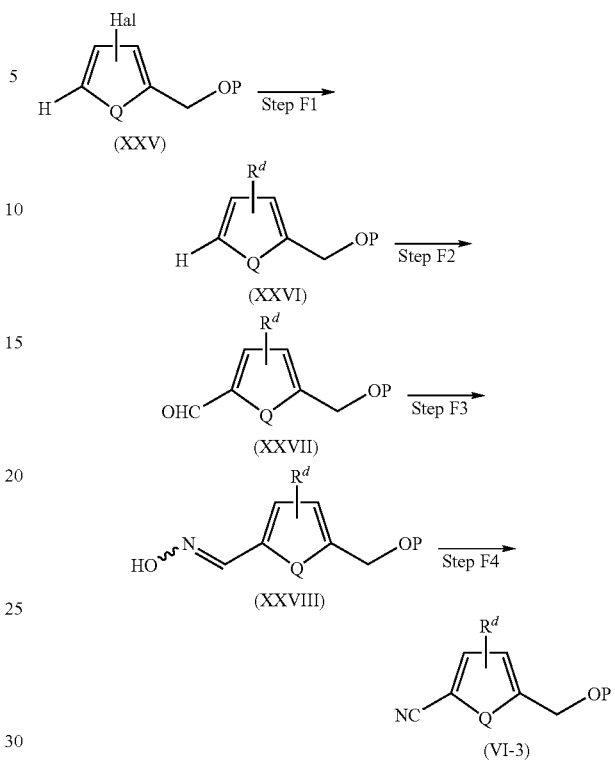

In the above reaction scheme, Hal represents a halogen atom as described above, and is preferably a bromine atom or an iodine atom, Q represents an oxygen atom or a sulfur atom, P represents a protecting group for a hydroxyl group as described above, and $R^d$ represents a $C_1$-$C_6$ alkyl group.

Step F1

Step F1 is a process for the preparation of a compound having the general formula (XXVI) by converting a halogen atom of a compound having the general formula (XXV) into an alkyl group.

This process can be accomplished by reacting a compound having the general formula (XXV) with an alkylating agent in a solvent. Additionally, many of the compounds having the general formula (XXV) employed as the starting compounds can be synthesized according to Method D described hereinbefore.

The alkylating agent employed in the above reaction can be, for example, a combination of a nickel catalyst, such as [1,3-bis(diphenylphosphino)propane]dichloronickel, bis(triphenylphosphine)dichloronickel or [1,1'-bis(diphenylphosphino)ferrocene]dichloronickel, and a Grignard reagent, such as an alkylmagnesium chloride, an alkylmagnesium bromide or an alkylmagnesium iodide; or a combination of a palladium catalyst, such as tetrakis(triphenylphosphine)palladium or dichlorobis(triphenylphosphine)palladium, and an alkylboric acid, such as a mono-alkylboric acid, an ester of mono-alkylboric acid, a dialkylboric acid or an ester of dialkylboric acid, and is preferably a combination of a nickel catalyst and a Grignard reagent and particularly preferably a combination of [1,3-bis(diphenylphosphino)propane]dichloronickel and an alkylmagnesium bromide.

The solvent employed in the above reaction is not particularly restricted provided that it has no adverse effect on the reaction and can be, for example, an ether such as diethyl ether, tetrahydrofuran, 1,2-dimethoxyethane, dioxane, or the like; or an aromatic hydrocarbon such as benzene, toluene or xylene, and is preferably an ether and particularly preferably tetrahydrofuran.

The reaction temperature employed in the above reaction is generally between −23° C. and 60° C., and preferably between −10° C. and 40° C.

The reaction time employed in the above reaction is different depending on the reaction temperature, the starting material, the reagent used or the solvent employed, but is generally from 15 minutes to 4 hours, and preferably from 1 hour to 2 hours.

After the reaction is completed, the desired compound of this reaction can, if necessary, be isolated from the reaction mixture and purified in the same manner as described in Step A1.

Step F2

Step F2 is a process for the preparation of a compound having the general formula (XXVII) by converting a hydrogen atom of a compound having the general formula (XXVI) into a formyl group.

This process can be accomplished by reacting a compound having the general formula (XXVI) with an appropriate base, followed by reacting the resulting product with a formylating agent in a solvent.

The base employed in the above reaction can be, for example, an alkyllithium such as n-butyllithium, sec-butyllithium or t-butyllithium; or a metal amide such as lithium diisopropylamide, lithium hexamethyldisilazide or potassium hexamethyldisilazide, and is preferably an alkyllithium and particularly preferably n-butyllithium.

The formylating agent employed in this reaction can be a formamide such as N,N-dimethylformamide, 1-formylpyrrolidine or 1-formylpiperidine; or an isocyanide such as t-butyl isocyanide, 1,1,3,3-tetramethylbutyl isocyanide, or the like, and is preferably a formamide and particularly preferably N,N-dimethylformamide.

The solvent employed in the above reaction is not particularly restricted provided that it has no adverse effect on the reaction and can be, for example, an ether such as diethyl ether, tetrahydrofuran, 1,2-dimethoxyethane, dioxane, or the like; or an aromatic hydrocarbon such as benzene, toluene or xylene, and is preferably an ether and particularly preferably tetrahydrofuran.

The reaction temperature employed in the above reaction is generally between −78° C. and room temperature, and preferably between −78° C. and 0° C.

The reaction time employed in the above reaction is different depending on the reaction temperature, the starting material, the reagent used or the solvent employed, but is generally from 30 minutes to 4 hours, and preferably from 1 hour to 3 hours.

After the reaction is completed, the desired compound of this reaction can, if necessary, be isolated from the reaction mixture and purified in the same manner as described in Step A1.

Step F3

Step F3 is a process for the preparation of a compound having the general formula (XXVIII) by converting a formyl group of a compound having the general formula (XXVII) into an oxime group.

This process can be accomplished by reacting a compound having the general formula (XXVII) with hydroxylamine or a hydroxylamine equivalent in a solvent.

The hydroxylamine equivalent can be a solution of hydroxylamine such as an aqueous solution of hydroxylamine, a mixed solution of hydroxylamine and methanol, a mixed solution of hydroxylamine and ethanol, or the like; or a combination of a hydroxylamine salt, such as hydroxylamine hydrochloride, hydroxylamine phosphate, hydroxylamine sulfate, or the like, and a tri-lower alkylamine, such as triethylamine, N,N-diisopropylethylamine or tributylamine, or an alkali metal carbonate, such as sodium hydrogencarbonate, potassium hydrogencarbonate, sodium carbonate, potassium carbonate, or the like, and is preferably a combination of a hydroxylamine salt and a tri-lower alkylamine and particularly preferably a combination of hydroxylamine hydrochloride and triethylamine.

The solvent employed in the above reaction is not particularly restricted provided that it has no adverse effect on the reaction and can be, for example, a halogenated hydrocarbon such as dichloromethane, chloroform, 1,2-dichloroethane, or the like; or an ether such as tetrahydrofuran, 1,2-dimethoxyethane, or the like; or an alcohol such as methanol, ethanol or isopropanol, and is preferably a halogenated hydrocarbon and particularly preferably dichloromethane.

The reaction temperature employed in the above reaction is generally between 0° C. and 80° C., and preferably between 20° C. and 60° C.

The reaction time employed in the above reaction is different depending on the reaction temperature, the starting material, the reagent used or the solvent employed, but is generally from 30 minutes to 5 hours, and preferably from 1 hour to 3 hours.

After the reaction is completed, the desired compound of this reaction can, if necessary, be isolated from the reaction mixture and purified in the same manner as described in Step A1.

Step F4

Step F4 is a process for the preparation of a compound having the general formula (VI-3) by converting an oxime group of a compound having the general formula (XXVIII) into a nitrile group.

This process can be accomplished by reacting a compound having the general formula (XXVIII) with an appropriate dehydrating agent in a solvent.

The dehydrating agent employed in the above reaction can be a carbodiimide such as N,N'-dicyclohexylcarbodiimide, N,N'-diisopropylcarbodiimide, 1-ethyl-3-(3'-dimethylaminopropyl)carbodiimide (WSCI), or the like; a phosphorus compound such as diphosphorus pentaoxide or phosphorus oxychloride; or thionyl chloride, or the like, and is preferably a carbodiimide and particularly preferably N,N'-dicyclohexylcarbodiimide.

The solvent employed in the above reaction is not particularly restricted provided that it has no adverse effect on the reaction and can be, for example, a halogenated hydrocarbon such as dichloromethane, chloroform, 1,2-dichloroethane, or the like; or an ether such as tetrahydrofuran, 1,2-dimethoxyethane, dioxane, or the like; or an aromatic hydrocarbon such as benzene, toluene, xylene, or the like, and is preferably an aromatic hydrocarbon and particularly preferably toluene.

The reaction temperature employed in the above reaction is generally between 20° C. and 150° C., and preferably between 60° C. and 110° C.

The reaction time employed in the above reaction is different depending on the reaction temperature, the starting material, the reagent used or the solvent employed, but is generally from 2 hours to 24 hours, and preferably from 6 hours to 12 hours.

After the reaction is completed, the desired compound of this reaction can, if necessary, be isolated from the reaction mixture and purified in the same manner as described in Step A1.

Method G

Method G is a method for the preparation of a compound having the general formula (VI-4), which is included in a compound having the general formula (VI), wherein the substituent W is a pyridine ring.

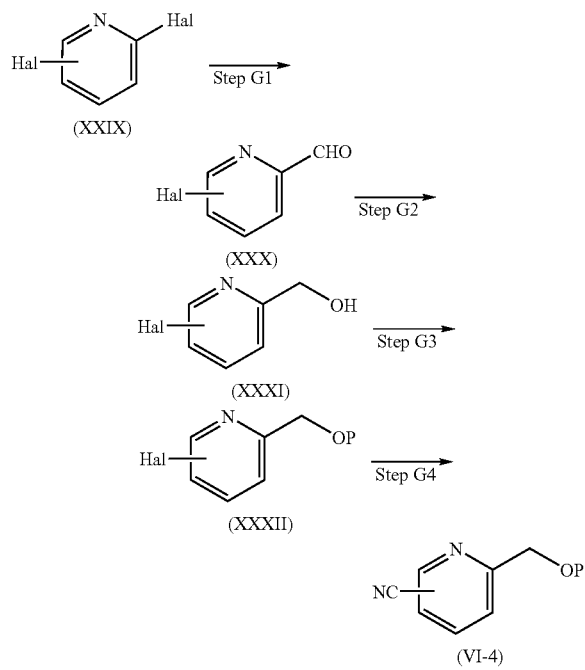

In the above reaction scheme, Hal represents a halogen atom as described above, and is preferably a bromine atom or an iodine atom, and P represents a protecting group for a hydroxyl group as described above.

Step G1

Step G1 is a process for the preparation of a compound having the general formula (XXX) by converting a halogen atom at the 2-position of a compound having the general formula (XXIX) into a formyl group.

This process is accomplished by carrying out a halogen-metal exchange on a compound having the general formula (XXIX), followed by reacting the resulting product with a suitable formylating agent in a solvent.

The metalating agent employed in the above reaction can be, for example, a metal such as metallic lithium, metallic magnesium, metallic zinc, or the like; or an alkyllithium such as n-butyllithium, s-butyllithium, t-butyllithium, or the like, and is preferably an alkyllithium and particularly preferably n-butyllithium.

The formylating agent employed in this reaction can be a formamide such as N,N-dimethylformamide, N-methylformanilide, N-formylpiperidine, or the like; or a formate such as methyl formate, ethyl formate, propyl formate, or the like, and is preferably a formamide and particularly preferably N,N-dimethylformamide.

The solvent employed in the above reaction is not particularly restricted provided that it has no adverse effect on the reaction and can be, for example, an ether such as diethyl ether, tetrahydrofuran, 1,2-dimethoxyethane, dioxane, or the like; or an aromatic hydrocarbon such as toluene, xylene, or the like, and is preferably an aromatic hydrocarbon and particularly preferably toluene.

The reaction temperature employed in the above reaction is generally between −100° C. and 0° C., and preferably between −78° C. and −45° C.

The reaction time employed in the above reaction is different depending on the reaction temperature, the starting material, the reagent used or the solvent employed, but is generally from 15 minutes to 5 hours, and preferably from 30 minutes to 3 hours.

After the reaction is completed, the desired compound of this reaction can, if necessary, be isolated from the reaction mixture and purified in the same manner as described in Step A1.

Step G2

Step G2 is a process for the preparation of a compound having the general formula (XXXI) by converting a formyl group of a compound having the general formula (XXX) into a hydroxymethyl group.

This process can be accomplished by reacting a compound having the general formula (XXX) with a reducing agent in a solvent.

The reducing agent employed in the above reaction can be, for example, an aluminum hydride such as lithium aluminum hydride, sodium aluminum hydride or diisobutylaluminum hydride; a borohydride such as lithium borohydride, sodium borohydride or borane, and is preferably a borohydride and particularly preferably sodium borohydride.

The solvent employed in the above reaction is not particularly restricted provided that it has no adverse effect on the reaction and can be, for example, an ether such as diethyl ether, tetrahydrofuran, 1,2-dimethoxyethane, dioxane, or the like; or an alcohol such as methanol, ethanol, isopropanol, or the like, and is preferably an alcohol and particularly preferably methanol.

The reaction temperature employed in the above reaction is generally between −23° C. and 50° C., and preferably between 0° C. and 30° C.

The reaction time employed in the above reaction is different depending on the reaction temperature, the starting material, the reagent used or the solvent employed, but is generally from 15 minutes to 2 hours, and preferably from 30 minutes to 1 hour.

After the reaction is completed, the desired compound of this reaction can, if necessary, be isolated from the reaction mixture and purified in the same manner as described in Step A1.

Step G3

Step G3 is a process for the preparation of a compound having the general formula (XXXII) by protecting a hydroxyl group of a compound having a general formula (XXXI) with an appropriate protecting group for a hydroxyl group. The protecting group employed in this reaction is not particularly restricted provided that it has no adverse effect on the reaction in succeeding processes and additionally can easily be removed, and is preferably a trialkylsilane. The general preparation method for the case that a trialkylsilane is employed as the protecting group is described hereinafter.

This process can be carried out by reacting a compound having the general formula (XXXI) with a silylating agent in the presence of a suitable base in a solvent.

The silylating agent employed in the above reaction can be, for example, a trialkylsilyl chloride such as triethylsilyl chloride, t-butyldimethylsilyl chloride, triisopropylsilyl chloride or t-butyldiphenylsilyl chloride; or a trialkylsilyl trifluoromethanesulfonate such as triethylsilyl trifluoromethanesulfonate, t-butyldimethylsilyl trifluoromethanesulfonate, triisopropylsilyl trifluoromethanesulfonate or t-butyldiphenylsilyl trifluoromethanesulfonate, and is preferably a trialkylsilyl chloride and particularly preferably t-butyldimethylsilyl chloride.

The base employed in the above reaction can be, for example, a trialkylamine such as triethylamine, N,N-diisopropylethylamine, or the like; an imidazole such as imidazole or 2-methylimidazole; or a pyridine such as pyridine, lutidine, collidine, or the like, and is preferably an imidazole and particularly preferably imidazole.

The solvent employed in the above reaction is not particularly restricted provided that it has no adverse effect on the reaction and can be, for example, an ether such as diethyl ether, tetrahydrofuran, 1,2-dimethoxyethane, dioxane, or the like; a halogenated hydrocarbon such as dichloromethane, 1,2-dichloroethane or chloroform; or an amide such as N,N-dimethylformamide, N,N-dimethylacetamide, or the like; and is preferably an amide and particularly preferably N,N-dimethylformamide.

The reaction temperature employed in the above reaction is generally between −23° C. and 50° C., and preferably between 0° C. and 30° C.

The reaction time employed in the above reaction is different depending on the reaction temperature, the starting material, the reagent used or the solvent employed, but is generally from 30 minutes to 4 hours, and preferably from 1 hour to 3 hours.

After the reaction is completed, the desired compound of this reaction can, if necessary, be isolated from the reaction mixture and purified in the same manner as described in Step A1.

Step G4

Step G4 is a process for the preparation of a compound having the general formula (VI-4) by converting a halogen atom of a compound having the general formula (XXXII) into a nitrile group.

This process is accomplished by reacting a compound having the general formula (XXXII) with an appropriate cyanating agent in a solvent.

The cyanating agent employed in this reaction can be, for example, a copper compound such as copper cyanide; or a combination of a palladium catalyst, such as tetrakis(triphenylphosphine)palladium, dichlorobis(triphenylphosphine)palladium, [1,1'-bis(diphenylphosphino)ferrocene]dichloropalladium, or the like, and a metal cyanide, such as zinc cyanide, trimethylsilyl cyanide or tributyltin cyanide, and is preferably a combination of palladium catalyst and zinc cyanide and particularly preferably a combination of [1,1'-bis(diphenylphosphino)ferrocene]dichloropalladium and zinc cyanide.

The solvent employed in the above reaction is not particularly restricted provided that it has no adverse effect on the reaction and can be, for example, an ether such as diethyl ether, tetrahydrofuran, 1,2-dimethoxyethane, dioxane, or the like; or an amide such as N,N-dimethylformamide, N,N-dimethylacetamide, N-methyl-2-pyrrolidinone, or the like; and is preferably an amide and particularly preferably N-methyl-2-pyrrolidinone.

The reaction temperature employed in the above reaction is generally between 20° C. and 180° C., and preferably between 80° C. and 120° C.

The reaction time employed in the above reaction is different depending on the reaction temperature, the starting material, the reagent used or the solvent employed, but is generally from 30 minutes to 4 hours, and preferably from 1 hour to 3 hours.

After the reaction is completed, the desired compound of this reaction can, if necessary, be isolated from the reaction mixture and purified in the same manner as described in Step A1.

Method H

Method H is a method for the preparation of a compound having the general formula (VI-5), which is included in a compound having the general formula (VI), wherein the substituent W is a pyridine ring and additionally, the ring is substituted with an alkyl group as a substituent.

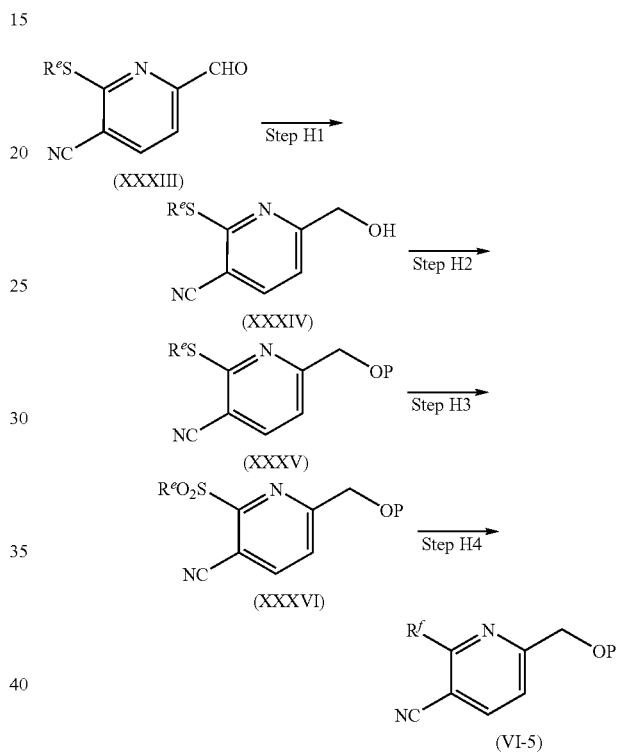

In the above reaction scheme, $R^e$ and $R^f$ are the same or different and each represents a $C_1$-$C_6$ alkyl group, and is preferably a methyl group or an ethyl group, and P represents a protecting group for a hydroxyl group as described above.

Step H1

Step H1 is a process for the preparation of a compound having the general formula (XXXIV) by converting a formyl group of a compound having the general formula (XXXIII) into a hydroxymethyl group. Additionally, as to the compound having the general formula (XXXIII) employed as the starting compounds, commercially available 6-formyl-2-(methylsulfanyl)nicotinonitrile, and the like (Maybridge Chemicals Ltd.) can be used.

This process can be accomplished by reacting a compound having the general formula (XXXIII) with a reducing agent in a solvent.

The reducing agent employed in the above reaction can be, for example, an aluminum hydride such as lithium aluminum hydride, sodium aluminum hydride, or diisobutylaluminum hydride; a borohydride such as lithium borohydride, sodium borohydride or borane, and is preferably a borohydride and particularly preferably sodium borohydride.

The solvent employed in the above reaction is not particularly restricted provided that it has no adverse effect on the reaction and can be, for example, an ether such as diethyl ether, tetrahydrofuran, 1,2-dimethoxyethane, dioxane, or the like; or an alcohol such as methanol, ethanol, isopropanol, or the like, and is preferably an alcohol and particularly preferably methanol.

The reaction temperature employed in the above reaction is generally between −23° C. and 50° C., and preferably between 0° C. and 30° C.

The reaction time employed in the above reaction is different depending on the reaction temperature, the starting material, the reagent used or the solvent employed, but is generally from 15 minutes to 2 hours, and preferably from 30 minutes to 1 hour.

After the reaction is completed, the desired compound of this reaction can, if necessary, be isolated from the reaction mixture and purified in the same manner as described in Step A1.

Step H2

Step H2 is a process for the preparation of a compound having the general formula (XXXV) by protecting a hydroxyl group of a compound having the general formula (XXXIV) with an appropriate protecting group for a hydroxyl group. The protecting group employed in this reaction is not particularly restricted provided that it has no adverse effect on the reaction in succeeding processes and additionally can easily be removed, and is preferably a trialkylsilane. The general preparation method for the case that a trialkylsilane is employed as the protecting group is described hereinafter.

This process can be carried out by reacting a compound having the general formula (XXXIV) with a silylating agent in the presence of a suitable base in a solvent.

The silylating agent employed in the above reaction can be, for example, a trialkylsilyl chloride such as triethylsilyl chloride, t-butyldimethylsilyl chloride, triisopropylsilyl chloride or t-butyldiphenylsilyl chloride; or a trialkylsilyl trifluoromethanesulfonate such as triethylsilyl trifluoromethanesulfonate, t-butyldimethylsilyl trifluoromethanesulfonate, triisopropylsilyl trifluoromethanesulfonate or t-butyldiphenylsilyl trifluoromethanesulfonate, and is preferably a trialkylsilyl chloride and particularly preferably triisopropylsilyl chloride.

The base employed in the above reaction can be, for example, a trialkylamine such as triethylamine, N,N-diisopropylethylamine, or the like; an imidazole such as imidazole, 2-methylimidazole, or the like; or a pyridine such as pyridine, lutidine, collidine, or the like, and is preferably an imidazole and particularly preferably imidazole.

The solvent employed in the above reaction is not particularly restricted provided that it has no adverse effect on the reaction and can be, for example, an ether such as diethyl ether, tetrahydrofuran, 1,2-dimethoxyethane, dioxane, or the like; a halogenated hydrocarbon such as dichloromethane, 1,2-dichloroethane or chloroform; or an amide such as N,N-dimethylformamide, N,N-dimethylacetamide, or the like; and is preferably an amide and particularly preferably N,N-dimethylformamide.

The reaction temperature employed in the above reaction is generally between −23° C. and 50° C., and preferably between 0° C. and 30° C.

The reaction time employed in the above reaction is different depending on the reaction temperature, the starting material, the reagent used or the solvent employed, but is generally from 30 minutes to 4 hours, and preferably from 1 hour to 3 hours.

After the reaction is completed, the desired compound of this reaction can, if necessary, be isolated from the reaction mixture and purified in the same manner as described in Step A1.

Step H3

Step H3 is a process for the preparation of a compound having the general formula (XXXVI) by oxidizing an alkylthio group of a compound having the general formula (XXXV).

This process is accomplished by reacting a compound having the general formula (XXXV) with an appropriate oxidizing agent in a solvent.

The oxidizing agent employed in the above reaction can be, for example, a peracid such as peracetic acid, perbenzoic acid, or m-chloroperbenzoic acid; a permanganate such as sodium permanganate or potassium permanganate, and is preferably a peracid and particularly preferably m-chloroperbenzoic acid.

The solvent employed in the above reaction is not particularly restricted provided that it has no adverse effect on the reaction and can be, for example, an alcohol such as methanol, ethanol, isopropanol, or the like; or a halogenated hydrocarbon such as dichloromethane, 1,2-dichloroethane, chloroform, or the like, and is preferably an alcohol and particularly preferably ethanol.

The reaction temperature employed in the above reaction is generally between −23° C. and 50° C., and preferably between 0° C. and 30° C.

The reaction time employed in the above reaction is different depending on the reaction temperature, the starting material, the reagent used or the solvent employed, but is generally from 30 minutes to 4 hours, and preferably from 1 hour to 3 hours.

After the reaction is completed, the desired compound of this reaction can, if necessary, be isolated from the reaction mixture and purified in the same manner as described in Step A1.

Step H4

Step H4 is a process for the preparation of a compound having the general formula (VI-5) by converting an alkylsulfone group of a compound having the general formula (XXXVI) into an alkyl group.

This process is carried out by reacting a compound having the general formula (XXXVI) with an alkylating agent in a solvent.

The alkylating agent employed in the above reaction can be, for example, a Grignard reagent such as an alkylmagnesium chloride, an alkylmagnesium bromide or an alkylmagnesium iodide; or an alkyllithium such as methyllithium, ethyllithium or isopropyllithium, and is preferably a Grignard reagent.

The solvent employed in the above reaction is not particularly restricted provided that it has no adverse effect on the reaction and can be, for example, an ether such as diethyl ether, tetrahydrofuran, 1,2-dimethoxyethane, dioxane, or the like; or an aromatic hydrocarbon such as benzene, toluene or xylene, and is preferably an ether and particularly preferably diethyl ether.

The reaction temperature employed in the above reaction is generally between −100° C. and 0° C., and preferably between −78° C. and −23° C.

The reaction time employed in the above reaction is different depending on the reaction temperature, the starting material, the reagent used or the solvent employed, but is generally from 15 minutes to 4 hours, and preferably from 1 hour to 2 hours.

After the reaction is completed, the desired compound of this reaction can, if necessary, be isolated from the reaction mixture and purified in the same manner as described in Step A1.

Method I

Method I is a method for the preparation of a compound having the general formula (VIII-1), which is included in a compound having the general formula (VIII), wherein the substituent Z is a phenoxy group which may optionally be substituted with substituent(s) and additionally, the substituent Y is a benzene ring which may optionally be substituted with substituent(s), and the LG is a hydroxyl group.

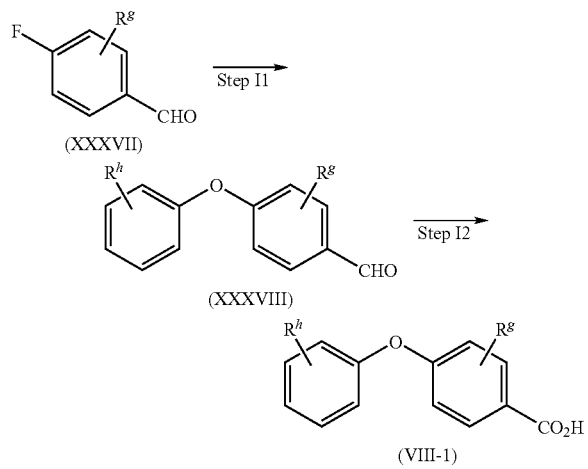

In the above reaction scheme, $R^g$ and $R^h$ are the same or different and each represents a group selected from Substituent group A described above.

Step I1

Step I1 is a process for the preparation of a compound having the general formula (XXXVIII) by substituting a fluorine atom of a compound having the general formula (XXXVII) with a phenoxy group, which may optionally be substituted with substituent(s).

This process is carried out by reacting a compound having the general formula (XXXVII) with various phenols in the presence of an appropriate base in a solvent.

The base employed in the above reaction can be, for example, an alkali metal carbonate such as lithium carbonate, sodium carbonate or potassium carbonate; or an alkali metal hydride such as lithium hydride, sodium hydride or potassium hydride, and is preferably an alkali metal carbonate and particularly preferably potassium carbonate.

The solvent employed in the above reaction is not particularly restricted provided that it has no adverse effect on the reaction and can be, for example, an amide such as N,N-dimethylformamide, N,N-dimethylacetamide, N-methyl-2-pyrrolidinone, or the like; or an ether such as diethyl ether, tetrahydrofuran, 1,2-dimethoxyethane, dioxane, or the like, and is preferably an amide and particularly preferably N,N-dimethylformamide.

The reaction temperature employed in the above reaction is generally between 0° C. and 140° C., and preferably between 60° C. and 100° C.

The reaction time employed in the above reaction is different depending on the reaction temperature, the starting material, the reagent used or the solvent employed, but is generally from 1 hour to 24 hours, and preferably from 3 hours to 12 hours.

After the reaction is completed, the desired compound of this reaction can, if necessary, be isolated from the reaction mixture and purified in the same manner as described in Step A1.

Step I2

Step I2 is a process for the preparation of a compound having the general formula (VIII-1) by oxidizing a formyl group of a compound having the general formula (XXXVIII).

This process is accomplished by reacting a compound having the general formula (XXXVIII) with an appropriate oxidizing agent in a solvent.

The oxidizing agent employed in the above reaction can be, for example, a hypochlorite such as sodium hypochlorite or potassium hypochlorite; a chlorite such as sodium chlorite or potassium chlorite; or a permanganate such as sodium permanganate or potassium permanganate, and is preferably a chlorite and particularly preferably sodium chlorite.

The solvent employed in the above reaction is not particularly restricted provided that it has no adverse effect on the reaction and can be, for example, a combination of water and a tertiary alcohol such as t-butanol or t-amyl alcohol; or a combination of water and a halogenated hydrocarbon such as dichloromethane, 1,2-dichloroethane, chloroform, or the like, and is preferably a combination of water and a tertiary alcohol and particularly preferably a combination of water and t-butanol.

The reaction temperature employed in the above reaction is generally between 0° C. and 60° C., and preferably between 0° C. and 40° C.

The reaction time employed in the above reaction is different depending on the reaction temperature, the starting material, the reagent used or the solvent employed, but is generally from 30 minutes to 24 hours, and preferably from 1 hour to 4 hours.

After the reaction is completed, the desired compound of this reaction can, if necessary, be isolated from the reaction mixture and purified in the same manner as described in Step A1.

Method J

Method J is a method for the preparation of a compound having the general formula (VIII-2), which is included in a compound having the general formula (VIII), wherein the substituent Z is an alkyl group which may optionally be branched and additionally, the substituent Y is a benzene ring which may optionally be substituted with substituent(s) and the LG is a hydroxyl group.

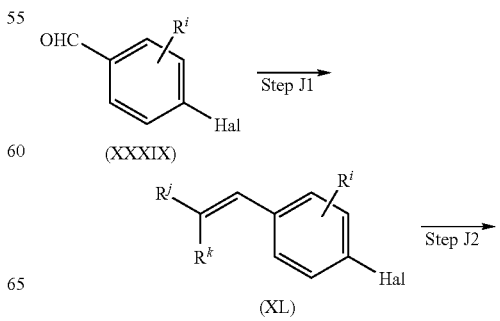

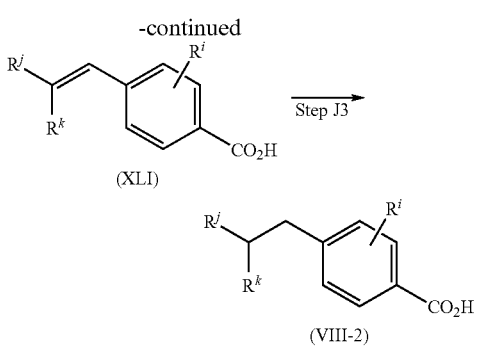

In the above reaction scheme, $R^i$ represents a group selected from Substituent group A described above, Hal represents a halogen atom as described above, and is preferably a bromine atom or an iodine atom, and $R^j$ and $R^k$ are the same or different and each represents a $C_1$-$C_6$ alkyl group which may optionally be substituted with group(s) selected from Substituent group A described above.

Step J1

Step J1 is a process for the preparation of a compound having the general formula (XL) by converting a formyl group of a compound having the general formula (XXXIX) into an alkenyl group.

This process is carried out by reacting a compound having the general formula (XXXIX) with various alkyltriphenylphosphonium salts in the presence of a suitable base in a solvent.

The base employed in the above reaction can be, for example, an alkoxide such as sodium methoxide, sodium ethoxide or potassium t-butoxide; an alkali metal hydride such as lithium hydride, sodium hydride or potassium hydride; or an alkyllithium such as n-butyllithium, s-butyllithium or t-butyllithium, and is preferably an alkoxide and particularly preferably potassium t-butoxide.

The solvent employed in the above reaction is not particularly restricted provided that it has no adverse effect on the reaction and can be, for example, an amide such as N,N-dimethylformamide, N,N-dimethylacetamide, N-methyl-2-pyrrolidinone, or the like; or an ether such as diethyl ether, tetrahydrofuran, 1,2-dimethoxyethane, dioxane, or the like, and is preferably an amide and particularly preferably N,N-dimethylformamide.

The reaction temperature employed in the above reaction is generally between −45° C. and 100° C., and preferably between 0° C. and 40° C.

The reaction time employed in the above reaction is different depending on the reaction temperature, the starting material, the reagent used or the solvent employed, but is generally from 15 minutes to 4 hours, and preferably from 30 minutes to 2 hours.

After the reaction is completed, the desired compound of this reaction can, if necessary, be isolated from the reaction mixture and purified in the same manner as described in Step A1.

Step J2

Step J2 is a process for the preparation of a compound having the general formula (XLI) by converting a halogen atom of a compound having the general formula (XL) into a carboxyl group.

This process is accomplished by carrying out a halogen-metal exchange on a compound having the general formula (XL), followed by reacting the resulting product with carbon dioxide in a solvent.

The metalating agent employed in the above reaction can be, for example, a metal such as metallic lithium, metallic magnesium, metallic zinc, or the like; or an alkyllithium such as n-butyllithium, s-butyllithium, t-butyllithium, or the like; and is preferably an alkyllithium and particularly preferably n-butyllithium.

The solvent employed in the above reaction is not particularly restricted provided that it has no adverse effect on the reaction and can be, for example, an ether such as diethyl ether, tetrahydrofuran, 1,2-dimethoxyethane, dioxane, or the like; or an aromatic hydrocarbon such as benzene, toluene, xylene, or the like, and is preferably an ether and particularly preferably tetrahydrofuran.

The reaction temperature employed in the above reaction is generally between −100° C. and 0° C., and preferably between −78° C. and −23° C.

The reaction time employed in the above reaction is different depending on the reaction temperature, the starting material, the reagent used or the solvent employed, but is generally from 15 minutes to 4 hours, and preferably from 30 minutes to 2 hours.

After the reaction is completed, the desired compound of this reaction can, if necessary, be isolated from the reaction mixture and purified in the same manner as described in Step A1.

Step J3

Step J3 is a process for the preparation of a compound having the general formula (VIII-2) by reducing a double bond moiety of a compound having the general formula (XLI).

This process is carried out by reacting a compound having the general formula (XLI) with hydrogen in the presence of an appropriate transition metal catalyst in a solvent.

The transition metal catalyst employed in the above reaction can be, for example, a heterogeneous catalyst such as palladium on carbon, platinum oxide or Raney nickel; a homogeneous catalyst such as chlorotris(triphenylphosphine)rhodium or tetrakis(triphenylphosphine)palladium, and is preferably a heterogeneous catalyst and particularly preferably palladium on carbon.

The solvent employed in the above reaction is not particularly restricted provided that it has no adverse effect on the reaction and can be, for example, an alcohol such as methanol, ethanol or isopropanol; an ether such as diethyl ether, tetrahydrofuran, 1,2-dimethoxyethane, dioxane, or the like; or an aromatic hydrocarbon such as benzene, toluene, or xylene, and is preferably an alcohol and particularly preferably ethanol.

The reaction temperature employed in the above reaction is generally between 0° C. and 80° C., and preferably between 20° C. and 40° C.

The reaction time employed in the above reaction is different depending on the reaction temperature, the starting material, the reagent used or the solvent employed, but is generally from 15 minutes to 4 hours, and preferably from 30 minutes to 2 hours.

After the reaction is completed, the desired compound of this reaction can, if necessary, be isolated from the reaction mixture and purified in the same manner as described in Step A1.

EXAMPLES

Example 1

1-[(4-{5-[4-Phenyl-5-(trifluoromethyl)-2-thienyl]-1,2,4-oxadiazol-3-yl}-2-furyl)methyl]azetidine-3-carboxylic acid

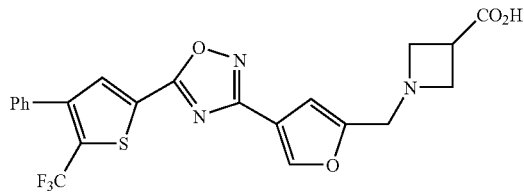

(1a) [(4-Bromo-2-furyl)methoxy](t-butyl)dimethylsilane

To a solution of 4-bromo-2-furaldehyde (5.0 g, 29 mmol) in methanol (40 ml) was added sodium borohydride (1.1 g, 29 mmol) at 0° C. with stirring, and the resulting mixture was stirred for 1 hour. After evaporating the reaction mixture in vacuo, the residue obtained was diluted with ether, poured into water and extracted with ether. The extract was washed with a saturated aqueous solution of sodium chloride and dried over magnesium sulfate. After filtration, the filtrate was evaporated in vacuo. Subsequently, to a solution of the residue obtained in N,N-dimethylformamide (30 ml) were added successively imidazole (3.9 g, 57 mmol) and t-butyldimethylchlorosilane (4.7 g, 31 mmol) with stirring, and the resulting mixture was stirred for 4 hours. After stirring, the reaction mixture was poured into water (50 ml) to quench the reaction and extracted with ether. The extract was washed with a saturated aqueous solution of sodium chloride and dried over magnesium sulfate. After filtration, the filtrate was evaporated in vacuo, and the crude product of the title compound thus obtained was purified by chromatography on a silica gel column using a mixed solvent of ethyl acetate and hexane (3:97) as the eluent to afford the title compound (7.4 g) in a yield of 89% as a colourless oily product.

$^1$HNMR (400 MHz, CDCl$_3$) δ ppm: 0.09 (s, 6H), 0.90 (s, 9H), 4.60 (s, 2H), 6.29 (s, 1H), 7.36 (s, 1H). IR Spectra (liquid film): 1230, 1257, 1464, 1473 cm$^{-1}$. Mass spectrum (EI$^+$) m/z: 290 (M$^+$).

(1b) 5-({[t-Butyl(dimethyl)silyl]oxy}methyl)-3-furaldehyde

To a solution of [(4-bromo-2-furyl)methoxy](t-butyl)dimethylsilane (7.3 g, 25 mmol) that was obtained in Example 1 (1a) in tetrahydrofuran (50 ml) was slowly added dropwise n-butyllithium (a 1.6 M solution in hexane, 17 ml, 28 mmol) at −78° C. with stirring, and the resulting mixture was stirred for 5 minutes. Subsequently, to the reaction mixture was furthermore added N,N-dimethylformamide (3.8 ml, 50 mmol) at the same temperature with stirring, and the resulting mixture was stirred for 45 minutes. After stirring, a saturated aqueous solution of ammonium chloride (10 ml) was added to the reaction mixture to quench the reaction, and the resulting mixture was poured into water (100 ml) and extracted with ether. The extract was washed with a saturated aqueous solution of sodium chloride and dried over magnesium sulfate. After filtration, the filtrate was evaporated in vacuo, and the crude product of the title compound thus obtained was purified by chromatography on a silica gel column using a mixed solvent of ethyl acetate and hexane (1:49 to 1:19) as the eluent to afford the title compound (3.3 g) in a yield of 55% as a colourless oily product.

$^1$HNMR Spectrum (500 MHz, CDCl$_3$) δ ppm: 0.10 (s, 6H), 0.91 (s, 9H), 4.65 (s, 2H), 6.62 (s, 1H), 8.00 (s, 1H), 9.90 (s, 1H). IR Spectrum (liquid film): 1083, 1139, 1258, 1473, 1544, 1693 cm$^{-1}$. Mass Spectrum (FAB$^+$) m/z: 241 ((M+H)$^+$).

(1c) 5-({[t-Butyl(dimethyl)silyl]oxy}methyl)-3-furonitrile

To a solution of 5-({[t-butyl(dimethyl)silyl]oxy}methyl)-3-furaldehyde (3.2 g, 13 mmol) that was obtained in Example 1 (1b) in dichloromethane (40 ml) were added successively hydroxylamine hydrochloride (1.0 g, 15 mmol) and triethylamine (3.7 ml, 27 mmol) with stirring, and the resulting mixture was stirred at room temperature for 2 hours. After stirring, the reaction mixture was evaporated in vacuo. Subsequently, to a solution of the residue obtained in toluene (40 ml) was added N,N'-dicyclohexylcarbodiimide (3.1 g, 15 mmol) with stirring, and the resulting mixture was stirred at 90° C. for 16 hours. After cooling to room temperature, hexane (40 ml) was added to the reaction mixture, and insoluble materials were removed by filtration with Celite. The filtrate was evaporated in vacuo, and the crude product of the title compound thus obtained was purified by chromatography on a silica gel column using a mixed solvent of ethyl acetate and hexane (3:97) as the eluent to afford the title compound (1.8 g) in a yield of 57% as a colourless oily product.

$^1$HNMR Spectrum (400 MHz, CDCl$_3$) δ ppm: 0.10 (s, 6H), 0.91 (s, 9H), 4.64 (s, 2H), 6.45 (s, 1H), 7.88 (s, 1H). IR Spectrum (liquid film): 1087, 1142, 1258, 1464, 1473, 1540, 2238 cm$^{-1}$. Mass Spectrum (FAB$^+$) m/z: 238 ((M+H)$^+$).

(1d) 5-({[t-Butyl(dimethyl)silyl]oxy}methyl)-N'-hydroxyfuran-3-carboximidamide

To a solution of 5-({[t-butyl(dimethyl)silyl]oxy}methyl)-3-furonitrile (1.8 g, 7.6 mmol) that was obtained in Example 1 (1c) in ethanol (10 ml) was added a 40% aqueous solution of hydroxylamine (1.0 ml) with stirring, and the resulting mixture was stirred at 60° C. for 1 hour. After evaporating the reaction mixture in vacuo, the residue obtained was diluted with ether, poured into water (40 ml) and extracted with ether. The extract was washed with a saturated aqueous solution of sodium chloride and dried over magnesium sulfate. After filtration, the filtrate was evaporated in vacuo, and the crude product of the title compound thus obtained was purified by chromatography on a silica gel column using a mixed solvent of ethyl acetate and hexane (1:1) as the eluent to afford the title compound (2.0 g) in a yield of 97% as a white crystalline solid.

$^1$HNMR Spectrum (400 MHz, CDCl$_3$) δ ppm: 0.09 (s, 6H), 0.90 (s, 9H), 4.62 (s, 2H), 4.69 (brs, 2H), 6.44 (s, 1H), 7.30 (br, 1H), 7.64 (s, 1H). IR Spectrum (KBr): 1059, 1594, 1613, 1671, 3203, 3376, 3498 cm$^{-1}$. Mass Spectrum (FAB$^+$) m/z: 271 ((M+H)$^+$), 309 ((M+K)$^+$).

(1e) (4-{5-[4-Phenyl-5-(trifluoromethyl)-2-thienyl]-1,2,4-oxadiazol-3-yl}-2-furyl)methanol To a solution of 5-({[t-butyl(dimethyl)silyl]oxy}methyl)-N'-hydroxyfuran-3-carboximidamide (0.14 g, 0.50 mmol)

that was obtained in Example 1 (1d) and 4-phenyl-5-(trifluoromethyl)thiophene-2-carbonyl chloride (0.17 g, 0.60 mmol) in dichloromethane (10 ml) was added N,N-diisopropylethylamine (0.17 ml, 1.0 mmol) at 0° C. with stirring, and the resulting mixture was stirred for 1 hour. After stirring, a saturated aqueous solution of sodium hydrogencarbonate (1.0 ml) was added to the reaction mixture to quench the reaction, and the resulting mixture was poured into water (20 ml) and extracted with ether. The extract was washed with a saturated aqueous solution of sodium chloride and dried over magnesium sulfate. After filtration, the filtrate was evaporated in vacuo. Subsequently, to a solution of the residue obtained in tetrahydrofuran (1.0 ml) was added tetrabutylammonium fluoride (a 1.0 M solution in tetrahydrofuran, 0.75 ml, 0.75 mmol) with stirring, and the resulting mixture was stirred at 60° C. for 3 hours. After stirring, the reaction mixture was poured into water (20 ml) to quench the reaction and extracted with ether. The extract was washed with a saturated aqueous solution of sodium chloride and dried over magnesium sulfate. After filtration, the filtrate was evaporated in vacuo, and the crude product of the title compound thus obtained was purified by chromatography on a silica gel column using a mixed solvent of ethyl acetate and hexane (1:1) as the eluent to afford the title compound (0.20 g) in a yield of 10% as a white crystalline solid.

$^1$HNMR Spectrum (500 MHz, CDCl$_3$) δ ppm: 4.69 (s, 2H), 6.83 (s, 1H), 7.47 (s, 5H), 7.88 (s, 1H), 8.12 (s, 1H). IR Spectrum (KBr): 1143, 1179, 1416, 1581, 1605, 1629, 3326 cm$^{-1}$. Mass Spectrum (FAB$^+$) m/z: 393 ((M+H)$^+$).

(1f) Ethyl 1-[(4-{5-[4-phenyl-5-(trifluoromethyl)-2-thienyl]-1,2,4-oxadiazol-3-yl}-2-furyl)methyl]azetidine-3-carboxylate A solution of (4-{5-[4-phenyl-5-(trifluoromethyl)-2-thienyl]-1,2,4-oxadiazol-3-yl}-2-furyl)methanol (0.20 g, 0.50 mmol) that was obtained in Example 1 (1e), carbon tetrabromide (0.20 g, 0.60 mmol), and triphenylphosphine (0.16 g, 0.60 mmol) in dichloromethane (1.0 ml) was stirred at 0° C. for 1 hour. Subsequently, to the reaction mixture were added successively ethyl 3-azetidinecarboxylate hydrochloride (0.12 g, 0.75 mmol) and N,N-diisopropylethylamine (0.26 ml, 1.5 mmol) at the same temperature with stirring, and the resulting mixture was stirred at room temperature for 2 hours. After stirring, a saturated aqueous solution of sodium hydrogencarbonate (1.0 ml) was added to the reaction mixture to quench the reaction, and the resulting mixture was poured into water (20 ml) and extracted with ethyl acetate. The extract was washed with a saturated aqueous solution of sodium chloride and dried over magnesium sulfate. After filtration, the filtrate was evaporated in vacuo, and the crude product of the title compound thus obtained was purified by chromatography on a silica gel column using a mixed solvent of ethyl acetate and hexane (1:1 to 2:1) as the eluent to afford the title compound (0.21 g) in a yield of 84% as a white crystalline solid.

$^1$HNMR Spectrum (500 MHz, CDCl$_3$) δ ppm: 1.27 (t, 3H, J=7.3 Hz), 3.35 (quintet, 1H, J=7.3 Hz), 3.41 (t, 2H, J=7.3 Hz), 3.62 (t, 2H, J=7.3 Hz), 3.66 (s, 2H) 4.16 (q, 2H, J=7.3 Hz), 6.72 (s, 1H), 7.46 (s, 5H), 7.87 (s, 1H), 8.09 (s, 1H). IR Spectrum (KBr): 1125, 1178, 1203, 1216, 1581, 1606, 1624, 1727 cm$^{-1}$. Mass Spectrum (FAB$^+$) m/z: 504 ((M+H)$^+$).

(1g) 1-[(4-{5-[4-Phenyl-5-(trifluoromethyl)-2-thienyl]-1,2,4-oxadiazol-3-yl}-2-furyl)methyl]azetidine-3-carboxylic acid To a solution of ethyl 1-[(4-{5-[4-phenyl-5-(trifluoromethyl)-2-thienyl]-1,2,4-oxadiazol-3-yl}-2-furyl)methyl]azetidine-3-carboxylate (0.20 g, 0.40 mmol) that was obtained in Example 1 (1f) in a mixed solvent of tetrahydrofuran (0.50 ml), methanol (0.50 ml) and water (0.50 ml) was added lithium hydroxide monohydrate (37 mg, 0.88 mmol) with stirring, and the resulting mixture was stirred at room temperature for 1 hour. After stirring, acetic acid (48 μl, 0.88 mmol) was added to the reaction mixture to quench the reaction. Subsequently, to the resulting mixture was added a solution of oxalic acid (18 mg, 0.20 mmol) in methanol (0.5 ml) with stirring, and the resulting mixture was stirred for 30 minutes. The white solid precipitated was collected by filtration using a Kiriyama funnel, washed with a mixed solvent of water and methanol (3:7), and dried in vacuo to afford the title compound (82 mg) in a yield of 39% as a white crystalline solid.

$^1$HNMR Spectrum (500 MHz, CD$_3$OD) δ ppm: 3.35 (quintet, 1H, J=7.8 Hz), 3.93 (t, 2H, J=8.3 Hz), 4.01 (t, 2H, J=9.3 Hz), 4.19 (s, 2H), 7.04 (s, 1H), 7.47-7.52 (m, 5H), 8.03 (s, 1H), 8.34 (s, 1H). IR Spectrum (KBr): 1135, 1177, 1379, 1410, 1594, 1626, 3421 cm$^{-1}$. Mass Spectrum (FAB$^+$) m/z: 476 ((M+H)$^+$).

Example 2

1-({5-[5-(4-Cyclohexylphenyl)-1,2,4-oxadiazol-3-yl]-2-furyl}methyl)azetidine-3-carboxylic acid

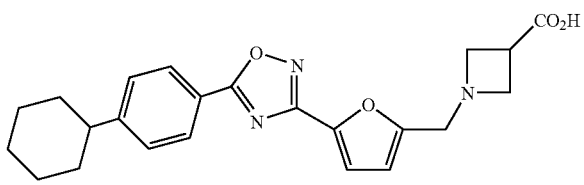

(2a) 5-({[t-Butyl(dimethyl)silyl]oxy}methyl)-2-furonitrile

The crude product of the title compound was synthesized by conducting the similar reaction to that mentioned in Example 1 (1c) using 5-({[t-butyl(dimethyl)silyl]oxy}methyl)-2-furaldehyde (9.1 g, 38 mmol) [reference literature: Tetrahedron, vol. 50 (23), 6767 (1994)], hydroxylamine hydrochloride (2.9 g, 42 mmol), triethylamine (11 ml, 76 mmol) and N,N'-dicyclohexylcarbodiimide (8.6 g, 42 mmol). Subsequently, the crude product of the title compound thus obtained was purified by chromatography on a silica gel column using a mixed solvent of ethyl acetate and hexane (1:9) as the eluent to afford the title compound (7.5 g) in a yield of 84% as a colourless oily product.

$^1$HNMR Spectrum (400 MHz, CDCl$_3$) δ ppm: 0.11 (s, 6H), 0.82 (s, 9H), 4.67 (s, 2H), 6.36 (d, 1H, J=3.4 Hz), 7.04 (d, 1H, J=3.4 Hz). IR Spectrum (liquid film): 1093, 1122, 1258, 1464, 1473, 1524, 2120, 2233 cm$^{-1}$. Mass Spectrum (EI$^+$) m/z: 238 (M$^+$).

(2b) 5-({[t-Butyl(dimethyl)silyl]oxy}methyl)-N'-hydroxyfuran-2-carboximidamide The crude product of the title compound was synthesized by conducting the similar reaction to that mentioned in Example 1 (1d) using 5-({[t-butyl(dimethyl)silyl]oxy}methyl)-2-furonitrile (7.5 g, 32 mmol) that was obtained in Example 2 (2a) and a 40% aqueous solution of hydroxylamine (4.0 ml). Subsequently, the crude product of the title compound thus obtained was purified by chromatography on a silica gel column using a mixed solvent of ethyl acetate and hexane (1:1) as the eluent to afford the title compound (8.1 g) in a yield of 95% as a white crystalline solid.

$^1$HNMR Spectrum (400 MHz, CDCl$_3$) δ ppm: 0.09 (s, 6H), 0.91 (s, 9H), 4.66 (s, 2H), 4.99 (brs, 2H), 6.28 (d, 1H, J=3.4 Hz), 6.70 (d, 1H, J=3.4 Hz), 8.76 (br, 1H). IR Spectrum (KBr): 1255, 1613, 1669, 3243, 3367, 3474 cm$^{-1}$. Mass Spectrum (EI$^+$) m/z: 270 (M$^+$).

(2c) {5-[5-(4-Cyclohexylphenyl)-1,2,4-oxadiazol-3-yl]-2-furyl}methanol

A solution of 5-({[t-butyl(dimethyl)silyl]oxy}methyl)-N'-hydroxyfuran-2-carboximidamide (0.19 g, 0.70 mmol) that was obtained in Example 2 (2b), 4-cyclohexylbenzoic acid (0.16 g, 0.77 mmol), and N,N'-dicyclohexylcarbodiimide (0.17 g, 0.84 mmol) in dichloromethane (1.5 ml) was stirred for 1 hour. After stirring, the reaction mixture was diluted with ether, and insoluble materials were removed by filtration with Celite, and then the filtrate was evaporated in vacuo. Subsequently, to a solution of the residue obtained in tetrahydrofuran (1.0 ml) was added tetrabutylammonium fluoride (a 1.0 M solution in tetrahydrofuran, 1.1 ml, 1.1 mmol) with stirring, and the resulting mixture was stirred at 60° C. for 1 hour. After stirring, the reaction mixture was poured into water (20 ml) to quench the reaction and extracted with ether. The extract was washed with a saturated aqueous solution of sodium chloride and dried over magnesium sulfate. After filtration, the filtrate was evaporated in vacuo, and the crude product of the title compound thus obtained was purified by chromatography on a silica gel column using a mixed solvent of ethyl acetate and hexane (1:1) as the eluent to afford the title compound (0.18 g) in a yield of 81% as a white crystalline solid.

$^1$HNMR Spectrum (500 MHz, CDCl$_3$) δ ppm: 1.24-1.51 (m, 5H), 1.75-1.81 (m, 1H), 1.84-1.96 (m, 4H), 2.56-2.64 (m, 1H), 4.74 (d, 2H, J=8.3 Hz), 6.50 (d, 1H, J=3.4 Hz), 7.16 (d, 1H, J=3.4 Hz), 7.38 (d, 2H, J=7.8 Hz), 8.11 (d, 2H, J=7.8 Hz). IR Spectrum (KBr): 1157, 1216, 1344, 1406, 1561, 1584, 1613, 3369 cm$^{-1}$. Mass Spectrum (FAB$^+$) m/z: 325 ((M+H)$^+$).

(2d) Ethyl 1-({5-[5-(4-cyclohexylphenyl)-1,2,4-oxadiazol-3-yl]-2-furyl}methyl)azetidine-3-carboxylate The crude product of the title compound was synthesized by conducting the similar reaction to that mentioned in Example 1 (1f) using {5-[5-(4-cyclohexylphenyl)-1,2,4-oxadiazol-3-yl]-2-furyl}methanol (0.18 g, 0.55 mmol) that was obtained in Example 2 (2c), carbon tetrabromide (0.22 g, 0.67 mmol), triphenylphosphine (0.18 g, 0.67 mmol), ethyl 3-azetidinecarboxylate hydrochloride (0.14 g, 0.83 mmol) and N,N-diisopropylethylamine (0.30 ml, 1.7 mmol). Subsequently, the crude product of the title compound thus obtained was purified by chromatography on a silica gel column using a mixed solvent of ethyl acetate and hexane (1:1 to 2:1) as the eluent to afford the title compound (0.23 g) in a yield of 96% as a white crystalline solid.

$^1$HNMR Spectrum (500 MHz, CDCl$_3$) δ ppm: 1.24-1.32 (m, 4H), 1.37-1.51 (m, 4H), 1.78 (d, 1H, J=12.7 Hz), 1.84-1.94 (m, 4H), 2.56-2.63 (m, 1H), 3.34 (quintet, 1H, J=7.8 Hz), 3.44 (t, 2H, J=7.8 Hz), 3.64 (t, 2H, J=7.8 Hz), 3.73 (s, 2H), 4.16 (q, 2H, J=7.3 Hz), 6.37 (d, 1H, J=3.4 Hz), 7.13 (d, 1H, J=3.4 Hz), 7.37 (d, 2H, J=8.3 Hz), 8.10 (d, 2H, J=8.3 Hz). IR Spectrum (KBr): 1374, 1561, 1614, 1736 cm$^{-1}$. Mass Spectrum (FAB$^+$) m/z: 436 ((M+H)$^+$).

(2e) 1-({5-[5-(4-Cyclohexylphenyl)-1,2,4-oxadiazol-3-yl]-2-furyl}methyl)azetidine-3-carboxylic acid To a solution of ethyl 1-({5-[5-(4-cyclohexylphenyl)-1,2,4-oxadiazol-3-yl]-2-furyl}methyl)azetidine-3-carboxylate (0.23 g, 0.53 mmol) that was obtained in Example 2 (2d) in a mixed solvent of tetrahydrofuran (0.50 ml), methanol (0.50 ml) and water (0.50 ml) was added lithium hydroxide monohydrate (50 mg, 1.2 mmol) with stirring, and the resulting mixture was stirred at room temperature for 1 hour. After stirring, acetic acid (65 µl, 1.2 mmol) was added to the reaction mixture to quench the reaction. The white solid precipitated was collected by filtration using a Kiriyama funnel, washed with a mixed solvent of water and methanol (3:7) and dried in vacuo to afford the title compound (122 mg) in a yield of 56% as a white crystalline solid.

$^1$HNMR Spectrum (500 MHz, CD$_3$OD) δ ppm: 1.30-1.40 (m, 1H), 1.43-1.57 (m, 4H), 1.79 (d, 1H, J=11.7 Hz), 1.87-1.94 (m, 4H), 2.63-2.69 (m, 1H), 3.36 (quintet, 1H, J=8.3 Hz), 3.97 (t, 2H, J=8.3 Hz), 4.05 (t, 2H, J=8.3 Hz), 4.27 (s, 2H), 6.77 (d, 1H, J=3.4 Hz), 7.26 (d, 1H, J=3.4 Hz), 7.48 (d, 2H, J=8.3 Hz), 8.11 (d, 2H, J=8.3 Hz). IR Spectrum (KBr): 1346, 1410, 1442, 1503, 1561, 1588, 1618, 3105, 3430 cm$^{-1}$. Mass Spectrum (FAB$^+$) m/z: 408 ((M+H)$^+$).

Example 3

1-[(4-{5-[4-Phenyl-5-(trifluoromethyl)-2-thienyl]-1,2,4-oxadiazol-3-yl}-2-thienyl)methyl]azetidine-3-carboxylic acid

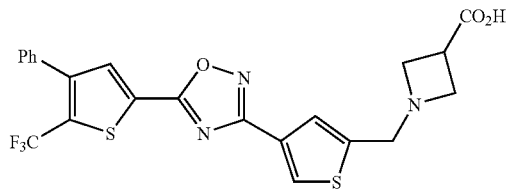

(3a) 5-({[t-Butyl(dimethyl)silyl]oxy}methyl)thiophene-3-carbonitrile

To a solution of [(4-bromo-2-thienyl)methoxy]t-butyldimethylsilane (9.0 g, 29 mmol) [reference literature: J. Med. Chem., vol. 45, 5005 (2002)] in N,N-dimethylformamide (20 ml) was added copper cyanide (4.7 g, 53 mmol) with stirring, and the resulting mixture was refluxed for 2 hours. After cooling to room temperature, the reaction mixture was diluted with ether (80 ml), and after adding a 28% aqueous solution of ammonia (50 ml), the resulting mixture was stirred at room temperature for 1 hour. After stirring, the reaction mixture was extracted with ether, and the extract was washed successively with water and a saturated aqueous solution of sodium chloride and dried over sodium sulfate. After filtration, the filtrate was evaporated in vacuo, and the crude product of the title compound thus obtained was purified by chromatography on a silica gel column using a mixed solvent of ethyl acetate and hexane (1:50 to 1:4) as the eluent to afford the title compound (4.3 g) in a yield of 58% as a colourless oily product.
¹HNMR Spectrum (400 MHz, CDCl₃) δ ppm: 0.11 (s, 6H), 0.93 (s, 9H), 4.85 (s, 2H), 7.06 (s, 1H), 7.82 (s, 1H). IR Spectrum (thin film): 1086, 1128, 1258, 2229 cm⁻¹. Mass Spectrum (EI⁺) m/z: 253 (M⁺).

(3b) 5-({[t-Butyl(dimethyl)silyl]oxy}methyl)-N'-hydroxythiophene-3-carboximidamide The crude product of the title compound was synthesized by conducting the similar reaction to that mentioned in Example 1 (1d) using 5-({[t-butyl(dimethyl)silyl]oxy}methyl)thiophene-3-carbonitrile (4.3 g, 17 mmol) that was obtained in Example 3 (3a) and a 40% aqueous solution of hydroxylamine (2.2 ml). Subsequently, the crude product of the title compound thus obtained was purified by chromatography on a silica gel column using a mixed solvent of ethyl acetate and hexane (1:10 to 2:5) as the eluent to afford the title compound (4.7 g) in a yield of 97% as a white crystalline solid.
¹HNMR Spectrum (400 MHz, CDCl₃) δ ppm: 0.10 (s, 6H), 0.93 (s, 9H) 1.69 (brs, 1H), 4.79 (brs, 2H), 4.84 (s, 2H), 7.02 (d, 1H, J=1.4 Hz), 7.31 (d, 1H, J=1.4 Hz). IR Spectrum (KBr): 1101, 1256, 1371, 1655, 3208, 3389, 3495 cm⁻¹ Mass Spectrum (FAB⁺) m/z: 287 ((M+H)⁺).

(3c) (4-{5-[4-Phenyl-5-(trifluoromethyl)-2-thienyl]-1,2,4-oxadiazol-3-yl}-2-thienyl)methanol The crude product of the title compound was synthesized by conducting the similar reaction to that mentioned in Example 1 (1e) using 5-({[t-butyl(dimethyl)silyl]oxy}methyl)-N'-hydroxythiophene-3-carboximidamide (0.43 g, 1.5 mmol) that was obtained in Example 3 (3b), 4-phenyl-5-(trifluoromethyl)thiophene-2-carbonyl chloride (0.52 g, 1.8 mmol), N,N-diisopropylethylamine (0.52 ml, 3.0 mmol), and a 1.0 M solution of tetrabutylammonium fluoride (3.0 ml, 3.0 mmol). Subsequently, the crude product of the title compound thus obtained was purified by chromatography on a silica gel column using a mixed solvent of ethyl acetate and hexane (1:2 to 1:1) as the eluent to afford the title compound (0.60 g) as a white crystalline solid.
¹HNMR Spectrum (400M Hz, CDCl₃) δ ppm: 1.95 (brs, 1H), 4.89 (s, 2H), 7.45 (s, 5H), 7.56 (s, 1H), 7.87 (d, 1H, J=1.2 Hz), 8.07 (d, 1H, J=1.2 Hz). IR Spectrum (KBr): 1126, 1183, 1268, 1313, 1417, 1578, 1606, 3324 cm⁻¹. Mass Spectrum (FAB⁺) m/z: 409 ((M+H)⁺).

(3d) Ethyl 1-[(4-{5-[4-phenyl-5-(trifluoromethyl)-2-thienyl]-1,2,4-oxadiazol-3-yl}-2-thienyl)methyl]azetidine-3-carboxylate The crude product of the title compound was synthesized by conducting the similar reaction to that mentioned in Example 1 (1f) using (4-{5-[4-phenyl-5-(trifluoromethyl)-2-thienyl]-1,2,4-oxadiazol-3-yl}-2-thienyl)methanol (0.10 g, 0.25 mmol) that was obtained in Example 3 (3c), carbon tetrabromide (0.17 g, 0.50 mmol), triphenylphosphine (0.13 g, 0.50 mmol), ethyl 3-azetidinecarboxylate hydrochloride (62 mg, 0.38 mmol), and N,N-diisopropylethylamine (0.11 ml, 0.63 mmol). Subsequently, the crude product of the title compound thus obtained was purified by thin layer chromatography on a silica gel plate using a mixed solvent of ethyl acetate and hexane (2:3) as the developing solvent to afford the title compound (73 mg) in a yield of 56% as a white crystalline solid.
¹HNMR Spectrum (400 MHz, CDCl₃) δ ppm: 1.27 (t, 3H, J=7.0 Hz), 3.31-3.41 (m, 3H), 3.55-3.68 (m, 2H), 3.83 (s, 2H), 4.17 (q, 2H, J=7.0 Hz), 7.47 (s, 6H), 7.89 (d, 1H, J=1.2 Hz), 8.04 (d, 1H, J=1.2 Hz). IR Spectrum (KBr): 1132, 1180, 1197, 1272, 1316, 1577, 1608, 1720 cm⁻¹. Mass Spectrum (FAB⁺) m/z: 520 ((M+H)⁺).

(3e) 1-[(4-{5-[4-Phenyl-5-(trifluoromethyl)-2-thienyl]-1,2,4-oxadiazol-3-yl}-2-thienyl)methyl]azetidine-3-carboxylic acid To a solution of ethyl 1-[(4-{5-[4-phenyl-5-(trifluoromethyl)-2-thienyl]-1,2,4-oxadiazol-3-yl}-2-thienyl)methyl]azetidine-3-carboxylate (70 mg, 0.13 mmol) that was obtained in Example 3 (3d) in dioxane (2 ml) was added a 1N aqueous solution of sodium hydroxide (0.39 ml, 0.39 mmol) with stirring, and the resulting mixture was stirred at room temperature for 2 hours. After stirring, acetic acid (22 μl, 0.39 mmol) was added to the reaction mixture to quench the reaction, and the resulting mixture was evaporated in vacuo. To the residue thus obtained were added successively methanol (1 ml) and water (1 ml) with stirring, and the white solid precipitated was collected by filtration using a Kiriyama funnel, washed with a mixed solvent of water and methanol (3:7) and dried in vacuo to afford the title compound (34 mg) in a yield of 53% as a crystalline white solid.
¹HNMR Spectrum (400 MHz, CD₃CO₂D) δ ppm: 3.75-3.88 (m, 1H), 4.35-4.46 (m, 2H), 4.46-4.58 (m, 2H), 4.76 (s, 2H), 7.45-7.60 (m, 5H), 7.93 (s, 1H), 8.03 (s, 1H), 8.37 (s, 1H). IR Spectrum (KBr): 1133, 1178, 1270, 1579, 1605, 3429 cm⁻¹ Mass Spectrum (FAB⁺) m/z: 492 ((M+H)⁺).

Example 4

1-[(5-{5-[4-Phenyl-5-(trifluoromethyl)-2-thienyl]-1,2,4-oxadiazol-3-yl}-2-thienyl)methyl]azetidine-3-carboxylic acid

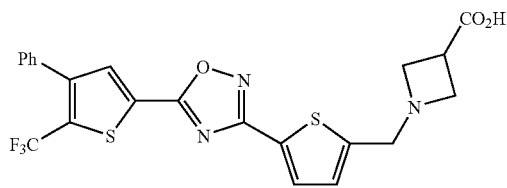

(4a) 5-({[t-Butyl(dimethyl)silyl]oxy}methyl)thiophene-2-carbonitrile

The crude product of the title compound was synthesized by conducting the similar reaction to that mentioned in Example 3 (3a) using [(5-bromo-2-thienyl)methoxy]t-butyldimethylsilane (2.4 g, 7.8 mmol) [reference literature: Tetrahedron, vol. 39, 2531 (1983)] and copper cyanide (1.3 g, 14 mmol). Subsequently, the crude product of the title compound thus obtained was purified by chromatography on a silica gel column using a mixed solvent of ethyl acetate and hexane (1:50 to 1:7) as the eluent to afford the title compound (1.1 g) in a yield of 56% as a white crystalline solid.

¹HNMR Spectrum (400 MHz, CDCl₃) δ ppm: 0.12 (s, 6H), 0.93 (s, 9H), 4.88 (d, 2H, J=1.2 Hz), 6.70 (dt, 1H, J=3.9 Hz, 1.2 Hz), 7.46 (d, 1H, J=3.9 Hz). IR Spectrum (thin film)]: 1096, 1258, 1377, 1464, 1472, 2219 cm⁻¹. Mass Spectrum (EI⁺) m/z: 253 (M⁺).

(4b) 5-({[t-Butyl(dimethyl)silyl]oxy}methyl)-N'-hydroxythiophene-2-carboximidamide The crude product of the title compound was synthesized by conducting the similar reaction to that mentioned in Example 1 (1d) using 5-({[t-butyl(dimethyl)silyl]oxy}methyl)thiophene-2-carbonitrile (1.3 g, 5.0 mmol) that was obtained in Example 4 (4a) and a 40% aqueous solution of hydroxylamine (0.7 ml). Subsequently, the crude product of the title compound thus obtained was purified by recrystallization from a mixed solvent of ethyl acetate and hexane to afford the title compound (1.2 g) in a yield of 81% as a white crystalline solid.

¹HNMR Spectrum (400 MHz, CDCl₃) δ ppm: 0.10 (s, 6H), 0.93 (s, 9H), 4.82 (brs, 2H), 4.84 (s, 2H), 6.81 (brs, 1H), 6.84 (d, 1H, J=3.7 Hz), 7.11 (d, 1H, J=3.7 Hz). IR Spectrum (KBr): 1067, 1250, 1256, 1368, 1387, 1588, 1658, 3206, 3384, 3498 cm⁻¹. Mass Spectrum (EI⁺) m/z: 286 (M⁺).

(4c) (5-{5-[4-Phenyl-5-(trifluoromethyl)-2-thienyl]-1,2,4-oxadiazol-3-yl}-2-thienyl)methanol The crude product of the title compound was synthesized by conducting the similar reaction to that mentioned in Example 1 (1e) using 5-({[t-butyl(dimethyl)silyl]oxy}methyl)-N'-hydroxythiophene-2-carboximidamide (0.43 g, 1.5 mmol) that was obtained in Example 4 (4b), 4-phenyl-5-(trifluoromethyl)thiophene-2-carbonyl chloride (0.52 g, 1.8 mmol), N,N-diisopropylethylamine (0.52 ml, 3.0 mmol), and a 1.0 M solution of tetrabutylammonium fluoride (3.0 ml, 3.0 mmol). Subsequently, the crude product of the title compound thus obtained was purified by chromatography on a silica gel column using a mixed solvent of ethyl acetate and hexane (1:2) as the eluent to afford the title compound (0.60 g) in a yield of 99% as a white crystalline solid.

¹HNMR Spectrum (400 MHz, CDCl₃) δ ppm: 1.97 (brs, 1H), 4.89 (s, 2H), 7.06 (d, 1H, J=3.7 Hz), 7.45 (s, 5H), 7.72 (d, 1H, J=3.7 Hz), 7.88 (q, 1H, J=1.6 Hz). IR Spectrum (KBr): 1108, 1126, 1176, 1269, 1373, 1572, 3322 cm⁻¹. Mass Spectrum (FAB⁺) m/z: 409 ((M+H)⁺).

(4d) Ethyl 1-[(5-{5-[4-phenyl-5-(trifluoromethyl)-2-thienyl]-1,2,4-oxadiazol-3-yl}-2-thienyl)methyl]azetidine-3-carboxylate The crude product of the title compound was synthesized by conducting the similar reaction to that mentioned in Example 1 (1f) using (5-{5-[4-phenyl-5-(trifluoromethyl)-2-thienyl]-1,2,4-oxadiazol-3-yl}-2-thienyl)methanol (0.12 g, 0.29 mmol) that was obtained in Example 4 (4c), carbon tetrabromide (0.19 g, 0.58 mmol), triphenylphosphine (0.15 g, 0.58 mmol), ethyl 3-azetidinecarboxylate hydrochloride (62 mg, 0.38 mmol), and N,N-diisopropylethylamine (0.13 ml, 0.73 mmol). Subsequently, the crude product of the title compound thus obtained was purified by thin layer chromatography on a silica gel plate using a mixed solvent of ethyl acetate and hexane (4:5) as the developing solvent to afford the title compound (0.12 g) in a yield of 80% as a colourless oily product.

¹HNMR Spectrum (400 MHz, CDCl₃) δ ppm: 1.28 (t, 3H, J=7.0 Hz), 3.30-3.42 (m, 3H), 3.59-3.69 (m, 2H), 3.84 (s, 2H), 4.17 (q, 2H, J=7.0 Hz), 6.96 (d, 1H, J=3.7 Hz), 7.45 (s, 5H), 7.69 (d, 1H, J=3.7 Hz), 7.87 (s, 1H). IR Spectrum (liquid film): 1133, 1182, 1214, 1269, 1284, 1373, 1571, 1734 cm⁻¹. Mass Spectrum (FAB⁺) m/z: 520 ((M+H)⁺).

(4e) 1-[(5-{5-[4-Phenyl-5-(trifluoromethyl)-2-thienyl]-1,2,4-oxadiazol-3-yl}-2-thienyl)methyl]azetidine-3-carboxylic acid The title compound (60 mg) was synthesized in a yield of 53% as a white crystalline solid by conducting the similar reaction to that mentioned in Example 3 (3e) using ethyl 1-[(5-{5-[4-phenyl-5-(trifluoromethyl)-2-thienyl]-1,2,4-oxadiazol-3-yl}-2-thienyl)methyl]azetidine-3-carboxylate (0.12 g, 0.23 mmol) that was obtained in Example 4 (4d) and a 1N aqueous solution of sodium hydroxide (0.69 ml, 0.69 mmol).

¹HNMR Spectrum (400 MHz, CD₃CO₂D) δ ppm: 3.80-3.92 (m, 1H), 4.33-4.48 (m, 2H), 4.52-4.65 (m, 2H), 4.80 (s, 2H), 7.45-7.57 (m, 6H), 7.87 (s, 1H), 8.02 (s, 1H). IR Spectrum (KBr): 1134, 1179, 1214, 1267, 1366, 1379, 1570, 1605, 3429 cm⁻¹. Mass Spectrum (FAB⁺) m/z: 492 ((M+H)⁺).

Example 5

1-({5-[5-(4-Phenoxyphenyl)-1,2,4-oxadiazol-3-yl]-2-thienyl}methyl)azetidine-3-carboxylic acid

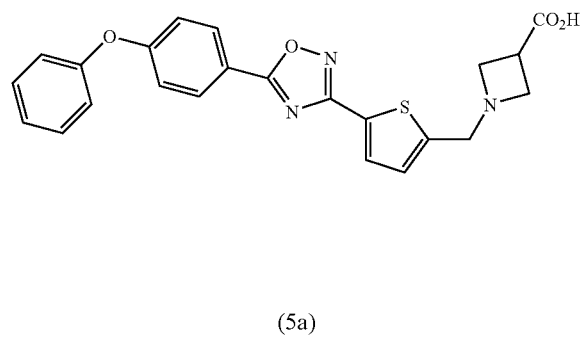

(5a)

{5-[5-(4-Phenoxyphenyl)-1,2,4-oxadiazol-3-yl]-2-thienyl}methanol

To a solution of 4-phenoxybenzoic acid (0.12 g, 0.55 mmol) in acetonitrile (5 ml) were added successively 1-hydroxybenzotriazole (88 mg, 0.65 mmol) 1-ethyl-3-(3-dimethylaminopropyl)carbodiimide hydrochloride (0.12 g, 0.60 mmol), 5-({[t-butyl(dimethyl)silyl]oxy}methyl)-N'-hydroxythiophene-2-carboximidamide (0.14 g, 0.5 mmol) that was obtained in Example 4 (4b) with stirring, and the resulting mixture was stirred at room temperature for 30 minutes. After stirring, water (5 ml) was added to the reaction mixture to quench the reaction, and the resulting mixture was extracted with ethyl acetate. The extract was washed successively with 0.1N hydrochloric acid, a saturated aqueous solution of sodium hydrogencarbonate and a saturated aqueous solution of sodium chloride and dried over sodium sulfate. After filtration, the filtrate was evaporated in vacuo. Subsequently, to a solution of the residue obtained in tetrahydrofuran (4.0 ml) was added tetrabutylammonium fluoride (a 1.0 M solution in tetrahydrofuran, 1.0 ml, 11.0 mmol) with stirring, and the resulting mixture was stirred at 60° C. for 3 hours. After stirring, the reaction mixture was poured into water (20 ml) to quench the reaction and extracted with ether. The extract was washed with a saturated aqueous solution of sodium chloride and dried over sodium sulfate. After filtration, the filtrate was evaporated in vacuo, and the crude product of the title compound thus obtained was purified by chromatography on a silica gel column using a mixed solvent of ethyl acetate and hexane (1:1) as the eluent to afford the title compound (97 mg) in a yield of 55% as a white crystalline solid.

$^1$HNMR Spectrum (400 MHz, CDCl$_3$) δ ppm: 1.89 (t, 1H, J=5.9 Hz), 4.89 (d, 2H, J=5.9 Hz), 7.03-7.10 (m, 4H), 7.19-7.28 (m, 2H), 7.35-7.44 (m, 2H), 7.71 (d, 1H, J=3.5 Hz), 8.61 (d, 2H, J=8.6 Hz). IR Spectrum (KBr): 1241, 1366, 1487, 1575, 1590, 1613, 3331 cm$^{-1}$. Mass Spectrum (FAB$^+$) m/z: 351 ((M+H)$^+$).

(5b) Ethyl 1-({5-[5-(4-phenoxyphenyl)-1,2,4-oxadiazol-3-yl]-2-thienyl}methyl)azetidine-3-carboxylate The crude product of the title compound was synthesized by conducting the similar reaction to that mentioned in Example 1 (1f) using {5-[5-(4-phenoxyphenyl)-1,2,4-oxadiazol-3-yl]-2-thienyl}methanol (97 m g, 0.28 mmol) that was obtained in Example 5 (5a), carbon tetrabromide (0.19 g, 0.56 mmol), triphenylphosphine (0.15 g, 0.56 mmol), ethyl 3-azetidinecarboxylate hydrochloride (70 mg, 0.42 mmol), and N,N-diisopropylethylamine (0.18 ml, 1.1 mmol). Subsequently, the crude product of the title compound thus obtained was purified by thin layer chromatography on a silica gel plate using a mixed solvent of ethyl acetate and hexane (4:3) as the developing solvent to afford the title compound (93 mg) in a yield of 72% as a colourless oily product.

$^1$HNMR Spectrum (400 MHz, CDCl$_3$) δ ppm: 1.27 (t, 3H, J=7.0 Hz), 3.29-3.41 (m, 3H), 3.59-3.68 (m, 2H), 3.84 (s, 2H), 4.17 (q, 2H, J=7.0 Hz), 6.96 (d, 1H, J=3.3 Hz), 7.06-7.15 (m, 4H), 7.23 (t, 1H, J=7.4 Hz), 7.42 (t, 2H, J=7.8 Hz), 7.70 (d, 1H, J=3.3 Hz), 8.14 (d, 2H, J=9.0 Hz). IR Spectrum (liquid film): 1168, 1196, 1246, 1367, 1489, 1732 cm$^{-1}$. Mass Spectrum (FAB$^+$) m/z: 462 ((M+H)$^+$).

(5c) 1-({5-[5-(4-Phenoxyphenyl)-1,2,4-oxadiazol-3-yl]-2-thienyl}methyl)azetidine-3-carboxylic acid The title compound (69 mg) was synthesized in a yield of 80% as a white crystalline solid by conducting the similar reaction to that mentioned in Example 3 (3e) using ethyl 1-({5-[5-(4-phenoxyphenyl)-1,2,4-oxadiazol-3-yl]-2-thienyl}methyl)azetidine-3-carboxylate (90 mg, 0.20 mmol) that was obtained in Example 5 (5b) and a 1N aqueous solution of sodium hydroxide (0.60 ml, 0.60 mmol).

$^1$HNMR Spectrum (400 MHz, CD$_3$CO$_2$D) δ ppm: 3.76-3.87 (m, 1H), 4.35-4.44 (m, 2H), 4.49-4.57 (m, 2H), 4.74 (s, 2H), 7.15 (d, 4H, J=8.6 Hz), 7.25 (t, 1H, J=7.8 Hz), 7.40-7.48 (m, 3H), 7.84 (d, 1H, J=3.9 Hz), 8.18 (d, 2H, J=8.6 Hz). IR Spectrum (KBr): 1243, 1366, 1488, 1569, 1591, 1613, 3469 cm$^{-1}$. Mass Spectrum (FAB$^+$) m/z: 434 ((M+H)$^+$).

Example 6

1-({4-[5-(4-Benzylphenyl)-1,2,4-oxadiazol-3-yl]-2-thienyl}methyl)azetidine-3-carboxylic acid

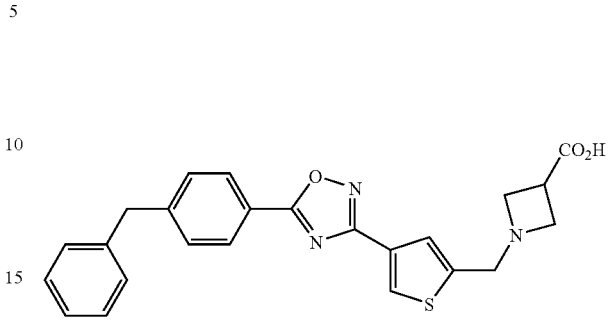

(6a) {4-[5-(4-Benzylphenyl)-1,2,4-oxadiazol-3-yl]-2-thienyl}methanol

The crude product of the title compound was synthesized by conducting the similar reaction to that mentioned in Example 5 (5a) using 4-benzylbenzoic acid (0.12 g, 0.55 mmol), 1-hydroxybenzotriazole (88 mg, 0.65 mmol), 1-ethyl-3-(3-dimethylaminopropyl)carbodiimide (0.12 g, 0.60 mmol), 5-({[t-butyl(dimethyl)silyl]oxy}methyl)-N'-hydroxythiophene-3-carboximidamide (0.14 g, 0.5 mmol) that was obtained in Example 3 (3b), and tetrabutylammonium fluoride (a 1.0 M solution in tetrahydrofuran, 1.0 ml, 1.0 mmol). Subsequently, the crude product of the title compound thus obtained was purified by recrystallization from a mixed solvent of ethyl acetate and hexane to afford the title compound (99 mg) in a yield of 57% as a white crystalline solid.

$^1$HNMR Spectrum (400 MHz, CDCl$_3$) δ ppm: 1.68 (brs, 1H), 4.08 (s, 2H), 4.90 (s, 2H), 7.18-7.43 (m, 7H), 7.59 (s, 1H), 8.07-8.15 (m, 3H). IR Spectrum (KBr): 1019, 1418, 1495, 1563, 1585, 16161, 3334 cm$^{-1}$. Mass Spectrum (FAB$^+$) m/z: 349 ((M+H)$^+$).

(6b) Ethyl 1-({4-[5-(4-benzylphenyl)-1,2,4-oxadiazol-3-yl]-2-thienyl}methyl)azetidine-3-carboxylate The crude product of the title compound was synthesized by conducting the similar reaction to that mentioned in Example 1 (1f) using {4-[5-(4-benzylphenyl)-1,2,4-oxadiazol-3-yl]-2-thienyl}methanol (95 mg, 0.27 mmol) that was obtained in Example 6 (6a), carbon tetrabromide (0.18 g, 0.54 mmol), triphenylphosphine (0.14 g, 0.54 mmol), ethyl 3-azetidinecarboxylate hydrochloride (67 mg, 0.41 mmol), and N,N-diisopropylethylamine (0.12 ml, 0.68 mmol). Subsequently, the crude product of the title compound thus obtained was purified by thin layer chromatography on a silica gel plate using a mixed solvent of ethyl acetate and hexane (6:4) as the developing solvent to afford the title compound (84 mg) in a yield of 68% as a white crystalline solid.

$^1$HNMR Spectrum (400 MHz, CDCl$_3$) δ ppm: 1.27 (t, 3H, J=7.0 Hz), 3.30-3.39 (m, 3H), 3.56-3.66 (m, 2H), 3.82 (s, 2H), 4.06 (s, 2H), 4.15 (q, 2H, J=7.0 Hz), 7.16-7.38 (m, 7H), 7.47 (s, 1H), 8.01 (s, 1H), 8.08 (d, 2H, J=8.2 Hz). IR Spectrum (KBr): 1184, 1296, 1356, 1423, 1585, 1735 cm$^{-1}$. Mass Spectrum (FAB$^+$) m/z: 460 ((M+H)$^+$).

(6c) 1-({4-[5-(4-Benzylphenyl)-1,2,4-oxadiazol-3-yl]-2-thienyl}methyl)azetidine-3-carboxylic acid The title compound (67 mg) was synthesized in a yield of 86% as a white crystalline solid by conducting the reaction similar to that mentioned in Example 3 (3e) using ethyl 1-({4-[5-(4-benzylphenyl)-1,2,4-oxadiazol-3-yl]-2-thienyl}methyl)azetidine-3-carboxylate (82 mg, 0.18 mmol) that was obtained in Example 6 (6b), and a 1N aqueous solution of sodium hydroxide (0.54 ml, 0.54 mmol).

$^1$HNMR Spectrum (400 MHz, $CD_3CO_2D$) δ ppm: 3.74-3.86 (m, 1H), 4.07 (s, 2H), 4.34-4.43 (m, 2H), 4.45-4.55 (m, 2H), 4.72 (s, 2H), 7.16-7.31 (m, 5H), 7.42 (d, 2H, J=8.2 Hz), 7.89 (s, 1H), 8.11 (d, 2H, J=7.8 Hz), 8.31 (s, 1H). IR Spectrum (KBr): 1323, 1387, 1428, 1562, 1587, 1604, 1616, 3427 $cm^{-1}$. Mass Spectrum ($FAB^+$) m/z: 432 (($M+H)^+$).

Example 7

1-{2-[5-(4-Isobutylphenyl)-1,2,4-oxadiazol-3-yl]-4,5,6,7-tetrahydro-1-benzofuran-4-yl}azetidine-3-carboxylic acid 1/2 oxalate

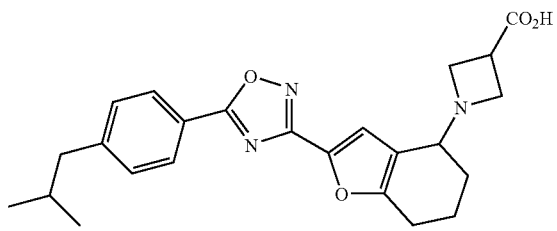

(7a) t-Butyl(dimethyl)(4,5,6,7-tetrahydro-1-benzofuran-4-yloxy)silane

To a solution of 6,7-dihydro-4-(5H)-benzofuranone (5.0 g, 37 mmol) in methanol (50 ml) was added sodium borohydride (1.4 g, 37 mmol) at 0° C. with stirring, and the resulting mixture was stirred for 1 hour. After evaporating the reaction mixture in vacuo, the residue obtained was diluted with ether, poured into water (40 ml), and extracted with ether. The extract was washed with a saturated aqueous solution of sodium chloride and dried over magnesium sulfate. After filtration, the filtrate was evaporated in vacuo. Subsequently, to a solution of the residue thus obtained in dimethylformamide (30 ml) were added successively imidazole (4.0 g, 59 mmol) and t-butyldimethylchlorosilane (4.9 g, 32 mmol) with stirring, and the resulting mixture was stirred for 2 hours. After stirring, the reaction mixture was poured into water (50 ml) to quench the reaction and extracted with ether. The extract was washed with a saturated aqueous solution of sodium chloride and dried over magnesium sulfate. After filtration, the filtrate was evaporated in vacuo, and the crude product of the title compound thus obtained was purified by chromatography on a silica gel column using a mixed solvent of ethyl acetate and hexane (1:49 to 3:97) as the eluent to afford the title compound (7.2 g) in a yield of 77% as a colourless oily product.

$^1$HNMR Spectrum (400 MHz, $CDCl_3$) δ ppm: 0.12 (s, 3H), 0.13 (s, 3H), 0.92 (s, 9H), 1.63-1.79 (m, 2H), 1.89-1.94 (m, 1H), 1.98-2.08 (m, 1H), 2.51 (dt, 1H, J=16.4 Hz, 6.3 Hz), 2.62 (dt, 1H, J=16.4 Hz, 6.3 Hz), 4.74 (t, 1H, J=6.3 Hz), 6.30 (d, 1H, J=1.6 Hz), 7.24 (d, 1H, J=1.6 Hz). IR Spectrum (liquid film): 1074, 1255, 2858, 2932 $cm^{-1}$. Mass Spectrum ($EI^+$) m/z: 252 ($M^+$).

(7b) 4-{[t-Butyl(dimethyl)silyl]oxy}-4,5,6,7-tetrahydro-1-benzofuran-2-carboxaldehyde To a solution of t-butyl(dimethyl)(4,5,6,7-tetrahydro-1-benzofuran-4-yloxy)silane (4.1 g, 16 mmol) that was obtained in Example 7 (7a) in tetrahydrofuran (30 ml) was slowly added dropwise n-butyllithium (a 1.6 M solution in hexane, 31 ml, 49 mmol) at −78° C. with stirring, and after raising the reaction temperature to 0° C., the resulting mixture was stirred for 30 minutes. After cooling again the reaction mixture to −78° C. while stirring, N,N-dimethylformamide (13 ml, 162 mmol) was added to the reaction mixture with stirring, and the resulting mixture was stirred for 30 minutes. After stirring, a saturated aqueous solution of ammonium chloride (10 ml) was added to the reaction mixture to quench the reaction, and the resulting mixture was poured into water (50 ml) and extracted with ether. The extract was washed with a saturated aqueous solution of sodium chloride and dried over magnesium sulfate. After filtration, the filtrate was evaporated in vacuo, and the crude product of the title compound thus obtained was purified by chromatography on a silica gel column using a mixed solvent of ethyl acetate and hexane (1:9) as the eluent to afford the title compound (4.3 g) in a yield of 94% as a white crystalline solid.

$^1$HNMR Spectrum (500 MHz, $CDCl_3$) δ ppm: 0.14 (s, 3H), 0.16 (s, 3H), 0.92 (s, 9H), 1.66-1.86 (m, 2H), 1.90-1.99 (m, 1H), 2.04-2.14 (m, 1H), 2.61 (dt, 1H, J=17.6 Hz, 6.3 Hz), 2.73 (dt, 1H, J=17.6 Hz, 6.3 Hz), 4.75 (t, 1H, J=5.9 Hz), 7.15 (s, 1H), 9.53 (s, 1H). IR Spectrum (KBr): 1074, 1085, 1525, 1678 $cm^{-1}$. Mass Spectrum ($FAB^+$) m/z: 280 (($M+H)^+$).

(7c) 4-{[t-Butyl(dimethyl)silyl]oxy}-4,5,6,7-tetrahydro-1-benzofuran-2-carbonitrile The crude product of the title compound was synthesized by conducting the similar reaction to that mentioned in Example 1 (1c) using 4-{[t-butyl(dimethyl)silyl]oxy}-4,5,6,7-tetrahydro-1-benzofuran-2-carboxaldehyde (4.3 g, 15.3 mmol) that was obtained in Example 7 (7b), hydroxylamine hydrochloride (1.2 g, 17 mmol), triethylamine (4.3 ml, 31 mmol), and N,N'-dicyclohexylcarbodiimide (3.5 g, 17 mmol). Subsequently, the crude product of the title compound thus obtained was purified by chromatography on a silica gel column using a mixed solvent of ethyl acetate and hexane (1:9) as the eluent to afford the title compound (3.0 g) in a yield of 71% as a colourless oily product.

$^1$HNMR Spectrum (400 MHz, $CDCl_3$) δ ppm: 0.12 (s, 3H), 0.14 (s, 3H), 0.91 (s, 9H), 1.16-1.38 (m, 1H), 1.65-1.82 (m, 1H), 1.86-1.96 (m, 1H), 2.02-2.12 (m, 1H), 2.55 (dt, 1H, J=17.2 Hz, 5.9 Hz), 2.66 (dt, 1H, J=17.2 Hz, 5.9 Hz), 4.70 (t, 1H, J=5.9 Hz), 6.99 (s, 1H). IR Spectrum (liquid film): 1087, 1255, 1526, 1616, 2120, 2227 $cm^{-1}$. Mass Spectrum ($FAB^+$) m/z: 278 (($M+H)^+$), 300 (($M+Na)^+$).

(7d) 4-{[t-Butyl(dimethyl)silyl]oxy}-N'-hydroxy-4,5,6,7-tetrahydro-1-benzofuran-2-carboximidamide The crude product of the title compound was synthesized by conducting the similar reaction to that mentioned in Example 1 (1d) using 4-{[t-butyl(dimethyl)silyl]oxy}-4,5,6,7-tetrahydro-1-benzofuran-2-carbonitrile (3.0 g, 11 mmol) that was obtained in Example 7 (7c) and a 40% aqueous solution of hydroxylamine (3.0 ml). Subsequently, the crude product of the title compound thus obtained was purified by chromatography on a silica gel column using a mixed solvent of ethyl acetate and hexane (3:7) as the eluent to afford the title compound (2.7 g) in a yield of 82% as a white crystalline solid.

$^1$HNMR Spectrum (500 MHz, CDCl$_3$) δ ppm: 0.12 (s, 3H), 0.13 (s, 3H), 0.91 (s, 9H), 1.64-1.81 (m, 2H), 1.85-1.93 (m, 1H), 2.00-2.10 (m, 1H), 2.54 (dt, 1H, J=17.4 Hz, 5.1 Hz), 2.65 (dt, 1H, J=17.2 Hz, 5.1 Hz), 4.72 (t, 1H, J=5.1 Hz), 4.85 (brs, 2H), 6.57 (brs, 1H), 6.62 (s, 1H). IR Spectrum (KBr): 1252, 1362, 1377, 1569, 1544, 1645, 1670, 3171, 3371, 3484 cm$^{-1}$. Mass Spectrum (FAB$^+$) m/z: 311 ((M+H)$^+$).

(7e) 2-[5-(4-Isobutylphenyl)-1,2,4-oxadiazol-3-yl]-4,5,6,7-tetrahydro-1-benzofuran-4-ol The crude product of the title compound was synthesized by conducting the similar reaction to that mentioned in Example 5 (5a) using 4-isobutylbenzoic acid (0.12 g, 0.66 mmol), 1-hydroxybenzotriazole (0.11 g, 0.78 mmol), 1-ethyl-3-(3-dimethylaminopropyl)carbodiimide hydrochloride (0.14 g, 0.72 mmol), 4-{[t-butyl(dimethyl)silyl]oxy}-N'-hydroxy-4,5,6,7-tetrahydro-1-benzofuran-2-carboximidamide (0.19 g, 0.6 mmol) that was obtained in Example 7 (7d), and tetrabutylammonium fluoride (a 1.0 M solution in tetrahydrofuran, 1.2 ml, 1.2 mmol). Subsequently, the crude product of the title compound thus obtained was purified by chromatography on a silica gel column using a mixed solvent of ethyl acetate and hexane (1:2-1:1) as the eluent to afford the title compound (0.15 g) in a yield of 75% as a pale yellowish oily product.

$^1$HNMR Spectrum (400 MHz, CDCl$_3$) δ ppm: 0.93 (d, 6H, J=6.7 Hz), 1.80-2.12 (m, 5H), 2.56 (d, 2H, J=7.4 Hz), 2.64-2.72 (m, 1H), 2.76-2.86 (m, 1H), 4.80 (brs, 1H), 7.21 (s, 1H), 7.29 (d, 2H, J=8.2 Hz), 8.08 (d, 2H, J=8.2 Hz). IR Spectrum (thin film): 1204, 1343, 1386, 1420, 1505, 1560, 1590, 1616, 3389 cm$^{-1}$. Mass Spectrum (FAB$^+$) m/z: 339 ((M+H)$^+$).

(7f) Ethyl 1-{2-[5-(4-isobutylphenyl)-1,2,4-oxadiazol-3-yl]-4,5,6,7-tetrahydro-1-benzofuran-4-yl}azetidine-3-carboxylate The crude product of the title compound was synthesized by conducting the similar reaction to that mentioned in Example 1 (1f) using 2-[5-(4-isobutylphenyl)-1,2,4-oxadiazol-3-yl]-4,5,6,7-tetrahydro-1-benzofuran-4-ol (0.15 g, 0.45 mmol) that was obtained in Example 7 (7e), carbon tetrabromide (0.30 g, 0.90 mmol), triphenylphosphine (0.24 g, 0.90 mmol), ethyl 3-azetidinecarboxylate hydrochloride (0.11 g, 0.68 mmol), and N,N-diisopropylethylamine (0.20 ml, 1.1 mmol). Subsequently, the crude product of the title compound thus obtained was purified by thin layer chromatography on a silica gel plate using a mixed solvent of ethyl acetate and hexane (4:3) as the developing solvent to afford the title compound (27 mg) in a yield of 13% as a white crystalline solid.

$^1$HNMR Spectrum (400 MHz, CDCl$_3$) δ ppm: 0.93 (d, 6H, J=6.6 Hz), 1.29 (t, 3H, J=7.4 Hz), 1.60-1.87 (m, 3H), 1.87-2.00 (m, 1H), 2.00-2.14 (m, 1H), 2.56 (d, 2H, J=7.4 Hz), 2.60-2.83 (m, 2H), 3.27-3.44 (m, 3H), 3.51 (t, 1H, J=6.8 Hz), 3.58-3.70 (m, 2H), 4.18 (q, 2H, J=7.4 Hz), 7.12 (s, 1H), 7.31 (d, 2H, J=8.0 Hz), 8.10 (d, 2H, J=8.0 Hz). IR Spectrum (liquid film): 1186, 1208, 1342, 1387, 1560, 1590, 1616, 1733 cm$^{-1}$. Mass Spectrum (FAB$^+$) m/z: 450 ((M+H)$^+$).

(7g) 1-{2-[5-(4-Isobutylphenyl)-1,2,4-oxadiazol-3-yl]-4,5,6,7-tetrahydro-1-benzofuran-4-yl}azetidine-3-carboxylic acid 1/2 oxalate The title compound (13 mg) was synthesized in a yield of 50% as a white crystalline solid by conducting the similar reaction to that mentioned in Example 3 (3e) using ethyl 1-{2-[5-(4-isobutylphenyl)-1,2,4-oxadiazol-3-yl]-4,5,6,7-tetrahydro-1-benzofuran-4-yl}azetidine-3-carboxylate (25 mg, 0.056 mmol) that was obtained in Example 7 (7f), a 1N aqueous solution of sodium hydroxide (0.17 ml, 0.17 mmol), and oxalic acid (3 mg, 0.028 mmol).

$^1$HNMR Spectrum (400 MHz, CD$_3$CO$_2$D) δ ppm: 0.94 (d, 6H, J=6.3 Hz), 1.90-2.23 (m, 5H), 2.60 (d, 2H, J=7.0 Hz), 2.69-2.79 (m, 1H), 2.79-2.90 (m, 1H), 3.79-3.92 (m, 1H), 4.38-4.73 (m, 5H), 7.40 (d, 2H, J=7.4 Hz), 7.43 (s, 1H), 8.13 (d, 2H, J=7.4 Hz). IR Spectrum (KBr): 1387, 1409, 1559, 1592, 1613, 3431 cm$^{-1}$. Mass Spectrum (FAB$^+$) m/z: 422 ((M+H)$^+$).

Example 8

1-{2-[5-(4-Isobutylphenyl)-1,2,4-oxadiazol-3-yl]-4,5,6,7-tetrahydro-1-benzothien-4-yl}azetidine-3-carboxylic acid

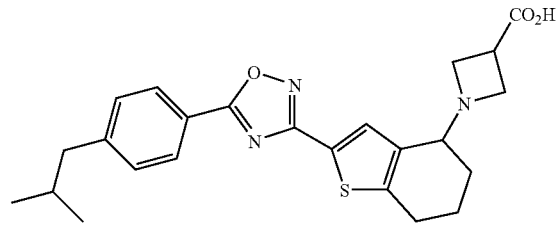

(8a) 2-Bromo-4,5,6,7-tetrahydro-1-benzothiophen-4-ol

To a solution of 4,5,6,7-tetrahydro-1-benzothien-4-yl acetate (5.1 g, 26 mmol) in chloroform (30 ml) was added N-bromosuccinimide (5 g, 28 mmol) at 0° C. with stirring, and the resulting mixture was stirred at room temperature for 3 hours. After stirring, the reaction mixture was poured into water (40 ml) and extracted with ether. The extract was washed with a saturated aqueous solution of sodium chloride and dried over magnesium sulfate. After filtration, the filtrate was evaporated in vacuo. Subsequently, to a solution of the residue thus obtained in a mixed solvent of tetrahydrofuran (20 ml) and water (20 ml) was added sodium hydroxide (2.3 g, 57 mmol) with stirring, and the resulting mixture was stirred for 2 hours. After stirring, the reaction mixture was poured into water (50 ml) to quench the reaction and extracted with ether. The extract was washed with a saturated aqueous solution of sodium chloride and dried over magnesium sulfate. After filtration, the filtrate was evaporated in vacuo, and the crude product of the title compound thus obtained was purified by chromatography on a silica gel column using a mixed solvent of ethyl acetate and hexane (3:7) as the eluent to afford the title compound (5.0 g) in a yield of 82% as a colourless oily product.

$^1$HNMR Spectrum (400 MHz, CDCl$_3$) δ ppm: 1.67 (d, 1H, J=6.6 Hz), 1.75-1.89 (m, 2H), 1.90-2.04 (m, 2H), 2.57-2.67 (m, 1H), 2.69-2.77 (m, 1H), 4.66-4.72 (m, 1H), 6.97 (s, 1H). IR Spectrum (liquid film): 1182, 1435, 1453, 3330 cm$^{-1}$. Mass Spectrum (EI$^+$) m/z: 232 (M$^+$).

(8b) [(2-Bromo-4,5,6,7-tetrahydro-1-benzothiophen-4-yl)oxy](t-butyl)dimethylsilane To a solution of 2-bromo-4,5,6,7-tetrahydro-1-benzothiophen-4-ol (5.0 g, 21 mmol) that was obtained in Example 8 (8a) in N,N-dimethylformamide (30 ml) were added successively imidazole (2.9 g, 43 mmol) and t-butyldimethylchlorosilane (3.5 g, 24 mmol) with stirring, and the resulting mixture was stirred for 2 hours. After stirring, the reaction mixture was poured into water (50 ml) to quench the reaction and extracted with ether. The extract was washed with a saturated aqueous solution of sodium chloride and dried over magnesium sulfate. After filtration, the filtrate was evaporated in vacuo, and the crude product of the title compound thus obtained was purified by chromatography on a silica gel column using a mixed solvent of ethyl acetate and hexane (1:9) as the eluent to afford the title compound (6.8 g) in a yield of 91% as a colourless oily product.

$^1$HNMR Spectrum (400 MHz, CDCl$_3$) δ ppm: 0.12 (s, 3H), 0.14 (s, 3H), 0.92 (s, 9H), 1.66-1.81 (m, 2H), 1.88-2.06 (m, 2H), 2.59 (dt, 1H, J=5.5 Hz, 16.4 Hz), 2.68 (dt, 1H, J=5.5 Hz, 16.4 Hz), 4.68 (t, 1H, J=5.5 Hz), 6.84 (s, 1H). IR Spectrum (liquid film): 1101, 1255, 2858, 2930 cm$^{-1}$. Mass Spectrum (EI$^+$) m/z: 346 (M$^+$).

(8c) 4-{[t-Butyl(dimethyl)silyl]oxy}-4,5,6,7-tetrahydro-1-benzothiophene-2-carboxaldehyde To a solution of [(2-bromo-4,5,6,7-tetrahydro-1-benzothiophen-4-yl)oxy](t-butyl)dimethylsilane (5.6 g, 16 mmol) that was obtained in Example 8 (8b) in tetrahydrofuran (30 ml) was slowly added dropwise n-butyllithium (a 1.6 M solution in hexane, 11 ml, 18 mmol) at −78° C. with stirring, and the resulting mixture was stirred for 5 minutes. Subsequently, to the resulting mixture was added N,N-dimethylformamide (2.5 ml, 32 mmol) at the same temperature with stirring, and the resulting mixture was stirred for 30 minutes. After stirring, a saturated aqueous solution of ammonium chloride (10 ml) was added to the reaction mixture to quench the reaction, and the resulting mixture was poured into water (50 ml) and extracted with ether. The extract was washed with a saturated aqueous solution of sodium chloride and dried over magnesium sulfate. After filtration, the filtrate was evaporated in vacuo, and the crude product of the title compound thus obtained was purified by chromatography on a silica gel column using a mixed solvent of ethyl acetate and hexane (1:9) as the eluent to afford the title compound (4.4 g) in a yield of 92% as a colourless oily product.

$^1$HNMR Spectrum (500 MHz, CDCl$_3$) δ ppm: 0.16 (s, 3H), 0.18 (s, 3H), 0.94 (s, 9H), 1.72-1.86 (m, 2H), 1.97-2.11 (m, 2H), 2.78 (dt, 1H, J=5.4 Hz, 16.5 Hz), 2.87 (dt, 1H, J=5.4 Hz, 16.5 Hz), 4.77 (t, 1H, J=5.4 Hz), 7.58 (s, 1H), 9.82 (s, 1H). IR Spectrum (liquid film): 1240, 1255, 1462, 1673 cm$^{-1}$. Mass Spectrum (EI$^+$) m/z: 296 (M$^+$).

(8d) 4-{[t-Butyl(dimethyl)silyl]oxy}-4,5,6,7-tetrahydro-1-benzothiophene-2-carbonitrile The crude product of the title compound was synthesized by conducting the similar reaction to that mentioned in Example 1 (1c) using 4-{[t-butyl(dimethyl)silyl]oxy}-4,5,6,7-tetrahydro-1-benzothiophene-2-carboxaldehyde (4.4 g, 15.3 mmol) that was obtained in Example 8 (8c), hydroxylamine hydrochloride (1.1 g, 16 mmol), triethylamine (4.1 ml, 30 mmol), and N,N'-dicyclohexylcarbodiimide (3.4 g, 16 mmol). Subsequently, the crude product of the title compound thus obtained was purified by chromatography on a silica gel column using a mixed solvent of ethyl acetate and hexane (1:9) as the eluent to afford the title compound (4.1 g) in a yield of 94% as a colourless oily product.

$^1$HNMR Spectrum (400 MHz, CDCl$_3$) δ ppm: 0.14 (s, 3H), 0.16 (s, 3H), 0.92 (s, 9H), 1.70-1.85 (m, 2H), 1.96-2.10 (m, 2H), 2.70-2.85 (m, 2H), 4.72 (t, 1H, J=5.5 Hz), 7.43 (s, 1H). IR Spectrum (liquid film): 1103, 1256, 1460, 2215 cm$^{-1}$. Mass Spectrum (FAB$^+$) m/z: 294 ((M+H)$^+$), 332 ((M+K)$^+$).

(8e) 4-{([t-Butyl(dimethyl)silyl]oxy}-N'-hydroxy-4,5,6,7-tetrahydro-1-benzothiophene-2-carboximidamide The crude product of the title compound was synthesized by conducting the similar reaction to that mentioned in Example 1 (1d) using 4-{[t-butyl(dimethyl)silyl]oxy}-4,5,6,7-tetrahydro-1-benzothiophene-2-carbonitrile (4.1 g, 13.9 mmol) that was obtained in Example 8 (8d) and a 40% aqueous solution of hydroxylamine (2.0 ml). Subsequently, the crude product of the title compound thus obtained was purified by chromatography on a silica gel column using a mixed solvent of ethyl acetate and hexane (3:7) as the eluent to afford the title compound (3.9 g) in a yield of 96% as a white crystalline solid.

$^1$HNMR Spectrum (500 MHz, CDCl$_3$) δ ppm: 0.14 (s, 3H), 0.16 (s, 3H), 0.93 (s, 9H), 1.70-1.82 (m, 2H), 1.94-2.07 (m, 2H), 2.69 (dt, 1H, J=16.5 Hz, 5.5 Hz), 2.76 (dt, 1H, J=16.5 Hz, 5.5 Hz), 4.73 (t, 1H, J=5.5 Hz), 4.78 (brs, 2H), 7.06 (s, 1H), 7.31 (brs, 1H). IR Spectrum (KBr): 1255, 1361, 1584, 1648, 3295, 3370, 3462 cm$^{-1}$. Mass Spectrum (FAB$^+$) m/z: 327 ((M+H)$^+$).

(8f) 2-[5-(4-Isobutylphenyl)-1,2,4-oxadiazol-3-yl]-4,5,6,7-tetrahydro-1-benzothiophen-4-ol The crude product of the title compound was synthesized by conducting the similar reaction to that mentioned in Example 2 (2c) using 4-{[t-butyl(dimethyl)silyl]oxy}-N'-hydroxy-4,5,6,7-tetrahydro-1-benzothiophene-2-carboximidamide (0.15 g, 0.50 mmol) that was obtained in Example 8 (8e), 4-isobutylbenzoic acid (89 mg, 0.50 mmol), N,N'-dicyclohexylcarbodiimide (0.11 g, 0.55 mmol), and a 1.0 M solution of tetrabutylammonium fluoride (0.75 ml, 0.75 mmol). Subsequently, the crude product of the title compound thus obtained was purified by chromatography on a silica gel column using a mixed solvent of ethyl acetate and hexane (1:1) as the eluent to afford the title compound (92 mg) in a yield of 52% as a colourless oily product.

$^1$HNMR Spectrum (400 MHz, CDCl$_3$) δ ppm: 0.93 (d, 6H, J=6.6 Hz), 1.84-1.97 (m, 2H), 1.97-2.11 (m, 2H), 2.56 (d, 2H, J=7.4 Hz), 2.78 (dt, 1H, J=16.0 Hz, 4.7 Hz), 2.90 (dt, 1H, J=16.0 Hz, 4.7 Hz), 4.80-4.85 (d, 2H, J=7.8 Hz), 7.31 (d, 2H, J=7.8 Hz), 7.81 (s, 1H), 8.08 (d, 2H, J=7.8 Hz). IR Spectrum (liquid film): 1363, 1519, 1559, 1584, 1614, 3385 cm$^{-1}$. Mass Spectrum (FAB$^+$) m/z: 355 ((M+H)$^+$).

(8g) Ethyl 1-{2-[5-(4-isobutylphenyl)-1,2,4-oxadiazol-3-yl]-4,5,6,7-tetrahydro-1-benzothien-4-yl}-azetidine-3-carboxylate The crude product of the title compound was synthesized by conducting the similar reaction to that mentioned in Example 1 (1f) using 2-[5-(4-isobutylphenyl)-1,2,4-oxadiazol-3-yl]-4,5,6,7-tetrahydro-1-benzothiophen-4-ol (92 mg, 0.26 mmol) that was obtained in Example 8 (8f), carbon tetrabromide (0.10 g, 0.31 mmol), triphenylphosphine (81 mg, 0.31 mmol), ethyl 3-azetidinecarboxylate hydrochloride (65 mg, 0.39 mmol), and N,N-diisopropylethylamine (0.14 ml, 0.78 mmol). Subsequently, the crude product of the title compound thus obtained was purified by chromatography on a silica gel column using a mixed solvent of ethyl acetate and hexane (1:1 to 2:1) as the eluent to afford the title compound (44 mg) in a yield of 36% as a colourless oily product.

$^1$HNMR Spectrum (500 MHz, CDCl$_3$) δ ppm: 0.93 (d, 6H, J=6.8 Hz), 1.29 (t, 3H, J=7.3 Hz), 1.70 (dt, 1H, J=11.2 Hz, 4.4 Hz), 1.75-1.83 (m, 3H), 1.93 (septet, 1H, J=6.8 Hz), 2.04-2.13 (m, 1H), 2.56 (d, 2H, J=7.3 Hz), 2.75-2.82 (m, 1H), 2.91 (dt, 1H, J=12.7 Hz, 4.5 Hz), 3.30 (quintet, 1H, J=7.8 Hz), 3.37 (t, 1H, J=6.8 Hz), 3.41 (t, 1H, J=3.9 Hz), 3.56 (t, 1H, J=7.3 Hz), 3.59-3.65 (m, 2H), 4.18 (q, 2H, J=6.8 Hz), 7.31 (d, 2H, J=8.3 Hz), 7.65 (s, 1H), 8.09 (d, 2H, J=8.3 Hz). IR Spectrum (thin film): 1186, 1332, 1363, 1450, 1517, 1560 cm$^{-1}$. Mass Spectrum (FAB$^+$) m/z: 466 ((M+H)$^+$).

(8h) 1-{2-[5-(4-Isobutylphenyl)-1,2,4-oxadiazol-3-yl]-4,5,6,7-tetrahydro-1-benzothien-4-yl}azetidine-3-carboxylic acid The title compound (26 mg) was synthesized in a yield of 64% as a white crystalline solid by conducting the reaction similar to that mentioned in Example 2 (2e) using ethyl 1-{2-[5-(4-isobutylphenyl)-1,2,4-oxadiazol-3-yl]-4,5,6,7-tetrahydro-1-benzothien-4-yl}-azetidine-3-carboxylate (44 mg, 0.094 mmol) that was obtained in Example 8 (8g), lithium hydroxide monohydrate (8.7 mg, 0.20 mmol), and acetic acid (11 μl, 0.20 mmol).

$^1$HNMR Spectrum (500 MHz, CD$_3$OD) δ ppm: 0.94 (d, 6H, J=6.8 Hz), 1.90-2.01 (m, 3H), 2.02-2.08 (m, 2H), 2.60 (d, 2H, J=7.3 Hz), 2.91 (dt, 1H, J=17.5 Hz, 7.3 Hz), 3.01 (dt, 1H, J=17.5 Hz, 5.4 Hz), 3.37 (quintet, 1H, J=7.8 Hz), 4.16-4.24 (m, 2H), 4.31 (t, 1H, J=9.3 Hz), 4.35-4.45 (m, 2H), 7.41 (d, 2H, J=8.3 Hz), 7.86 (s, 1H), 8.09 (d, 2H, J=8.3 Hz). IR Spectrum (thin film): 1517, 1559, 1613, 1714, 3428 cm$^{-1}$. Mass Spectrum (FAB$^+$) m/z: 438 ((M+H)$^+$).

Example 9

1-({4-[3-(4-Isobutylphenyl)isoxazol-5-yl]-2-thienyl}methyl)azetidine-3-carboxylic acid

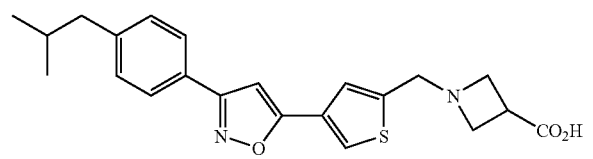

(9a) 4-[(Trimethylsilyl)ethynyl]thiophene-2-carboxaldehyde

To a solution of 4-bromo-2-thiophenecarboxaldehyde (3.0 g, 16 mmol) in N,N-dimethylformamide (30 ml) were added successively (trimethylsilyl)acetylene (11 ml, 79 mmol), triethylamine (13 ml, 94 mmol), and dichlorobis(triphenylphosphine)palladium (1.1 g, 1.6 mmol) under a nitrogen atmosphere with stirring, and the resulting mixture was stirred at 80° C. for 2 hours under a nitrogen atmosphere. After stirring, the reaction mixture was diluted with ethyl acetate, poured into a saturated aqueous solution of ammonium chloride (250 ml) and extracted with ethyl acetate. The extract was washed with a saturated aqueous solution of sodium chloride and dried over magnesium sulfate. After filtration, the filtrate was evaporated in vacuo, and the crude product of the title compound thus obtained was purified by chromatography on a silica gel column using a mixed solvent of ethyl acetate and hexane (0:1 to 1:19) as the eluent to afford the title compound (3.3 g) in a yield of 100% as a brown oily product.

$^1$HNMR Spectrum (500 MHz, CDCl$_3$) δ ppm: 0.25 (s, 9H), 7.77 (s, 1H), 7.81 (s, 1H), 9.88 (s, 1H). IR Spectrum (liquid film): 665, 761, 847, 966, 1182, 1230, 1250, 1434, 1684, 2163, 2823, 2899, 2960, 3097 cm$^{-1}$. Mass Spectrum (EI$^+$) m/z: 208 (M$^+$).

(9b) 4-Ethynylthiophene-2-carboxaldehyde

To a solution of 4-[(trimethylsilyl)ethynyl]thiophene-2-carboxaldehyde (3.3 g, 16 mmol) that was obtained in Example 9 (9a) in methanol (160 ml) was added potassium carbonate (4.3 g, 31 mmol) with stirring, and the resulting mixture was stirred at room temperature for 1 hour. After stirring, insoluble materials were removed by filtration, and the filtrate was evaporated in vacuo. The residue thus obtained was diluted with ethyl acetate, poured into water (100 ml) and extracted with ethyl acetate. The extract was washed with a saturated aqueous solution of sodium chloride and dried over magnesium sulfate. After filtration, the filtrate was evaporated in vacuo, and the crude product of the title compound thus obtained was purified by chromatography on a silica gel column using a mixed solvent of ethyl acetate and hexane (0:1 to 1:19) as the eluent to afford the title compound (1.5 g) in a yield of 69% as a brown solid.

$^1$HNMR Spectrum (400 MHz, CDCl$_3$) δ ppm: 3.10 (s, 1H), 7.79 (s, 1H), 7.86 (s, 1H), 9.90 (s, 1H). IR Spectrum (KBr): 616, 661, 726, 800, 858, 1124, 1190, 1231, 1364, 1432, 1673, 3098, 3426 cm$^{-1}$. Mass Spectrum (EI$^+$) m/z: 136 (M$^+$).

(9c) (4-Ethynyl-2-thienyl)methanol

To a solution of 4-ethynylthiophene-2-carboxaldehyde (1.5 g, 11 mmol) that was obtained in Example 9 (9b) in methanol (30 ml) was added sodium borohydride (0.49 g, 13 mmol) at 0° C. with stirring, and then the resulting mixture was stirred at room temperature for 15 minutes. After cooling the reaction mixture to 0° C., water (100 ml) was added to the reaction mixture, and the resulting mixture was extracted with ethyl acetate. The extract was washed with a saturated aqueous solution of sodium chloride and dried over magnesium sulfate. After filtration, the filtrate was evaporated in vacuo, and the crude product of the title compound thus obtained was purified by chromatography on a silica gel column using a mixed solvent of ethyl acetate and hexane (1:9 to 3:7) as the eluent to afford the title compound (0.88 g) in a yield of 60% as a brown oily product.

$^1$HNMR Spectrum (400 MHz, CDCl$_3$) δ ppm: 1.82 (t, 1H, J=6.1 Hz), 3.01 (s, 1H), 4.75 (d, 1H, J=6.1 Hz), 4.79 (d, 1H, J=6.1 Hz), 7.04 (d, 1H, J=1.0 Hz), 7.46 (d, 1H, J=1.0 Hz). IR Spectrum (liquid film): 609, 660, 761, 846, 1012, 1116, 1165, 1185, 1356, 1370, 2111, 2875, 2932, 3107, 3289 cm$^{-1}$. Mass Spectrum (EI$^+$) m/z: 138 (M$^+$).

(9d) t-Butyl[(4-ethynyl-2-thienyl)methoxy]dimethylsilane

To a solution of (4-ethynyl-2-thienyl)methanol (0.88 g, 6.4 mmol) that was obtained in Example 9 (9c) in dichloromethane (20 ml) were added successively triethylamine (1.3 ml, 9.6 mmol), t-butyldimethylchlorosilane (1.2 g, 7.6 mmol), and 4-dimethylaminopyridine (78 mg, 0.64 mmol)

with stirring, and the resulting mixture was stirred at room temperature for 1 hour. After stirring, water (50 ml) was added to the reaction mixture, and the resulting mixture was extracted with dichloromethane. The extract was washed with a saturated aqueous solution of sodium chloride and dried over magnesium sulfate. After filtration, the filtrate was evaporated in vacuo, and the crude product of the title compound thus obtained was purified by chromatography on a silica gel column using a mixed solvent of ethyl acetate and hexane (0:1 to 1:9) as the eluent to afford the title compound (1.5 g) in a yield of 94% as a brown oily product.

$^1$HNMR Spectrum (400 MHz, CDCl$_3$) δ ppm: 0.10 (s, 6H), 0.92 (s, 9H), 2.98 (s, 1H), 4.80 (s, 2H), 6.91 (d, 1H, J=1.2 Hz), 7.38 (d, 1H, J=1.2 Hz). IR Spectrum (liquid film): 778, 838, 1080, 1122, 1171, 1257, 1374, 1464, 1472, 2858, 2930, 2956, 3313 cm$^{-1}$. Mass Spectrum (EI$^+$) m/z: 252 (M$^+$).

(9e) 4-Isobutylbenzaldehyde oxime

To a solution of 4-isobutylbenzaldehyde (5.0 g, 31 mmol) in a mixed solvent of ethanol (25 ml) and pyridine (25 ml) was added hydroxylamine hydrochloride (2.4 g, 34 mmol) with stirring, and the resulting mixture was stirred at room temperature for 18 hours. After evaporating the reaction mixture in vacuo, the residue thus obtained was diluted with ether, poured into water (150 ml) and extracted with ether. The extract was washed successively with 1N hydrochloric acid and a saturated aqueous solution of sodium chloride and dried over magnesium sulfate. After filtration, the filtrate was evaporated in vacuo, and the crude product of the title compound thus obtained was purified by chromatography on a silica gel column using a mixed solvent of ethyl acetate and hexane (1:19 to 1:9) as the eluent to afford the title compound (4.6 g) in a yield of 84% as a colourless oily product.

$^1$HNMR Spectrum (500 MHz, CDCl$_3$) δ ppm: 0.90 (d, 6H, J=6.8 Hz), 1.87 (m, 1H), 2.49 (d, 2H, J=7.3 Hz), 7.16 (d, 2H, J=8.3 Hz), 7.48 (d, 2H, J=8.3 Hz), 7.63 (brs, 1H), 8.12 (s, 1H). IR Spectrum (liquid film): 534, 790, 845, 962, 1296, 1466, 1517, 1611, 2869, 2925, 2957, 3308 cm$^{-1}$. Mass Spectrum (EI$^+$) m/z: 177 (M$^+$).

(9f) N-Hydroxy-4-isobutylbenzenecarboximidoyl chloride

To a solution of 4-isobutylbenzaldehyde oxime (1.0 g, 5.6 mmol) that was obtained in Example 9 (9e) in N,N-dimethylformamide (10 ml) was added N-chlorosuccinimide (0.15 g, 1.1 mmol) with stirring, and furthermore, a small amount of gaseous hydrochloric acid was bubbled into the resulting mixture under stirring, and then the resulting mixture was stirred at room temperature for 10 minutes. After repeating the series of the same procedures described above five times in total, the reaction mixture was poured into ice water (100 ml) and extracted with ether. The extract was washed successively with water and a saturated aqueous solution of sodium chloride and dried over magnesium sulfate. After filtration, the filtrate was evaporated in vacuo to afford the title compound (1.2 g) in a yield of 100% as a yellow oily product.

$^1$HNMR Spectrum (500M Hz, CDCl$_3$) δ ppm: 0.91 (d, 6H, J=6.8 Hz), 1.88 (m, 1H), 2.51 (d, 2H, J=7.3 Hz), 7.18 (d, 2H, J=8.3 Hz), 7.75 (d, 2H, J=8.3 Hz), 7.82 (s, 1H). IR Spectrum (liquid film): 795, 850, 937, 994, 1185, 1249, 1413, 1466, 1609, 2957, 3380 cm$^{-1}$. Mass Spectrum (EI$^+$) m/z: 211 (M$^+$).

(9g) {4-[3-(4-Isobutylphenyl)isoxazol-5-yl]-2-thienyl}methanol

To a solution of N-hydroxy-4-isobutylbenzenecarboximidoyl chloride (0.50 g, 2.4 mmol) that was obtained in Example 9 (9f) and t-butyl[(4-ethynyl-2-thienyl)methoxy]dimethylsilane (0.72 g, 2.8 mmol) that was obtained in Example 9 (9d) in ethyl acetate (10 ml) was added triethylamine (0.40 ml, 2.8 mmol) at 0° C. with stirring, and the resulting mixture was stirred at room temperature for 18 hours. After stirring, the reaction mixture was poured into water (50 ml) and extracted with ethyl acetate. The extract was washed with a saturated aqueous solution of sodium chloride and dried over magnesium sulfate. After filtration, the filtrate was evaporated in vacuo. Subsequently, to a solution of the residue thus obtained in tetrahydrofuran (15 ml) was added tetrabutylammonium fluoride (a 1.0 M solution in tetrahydrofuran, 2.8 ml, 2.8 mmol) at 0° C. with stirring, and the resulting mixture was stirred at room temperature for 1 hour. After stirring, the reaction mixture was poured into water (50 ml) and extracted with ethyl acetate. The extract was washed with a saturated aqueous solution of sodium chloride and dried over magnesium sulfate. After filtration, the filtrate was evaporated in vacuo. Subsequently, to the residue obtained was added a mixed solvent of ethyl acetate and hexane (1:3) with stirring, and the solid precipitated was collected by filtration using a Kiriyama funnel and washed with the same solvent to afford the title compound (0.44 g) in a yield of 59% as a white crystalline solid.

$^1$HNMR Spectrum (500 MHz, CDCl$_3$) δ ppm: 0.93 (d, 6H, J=6.3 Hz), 1.91 (m, 1H), 1.98 (brs, 1H), 2.53 (d, 2H, J=6.8 Hz), 4.89 (s, 2H), 6.64 (s, 1H), 7.25 (d, 2H, J=8.3 Hz), 7.35 (s, 1H), 7.73-7.77 (m, 3H). IR Spectrum (KBr): 774, 794, 847, 1018, 1380, 1440, 1467, 1615, 2869, 2926, 2953, 3344 cm$^{-1}$. Mass Spectrum (EI$^+$) m/z: 313 (M$^+$).

(9h) Ethyl 1-({4-[3-(4-isobutylphenyl)isoxazol-5-yl]-2-thienyl}methyl)azetidine-3-carboxylate A solution of {4-[3-(4-isobutylphenyl)isoxazol-5-yl]-2-thienyl}methanol (0.43 g, 1.4 mmol) that was obtained in Example 9 (9g), carbon tetrabromide (0.68 g, 2.1 mmol) and triphenylphosphine (0.54 g, 2.1 mmol) in dichloromethane (15 ml) was stirred at 0° C. for 5 minutes. Subsequently, to the reaction mixture were added successively ethyl 3-azetidinecarboxylate hydrochloride (0.34 mg, 2.1 mmol) and N,N-diisopropylethylamine (0.60 ml, 3.4 mmol) with stirring, and the resulting mixture was stirred at room temperature for 18 hours. After stirring, a saturated aqueous solution of sodium hydrogencarbonate (5 ml) was added to the reaction mixture to quench the reaction, and the resulting mixture was poured into water (50 ml) and extracted with dichloromethane. The extract was washed with a saturated aqueous solution of sodium chloride and dried over magnesium sulfate. After filtration, the filtrate was evaporated in vacuo, and the crude product of the title compound thus obtained was purified by chromatography on a silica gel column using a mixed solvent of ethyl acetate and hexane (1:4 to 3:2) as the eluent to afford the title compound (0.48 g) in a yield of 82% as a white crystalline solid.

$^1$HNMR Spectrum (500 MHz, CDCl$_3$) δ ppm: 0.93 (d, 6H, J=6.7 Hz), 1.27 (t, 3H, J=7.0 Hz), 1.90 (m, 1H), 2.52 (d, 2H, J=7.0 Hz), 3.32-3.38 (m, 3H), 3.56-3.64 (m, 2H), 3.81 (s, 2H), 4.16 (q, 2H, J=7.0 Hz), 6.60 (s, 1H), 7.21-7.26 (m, 3H), 7.68 (s, 1H), 7.72 (d, 2H, J=8.2 Hz). IR Spectrum (KBr): 797, 1193, 1369, 1436, 1607, 1731, 2955, 3115 cm$^{-1}$. Mass Spectrum (FAB$^+$) m/z: 425 ((M+H)$^+$).

(9i) 1-({4-[3-(4-Isobutylphenyl)isoxazol-5-yl]-2-thienyl}methyl)azetidine-3-carboxylic acid To a solution of ethyl 1-({4-[3-(4-isobutylphenyl)isoxazol-5-yl]-2-thienyl}methyl)azetidine-3-carboxylate (0.47 g, 1.1 mmol) that was obtained in Example 9 (9h) in 1,4-dioxane (15 ml) was added a 1N aqueous solution of sodium hydroxide (3.3 ml, 3.3 mmol) at 0° C. with stirring, and then the resulting mixture was stirred at room temperature for 30 minutes. After adding methanol (15 ml) and water (5 ml) to the reaction mixture, the resulting mixture was heated under stirring until the white solid precipitated was dissolved, and then acetic acid (0.19 ml, 3.3 mmol) was added. The white solid precipitated was collected by filtration using a Kiriyama funnel, washed with methanol and dried in vacuo to afford the title compound (0.35 g) in a yield of 78% as a white crystalline solid.

$^1$HNMR Spectrum (500 MHz, $CD_3CO_2D$) δ ppm: 0.93 (d, 6H, J=6.6 Hz), 1.92 (m, 1H), 2.54 (d, 2H, J=7.3 Hz), 3.77-3.87 (m, 1H), 4.35-4.60 (m, 4H), 4.73 (s, 2H), 6.98 (s, 1H), 7.30 (d, 2H, J=8.2 Hz), 7.77 (d, 1H, J=1.4 Hz), 7.82 (d, 2H, J=8.2 Hz), 8.06 (d, 1H, J=1.4 Hz). IR Spectrum (KBr): 792, 826, 951, 1386, 1440, 1614, 2924, 2954, 3.103, 3423 $cm^{-1}$. Mass Spectrum ($FAB^+$) m/z: 397 (($M+H)^+$).

Example 10

1-[(4-Ethyl-5-{5-[4-(2-fluorophenoxy)phenyl]-1,2,4-oxadiazol-3-yl}-2-thienyl)methyl]azetidine-3-carboxylic acid 1/2 oxalate

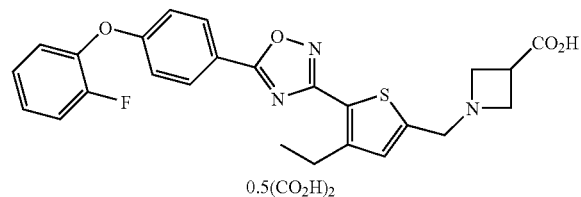

0.5$(CO_2H)_2$

(10a) t-Butyl[(4-ethyl-2-thienyl)methoxy]dimethylsilane

To a solution of [(4-bromo-2-thienyl)methoxy](t-butyl)dimethylsilane (0.61 g, 2.0 mmol) and [1,3-bis(diphenylphosphino)propane]dichloronickel (54 mg, 0.1 mmol) in ether (5 ml) was added slowly a 1.0 M solution of ethylmagnesium bromide in tetrahydrofuran (3.0 ml, 3.0 mmol) at 0° C. with stirring, and after raising the reaction temperature to room temperature, the resulting mixture was stirred for 1 hour. After stirring, a saturated aqueous solution of ammonium chloride (5 ml) was added to the reaction mixture to quench the reaction, and the resulting mixture was poured into water (20 ml) and extracted with ether. The extract was washed with a saturated aqueous solution of sodium chloride and dried over magnesium sulfate. After filtration, the filtrate was evaporated in vacuo, and the crude product of the title compound thus obtained was purified by chromatography on a silica gel column using a mixed solvent of ethyl acetate and hexane (0:10 to 5:95) as the eluent to afford the title compound (0.44 g) in a yield of 95% as a pale yellow oily product.

$^1$HNMR Spectrum (400 MHz, $CDCl_3$) δ ppm: 0.10 (s, 6H), 0.93 (s, 9H), 1.21 (t, 3H, J=7.4 Hz), 2.58 (q, 2H, J=7.4 Hz), 4.82 (s, 2H), 6.77 (s, 1H), 6.81 (s, 1H). IR Spectrum (liquid film): 1077, 1131, 1174, 1255, 1463, 1471 $cm^{-1}$. Mass Spectrum ($FAB^+$) m/z: 255 (($M-H)^+$).

(10b) 5-({[t-Butyl(dimethyl)silyl]oxy}methyl)-3-ethylthiophene-2-carboxaldehyde To a solution of t-butyl[(4-ethyl-2-thienyl)methoxy]dimethylsilane (1.3 g, 5.6 mmol) that was obtained in Example 10 (10a) in tetrahydrofuran (10 ml) was slowly added a 1.6 M solution of n-butyllithium in hexane (4.2 ml, 6.7 mmol) at −78° C. with stirring, and after raising the reaction temperature to 0° C., the resulting mixture was stirred for 30 minutes. Subsequently, the reaction temperature was lowered to −78° C. again under stirring, and to the reaction mixture was added N,N-dimethylformamide (0.86 ml, 11 mmol) with stirring, and the resulting mixture was stirred for 30 minutes. After stirring, a saturated aqueous solution of ammonium chloride (5 ml) was added to the reaction mixture to quench the reaction, and the resulting mixture was poured into water (20 ml) and extracted with ether. The extract was washed with a saturated aqueous solution of sodium chloride and dried over magnesium sulfate. After filtration, the filtrate was evaporated in vacuo, and the crude product of the title compound thus obtained was purified by chromatography on a silica gel column using a mixed solvent of ethyl acetate and hexane (0:10 to 5:95) as the eluent to afford the title compound (1.3 g) in a yield of 86% as a pale yellow oily product.

$^1$HNMR Spectrum (400 MHz, $CDCl_3$) δ ppm: 0.12 (s, 6H), 0.94 (s, 9H), 1.29 (t, 3H, J=7.4 Hz), 2.94 (q, 2H, J=7.4 Hz), 4.86 (s, 2H), 6.84 (s, 1H), 9.99 (s, 1H). IR Spectrum (liquid film): 1092, 1156, 1225, 1256, 1461, 1659 $cm^{-1}$. Mass Spectrum ($EI^+$) m/z: 285 ($M^+$).

(10c) 5-({[t-Butyl(dimethyl)silyl]oxy}methyl)-3-ethylthiophene-2-carbonitrile To a suspension of 5-({[t-butyl(dimethyl)silyl]oxy}methyl)-3-ethylthiophene-2-carboxaldehyde (1.3 g, 4.8 mmol) that was obtained in Example 10 (10b) and hydroxylamine hydrochloride (0.37 g, 5.3 mmol) in dichloromethane (20 ml) were added successively methanol (2 ml) and triethylamine (1.3 ml, 9.6 mmol) with stirring, and the resulting mixture was stirred at room temperature for 2 hours. After removing the solvent in vacuo, toluene (10 ml) was added to the residue and the resulting mixture was evaporated azeotropically in vacuo. Subsequently, the residue obtained and N,N'-dicyclohexylcarbodiimide (1.1 g, 5.3 mmol) were suspended in toluene (20 ml) and stirred at 90° C. for 15 hours. After cooling to room temperature, hexane (20 ml) was added to the reaction mixture, and the resulting mixture was filtered with Celite. The filtrate was evaporated in vacuo, and the crude product of the title compound thus obtained was purified by chromatography on a silica gel column using a mixed solvent of ethyl acetate and hexane (0:10 to 5:95) as the eluent to afford the title compound (0.94 g) in a yield of 69% as a pale yellow oily product.

$^1$HNMR Spectrum (400 MHz, $CDCl_3$) δ ppm: 0.11 (s, 6H), 0.93 (s, 9H), 1.25 (t, 3H, J=7.8 Hz), 2.75 (q, 2H, J=7.8 Hz), 4.83 (s, 2H), 6.74 (s, 1H). IR Spectrum (liquid film): 1093, 1149, 1256, 2212 $cm^{-1}$. Mass Spectrum ($EI^+$) m/z: 282 ($M^+$).

(10d) 5-({[t-Butyl(dimethyl)silyl]oxy}methyl)-3-ethyl-N'-hydroxythiophene-2-carboximidamide The crude product of the title compound was synthesized by conducting the reaction similar to that mentioned in Example 1 (1d) using 5-({[t-butyl(dimethyl)silyl]oxy}methyl)-3-ethylthiophene-2-carbonitrile (0.93 g, 3.3 mmol) that was obtained in Example 10 (10c) and a 40% aqueous solution of hydroxylamine (0.5 mL)). Subsequently, the crude product of the title compound thus obtained was purified by recrystallization from hexane (6:4) to afford the title compound (0.60 g) in a yield of 60% as a white crystalline solid.

$^1$HNMR Spectrum (400 MHz, CDCl$_3$) δ ppm: 0.11 (s, 6H), 0.93 (s, 9H), 1.20 (t, 3H, J=7.8 Hz), 2.76 (q, 2H, J=7.8 Hz), 4.80 (s, 4H), 6.76 (s, 1H), 7.10 (br, 1H). IR Spectrum (KBr): 1059, 1590, 1643, 3284, 3357, 3491 cm$^{-1}$. Mass Spectrum (EI$^+$) m/z: 315 (M$^+$).

(10e) 4-(2-Fluorophenoxy)benzoic acid

To a solution of 4-fluorobenzaldehyde (1.2 g, 10 mmol) and 2-fluorophenol (1.3 g, 12 mmol) in N,N-dimethylformamide (10 ml) was added potassium carbonate (2.8 g, 20 mmol) with stirring, and the resulting mixture was stirred at 100° C. for 16 hours. After cooling to room temperature, the reaction mixture was poured into water (20 ml) and extracted with ether. The extract was washed with a saturated aqueous solution of sodium chloride and dried over magnesium sulfate. After filtration, the filtrate was evaporated in vacuo. Subsequently, to a solution of the residue obtained in a mixture of tetrahydrofuran (5 ml), t-butanol (10 ml), and water (5 ml) were added successively 2-methyl-2-butene (5.3 ml, 50 mmol), potassium dihydrogenphosphate (3.4 g, 25 mmol), and sodium hypochlorite (2.7 g, 30 mmol) with stirring, and the resulting mixture was stirred at room temperature for 2 hours. After stirring, the reaction mixture was poured into water (20 ml) and extracted with ether. Subsequently, to the aqueous layer was added a 1M aqueous sodium hydroxide solution (20 ml), and the resulting aqueous layer was acidified with a 10M aqueous hydrochloric acid solution (2 ml) and extracted again with ether. The extract was washed with a saturated aqueous solution of sodium chloride and dried over magnesium sulfate. After filtration, the filtrate was evaporated in vacuo to afford the title compound (2.0 g) in a yield of 87% as a white crystalline solid.

$^1$HNMR Spectrum (400 MHz, CDCl$_3$) δ ppm: 6.98 (d, 2H, J=8.6 Hz), 7.15-7.24 (m, 4H), 8.07 (d, 2H, J=8.6 Hz). IR Spectrum (KBr): 1266, 1290, 1428, 1498, 1594, 1682, 2544, 2672, 2884, 2990 cm$^{-1}$. Mass Spectrum (EI$^+$) m/z: 232 (M$^+$).

(10f) (4-Ethyl-5-{5-[4-(2-fluorophenoxy)phenyl]-1,2,4-oxadiazol-3-yl}-2-thienyl)methanol To a solution of 5-({[t-butyl(dimethyl)silyl]oxy}methyl)-3-ethyl-N'-hydroxythiophene-2-carboximidamide (0.16 g, 0.50 mmol) that was obtained in Example 10 (10d) and 4-(2-fluorophenoxy)benzoic acid (0.13 g, 0.55 mmol) that was obtained in Example 10 (10e) in dichloromethane (1.5 ml) was added N,N'-dicyclohexylcarbodiimide (0.11 g, 0.55 mmol) with stirring, and the resulting mixture was stirred at room temperature for 30 minutes. After stirring, hexane (2 ml) was added to the reaction mixture, and insoluble materials were removed by filtration, and the filtrate obtained was evaporated in vacuo. Subsequently, to a solution of the residue obtained in tetrahydrofuran (1 ml) was added a 1.0 M solution of tetrabutylammonium fluoride in tetrahydrofuran (0.75 ml, 0.75 mmol) with stirring, and the resulting mixture was stirred at 60° C. for 1 hour. After cooling to room temperature, the reaction mixture was poured into water (10 ml) and extracted with ether. The extract was washed with a saturated aqueous solution of sodium chloride and dried over magnesium sulfate. After filtration, the filtrate was evaporated in vacuo, and the crude product of the title compound thus obtained was purified by chromatography on a silica gel column using a mixed solvent of ethyl acetate and hexane (3:7 to 5:5) as the eluent to afford the title compound (0.18 g) in a yield of 89% as a white crystalline solid.

$^1$HNMR Spectrum (400 MHz, CDCl$_3$) δ ppm: 1.29 (t, 3H, J=7.8 Hz), 3.05 (q, 2H, J=7.8 Hz), 4.83 (s, 2H), 6.98 (s, 1H), 7.07 (d, 2H, J=8.6 Hz), 7.17-7.25 (m, 4H), 8.15 (d, 2H, J=8.6 Hz). IR Spectrum (KBr): 1270, 1353, 1497, 1602, 3340 cm$^{-1}$. Mass Spectrum (FAB$^+$) m/z: 397 ((M+H)$^+$).

(10g) Methyl 1-[(4-ethyl-5-{5-[4-(2-fluorophenoxy)phenyl]-1,2,4-oxadiazol-3-yl}-2-thienyl)methyl]azetidine-3-carboxylate The crude product of the title compound was synthesized by conducting the reaction similar to that mentioned in Example 1 (1f) using (4-ethyl-5-{5-[4-(2-fluorophenoxy)phenyl]-1,2,4-oxadiazol-3-yl}-2-thienyl)methanol (0.17 g, 0.43 mmol) that was obtained in Example 10 (10f), carbon tetrabromide (0.17 g, 0.51 mmol), triphenylphosphine (0.13 g, 0.51 mmol), methyl 3-azetidinecarboxylate hydrochloride (0.10 g, 0.65 mmol), N,N-diisopropylethylamine (0.23 mL, 1.3 mmol). Subsequently, the crude product of the title compound thus obtained was purified by chromatography using a mixed solvent of ethyl acetate and hexane (5:5) to afford the title compound (0.19 g) in a yield of 90% as a white crystalline solid.

$^1$HNMR Spectrum (500 MHz, CDCl$_3$) δ ppm: 1.28 (t, 3H, J=7.8 Hz), 3.03 (q, 2H, J=7.8 Hz), 3.32-3.40 (m, 4H), 3.60-3.66 (m, 1H), 3.72 (s, 3H), 3.79 (s, 2H), 6.86 (s, 1H), 7.07 (d, 2H, J=8.8 Hz), 7.17-7.25 (m, 4H), 8.13 (d, 2H, J=8.8 Hz). IR Spectrum (liquid film): 1497, 1514, 1557, 1604, 1737 cm$^{-1}$. Mass Spectrum (FAB$^+$) m/z: 494 ((M+H)$^+$).

(10h) 1-[(4-Ethyl-5-{5-[4-(2-fluorophenoxy)phenyl]-1,2,4-oxadiazol-3-yl}-2-thienyl)methyl]azetidine-3-carboxylic acid 1/2 oxalate The title compound (77 mg) was synthesized in a yield of 39% as a white crystalline solid by conducting the reaction similar to that mentioned in Example 1 (1g) using methyl 1-[(4-ethyl-5-{5-[4-(2-fluorophenoxy)phenyl]-1,2,4-oxadiazol-3-yl}-2-thienyl)methyl]azetidine-3-carboxylate (0.19 g, 0.38 mmol) that was obtained in Example 10 (10g), lithium hydroxide monohydrate (36 mg, 0.85 mmol), acetic acid (46 μL, 0.85 mmol), and oxalic acid (17 mg, 0.19 mmol).

$^1$HNMR Spectrum (400 MHz, CD$_3$OD) δ ppm: 1.26 (t, 3H, J=7.4 Hz), 3.03 (q, 2H, J=7.4 Hz), 3.22 (quintet, 1H, J=8.6 Hz), 3.37 (t, 2H, J=8.2 Hz), 3.62 (t, 2H, J=7.0 Hz), 3.82 (s, 2H), 6.98 (s, 1H), 7.12 (d, 2H, J=9.0 Hz), 7.25-7.33 (m, 4H), 8.16 (d, 2H, J=9.0 Hz). IR Spectrum (KBr): 1420, 1497, 1601, 1659, 3413 cm$^{-1}$. Mass Spectrum (FAB$^+$) m/z: 480 ((M+H)$^+$).

Example 11

1-({5-[5-(3-Fluoro-4-phenoxyphenyl)-1,2,4-oxadiazol-3-yl]-4-methyl-2-thienyl}methyl)azetidine-3-carboxylic acid

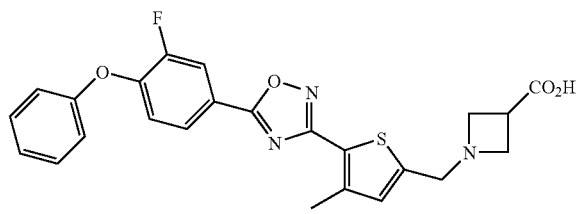

(11a) t-Butyl(dimethyl)[(4-methyl-2-thienyl)methoxy]silane

To a solution of 2-hydroxymethyl-4-methylthiophene (1.8 g, 14 mmol) (reference literature: J. Heterocycl. Chem., vol. 19, 1125 (1982)) and imidazole (1.9 g, 28 mmol) in N,N-dimethylformamide (20 ml) was added t-butyldimethylsilyl chloride (2.3 g, 15 mmol) with stirring, and the resulting mixture was stirred at room temperature for 2 hours. After stirring, the reaction mixture was poured into water (20 ml) and extracted with ether. The extract was washed with a saturated aqueous solution of sodium chloride and dried over magnesium sulfate. After filtration, the filtrate was evaporated in vacuo, and the crude product of the title compound thus obtained was purified by chromatography on a silica gel column using a mixed solvent of ethyl acetate and hexane (0:10 to 1:19) as the eluent to afford the title compound (2.5 g) in a yield of 74% as a colourless oily product.

$^1$HNMR Spectrum (400 MHz, CDCl$_3$) δ ppm: 0.10 (s, 6H), 0.93 (s, 9H), 2.22 (s, 3H), 4.81 (s, 2H), 6.72 (s, 1H), 6.78 (s, 1H). IR Spectrum (liquid film): 1077, 1130, 1256, 1464 cm$^{-1}$. Mass Spectrum (EI$^+$) m/z: 242 ((M+H)$^+$).

(11b) 5-({[t-Butyl(dimethyl)silyl]oxy}methyl)-3-methylthiophene-2-carboxaldehyde The crude product of the title compound was synthesized by conducting the reaction similar to that mentioned in Example 10 (10b) using t-butyl(dimethyl)[(4-methyl-2-thienyl)methoxy]silane (2.5 g, 10 mmol) that was obtained in Example 11 (11a), 1.6 M solution of n-butyllithium in hexane (7.8 mL, 12 mmol), and N,N-dimethylformamide (1.6 mL, 21 mmol). Subsequently, the crude product of the title compound thus obtained was purified by chromatography on a silica gel column using a mixed solvent of ethyl acetate and hexane (0:10 to 5:95) as the eluent to afford the title compound (2.5 g) in a yield of 89% as a pale yellowish oily product.

$^1$HNMR Spectrum (400 MHz, CDCl$_3$) δ ppm: 0.12 (s, 6H), 0.94 (s, 9H), 2.52 (s, 3H), 4.85 (s, 2H), 6.78 (s, 1H), 9.98 (s, 1H). IR Spectrum (liquid film): 1092, 1363, 1393, 1472, 1661 cm$^{-1}$. Mass Spectrum (FAB$^+$) m/z: 271 ((M+H)$^+$).

(11c) 5-({[t-Butyl(dimethyl)silyl]oxy}methyl)-3-methylthiophene-2-carbonitrile The crude product of the title compound was synthesized by conducting the reaction similar to that mentioned in Example 10 (10c) using 5-({[t-butyl(dimethyl)silyl]oxy}methyl)-3-methylthiophene-2-carboxaldehyde (2.5 g, 9.2 mmol) that was obtained in Example 11 (11b), hydroxylamine hydrochloride (0.71 g, 10 mmol), triethylamine (2.6 mL, 18 mmol), and N,N'-dicyclohexylcarbodiimide (2.1 g, 10 mmol). Subsequently, the crude product of the title compound thus obtained was purified by chromatography on a silica gel column using a mixed solvent of ethyl acetate and hexane (0:10 to 5:95) as the eluent to afford the title compound (2.5 g) in a yield of 100% as a pale yellowish oily product.

$^1$HNMR Spectrum (400 MHz, CDCl$_3$) δ ppm: 0.11 (s, 6H), 0.93 (s, 9H), 2.39 (s, 3H), 4.83 (s, 2H), 6.71 (s, 1H). IR Spectrum (liquid film): 1093, 1150, 1258, 2120, 2214 cm$^{-1}$. Mass Spectrum (FAB$^+$) m/z: 268 ((M+H)$^+$).

(11d) 5-({[t-Butyl(dimethyl)silyl]oxy}methyl)-N'-hydroxy-3-methylthiophene-2-carboximidamide The crude product of the title compound was synthesized by conducting the reaction similar to that mentioned in Example 1 (1d) using 5-({[t-butyl(dimethyl)silyl]oxy}methyl)-3-methylthiophene-2-carbonitrile (2.5 g, 9.2 mmol) that was obtained in Example 11 (11c) and a 40% aqueous solution of hydroxylamine (20 mL). Subsequently, the crude product of the title compound thus obtained was purified by chromatography on a silica gel column using a mixed solvent of ethyl acetate and hexane (0:10 to 5:95) as the eluent to afford the title compound (1.4 g) in a yield of 52% as a white crystalline solid.

$^1$HNMR Spectrum (400 MHz, CDCl$_3$) δ ppm: 0.10 (s, 6H), 0.93 (s, 9H), 2.35 (s, 3H), 4.79 (s, 4H), 6.68 (s, 1H), 7.16 (br, 1H). IR Spectrum (KBr): 1255, 1651, 3277, 3353, 3455 cm$^{-1}$. Mass Spectrum (FAB) m/z: 301 ((M+H)$^+$).

(11e) 3-Fluoro-4-phenoxybenzoic acid

The title compound (1.1 g) was synthesized in a yield of 93% as a white crystalline solid by conducting a reaction similar to that mentioned in Example 10 (10e) using 3,4-difluorobenzaldehyde (0.71 g, 5.0 mmol), phenol (0.56 g, 6.0 mmol), potassium carbonate (1.4 g, 10 mmol), 2-methyl-2-butene (2.5 mL, 23 mmol), potassium dihydrogenphosphate (1.6 g, 12 mmol), and sodium hypochlorite (1.3 g, 14 mmol).

$^1$HNMR Spectrum (400 MHz, CDCl$_3$) δ ppm: 6.96 (t, 1H, J=8.2 Hz)), 7.04-7.07 (m, 2H), 7.19 (t, 1H, J=7.4 Hz), 7.37 (d, 1H, J=7.4 Hz), 7.39 (d, 1H, J=7.4 Hz), 7.80-7.83 (m, 1H), 7.89 (dd, 1H, J=11.0 Hz, 2.0 Hz). IR Spectrum (KBr): 1025, 1275, 1444, 1492, 1692, 2596, 2673, 2983, 3065 cm$^{-1}$. Mass Spectrum (EI$^+$) m/z: 232 (M$^+$).

(11f) {5-[5-(3-Fluoro-4-phenoxyphenyl]-1,2,4-oxadiazol-3-yl)-4-methyl-2-thienyl}methanol The crude product of the title compound was synthesized by conducting the reaction similar to that mentioned in Example 10 (10f) using 5-({[t-butyl(dimethyl)silyl]oxy}methyl)-N'-hydroxy-3-methylthiophene-2-carboximidamide (0.18 g, 0.60 mmol) that was obtained in Example 11 (11d), 3-fluoro-4-phenoxybenzoic acid (0.15 g, 0.66 mmol) that was obtained in Example 11 (11e), N,N'-dicyclohexylcarbodiimide (0.14 g, 0.66 mmol), and 1.0 M solution of tetrabutylammonium fluoride in tetrahydrofuran (0.90 mL, 0.90 mmol). Subsequently, the crude product of the title compound thus obtained was purified by chromatography on a silica gel column using a mixed solvent of ethyl acetate and hexane (1:1) as the eluent to afford the title compound (0.21 g) in a yield of 93% as a white crystalline solid.

$^1$HNMR Spectrum (400 MHz, CDCl$_3$) δ ppm: 2.60 (s, 3H), 4.84 (d, 2H, J=5.9 Hz), 6.92 (s, 1H), 7.06-7.11 (m, 3H), 7.22 (t, 1H, J=7.4 Hz), 7.42 (t, 2H, J=6.6 Hz), 7.91 (dd, 1H, J=1.2 Hz, 8.6 Hz), 8.01 (dd, 1H, J=2.3 Hz, 10.9 Hz). IR Spectrum (KBr): 1444, 1488, 1577, 1590, 1626, 3264, 3327 cm$^{-1}$. Mass Spectrum (FAB$^+$) m/z: 383 ((M+H)$^+$).

(11g) Methyl 1-({5-[5-(3-fluoro-4-phenoxyphenyl)-1,2,4-oxadiazol-3-yl]-4-methyl-2-thienyl}methyl)azetidine-3-carboxylate The crude product of the title compound was synthesized by conducting the reaction similar to that mentioned in Example 1 (1f) using {5-[5-(3-fluoro-4-phenoxyphenyl)-1,2,4-oxadiazol-3-yl)-4-methyl-2-thienyl}methanol (0.21 g, 0.55 mmol) that was obtained in Example 11 (11f), carbon tetrabromide (0.22 g, 0.66 mmol), triphenylphosphine (0.17 g, 0.66 mmol), methyl 3-azetidinecarboxylate hydrochloride (0.13 g, 0.83 mmol), and N,N-diisopropylethylamine (0.30 mL, 1.7 mmol). Subsequently, the crude product of the title compound thus obtained was purified by chromatography using a mixed solvent of ethyl acetate and hexane (5:5) to afford the title compound (0.23 g) in a yield of 86% as a colourless oily product.

$^1$HNMR Spectrum (500 MHz, CDCl$_3$) δ ppm: 2.56 (s, 3H), 3.30-3.39 (m, 4H), 3.58-3.64 (m, 1H), 3.71 (s, 3H), 3.76 (s, 2H), 7.02-7.08 (m, 3H), 7.19 (t, 1H, J=7.4 Hz), 7.38 (t, 2H, J=7.4 Hz), 7.85-7.89 (m, 1H), 7.97 (dd, 1H, J=2.0 Hz, 10.5 Hz). IR Spectrum (liquid film): 1489, 1514, 1562, 1590, 1621, 1737 cm$^{-1}$. Mass Spectrum (FAB$^+$) m/z: 480 ((M+H)$^+$).

(11h) 1-({5-[5-(3-Fluoro-4-phenoxyphenyl)-1,2,4-oxadiazol-3-yl]-4-methyl-2-thienyl}methyl)azetidine-3-carboxylic acid The title compound (0.17 g) was synthesized in a yield of 74% as a white crystalline solid by conducting the reaction similar to that mentioned in Example 2 (2e) using methyl 1-({5-[5-(3-fluoro-4-phenoxyphenyl)-1,2,4-oxadiazol-3-yl]-4-methyl-2-thienyl}methyl)azetidine-3-carboxylate (0.23 g, 0.48 mmol) that was obtained in Example 11 (11g), lithium hydroxide monohydrate (46 mg, 1.1 mmol), and acetic acid (60 µL, 1.1 mmol).

$^1$HNMR Spectrum (400 MHz, CD$_3$OD) δ ppm: 2.61 (s, 3H), 3.50-3.62 (m, 1H), 4.22-4.33 (m, 4H), 4.58 (s, 2H), 7.09 (d, 2H, J=7.8 Hz), 7.15 (t, 1H, J=8.6 Hz), 7.19-7.24 (m, 2H), 7.42 (t, 2H, J=7.8 Hz), 7.94 (d, 1H, J=8.2 Hz), 8.02 (d, 1H, J=11.0 Hz). IR Spectrum (KBr): 1272, 1340, 1507, 1515, 1561, 1591, 1619, 3404 cm$^{-1}$. Mass Spectrum (FAB$^+$) m/z: 466 ((M+H)$^+$).

Example 12

1-({4-Methyl-5-[5-(4-phenoxyphenyl)-1,2,4-oxadiazol-3-yl]-2-thienyl}methyl)azetidine-3-carboxylic acid

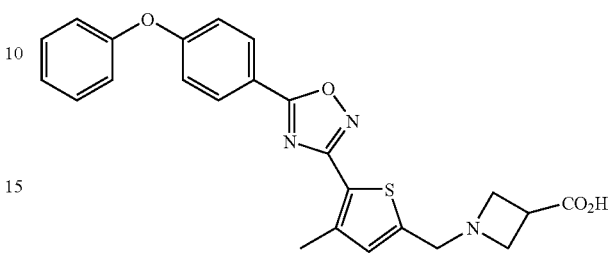

(12a) {4-Methyl-5-[5-(4-phenoxyphenyl)-1,2,4-oxadiazol-3-yl]-2-thienyl}methanol

To a solution of 4-phenoxybenzoic acid (0.14 g, 0.63 mmol) in a mixture of acetonitrile (4 ml) and tetrahydrofuran (2 ml) were added successively 1-hydroxybenzotriazole (89 mg, 0.66 mmol), 1-ethyl-3-(3-dimethylaminopropyl)carbodiimide hydrochloride (0.13 g, 0.66 mmol) and 5-({[t-butyl(dimethyl)silyl]oxy}methyl)-N'-hydroxy-3-methylthiophene-2-carboximidamide (0.18 g, 0.60 mmol) that was obtained in Example 11 (11d) with stirring, and the resulting mixture was stirred at 50° C. for 30 minutes. After stirring, water (5 ml) was added to the reaction mixture to quench the reaction, and the resulting mixture was extracted with ethyl acetate. The extract was washed successively with 0.1N hydrochloric acid, a saturated aqueous solution of sodium hydrogencarbonate and a saturated aqueous solution of sodium chloride and dried over sodium sulfate. After filtration, the filtrate was evaporated in vacuo. Subsequently, to a solution of the residue obtained in tetrahydrofuran (5 ml) was added a 1.0 M solution of tetrabutylammonium fluoride in tetrahydrofuran (1.2 ml, 1.2 mmol) with stirring, and the resulting mixture was stirred at 50° C. for 2 hours. After stirring, the reaction mixture was poured into water (20 ml) to quench the reaction and extracted with ether. The extract was washed with a saturated aqueous solution of sodium chloride and dried over sodium sulfate. After filtration, the filtrate was evaporated in vacuo, and the crude product of the title compound thus obtained was purified by chromatography on a silica gel column using a mixed solvent of ethyl acetate and hexane (1:3 to 1:2) as the eluent to afford the title compound (0.19 g) in a yield of 86% as a white crystalline solid.

$^1$HNMR Spectrum (400 MHz, CDCl$_3$) δ ppm: 1.87 (bs, 1H), 2.59 (s, 3H), 4.83 (s, 2H), 6.91 (s, 1H), 7.09 (d, 2H, J=8.8 Hz), 7.10 (d, 2H, J=8.3 Hz), 7.22 (t, 1H, J=7.1 Hz), 7.42 (t, 2H, J=7.8 Hz), 8.14 (d, 2H, J=8.3 Hz). IR Spectrum (KBr): 1249, 1341, 1489, 1514, 1588, 1612, 3279, 3393 cm$^{-1}$. Mass Spectrum (FAB$^+$) m/z: 365 ((M+H)$^+$).

(12b) Methyl 1-({4-methyl-5-[5-(4-phenoxyphenyl)-1,2,4-oxadiazol-3-yl]-2-thienyl}methyl)azetidine-3-carboxylate The crude product of the title compound was synthesized by conducting the reaction similar to that mentioned in Example 1 (1f) using {4-methyl-5-[5-(4-phenoxyphenyl)-1,2,4-oxadiazol-3-yl]-2-thienyl}methanol (0.19 g, 0.51 mmol)

that was obtained in Example 12 (12a), carbon tetrabromide (0.22 g, 0.66 mmol), triphenylphosphine (0.17 g, 0.66 mmol), methyl 3-azetidinecarboxylate hydrochloride (0.12 g, 0.77 mmol), and N,N-diisopropylethylamine (0.27 mL, 1.5 mmol). Subsequently, the crude product of the title compound thus obtained was purified by chromatography on a silica gel column using a mixed solvent of ethyl acetate and hexane (2:3) as the eluent to afford the title compound (0.20 g) in a yield of 85% as a pale yellowish oily product.

$^1$HNMR Spectrum (400 MHz, CDCl$_3$) δ ppm: 2.57 (s, 3H), 3.31-3.40 (m, 3H), 3.59-3.61 (m, 2H), 3.72 (s, 3H), 3.77 (s, 2H), 6.80 (s, 1H), 7.07-7.13 (m, 4H), 7.22 (t, 1H, J=7.1 Hz), 7.42 (t, 2H, J=7.8 Hz), 8.14 (d, 2H, J=8.3 Hz). IR Spectrum (KBr): 1166, 1201, 1242, 1341, 1488, 1516, 1592, 1613, 1732 cm$^{-1}$. Mass Spectrum (FAB$^+$) m/z: 462 ((M+H)$^+$).

(12c) 1-({4-Methyl-5-[5-(4-phenoxyphenyl)-1,2,4-oxadiazol-3-yl]-2-thienyl}methyl)azetidine-3-carboxylic acid The title compound (0.16 g) was synthesized in a yield of 85% as a white crystalline solid by conducting the reaction similar to that mentioned in Example 3 (3e) using methyl 1-({4-methyl-5-[5-(4-phenoxyphenyl)-1,2,4-oxadiazol-3-yl]-2-thienyl}methyl)azetidine-3-carboxylate (0.20 g, 0.42 mmol) that was obtained in Example 12 (12b) and a 1 N aqueous solution of sodium hydroxide (1.3 mL, 1.3 mmol).

$^1$HNMR Spectrum (400 MHz, CD$_3$CO$_2$D) δ ppm: 2.61 (s, 3H), 3.77-3.86 (m, 1H), 4.34-4.44 (m, 2H), 4.50-4.58 (m, 2H), 4.67 (s, 2H), 7.15 (d, 4H, J=8.6 Hz), 7.21-7.26 (m, 1H), 7.26 (s, 1H), 7.45 (t, 2H, J=7.8 Hz), 8.18 (d, 2H, J=9.0 Hz). IR Spectrum (KBr): 1244, 1336, 1488, 1593, 1612, 3429 cm$^{-1}$. Mass Spectrum (FAB$^+$) m/z: 448 ((M+H)$^+$).

Example 13

1-({4-Ethyl-5-[5-(4-phenoxyphenyl)-1,2,4-oxadiazol-3-yl]-2-thienyl}methyl)azetidine-3-carboxylic acid

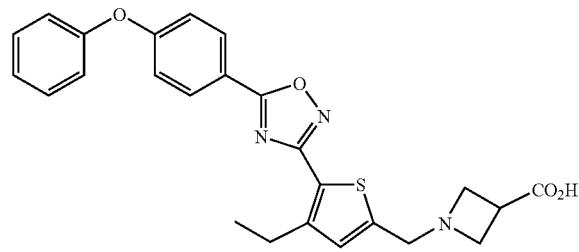

(13a) {4-Ethyl-5-[5-(4-phenoxyphenyl)-1,2,4-oxadiazol-3-yl]-2-thienyl}methanol

The crude product of the title compound was synthesized by conducting the reaction similar to that mentioned in Example 12 (12a) using 4-phenoxybenzoic acid (0.12 g, 0.53 mmol), 1-hydroxybenzotriazole (74 mg, 0.55 mmol), 1-ethyl-3-(3-dimethylaminopropyl)carbodiimide hydrochloride (0.11 g, 0.55 mmol), 5-({[t-butyl(dimethyl)silyl]oxy}methyl)-3-ethyl-N'-hydroxythiophene-2-carboximidamide (0.16 g, 0.50 mmol) that was obtained in Example 10 (10d), and 1.0 M solution of tetrabutylammoniumfluoride in tetrahydrofuran (1.0 mL, 1.0 mmol). Subsequently, the crude product of the title compound thus obtained was purified by chromatography on a silica gel column using a mixed solvent of ethyl acetate and hexane (1:3) as the eluent to afford the title compound (0.17 g) in a yield of 89% as a pale yellowish crystalline solid.

$^1$HNMR Spectrum (400 MHz, CDCl$_3$) δ ppm: 1.29 (t, 3H, J=7.4 Hz), 1.88 (t, 1H, J=5.9 Hz), 3.05 (q, 2H, J=7.4 Hz), 4.83 (d, 2H, J=5.9 Hz), 6.96 (s, 1H), 7.04-7.10 (m, 4H), 7.20 (t, 1H, J=7.4 Hz), 7.39 (t, 2H, J=7.4 Hz), 8.12 (d, 2H, J=9.0 Hz). IR Spectrum (KBr): 1248, 1353, 1490, 1496, 1515, 1588, 1612, 3356 cm$^{-1}$. Mass Spectrum (FAB$^+$) m/z: 379 ((M+H)$^+$).

(13b) Methyl 1-({4-ethyl-5-[5-(4-phenoxyphenyl)-1,2,4-oxadiazol-3-yl]-2-thienyl}methyl)azetidine-3-carboxylate The crude product of the title compound was synthesized by conducting the reaction similar to that mentioned in Example 1 (1f) using {4-ethyl-5-[5-(4-phenoxyphenyl)-1,2,4-oxadiazol-3-yl]-2-thienyl}methanol (0.17 g, 0.44 mmol) that was obtained in Example 13 (13a), carbon tetrabromide (0.19 g, 0.57 mmol), triphenylphosphine (0.15 g, 0.57 mmol), methyl 3-azetidinecarboxylate hydrochloride (0.10 g, 0.66 mmol), and N,N-diisopropylethylamine (0.23 mL, 1.3 mmol). Subsequently, the crude product of the title compound thus obtained was purified by chromatography on a silica gel column using a mixed solvent of ethyl acetate and hexane (1:3 to 1:2) as the eluent to afford the title compound (0.19 g) in a yield of 89% as a pale yellow oily product.

$^1$HNMR Spectrum (400 MHz, CDCl$_3$) δ ppm: 1.27 (t, 3H, J=7.4 Hz), 3.03 (q, 2H, J=7.4 Hz), 3.30-3.40 (m, 3H), 3.59-3.67 (m, 2H), 3.71 (s, 3H), 3.78 (s, 2H), 6.84 (s, 1H), 7.04-7.10 (m, 4H), 7.20 (t, 1H, J=7.4 Hz), 7.39 (t, 2H, J=7.4 Hz), 8.11 (d, 2H, J=9.0 Hz). IR Spectrum (liquid film): 1168, 1200, 1245, 1346, 1489, 1514, 1589, 1613, 1737 cm$^{-1}$. Mass Spectrum (FAB$^+$) m/z: 476 ((M+H)$^+$).

(13c) 1-({4-Ethyl-5-[5-(4-phenoxyphenyl)-1,2,4-oxadiazol-3-yl]-2-thienyl}methyl)azetidine-3-carboxylic acid The title compound (0.15 g) was synthesized in a yield of 86% as a white crystalline solid using by conducting the similar reaction to that mentioned in Example 3 (3e) using methyl 1-({4-ethyl-5-[5-(4-phenoxyphenyl)-1,2,4-oxadiazol-3-yl]-2-thienyl}methyl)azetidine-3-carboxylate (0.180 g, 0.39 mmol) that was obtained in Example 13 (13b) and a 1N aqueous solution of sodium hydroxide (1.2 ml, 1.2 mmol).

$^1$HNMR Spectrum (400 MHz, CD$_3$CO$_2$D) δ ppm: 1.30 (t, 3H, J=7.4 Hz), 3.09 (q, 2H, J=7.4 Hz), 3.76-3.87 (m, 1H), 4.33-4.45 (m, 2H), 4.45-4.57 (m, 2H), 4.68 (s, 2H), 7.15 (d, 4H, J=9.0 Hz), 7.24 (t, 1H, J=7.4 Hz), 7.32 (s, 1H), 7.45 (t, 2H, J=7.4 Hz), 8.17 (d, 2H, J=9.0 Hz). IR Spectrum (KBr): 1167, 1249, 1347, 1489, 1517, 1557, 1592, 1613, 3422 cm$^{-1}$. Mass Spectrum (FAB$^+$) m/z: 462 ((M+H)$^+$).

Example 14

1-({4-Ethyl-5-[5-(3-fluoro-4-phenoxyphenyl)-1,2,4-oxadiazol-3-yl]-2-thienyl}methyl)azetidine-3-carboxylic acid

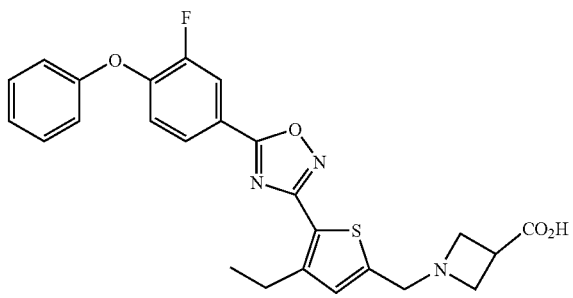

(14a) {4-Ethyl-5-[5-(3-fluoro-4-phenoxyphenyl)-1,2,4-oxadiazol-3-yl]-2-thienyl}methanol The crude product of the title compound was synthesized by conducting the similar reaction to that mentioned in Example 12 (12a) using 3-fluoro-4-phenoxybenzoic acid (0.12 g, 0.50 mmol) that was obtained in Example 11 (11e), 1-hydroxybenzotriazole (72 mg, 0.53 mmol), 1-ethyl-3-(3-dimethylaminopropyl)carbodiimide hydrochloride (0.10 g, 0.53 mmol), 5-({[t-butyl(dimethyl)silyl]oxy}methyl)-3-ethyl-N'-hydroxythiophene-2-carboximidamide (0.15 g, 0.48 mmol) that was obtained in Example 10 (10d), and a 1.0 M solution of tetrabutylammonium fluoride in tetrahydrofuran (0.96 ml, 0.96 mmol). Subsequently, the crude product of the title compound thus obtained was purified by chromatography on a silica gel column using a mixed solvent of ethyl acetate and hexane (1:3) as the eluent to afford the title compound (0.16 g) in a yield of 85% as a pale yellowish crystalline solid.

$^1$HNMR Spectrum (400 MHz, CDCl$_3$) δ ppm: 1.29 (t, 3H, J=7.4 Hz), 1.91 (t, 1H, J=5.9 Hz), 3.05 (q, 2H, J=7.4 Hz), 4.84 (d, 2H, J=5.9 Hz), 6.96 (s, 1H), 7.02-7.09 (m, 3H), 7.19 (t, 1H, J=7.4 Hz), 7.39 (t, 2H, J=7.4 Hz), 7.88 (dd, 1H, J=8.4 Hz, 1.4 Hz), 7.99 (dd, 1H, J=10.6 Hz, 2.0 Hz). IR Spectrum (KBr): 1207, 1270, 1283, 1342, 1436, 1456, 1492, 1513, 1576, 1595, 3433 cm$^{-1}$. Mass Spectrum (FAB$^+$) m/z: 397 ((M+H)$^+$).

(14b) Methyl 1-({4-ethyl-5-[5-(3-fluoro-4-phenoxyphenyl)-1,2,4-oxadiazol-3-yl]-2-thienyl}methyl)azetidine-3-carboxylate The crude product of the title compound was synthesized by conducting the reaction similar to that mentioned in Example 1 (1f) using {4-ethyl-5-[5-(3-fluoro-4-phenoxyphenyl)-1,2,4-oxadiazol-3-yl]-2-thienyl}methanol (0.16 g, 0.40 mmol) that was obtained in Example 14 (14a), carbon tetrabromide (0.17 g, 0.52 mmol), triphenylphosphine (0.14 g, 0.52 mmol), methyl 3-azetidinecarboxylate hydrochloride (91 mg, 0.60 mmol), and N,N-diisopropylethylamine (0.21 mL, 1.2 mmol). Subsequently, the crude product of the title compound thus obtained was purified by chromatography on a silica gel column using a mixed solvent of ethyl acetate and hexane (1:3 to 1:2) as the eluent to afford the title compound (0.15 g) in a yield of 77% as a pale yellow oily product.

$^1$HNMR Spectrum (400 MHz, CDCl$_3$) δ ppm: 1.28 (t, 3H, J=7.4 Hz), 3.02 (q, 2H, J=7.4 Hz), 3.31-3.40 (m, 3H), 3.58-3.67 (m, 2H), 3.71 (s, 3H), 3.78 (s, 2H), 6.85 (s, 1H), 7.02-7.09 (m, 3H), 7.19 (t, 1H, J=7.4 Hz), 7.38 (t, 2H, J=7.4 Hz), 7.87 (dt, 1H, J=9.0 Hz, 1.7 Hz), 7.98 (dd, 1H, J=10.8 Hz, 2.2 Hz). IR Spectrum (liquid film): 1204, 1272, 1348, 1454, 1489, 1523, 1559, 1590, 1737 cm$^{-1}$. Mass Spectrum (FAB$^+$) m/z: 494 ((M+H)$^+$).

(14c) 1-({4-Ethyl-5-[5-(3-fluoro-4-phenoxyphenyl)-1,2,4-oxadiazol-3-yl]-2-thienyl}methyl)azetidine-3-carboxylic acid The title compound (0.11 g) was synthesized in a yield of 77% as a white crystalline solid by conducting the reaction similar to that mentioned in Example 3 (3e) using methyl 1-({4-ethyl-5-[5-(3-fluoro-4-phenoxyphenyl)-1,2,4-oxadiazol-3-yl]-2-thienyl}methyl)azetidine-3-carboxylate (0.15 g, 0.30 mmol) that was obtained in Example 14 (14b) and a 1 N aqueous solution of sodium hydroxide (0.9 mL, 0.9 mmol).

$^1$HNMR Spectrum (400 MHz, CD$_3$CO$_2$D) δ ppm: 1.31 (t, 3H, J=7.4 Hz), 3.09 (q, 2H, J=7.4 Hz), 3.75-3.87 (m, 1H), 4.33-4.44 (m, 2H), 4.44-4.58 (m, 2H), 4.68 (s, 2H), 7.09-7.20 (m, 3H), 7.23 (t, 1H, J=7.6 Hz), 7.33 (s, 1H), 7.44 (t, 2H, J=7.6 Hz), 7.97 (d, 1H, J=9.0 Hz), 8.04 (d, 1H, J=10.6 Hz). IR Spectrum (KBr): 1201, 1275, 1349, 1491, 1515, 1556, 1591, 3427 cm$^{-1}$. Mass Spectrum (FAB$^+$) m/z: 480 ((M+H)$^+$).

Example 15

1-({5-[5-(3-Chloro-4-phenoxyphenyl)-1,2,4-oxadiazol-3-yl]-4-ethyl-2-thienyl}methyl)azetidine-3-carboxylic acid

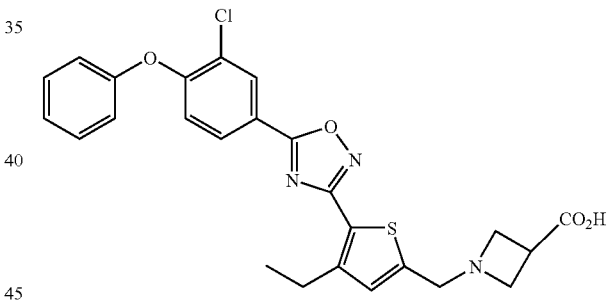

(15a) 3-Chloro-4-phenoxybenzoic acid

The title compound (0.95 g) was synthesized in a yield of 77% as a white crystalline solid by conducting the similar reaction to that mentioned in Example 10 (10e) using 3-chloro-4-fluorobenzaldehyde (0.80 g, 5.0 mmol), phenol (0.66 g, 7.0 mmol), potassium carbonate (1.7 g, 13 mmol), 2-methyl-2-butene (2.7 ml, 25 mmol), potassium dihydrogenphosphate (1.7 g, 13 mmol) and sodium hypochlorite (1.4 g, 15 mmol).

$^1$HNMR Spectrum (400 MHz, CDCl$_3$) δ ppm: 6.87 (d, 1H, J=8.6 Hz), 7.05 (dd, 2H, J=7.4 Hz, 1.2 Hz), 7.21 (t, 1H, J=7.4 Hz), 7.39 (t, 2H, J=7.4 Hz), 7.88 (dd, 1H, J=8.6 Hz, 2.0 Hz), 8.19 (d, 1H, J=2.0 Hz).

(15b) {5-[5-(3-Chloro-4-phenoxyphenyl)-1,2,4-oxadiazol-3-yl]-4-ethyl-2-thienyl}methanol The crude product of the title compound was synthesized by conducting the reaction similar to that mentioned in Example 12 (12a) using 3-chloro-4-phenoxybenzoic acid (0.12 g, 0.50 mmol) that was obtained in Example 15 (15a), 1-hydroxybenzotriazole (72 mg, 0.53 mmol), 1-ethyl-3-(3-dimethylaminopropyl)carbodiimide hydrochloride (0.10 g, 0.53 mmol), 5-({[t-butyl(dimethyl)silyl]oxy}methyl)-3-ethyl-N'-hydroxythiophene-2-carboximidamide (0.15 g, 0.48 mmol) that was obtained in Example 10 (10d), and 1.0 M solution of tetrabutylammoniumfluoride in tetrahydrofuran (0.96 mL, 0.96 mmol). Subsequently, the crude product of the title compound thus obtained was purified by chromatography on a silica gel column using a mixed solvent of ethyl acetate and hexane (1:3) as the eluent to afford the title compound (0.17 g) in a yield of 87% as a pale yellow crystalline solid.

¹HNMR Spectrum (400 MHz, CDCl₃) δ ppm: 1.30 (t, 3H, J=7.4 Hz), 1.90 (t, 1H, J=5.8 Hz), 3.06 (q, 2H, J=7.4 Hz), 4.85 (d, 2H, J=5.8 Hz), 6.98 (d, 1H, J=8.6 Hz), 6.99 (s, 1H), 7.09 (d, 2H, J=8.6 Hz), 7.23 (t, 1H, J=7.4 Hz), 7.43 (t, 2H, J=7.4 Hz), 7.99 (dd, 1H, J=8.6 Hz, 2.1 Hz), 8.31 (d, 1H, J=2.1 Hz). IR Spectrum (KBr): 1242, 1265, 1393, 1480, 1591, 3250, 3335 cm⁻¹. Mass Spectrum (FAB⁺) m/z: 413 ((M+H)⁺).

(15c) Methyl 1-({5-[5-(3-chloro-4-phenoxyphenyl)-1,2,4-oxadiazol-3-yl]-4-ethyl-2-thienyl}methyl)azetidine-3-carboxylate The crude product of the title compound was synthesized by conducting the reaction similar to that mentioned in Example 1 (1f) using {5-[5-(3-chloro-4-phenoxyphenyl)-1,2,4-oxadiazol-3-yl]-4-ethyl-2-thienyl}methanol (0.17 g, 0.41 mmol) that was obtained in Example 15 (15b), carbon tetrabromide (0.18 g, 0.53 mmol), triphenylphosphine (0.14 g, 0.53 mmol), methyl 3-azetidinecarboxylate hydrochloride (93 mg, 0.62 mmol), and N,N-diisopropylethylamine (0.21 mL, 1.2 mmol). Subsequently, the crude product of the title compound thus obtained was purified by chromatography on a silica gel column using a mixed solvent of ethyl acetate and hexane (1:3) as the eluent to afford the title compound (0.15 g) in a yield of 73% as a pale yellowish oily product.

¹HNMR Spectrum (400 MHz, CDCl₃) δ ppm: 1.28 (t, 3H, J=7.8 Hz), 3.03 (q, 2H, J=7.8 Hz), 3.32-3.43 (m, 3H), 3.59-3.69 (m, 2H), 3.79 (s, 3H), 3.84 (s, 2H), 6.87 (s, 1H), 6.98 (d, 1H, J=8.6 Hz), 7.09 (d, 2H, J=7.4 Hz), 7.24 (t, 1H, J=7.4 Hz), 7.43 (t, 2H, J=7.4 Hz), 7.98 (dd, 1H, J=8.6 Hz, 2.2 Hz), 8.30 (d, 1H, J=2.2 Hz). IR Spectrum (thin film): 1198, 1245, 1266, 1343, 1483, 1513, 1737 cm⁻¹. Mass Spectrum (FAB⁺) m/z: 510 ((M+H)⁺).

(15d) 1-({5-[5-(3-Chloro-4-phenoxyphenyl)-1,2,4-oxadiazol-3-yl]-4-ethyl-2-thienyl}methyl)azetidine-3-carboxylic acid The title compound (0.13 g) was synthesized in a yield of 88% as a white crystalline solid by conducting the reaction similar to that mentioned in Example 3 (3e) using methyl 1-({5-[5-(3-chloro-4-phenoxyphenyl)-1,2,4-oxadiazol-3-yl]-4-ethyl-2-thienyl}methyl)azetidine-3-carboxylate (0.15 g, 0.29 mmol) that was obtained in Example 15 (15c) and a 1 N aqueous solution of sodium hydroxide (0.87 mL, 0.87 mmol).

¹HNMR Spectrum (400 MHz, CD₃CO₂D) δ ppm: 1.31 (t, 3H, J=7.6 Hz), 3.09 (q, 2H, J=7.6 Hz), 3.75-3.87 (m, 1H), 4.33-4.44 (m, 2H), 4.48-4.59 (m, 2H), 4.68 (s, 2H), 7.07 (d, 1H, J=8.6 Hz), 7.13 (d, 2H, J=7.8 Hz), 7.25 (t, 1H, J=7.8 Hz), 7.33 (s, 1H), 7.45 (t, 2H, J=7.8 Hz), 8.06 (dd, 1H, J=8.6 Hz, 2.2 Hz), 8.31 (s, 1H). IR Spectrum (KBr): 1265, 1344, 1392, 1484, 1514, 1591, 1609, 3414 cm⁻¹. Mass Spectrum (FAB⁺) m/z: 496 ((M+H)⁺).

Example 16

1-[(5-{5-[3-Chloro-4-(3-fluorophenoxy)phenyl]-1,2,4-oxadiazol-3-yl}-4-ethyl-2-thienyl)methyl]azetidine-3-carboxylic acid

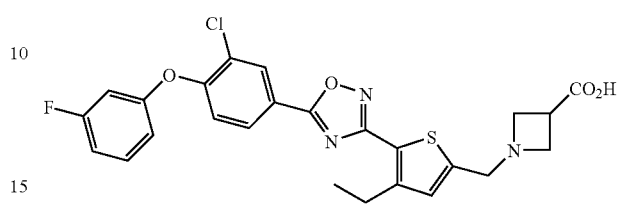

(16a) 3-Chloro-4-(3-fluorophenoxy)benzoic acid

The title compound (1.3 g) was synthesized in a yield of 79% as a pale yellow crystalline solid by conducting the similar reaction to that mentioned in Example 10 (10e) using 3-chloro-4-fluorobenzaldehyde (1.0 g, 6.3 mmol), 2-fluorophenol (1.1 g, 9.5 mmol) potassium carbonate (2.2 g, 16 mmol), 2-methyl-2-butene (3.0 ml, 28 mmol), potassium dihydrogenphosphate (1.9 g, 14 mmol), and sodium hypochlorite (1.5 g, 17 mmol).

¹HNMR Spectrum (400 MHz, CDCl₃) δ ppm: 6.75-6.95 (m, 3H), 7.04 (d, 1H, J=8.6 Hz), 7.33-7.38 (m, 1H), 7.96 (dd, 1H, J=8.6 Hz, 2.2 Hz), 8.23 (d, 1H, J=2.2 Hz). IR Spectrum (KBr): 1123, 1269, 1423, 1486, 1592, 1705, 2663, 2982, 3078 cm⁻¹. Mass Spectrum (EI⁺) m/z: 266 (M⁺).

(16b) (5-{5-[3-Chloro-4-(3-fluorophenoxy)phenyl]-1,2,4-oxadiazol-3-yl}-4-ethyl-2-thienyl)methanol The crude product of the title compound was synthesized by conducting the reaction similar to that mentioned in Example 5 (5a) using 3-chloro-4-(3-fluorophenoxy)benzoic acid (0.14 g, 0.53 mmol) that was obtained in Example 16 (16a), 1-hydroxybenzotriazole (0.086 g, 0.56 mmol), 1-ethyl-3-(3-dimethylaminopropyl)carbodiimide hydrochloride (0.11 g, 0.56 mmol), 5-({[t-butyl(dimethyl)silyl]oxy}methyl)-3-ethyl-N'-hydroxythiophene-2-carboximidamide (0.16 g, 0.51 mmol) that was obtained in Example 10 (10d), and 1.0M solution of tetrabutylammoniumfluoride in tetrahydrofuran (1.0 mL, 1.0 mmol). Subsequently, the crude product of the title compound thus obtained was purified by chromatography on a silica gel column using a mixed solvent of ethyl acetate and hexane (2:8 to 5:5) as the eluent to afford the title compound (0.17 g) in a yield of 89% as a pale yellowish crystalline solid.

¹HNMR Spectrum (400 MHz, CDCl₃) δ ppm: 1.30 (t, 3H, J=7.6 Hz), 1.89 (t, 1H, J=5.9 Hz), 3.06 (q, 2H, J=7.6 Hz), 4.86 (d, 2H, J=5.9 Hz), 6.75-6.97 (m, 3H), 6.99 (s, 1H), 7.09 (d, 1H, J=8.6 Hz), 7.33-7.40 (m, 1H), 8.04 (dd, 1H, J=8.6 Hz, 2.0 Hz), 8.32 (d, 1H, J=2.0 Hz). IR Spectrum (KBr): 759, 958, 1120, 1269, 1393, 1480, 1603, 2928, 2973, 3334 cm⁻¹. Mass Spectrum (FAB⁺) m/z: 431 ((M+H)⁺).

(16c) Methyl 1-[(5-{5-[3-chloro-4-(3-fluorophenoxy)phenyl]-1,2,4-oxadiazol-3-yl}-4-ethyl-2-thienyl)methyl]azetidine-3-carboxylate The crude product of the title compound was synthesized by conducting the reaction similar to that mentioned in Example 1 (1f) using (5-{5-[3-chloro-4-(3-fluorophenoxy)phenyl]-1,2,4-oxadiazol-3-yl}-4-ethyl-2-thienyl)methanol (0.15 g, 0.34 mmol) that was obtained in Example 16 (16b), carbon tetrabromide (0.16 g, 0.51 mmol), triphenylphosphine (0.13 g, 0.51 mmol), methyl 3-azetidinecarboxylate hydrochloride (0.073 g, 0.51 mmol), and N,N-diisopropylethylamine (0.14 mL, 0.84 mmol). Subsequently, the crude product of the title compound thus obtained was purified by chromatography on a silica gel column using a mixed solvent of ethyl acetate and hexane (2:8 to 5:15) as the eluent to afford the title compound (0.16 g) in a yield of 88% as a colourless oily product.

$^1$HNMR Spectrum (400 MHz, CDCl$_3$) δ ppm: 1.28 (t, 3H, J=7.4 Hz), 3.02 (q, 2H, J=7.4 Hz), 3.32-3.42 (m, 3H), 3.60-3.67 (m, 2H), 3.71 (s, 3H), 3.78 (s, 2H), 6.75-6.93 (m, 4H), 7.06 (d, 1H, J=8.2 Hz), 7.30-7.37 (m, 1H), 7.99-8.03 (m, 1H), 8.29 (d, 1H, J=2.0 Hz). IR Spectrum (liquid film): 959, 1120, 1270, 1343, 1483, 1513, 1604, 1738, 2846, 2966 cm$^{-1}$. Mass Spectrum (FAB$^+$) m/z: 528 ((M+H)$^+$).

(16d) 1-[(5-{5-[3-Chloro-4-(3-fluorophenoxy)phenyl]-1,2,4-oxadiazol-3-yl}-4-ethyl-2-thienyl)methyl]azetidine-3-carboxylic acid The title compound (0.14 g) was synthesized in a yield of 92% as a white crystalline solid by conducting the reaction similar to that mentioned in Example 3 (3e) using methyl 1-[(5-{5-[3-chloro-4-(3-fluorophenoxy)phenyl]-1,2,4-oxadiazol-3-yl}-4-ethyl-2-thienyl)methyl]azetidine-3-carboxylate (0.16 g, 0.30 mmol) that was obtained in Example 16 (16c), a 1 N aqueous solution of sodium hydroxide (0.89 mL, 0.89 mmol), and acetic acid (51 μL, 0.89 mmol).

$^1$HNMR Spectrum (400 MHz, CD$_3$CO$_2$D) δ ppm: 1.31 (t, 3H, J=7.5 Hz), 3.10 (q, 2H, J=7.5 Hz), 3.78-3.89 (m, 1H), 4.30-4.65 (m, 4H), 4.71 (s, 2H), 6.87-7.01 (m, 3H), 7.20 (d, 1H, J=8.6 Hz), 7.38 (s, 1H), 7.39-7.46 (m, 1H), 8.12 (dd, 1H, J=8.6 Hz, 2.1 Hz), 8.33 (d, 1H, J=2.1 Hz). IR Spectrum (KBr): 769, 847, 959, 1118, 1231, 1272, 1344, 1393, 1447, 1486, 1514, 1552, 1603, 2969, 3429 cm$^{-1}$. Mass Spectrum (FAB$^+$) m/z: 514 ((M+H)$^+$).

Example 17

1-[(4-Ethyl-5-{5-[4-(3-fluorophenoxy)phenyl]-1,2,4-oxadiazol-3-yl}-2-thienyl)methyl]azetidine-3-carboxylic acid

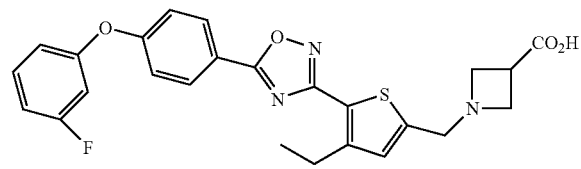

(17a) 4-(3-Fluorophenoxy)benzoic acid

The title compound (2.0 g) was synthesized in a yield of 96% as a white crystalline solid by conducting the similar reaction to that mentioned in Example 10 (10e) using 4-fluorobenzaldehyde (1.5 g, 12 mmol), 3-fluorophenol (1.2 ml, 13 mmol), potassium carbonate (3.3 g, 24 mmol), 2-methyl-2-butene (4.8 ml, 45 mmol), potassium dihydrogenphosphate (3.1 g, 23 mmol), and sodium hypochlorite (2.5 g, 27 mmol).

$^1$HNMR Spectrum (400 MHz, CDCl$_3$) δ ppm: 6.75-6.92 (m, 3H), 7.03 (d, 2H, J=8.6 Hz), 7.27-7.37 (m, 1H), 8.08 (d, 2H, J=8.6 Hz). IR Spectrum (KBr): 1117, 1226, 1271, 1293, 1314, 1484, 1597, 1689, 2553, 2671, 2842, 2984 cm$^{-1}$. Mass Spectrum (EI$^+$) m/z: 232 (M$^+$).

(17b) (4-Ethyl-5-{5-[4-(3-fluorophenoxy)phenyl]-1,2,4-oxadiazol-3-yl}-2-thienyl)methanol The crude product of the title compound was synthesized by conducting the reaction similar to that mentioned in Example 10 (10f) using 5-({[t-butyl(dimethyl)silyl]oxy}methyl)-3-ethyl-N'-hydroxythiophene-2-carboximidamide (0.16 g, 0.50 mmol) that was obtained in Example 10 (10d), 4-(3-fluorophenoxy)benzoic acid (0.13 g, 0.55 mmol) that was obtained in Example 17 (17a), N,N'-dicyclohexylcarbodiimide (0.11 g, 0.55 mmol), and 1.0 M solution of tetrabutylammonium fluoride in tetrahydrofuran (0.75 mL, 0.75 mmol). Subsequently, the crude product of the title compound thus obtained was purified by chromatography on a silica gel column using a mixed solvent of ethyl acetate and hexane (3:7 to 5:5) as the eluent to afford the title compound (0.15 g) in a yield of 73% as a white crystalline solid.

$^1$HNMR Spectrum (400 MHz, CDCl$_3$) δ ppm: 1.30 (t, 3H, J=7.4 Hz), 1.87 (br, 1H), 3.07 (q, 2H, J=7.8 Hz), 4.85 (d, 2H, J=4.7 Hz), 6.82 (dt, 1H, J=7.4 Hz, 2.3 Hz), 6.85-6.95 (m, 3H), 6.99 (s, 1H), 7.14 (d, 2H, J=9.0 Hz), 7.35-7.40 (m, 1H), 8.18 (d, 2H, J=9.0 Hz). IR Spectrum (KBr): 1341, 1486, 1515, 1557, 1603, 3373 cm$^{-1}$. Mass Spectrum (FAB$^+$) m/z: 397 ((M+H)$^+$).

(17c) Methyl 1-[(4-ethyl-5-{5-[4-(3-fluorophenoxy)phenyl]-1,2,4-oxadiazol-3-yl}-2-thienyl)methyl]azetidine-3-carboxylate The crude product of the title compound was synthesized by conducting the reaction similar to that mentioned in Example 1 (1f) using (4-ethyl-5-{5-[4-(3-fluorophenoxy)phenyl]-1,2,4-oxadiazol-3-yl}-2-thienyl)methanol (0.15 g, 0.38 mmol) that was obtained in Example 17 (17b), carbon tetrabromide (0.15 g, 0.45 mmol), triphenylphosphine (0.12 g, 0.45 mmol), methyl 3-azetidinecarboxylate hydrochloride (86 mg, 0.57 mmol), and N,N-diisopropylethylamine (0.19 mL, 1.1 mmol). Subsequently, the crude product of the title compound thus obtained was purified by chromatography using a mixed solvent of ethyl acetate and hexane (5:5) to afford the title compound (0.16 g) in a yield of 85% as a pale yellow oily product.

$^1$HNMR Spectrum (500 MHz, CDCl$_3$) δ ppm: 1.28 (t, 3H, J=7.8 Hz), 3.03 (q, 2H, J=7.8 Hz), 3.33-3.40 (m, 4H), 3.60-3.66 (m, 1H), 3.72 (s, 3H), 3.79 (s, 2H), 6.80 (dt, 1H, J=7.4 Hz, 2.4 Hz), 6.86-6.94 (m, 3H), 7.13 (d, 2H, J=8.8 Hz), 7.35 (q, 1H, J=8.3 Hz), 8.17 (d, 2H, J=8.8 Hz). IR Spectrum (liquid film): 1346, 1485, 1498, 1514, 1603, 1737 cm$^{-1}$. Mass Spectrum (FAB$^+$) m/z: 494 ((M+H)$^+$).

(17d) 1-[(4-Ethyl-5-{5-[4-(3-fluorophenoxy)phenyl]-1,2,4-oxadiazol-3-yl}-2-thienyl)methyl]azetidine-3-carboxylic acid The title compound (83 mg) was synthesized in a yield of 54% as a white crystalline solid by conducting the reaction similar to that mentioned in Example 2 (2e) using methyl 1-[(4-ethyl-5-{5-[4-(3-fluorophenoxy)phenyl]-1,2,4-oxadiazol-3-yl}-2-thienyl)methyl]azetidine-3-carboxylate (0.16 mg, 0.32 mmol) that was obtained in Example 17 (17c), lithium hydroxide monohydrate (30 mg, 0.71 mmol), and acetic acid (39 µL, 0.71 mmol).

$^1$HNMR Spectrum (500 MHz, CD$_3$OD) δ ppm: 1.29 (t, 3H, J=7.3 Hz), 3.07 (q, 2H, J=7.3 Hz), 3.34 (quintet, 1H, J=8.8 Hz), 3.84-3.90 (m, 2H), 3.94-4.01 (m, 2H), 4.27 (s, 2H), 6.88-7.01 (m, 3H), 7.17 (s, 1H), 7.20 (d, 2H, J=8.8 Hz), 7.44 (q, 1H, J=7.8 Hz), 8.20 (d, 2H, J=8.8 Hz). IR Spectrum (KBr): 1224, 1273, 1342, 1498, 1514, 3428 cm$^{-1}$. Mass Spectrum (FAB$^+$) m/z: 480 ((M+H)$^+$).

Example 18

1-[(5-{5-[4-(2,3-Difluorophenoxy)phenyl]-1,2,4-oxadiazol-3-yl}-4-ethyl-2-thienyl)methyl]azetidine-3-carboxylic acid

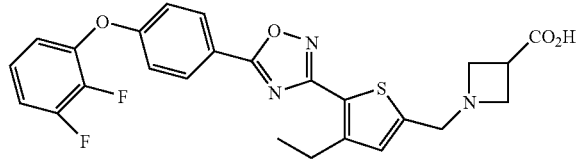

(18a) 4-(2,3-Difluorophenoxy)benzoic acid

The title compound (2.2 g) was synthesized in a yield of 94% as a white crystalline solid by conducting the similar reaction to that mentioned in Example 10 (10e) using 4-fluorobenzaldehyde (1.3 g, 10 mmol), 2,3-difluorophenol (2.0 g, 15 mmol), potassium carbonate (2.8 g, 20 mmol), 2-methyl-2-butene (4.9 ml, 46 mmol), potassium dihydrogenphosphate (3.1 g, 23 mmol) and sodium hypochlorite (2.5 g, 27 mmol).

$^1$HNMR Spectrum (400 MHz, CDCl$_3$) δ ppm: 6.88-6.95 (m, 1H), 6.98-7.12 (m, 4H), 8.08 (d, 2H, J=9.0 Hz). IR Spectrum (KBr): 1170, 1249, 1297, 1498, 1603, 1678, 1703, 2565, 2683, 2839, 2991 cm$^1$. Mass Spectrum (EI$^+$) m/z: 250 (M$^+$).

(18b) (5-{5-[4-(2,3-Difluorophenoxy)phenyl]-1,2,4-oxadiazol-3-yl}-4-ethyl-2-thienyl)methanol The crude product of the title compound was synthesized by conducting the reaction similar to that mentioned in Example 10 (10f) using 5-({[t-butyl(dimethyl)silyl]oxy}methyl)-3-ethyl-N'-hydroxythiophene-2-carboximidamide (0.16 g, 0.50 mmol) that was obtained in Example 10 (10d), 4-(2,3-difluorophenoxy)benzoic acid (0.14 g, 0.55 mmol) that was obtained in Example 18 (18a), N,N'-dicyclohexylcarbodiimide (0.11 g, 0.55 mmol), and 1.0M solution of tetrabutylammonium fluoride in tetrahydrofuran (0.75 mL, 0.75 mmol). Subsequently, the crude product of the title compound thus obtained was purified by chromatography on a silica gel column using a mixed solvent of ethyl acetate and hexane (2:8 to 3:7) as the eluent to afford the title compound (0.18 g) in a yield of 88% as a white crystalline solid.

$^1$HNMR Spectrum (400 MHz, CDCl$_3$) δ ppm: 1.29 (t, 3H, J=7.4 Hz), 3.04 (q, 2H, J=7.4 Hz), 4.84 (s, 2H), 6.90-7.13 (m, 5H), 8.14 (d, 2H, J=9.0 Hz). IR Spectrum (KBr): 1248, 1352, 1474, 1512, 1607, 1628, 3305 cm$^{-1}$. Mass Spectrum (FAB$^+$) m/z: 415 ((M+H)$^+$).

(18c) Methyl 1-[(5-{5-[4-(2,3-difluorophenoxy)phenyl]-1,2,4-oxadiazol-3-yl}-4-ethyl-2-thienyl)methyl]azetidine-3-carboxylate The crude product of the title compound was synthesized by conducting the reaction similar to that mentioned in Example 1 (1f) using (5-{5-[4-(2,3-difluorophenoxy)phenyl]-1,2,4-oxadiazol-3-yl}-4-ethyl-2-thienyl)methanol (0.18 g, 0.43 mmol) that was obtained in Example 18 (18b), carbon tetrabromide (0.17 g, 0.52 mmol), triphenylphosphine (0.14 g, 0.52 mmol), methyl 3-azetidinecarboxylate hydrochloride (0.10 g, 0.86 mmol), and N,N-diisopropylethylamine (0.15 mL, 1.1 mmol). Subsequently, the crude product of the title compound thus obtained was purified by chromatography using a mixed solvent of ethyl acetate and hexane (5:5) to afford the title compound (0.20 g) in a yield of 91% as a pale yellow oily product.

$^1$HNMR Spectrum (500 MHz, CDCl$_3$) δ ppm: 1.28 (t, 3H, J=7.4 Hz), 3.03 (q, 2H, J=7.4 Hz), 3.32-3.40 (m, 4H), 3.58-3.68 (m, 1H), 3.72 (s, 3H), 3.79 (s, 2H), 6.92-6.97 (m, 1H), 7.03-7.16 (m, 4H), 8.16 (d, 2H, J=9.0 Hz). IR Spectrum (liquid film): 1250, 1346, 1476, 1498, 1512, 1557, 1608, 1737 cm$^{-1}$. Mass Spectrum (FAB$^+$) m/z: 512 ((M+H)$^+$).

(18d) 1-[(5-{5-[4-(2,3-Difluorophenoxy)phenyl]-1,2,4-oxadiazol-3-yl}-4-ethyl-2-thienyl)methyl]azetidine-3-carboxylic acid The title compound (77 mg) was synthesized in a yield of 38% as a white crystalline solid by conducting the reaction similar to that mentioned in Example 2 (2e) using methyl 1-[(5-{5-[4-(2,3-difluorophenoxy)phenyl]-1,2,4-oxadiazol-3-yl}-4 ethyl-2-thienyl)methyl]azetidine-3-carboxylate (0.20 g, 0.39 mmol) that was obtained in Example 18 (18c), lithium hydroxide monohydrate (36 mg, 0.86 mmol), and acetic acid (47 µL, 0.86 mmol).

$^1$HNMR Spectrum (500 MHz, CD$_3$OD) δ ppm: 1.29 (t, 3H, J=7.4 Hz), 3.07 (q, 2H, J=7.4 Hz), 3.40 (quintet, 1H, J=6.1 Hz), 4.07 (t, 2H, J=10.2 Hz), 4.13 (t, 2H, J=9.8 Hz), 4.44 (s, 2H), 7.04-7.10 (m, 1H), 7.16-7.28 (m, 4H), 8.19 (d, 2H, J=8.6 Hz). IR Spectrum (KBr): 1498, 1511, 1607, 3320, 3444 cm$^{-1}$. Mass Spectrum (FAB$^+$) m/z: 498 ((M+H)$^+$).

Example 19

1-[(5-{5-[4-(2-Chlorophenoxy)phenyl]-1,2,4-oxadiazol-3-yl}-4-ethyl-2-thienyl)methyl]azetidine-3-carboxylic acid 1/2 oxalate

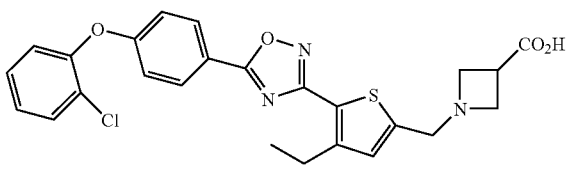

(19a) 4-(2-Chlorophenoxy)benzoic acid

The title compound (1.0 g) was synthesized in a yield of 84% as a yellowish white crystalline solid by conducting the similar reaction to that mentioned in Example 10 (10e) using 4-fluorobenzaldehyde (0.60 g, 5.0 mmol), 2-chlorophenol (0.90 g, 7.0 mmol), potassium carbonate (1.7 g, 13 mmol), 2-methyl-2-butene (2.7 ml, 25 mmol), potassium dihydrogenphosphate (1.7 g, 13 mmol) and sodium hypochlorite (1.4 g, 15 mmol).

$^1$HNMR Spectrum (400 MHz, CDCl$_3$) δ ppm: 6.95 (d, 2H, J=8.9 Hz), 7.13 (dd, 1H, J=7.8 Hz, 1.5 Hz), 7.20 (td, 1H, J=7.8 Hz, 1.5 Hz), 7.31 (td, 1H, J=7.8 Hz, 1.5 Hz), 7.50 (dd, 1H, J=7.8 Hz, 1.5 Hz), 8.08 (d, 2H, J=8.9 Hz).

(19b) (5-{5-[4-(2-Chlorophenoxy)phenyl]-1,2,4-oxadiazol-3-yl}-4-ethyl-2-thienyl)methanol The crude product of the title compound was synthesized by conducting the reaction similar to that mentioned in Example 10 (10f) using 5-({[t-butyl(dimethyl)silyl]oxy}methyl)-3-ethyl-N'-hydroxythiophene-2-carboximidamide (0.16 g, 0.50 mmol) that was obtained in Example 10 (10d), 4-(2-chlorophenoxy)benzoic acid (0.14 g, 0.55 mmol) that was obtained in Example 19 (19a), dicyclohexylcarbodiimide (0.11 g, 0.55 mmol), and 1.0 M solution of tetrabutylammonium fluoride in tetrahydrofuran (0.75 mL, 0.75 mmol). Subsequently, the crude product of the title compound thus obtained was purified by chromatography on a silica gel column using a mixed solvent of ethyl acetate and hexane (3:7 to 5:5) as the eluent to afford the title compound (0.19 g) in a yield of 92% as a white crystalline solid.

$^1$HNMR Spectrum (400 MHz, CDCl$_3$) δ ppm: 1.29 (t, 3H, J=7.4 Hz), 3.04 (q, 2H, J=7.4 Hz), 4.83 (s, 2H), 6.96 (s, 1H), 7.01 (d, 2H, J=8.6 Hz), 7.13 (dd, 1H, J=1.2 Hz, 7.8 Hz), 7.19 (dt, 1H, J=1.2 Hz, 7.4 Hz), 7.30 (dt, 1H, J=1.2 Hz, 7.4 Hz), 7.49 (dd, 1H, J=1.2 Hz, 7.8 Hz), 8.12 (d, 2H, J=9.0 Hz). IR Spectrum (KBr): 1245, 1259, 1353, 1473, 1498, 1517, 1556, 1612, 3329 cm$^{-1}$. Mass Spectrum (FAB$^+$) m/z: 413 ((M+H)$^+$).

(19c) Methyl 1-[(5-{5-[4-(2-chlorophenoxy)phenyl]-1,2,4-oxadiazol-3-yl}-4-ethyl-2-thienyl)methyl]azetidine-3-carboxylate The crude product of the title compound was synthesized by conducting the reaction similar to that mentioned in Example 1 (1f) using (5-{5-[4-(2-chlorophenoxy)phenyl]-1,2,4-oxadiazol-3-yl}-4-ethyl-2-thienyl)methanol (0.19 g, 0.46 mmol) that was obtained in Example 19 (19b), carbon tetrabromide (0.18 g, 0.55 mmol), triphenylphosphine (0.14 g, 0.55 mmol), methyl 3-azetidinecarboxylate hydrochloride (0.10 g, 0.69 mmol), and N,N-diisopropylethylamine (0.16 mL, 0.92 mmol). Subsequently, the crude product of the title compound thus obtained was purified by chromatography using a mixed solvent of ethyl acetate and hexane (5:5) to afford the title compound (0.21 g) in a yield of 91% as a pale yellow oily product.

$^1$HNMR Spectrum (400 MHz, CDCl$_3$) δ ppm: 1.28 (t, 3H, J=7.4 Hz), 3.03 (q, 2H, J=7.4 Hz), 3.32-3.40 (m, 4H), 3.58-3.66 (m, 1H), 3.72 (s, 3H), 3.78 (s, 2H), 6.86 (s, 1H), 7.03 (d, 2H, J=7.9 Hz), 7.15 (dd, 1H, J=1.6 Hz, 7.8 Hz), 7.21 (dt, 1H, J=1.6 Hz, 7.4 Hz), 7.32 (dt, 1H, J=1.6 Hz, 7.4 Hz), 7.51 (dd, 1H, J=1.6 Hz, 7.8 Hz), 8.14 (d, 2H, J=9.0 Hz). IR Spectrum (liquid film): 1475, 1514, 1557, 1581, 1613, 1737 cm$^{-1}$. Mass Spectrum (FAB$^+$) m/z: 510 ((M+H)$^+$).

(19d) 1-[(5-{5-[4-(2-Chlorophenoxy)phenyl]-1,2,4-oxadiazol-3-yl}-4-ethyl-2-thienyl)methyl]azetidine-3-carboxylic acid 1/2 oxalate The title compound (140 mg) was synthesized in a yield of 67% as a white crystalline solid by conducting the reaction similar to that mentioned in Example 1 (1g) using methyl 1-[(5-{5-[4-(2-chlorophenoxy)phenyl]-1,2,4-oxadiazol-3-yl}-4-ethyl-2-thienyl)methyl]azetidine-3-carboxylate (0.21 g, 0.41 mmol) that was obtained in Example 19 (19c), lithium hydroxide monohydrate (38 mg, 0.90 mmol), acetic acid (49 μL, 0.90 mmol), and oxalic acid (18 mg, 0.20 mmol).

$^1$HNMR Spectrum (400 MHz, CD$_3$OD+CD$_3$CO$_2$D (5:1)) δ ppm: 1.29 (t, 3H, J=7.4 Hz), 3.08 (q, 2H, J=7.4 Hz), 3.56 (quintet, 1H, J=7.4 Hz), 4.25 (t, 2H, J=10.2 Hz), 4.29 (t, 2H, J=10.2 Hz), 4.58 (s, 2H), 7.08 (d, 2H, J=9.0 Hz), 7.24 (dd, 1H, J=1.6 Hz, 7.8 Hz), 7.30 (dt, 1H, J=1.6 Hz, 8.2 Hz), 7.42 (dt, 1H, J=1.6 Hz, 8.2 Hz), 7.57 (dd, 1H, J=1.6 Hz, 7.8 Hz), 8.17 (d, 2H, J=9.0 Hz). IR Spectrum (KBr): 1475, 1497, 1515, 1613, 1665, 3418 cm$^{-1}$. Mass Spectrum (FAB$^+$) m/z: 496 ((M+H)$^+$).

Example 20

1-[(4-Ethyl-5-{5-[3-fluoro-4-(3-fluorophenoxy)phenyl]-1,2,4-oxadiazol-3-yl}-2-thienyl)methyl]azetidine-3-carboxylic acid

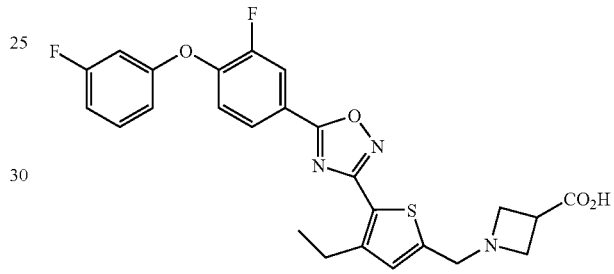

(20a) 3-Fluoro-4-(3-fluorophenoxy)benzoic acid

The title compound (2.0 g) was synthesized in a yield of 84% as a yellowish white crystalline solid by conducting the similar reaction to that mentioned in Example 10 (10e) using 3,4-difluorobenzaldehyde (1.4 g, 10 mmol), 3-fluorophenol (1.6 g, 14 mmol), potassium carbonate (3.5 g, 25 mmol), 2-methyl-2-butene (5.1 ml, 48 mmol), potassium dihydrogenphosphate (3.3 g, 24 mmol), and sodium hypochlorite (2.6 g, 29 mmol).

$^1$HNMR Spectrum (400 MHz, CDCl$_3$) δ ppm: 6.76 (dt, 1H, J=9.8 Hz, 2.3 Hz), 6.82 (dd, 1H, J=8.2 Hz, 2.3 Hz), 6.88 (tdd, 1H, J=8.2 Hz, 2.3 Hz, 0.8 Hz), 7.06 (t, 1H, J=8.2 Hz), 7.31 (td, 1H, J=8.2 Hz, 6.7 Hz), 7.86 (ddd, 1H, J=8.6 Hz, 2.0 Hz, 1.2 Hz), 7.91 (dd, 1H, J=11.0 Hz, 2.0 Hz).

(20b) (4-Ethyl-5-{5-[3-fluoro-4-(3-fluorophenoxy)phenyl]-1,2,4-oxadiazol-3-yl}-2-thienyl)methanol The crude product of the title compound was synthesized by conducting the reaction similar to that mentioned in Example 12 (12a) using 3-fluoro-4-(3-fluorophenoxy)benzoic acid (0.13 g, 0.53 mmol) that was obtained in Example 20 (20a), 1-hydroxybenzotriazole (74 mg, 0.55 mmol), 1-ethyl-3-(3-dimethylaminopropyl)carbodiimide hydrochloride (0.11 g, 0.55 mmol), 5-({[t-butyl(dimethyl)silyl]oxy}methyl)-3-ethyl-N'-hydroxythiophene-2-carboximidamide (0.16 g, 0.50 mmol) that was obtained in Example 10 (10d), and 1.0 M solution of tetrabutylammoniumfluoride in tetrahydrofuran (1.0 mL, 1.0 mmol). Subsequently, the crude product of the title compound thus obtained was purified by chromatography on a silica gel column using a mixed solvent of ethyl acetate and hexane (1:3) as the eluent to afford the title compound (0.18 g) in a yield of 87% as a pale yellow crystalline solid.

$^1$HNMR Spectrum (400 MHz, CDCl$_3$) δ ppm: 1.30 (t, 3H, J=7.4 Hz), 1.89 (t, 1H, J=6.3 Hz), 3.06 (q, 2H, J=7.4 Hz), 4.86 (d, 2H, J=6.3 Hz), 6.79 (dt, 1H, J=9.8 Hz, 2.3 Hz), 6.84 (dd, 1H, J=8.2 Hz, 2.3 Hz), 6.90 (td, 1H, J=8.2 Hz, 2.3 Hz), 6.99 (s, 1H), 7.17 (t, 1H, J=8.2 Hz), 7.34 (td, 1H, J=8.2 Hz, 6.6 Hz), 7.96 (dt, 1H, J=9.0 Hz, 2.0 Hz), 8.03 (dd, 1H, J=10.6 Hz, 2.0 Hz). IR Spectrum (KBr): 1127, 1277, 1354, 1488, 1516, 1558, 1607, 3318 cm$^{-1}$. Mass Spectrum (FAB$^+$) m/z: 415 ((M+H)$^+$).

(20c) Methyl 1-[(4-ethyl-5-{5-[3-fluoro-4-(3-fluorophenoxy)phenyl]-1,2,4-oxadiazol-3-yl}-2-thienyl)methyl]azetidine-3-carboxylate The crude product of the title compound was synthesized by conducting the reaction similar to that mentioned in Example 1 (1f) using (4-ethyl-5-{5-[3-fluoro-4-(3-fluorophenoxy)phenyl]-1,2,4-oxadiazol-3-yl}-2-thienyl)methanol (0.18 g, 0.43 mmol) that was obtained in Example 20 (20b), carbon tetrabromide (0.22 g, 0.65 mmol), triphenylphosphine (0.17 g, 0.65 mmol), methyl 3-azetidinecarboxylate hydrochloride (99 mg, 0.65 mmol), N,N-diisopropylethylamine (0.22 mL, 1.3 mmol). Subsequently, the crude product of the title compound thus obtained was purified by chromatography on a silica gel column using a mixed solvent of ethyl acetate and hexane (1:3 to 1:2) as the eluent to afford the title compound (0.14 g) in a yield of 64% as a pale yellow oily product.

$^1$HNMR Spectrum (400 MHz, CDCl$_3$) δ ppm: 1.28 (t, 3H, J=7.4 Hz), 3.03 (q, 2H, J=7.4 Hz), 3.32-3.43 (m, 3H), 3.60-3.68 (m, 2H), 3.72 (s, 3H), 3.79 (s, 2H), 6.79 (dt, 1H, J=9.8 Hz, 2.3 Hz), 6.85 (dd, 1H, J=8.2 Hz, 2.3 Hz), 6.87 (s, 1H), 6.90 (td, 1H, J=8.6 Hz, 0.8 Hz), 7.17 (t, 1H, J=8.2 Hz), 7.34 (td, 1H, J=8.2 Hz, 6.6 Hz), 7.95 (dt, 1H, J=8.6 Hz, 2.0 Hz), 8.02 (dd, 1H, J=10.6 Hz, 2.0 Hz). IR Spectrum (liquid film): 1128, 1200, 1275, 1348, 1451, 1486, 1513, 1605, 1737 cm$^{-1}$. Mass Spectrum (FAB$^+$) m/z: 512 ((M+H)$^+$).

(20d) 1-[(4-Ethyl-5-{5-[3-fluoro-4-(3-fluorophenoxy)phenyl]-1,2,4-oxadiazol-3-yl}-2-thienyl)methyl]azetidine-3-carboxylic acid The title compound (0.11 g) was synthesized in a yield of 83% as a white crystalline solid by conducting the reaction similar to that mentioned in Example 3 (3e) using methyl 1-[(4-ethyl-5-{5-[3-fluoro-4-(3-fluorophenoxy)phenyl]-1,2,4-oxadiazol-3-yl}-2-thienyl)methyl]azetidine-3-carboxylate (0.14 g, 0.27 mmol) that was obtained in Example 20 (20c) and a 1 N aqueous solution of sodium hydroxide (0.81 mL, 0.81 mmol).

$^1$HNMR Spectrum (400 MHz, CD$_3$CO$_2$D) δ ppm: 1.31 (t, 3H, J=7.4 Hz), 3.10 (q, 2H, J=7.4 Hz), 3.75-3.87 (m, 1H), 4.34-4.45 (m, 2H), 4.50-4.59 (m, 2H), 4.69 (s, 2H), 6.88-7.00 (m, 3H), 7.28 (t, 1H, J=8.6 Hz), 7.34 (s, 1H), 7.37-7.47 (m, 1H), 8.02 (d, 1H, J=8.6 Hz), 8.06 (d, 1H, J=11.0 Hz). IR Spectrum (KBr): 1130, 1278, 1488, 1515, 1607, 3434 cm$^{-1}$. Mass Spectrum (FAB$^+$) m/z: 498 ((M+H)$^+$).

Example 21

1-[(4-Ethyl-5-{5-[4-(2-methoxyphenoxy)phenyl]-1,2,4-oxadiazol-3-yl}-2-thienyl)methyl]azetidine-3-carboxylic acid 1/2 oxalate

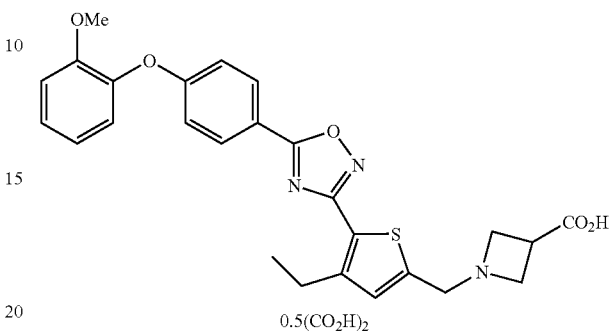

(21a) 4-(2-Methoxyphenoxy)benzoic acid

The title compound (1.6 g) was synthesized in a yield of 89% as a yellowish white crystalline solid by conducting the similar reaction to that mentioned in Example 10 (10e) using 4-fluorobenzaldehyde (1.2 g, 10 mmol), 2-methoxyphenol (1.7 g, 14 mmol), potassium carbonate (3.5 g, 25 mmol), 2-methyl-2-butene (3.9 ml, 37 mmol), potassium dihydrogenphosphate (2.5 g, 19 mmol) and sodium hypochlorite (2.0 g, 22 mmol).

$^1$HNMR Spectrum (400 MHz, CDCl$_3$) δ ppm: 3.80 (s, 3H), 6.93 (dd, 2H, J=8.6 Hz, 2.0 Hz), 6.99 (td, 1H, J=7.4 Hz, 1.6 Hz), 7.04 (dd, 1H, J=8.2 Hz, 1.6 Hz), 7.09 (dd, 1H, J=8.2 Hz, 1.6 Hz), 7.23 (td, 1H, J=7.4 Hz, 1.6 Hz), 8.04 (dd, 1H, J=8.6 Hz, 2.0 Hz).

(21b) (4-Ethyl-5-{5-[4-(2-methoxyphenoxy)phenyl]-1,2,4-oxadiazol-3-yl}-2-thienyl)methanol The crude product of the title compound was synthesized by conducting the reaction similar to that mentioned in Example 12 (12a) using 4-(2-methoxyphenoxy)benzoic acid (0.13 g, 0.53 mmol) that was obtained in Example 21 (21a), 1-hydroxybenzotriazole (74 mg, 0.55 mmol), 1-ethyl-3-(3-dimethylaminopropyl)carbodiimide hydrochloride (0.11 g, 0.55 mmol), 5-({[t-butyl(dimethyl)silyl]oxy}methyl)-3-ethyl-N'-hydroxythiophene-2-carboximidamide (0.16 g, 0.50 mmol) that was obtained in Example 10 (10d), and 1.0 M solution of tetrabutylammoniumfluoride in tetrahydrofuran (1.0 mL, 1.0 mmol). Subsequently, the crude product of the title compound thus obtained was purified by chromatography on a silica gel column using a mixed solvent of ethyl acetate and hexane (2:5) as the eluent to afford the title compound (0.15 g) in a yield of 72% as a yellowish white crystalline solid.

$^1$HNMR Spectrum (400 MHz, CDCl$_3$) δ ppm: 1.29 (t, 3H, J=7.4 Hz), 1.85 (t, 1H, J=6.3 Hz), 3.06 (q, 2H, J=7.4 Hz), 3.81 (s, 3H), 4.85 (d, 2H, J=6.3 Hz), 6.98 (s, 1H), 6.99-7.07 (m, 4H), 7.11 (dd, 1H, J=7.8 Hz, 1.6 Hz), 7.24 (dt, 1H, J=7.8 Hz, 1.6 Hz), 8.11 (dd, 2H, J=9.0 Hz, 2.0 Hz). IR Spectrum (KBr): 1228, 1262, 1354, 1497, 1513, 1612, 3316, 3379 cm$^{-1}$. Mass Spectrum (FAB$^+$) m/z: 409 ((M+H)$^+$).

(21c) Methyl 1-[(4-ethyl-5-{5-[4-(2-methoxyphenoxy)phenyl]-1,2,4-oxadiazol-3-yl}-2-thienyl)methyl]azetidine-3-carboxylate The crude product of the title compound was synthesized by conducting the reaction similar to that mentioned in Example 1 (1f) using (4-ethyl-5-{5-[4-(2-methoxyphenoxy)phenyl]-1,2,4-oxadiazol-3-yl}-2-thienyl)methanol (0.14 g, 0.35 mmol) that was obtained in Example 21 (21b), carbon tetrabromide (0.17 g, 0.53 mmol), triphenylphosphine (0.14 g, 0.53 mmol), methyl 3-azetidinecarboxylate hydrochloride (80 mg, 0.53 mmol), and N,N-diisopropylethylamine (0.18 mL, 1.1 mmol). Subsequently, the crude product of the title compound thus obtained was purified by chromatography on a silica gel column using a mixed solvent of ethyl acetate and hexane (2:5 to 1:2) as the eluent to afford the title compound (89 mg) in a yield of 50% as a colourless oily product.

$^1$HNMR Spectrum (400 MHz, CDCl$_3$) δ ppm: 1.27 (t, 3H, J=7.4 Hz), 3.03 (q, 2H, J=7.4 Hz), 3.31-3.41 (m, 3H), 3.59-3.68 (m, 2H), 3.72 (s, 3H), 3.78 (s, 2H), 3.81 (s, 3H), 6.86 (s, 1H), 6.97-7.07 (m, 4H), 7.11 (dd, 1H, J=8.2 Hz, 1.6 Hz), 7.24 (td, 1H, J=7.4 Hz, 1.6 Hz), 8.10 (dd, 2H, J=9.0 Hz, 2.2 Hz). IR Spectrum (thin film): 1168, 1176, 1201, 1265, 1346, 1455, 1496, 1513, 1613, 1737 cm$^{-1}$. Mass Spectrum (FAB$^+$) m/z: 506 ((M+H)$^+$).

(21d) 1-[(4-Ethyl-5-{5-[4-(2-methoxyphenoxy)phenyl]-1,2,4-oxadiazol-3-yl}-2-thienyl)methyl]azetidine-3-carboxylic acid 1/2 oxalate To a solution of methyl 1-[(4-ethyl-5-{5-[4-(2-methoxyphenoxy)phenyl]-1,2,4-oxadiazol-3-yl}-2-thienyl)methyl]azetidine-3-carboxylate (86 mg, 0.17 mmol) that was obtained in Example 21 (21c) in dioxane (3 ml) was added a 1N aqueous solution of sodium hydroxide (0.51 ml, 0.51 mmol) with stirring, and the resulting mixture was stirred at room temperature for 2 hours. After stirring, acetic acid (29 μl, 0.51 mmol) was added to the reaction mixture to quench the reaction, and the resulting mixture was evaporated in vacuo. Subsequently, to the residue obtained were added successively methanol (2 ml) and water (1 ml) with stirring, and furthermore a solution of oxalic acid (8 mg, 0.09 mmol) in methanol (0.5 ml) was added, and then the resulting mixture was stirred for 30 minutes. The white solid precipitated was collected by filtration using a Kiriyama funnel, washed with a mixed solvent of water and methanol (3:7) and dried in vacuo to afford the title compound (63 mg) in a yield of 69% as a white crystalline solid.

$^1$HNMR Spectrum (400 MHz, CD$_3$CO$_2$D) δ ppm: 1.30 (t, 3H, J=6.8 Hz), 3.09 (q, 2H, J=6.8 Hz), 3.78 (s, 3H), 3.76-3.89 (m, 1H), 4.33-4.43 (m, 2H), 4.50-4.61 (m, 2H), 4.68 (s, 2H), 6.98-7.07 (m, 3H), 7.10-7.18 (m, 2H), 7.27 (t, 1H, J=6.6 Hz), 7.34 (s, 1H), 8.12 (d, 2H, J=8.6 Hz). IR Spectrum (KBr): 1233, 1265, 1346, 1497, 1515, 1614, 3422 cm$^{-1}$. Mass Spectrum (FAB$^+$) m/z: 492 ((M+H)$^+$).

Example 22

1-({3-Ethyl-5-[5-(4-phenoxyphenyl)-1,2,4-oxadiazol-3-yl]-2-thienyl}methyl)azetidine-3-carboxylic acid

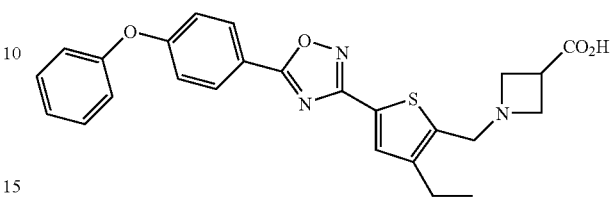

(22a) [5-({[t-Butyl(dimethyl)silyl]oxy}methyl)-3-ethyl-2-thienyl]methanol

To a solution of 5-({[t-butyl(dimethyl)silyl]oxy}methyl)-3-ethylthiophene-2-carboxaldehyde that was obtained in Example 10 (10b) (1.5 g, 5.8 mmol) in methanol (10 mL) were slowly added sodium borohydride (0.22 g, 5.8 mmol) at 0° C. with stirring, and the resulting mixture was stirred for 30 minutes. After stirring, the solvent was evaporated in vacuo. Subsequently, a solution of the residue obtained in ether was poured into water (20 mL) and extracted with ether. The extract was washed with a saturated aqueous solution of sodium chloride and dried over magnesium sulfate. After filtration, the filtrate was evaporated in vacuo, and the crude product of the title compound thus obtained was purified by chromatography on a silica gel column using a mixed solvent of ethyl acetate and hexane (1:4 to 3:7) as the eluent to afford the pure title compound (1.4 g) in a yield of 94% as a colourless oily product.

$^1$HNMR Spectrum (400 MHz, CDCl$_3$) δ ppm: 0.11 (s, 6H), 0.93 (s, 9H), 1.18 (t, 3H, J=7.4 Hz), 2.57 (q, 2H, J=7.4 Hz), 4.71 (d, 2H, J=5.9 Hz), 4.80 (s, 2H), 6.72 (s, 1H). IR Spectrum (liquid film): 1075, 1149, 1255, 1362, 1390, 1463, 3352 cm$^{-1}$. Mass Spectrum (FAB$^+$) m/z: 285 ((M−H)$^+$).

(22b) 4-Ethyl-5-[(tetrahydro-2H-pyran-2-yloxy)methyl]thiophene-2-carboxaldehyde To a solution of [5-({[t-butyl(dimethyl)silyl]oxy}methyl)-3-ethyl-2-thienyl]methanol (1.4 g, 5.3 mmol) that was obtained in Example 22 (22a) in dichloromethane (10 ml) were added successively 3,4-dihydro-2H-pyran (0.58 ml, 6.4 mmol) and p-toluenesulfonic acid (10 mg, 0.04 mmol) at 0° C. with stirring, and the resulting mixture was stirred at room temperature for 30 minutes. After stirring, a saturated aqueous solution of sodium hydrogencarbonate (5 ml) was added to the reaction mixture to quench the reaction, and the resulting mixture was poured into water (20 ml) and extracted with ether. The extract was washed with a saturated aqueous solution of sodium chloride and dried over magnesium sulfate. After filtration, the filtrate was evaporated in vacuo. Subsequently, to a solution of the residue obtained in tetrahydrofuran (5 ml) was added a 1.0 M solution of tetrabutylammonium fluoride in tetrahydrofuran (6.4 ml, 6.4 mmol) with stirring, and the resulting mixture was stirred at room temperature for 30 minutes. After stirring, the reaction mixture was poured into water (20 ml) and extracted with ether. The extract was washed with a saturated aqueous solution of sodium chloride and dried over magnesium sulfate. After filtration, the filtrate was evaporated in vacuo. Subsequently, to a solution of the residue obtained in dichloromethane (30 ml) was added molecular sieves 4A (10g), and after cooling to 0° C., pyridinium dichromate (3.3 g, 8.7 mmol) was furthermore added to the resulting mixture with stirring, and the resulting mixture was stirred at room temperature for 2 hours. After stirring, ether (150 ml) was added to the reaction mixture with stirring, and insoluble materials were removed by filtration with silica gel. The filtrate was evaporated in vacuo, and the crude product of the title compound thus obtained was purified by chromatography on a silica gel column using a mixed solvent of ethyl acetate and hexane (0:10 to 2:8) as the eluent to afford the title compound (0.97 g) in a yield of 78% as a colourless oily product.

$^1$HNMR Spectrum (400 MHz, CDCl$_3$) δ ppm: 1.23 (t, 3H, J=7.6 Hz), 1.50-1.92 (m, 6H), 2.61 (q, 2H, J=7.6 Hz), 3.53-3.59 (m, 1H), 3.84-3.92 (m, 1H), 4.65 (d, 1H, J=13.5 Hz), 4.74 (t, 1H, J=3.5 Hz), 4.87 (d, 1H, J=13.5 Hz), 7.55 (s, 1H), 9.80 (s, 1H). IR Spectrum (liquid film): 1023, 1036, 1121, 1158, 1454, 1670, 2873, 2942, 3440 cm$^{-1}$. Mass Spectrum (EI$^+$) m/z: 254 (M$^+$).

(22c) 4-Ethyl-5-[(tetrahydro-2H-pyran-2-yloxy)methyl]thiophene-2-carbonitrile The crude product of the title compound was synthesized by conducting the reaction similar to that mentioned in Example 1 (1c) using 4-ethyl-5-[(tetrahydro-2H-pyran-2-yloxy)methyl]thiophene-2-carbonitrile (0.97 g, 3.6 mmol) that was obtained in Example 22 (22b), hydroxylamine hydrochloride (0.29 g, 3.9 mmol), triethylamine (1.1 mL, 7.2 mmol), and N,N'-dicyclohexylcarbodiimide (0.87 g, 3.9 mmol). Subsequently, the crude product of the title compound thus obtained was purified by chromatography on a silica gel column using a mixed solvent of ethyl acetate and hexane (0:10 to 10:90) as the eluent to afford the title compound (0.86 g) in a yield of 95% as a colourless oily product.

$^1$HNMR Spectrum (400 MHz, CDCl$_3$) δ ppm: 1.19 (t, 3H, J=7.6 Hz), 1.52-1.90 (m, 6H), 2.58 (q, 2H, J=7.6 Hz), 3.52-3.59 (m, 1H), 3.82-3.90 (m, 1H), 4.62 (d, 1H, J=13.3 Hz), 4.71 (t, 1H, J=3.3 Hz), 4.84 (d, 1H, J=13.3 Hz), 7.38 (s, 1H). IR Spectrum (liquid film): 903, 1024, 1036, 1066, 1077, 1123, 1174, 1201, 1342, 1454, 2216, 2873, 2942 cm$^{-1}$. Mass Spectrum (EI$^+$) m/z: 251 (M$^+$).

(22d) 4-Ethyl-N'-hydroxy-5-[(tetrahydro-2H-pyran-2-yloxy)methyl]thiophene-2-carboximidamide The crude product of the title compound was synthesized by conducting the reaction similar to that mentioned in Example 1 (1d) using 4-ethyl-5-[(tetrahydro-2H-pyran-2-yloxy)methyl]thiophene-2-carbonitrile (0.86 g, 3.4 mmol) that was obtained in Example 22 (22c) and a 50% aqueous solution of hydroxylamine (0.5 mL). Subsequently, the crude product of the title compound thus obtained was purified by chromatography on a silica gel column using a mixed solvent of ethyl acetate and hexane (1:3 to 5:5) as the eluent to afford the title compound (0.96 g) in a yield of 98% as a colourless oily product.

$^1$HNMR Spectrum (400 MHz, CDCl$_3$) δ ppm: 1.20 (t, 3H, J=7.6 Hz), 1.47-1.89 (m, 6H), 2.59 (q, 2H, J=7.6 Hz), 3.52-3.59 (m, 1H), 3.87-3.94 (m, 1H), 4.61 (d, 1H, J=12.9 Hz), 4.71 (t, 1H, J=3.3 Hz), 4.80 (d, 1H, J=12.9 Hz), 4.82 (br, 2H), 7.07 (s, 1H), 7.23 (br, 1H). IR Spectrum (liquid film): 1022, 1117, 1344, 1390, 1588, 1635, 2872, 2942, 3353 cm$^{-1}$. Mass Spectrum (FAB$^+$) m/z: 285 ((M+H)$^+$).

(22e) 3-{4-Ethyl-5-[(tetrahydro-2H-pyran-2-yloxy)methyl]-2-thienyl}-5-(4-phenoxyphenyl)-1,2,4-oxadiazole The crude product of the title compound was synthesized by conducting the similar reaction to that mentioned in Example 5 (5a) using 4-phenoxybenzoic acid (0.16 g, 0.73 mmol), 1-hydroxybenzotriazole (0.12 g, 0.76 mmol), 1-ethyl-3-(3-dimethylaminopropyl)carbodiimide hydrochloride (0.15 g, 0.76 mmol), 4-ethyl-N'-hydroxy-5-[(tetrahydro-2H-pyran-2-yloxy)methyl]thiophene-2-carboximidamide (0.17 g, 0.69 mmol) that was obtained in Example 22 (22d) and tetrabutylammonium fluoride (a 1.0 M solution in tetrahydrofuran, 14 ml, 1.4 mmol). Subsequently, the crude product of the title compound thus obtained was purified by chromatography on a silica gel column using a mixed solvent of ethyl acetate and hexane (0:10 to 2:8) as the eluent to afford the title compound (0.25 g) in a yield of 78% as a colourless oily product.

$^1$HNMR Spectrum (400 MHz, CDCl$_3$) δ ppm: 1.26 (t, 3H, J=7.6 Hz), 1.50-1.93 (m, 6H), 2.65 (q, 2H, J=7.6 Hz), 3.55-3.61 (m, 1H), 3.89-3.96 (m, 1H), 4.69 (d, 1H, J=12.9 Hz), 4.77 (t, 1H, J=3.5 Hz), 4.88 (d, 1H, J=12.9 Hz), 7.07-7.12 (m, 4H), 7.20-7.25 (m, 1H), 7.41 (d, 1H, J=7.4 Hz), 7.43 (d, 1H, J=7.4 Hz), 7.66 (s, 1H), 8.15 (d, 2H, J=9.0 Hz). IR Spectrum (liquid film): 761, 1022, 1167, 1245, 1488, 1589, 1613, 2872, 2940 cm$^{-1}$. Mass Spectrum (FAB$^+$) m/z: 463 ((M+H)$^+$).

(22f) {3-Ethyl-5-[5-(4-phenoxyphenyl)-1,2,4-oxadiazol-3-yl]-2-thienyl}methanol To a solution of 3-{4-ethyl-5-[(tetrahydro-2H-pyran-2-yloxy)methyl]-2-thienyl}-5-(4-phenoxyphenyl)-1,2,4-oxadiazole (0.25 g, 0.54 mmol) that was obtained in Example 22 (22e) in ethanol (5 ml) was added pyridinium p-toluenesulfonate (0.014 g, 0.54 mmol) with stirring, and the resulting mixture was stirred at 60° C. for 4 hours. After stirring, the reaction mixture was poured into water (20 ml) to quench the reaction and extracted with ethyl acetate. The extract was washed with a saturated aqueous solution of sodium chloride and dried over magnesium sulfate. After filtration, the filtrate was evaporated in vacuo to afford the title compound (0.19 g) in a yield of 92% as a crystalline white solid.

$^1$HNMR Spectrum (400 MHz, CDCl$_3$) δ ppm: 1.27 (t, 3H, J=7.6 Hz), 1.79 (t, 1H, J=5.9 Hz), 2.67 (q, 2H, J=7.6 Hz), 4.83 (d, 2H, J=5.9 Hz), 7.07-7.12 (m, 4H), 7.20-7.25 (m, 1H), 7.41 (d, 1H, J=7.4 Hz), 7.43 (d, 1H, J=7.4 Hz), 7.67 (s, 1H), 8.15 (d, 2H, J=8.6 Hz). IR Spectrum (KBr): 760, 998, 1232, 1422, 1487, 1579, 1591, 1615, 2964, 3452 cm$^{-1}$. Mass Spectrum (FAB$^+$) m/z: 379 ((M+H)$^+$).

(22g) Methyl 1-({3-ethyl-5-[5-(4-phenoxyphenyl)-1,2,4-oxadiazol-3-yl]-2-thienyl}methyl)azetidine-3-carboxylate The crude product of the title compound was synthesized by conducting the reaction similar to that mentioned in Example 1 (1f) using {3-ethyl-5-[5-(4-phenoxyphenyl)-1,2,4-oxadiazol-3-yl]-2-thienyl}methanol (0.19 g, 0.50 mmol) that was obtained in Example 22 (22f), carbon tetrabromide (0.33 g, 0.99 mmol), triphenylphosphine (0.26 g, 0.99 mmol), methyl 3-azetidinecarboxylate hydrochloride (0.11 g, 0.75 mmol), N,N-diisopropylethylamine (0.22 mL, 1.2 mmol). Subsequently, the crude product of the title compound thus obtained was purified by chromatography on a silica gel column using a mixed solvent of ethyl acetate and hexane (2:8 to 4:6) as the eluent to afford the title compound (0.17 g) in a yield of 72% as a pale yellow crystalline solid.

$^1$HNMR Spectrum (500 MHz, CDCl$_3$) δ ppm: 1.23 (t, 3H, J=7.6 Hz), 2.61 (q, 2H, J=7.6 Hz), 3.33-3.41 (m, 3H), 3.62-3.70 (m, 2H), 3.72 (s, 3H), 3.77 (s, 2H), 7.06-7.12 (m, 4H), 7.20-7.24 (m, 1H), 7.38-7.43 (m, 2H), 7.62 (s, 1H), 8.14 (d, 2H, J=8.8 Hz). IR Spectrum (KBr): 1167, 1249, 1367, 1490, 1589, 1736, 2963 cm$^{-1}$. Mass Spectrum (FAB$^+$) m/z: 476 ((M+H)$^+$).

(22h) 1-({3-Ethyl-5-[5-(4-phenoxyphenyl)-1,2,4-oxadiazol-3-yl]-2-thienyl}methyl)azetidine-3-carboxylic acid The title compound (0.16 g) was synthesized in a yield of 95% as a white crystalline solid by conducting the reaction similar to that mentioned in Example 3 (3e) using methyl 1-({3-ethyl-5-[5-(4-phenoxyphenyl)-1,2,4-oxadiazol-3-yl]-2-thienyl}methyl)azetidine-3-carboxylate (0.17 g, 0.36 mmol) that was obtained in Example 22 (22g), a 1 N aqueous solution of sodium hydroxide (1.1 mL, 1.1 mmol), and acetic acid (62 μL, 1.1 mmol).

$^1$HNMR Spectrum (400 MHz, CD$_3$CO$_2$D) δ ppm: 1.29 (t, 3H, J=7.5 Hz), 2.78 (q, 2H, J=7.5 Hz), 3.75-3.86 (m, 1H), 4.30-4.60 (m, 2H), 4.71 (s, 2H), 7.11-7.17 (m, 4H), 7.22-7.27 (m, 1H), 7.41-7.48 (m, 2H), 7.80 (s, 1H), 8.15-8.21 (m, 2H). IR Spectrum (KBr): 761, 1170, 1241, 1368, 1487, 1591, 1614, 2969, 3536 cm$^{-1}$. Mass Spectrum (FAB$^+$) m/z: 462 ((M+H)$^+$).

Example 23

1-({5-[5-(3-Fluoro-4-isobutylphenyl)-1,2,4-oxadiazol-3-yl]pyridin-2-yl}methyl)azetidine-3-carboxylic acid

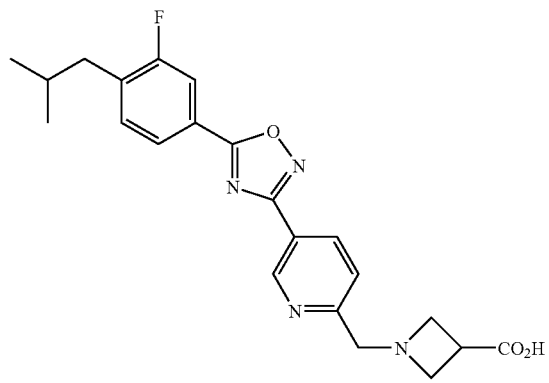

(23a) 5-Bromo-2-({[t-butyl(dimethyl)silyl]oxy}methyl)pyridine

To a solution of 5-bromo-2-formylpyridine (4.6 g, 25 mmol) in methanol (30 ml) was added sodium borohydride (0.93 g, 25 mmol) at 0° C. with stirring, and the resulting mixture was stirred for 1 hour. After evaporating the solvent in vacuo, the residue obtained was diluted with ether, poured into water (20 ml) and extracted with ethyl acetate. The extract was washed with a saturated aqueous solution of sodium chloride and dried over magnesium sulfate. After filtration, the filtrate was evaporated in vacuo. Subsequently, to a solution of the residue obtained and imidazole (3.4 g, 49 mmol) in N,N-dimethylformamide (30 ml) was added t-butyldimethylsilyl chloride (4.1 g, 27 mmol) with stirring, and the resulting mixture was stirred at room temperature for 1 hour. After stirring, the reaction mixture was poured into water (50 ml) and extracted with ether. The extract was washed with a saturated aqueous solution of sodium chloride and dried over magnesium sulfate. After filtration, the filtrate was evaporated in vacuo, and the crude product of the title compound thus obtained was purified by chromatography on a silica gel column using a mixed solvent of ethyl acetate and hexane (1:49 to 1:9) as the eluent to afford the title compound (6.8 g) in a yield of 90% as a white crystalline solid.

$^1$HNMR Spectrum (400 MHz, CDCl$_3$) δ ppm: 0.12 (s, 6H), 0.95 (s, 9H), 4.78 (s, 2H), 7.42 (d, 1H, J=8.6 Hz), 7.82 (dd, 1H, J=2.3 Hz, 8.6 Hz), 8.56 (d, 1H, J=2.3 Hz). IR Spectrum (KBr): 1008, 1104, 1258, 1377, 1471, 1578 cm$^{-1}$. Mass Spectrum (FAB$^+$) m/z: 302 ((M+H)$^+$).

(23b) 6-({[t-Butyl(dimethyl)silyl]oxy}methyl)nicotinonitrile

A solution of 5-bromo-2-({[t-butyl(dimethyl)silyl]oxy}methyl)pyridine (0.30 g, 1.0 mmol) that was obtained in Example 23 (23a), zinc cyanide (0.18 g, 1.5 mmol), bis(dibenzylideneacetone)palladium (18 mg, 0.02 mmol) and 1,1'-bis(diphenylphosphino)ferrocene (44 mg, 0.08 mmol) in N-methyl-2-pyrrolidinone (4 ml) was stirred at 100° C. for 1 hour. After cooling to room temperature, the reaction mixture was poured into water and extracted with ether. The extract was washed with a saturated aqueous solution of sodium chloride and dried over magnesium sulfate. After filtration, the filtrate was evaporated in vacuo, and the crude product of the title compound thus obtained was purified by chromatography on a silica gel column using a mixed solvent of ethyl acetate and hexane (1:9) as the eluent to afford the title compound (0.23 g) in a yield of 93% as a white crystalline solid.

$^1$HNMR Spectrum (400 MHz, CDCl$_3$) δ ppm: 0.14 (s, 6H), 0.96 (s, 9H), 4.87 (s, 2H), 7.67 (d, 1H, J=8.2 Hz), 7.98 (dd, 1H, J=2.0 Hz, 8.2 Hz), 8.78 (d, 1H, J=2.0 Hz). IR Spectrum (KBr): 1110, 1254, 1470, 1594, 2230 cm$^{-1}$. Mass Spectrum (FAB$^+$) m/z: 249 ((M+H)$^+$).

(23c) 6-({[t-Butyl(dimethyl)silyl]oxy}methyl)-N'-hydroxypyridine-3-carboximidamide The crude product of the title compound was synthesized by conducting the similar reaction to that mentioned in Example 1 (1d) using 6-({[t-butyl(dimethyl)silyl]oxy}methyl)nicotinonitrile (2.0 g, 8.1 mmol) that was obtained in Example 23 (23b) and a 40% aqueous solution of hydroxylamine (1 ml). Subsequently, the crude product of the title compound thus obtained was purified by recrystallization from a mixed solvent of ethyl acetate and hexane (1:9) to afford the title compound (2.1 g) in a yield of 94% as a white crystalline solid.

$^1$HNMR Spectrum (500 MHz, CDCl$_3$) δ ppm: 0.13 (s, 6H), 0.96 (s, 9H), 4.86 (s, 2H), 4.89 (br, 2H), 7.56 (d, 1H, J=8.3 Hz), 7.95 (dd, 1H, J=2.4 Hz, 8.3 Hz), 8.77 (d, 1H, J=2.4 Hz). IR Spectrum (KBr): 1258, 1380, 1397, 1645, 3166, 3299, 3467 cm$^{-1}$. Mass Spectrum (FAB$^+$) m/z: 282 ((M+H)$^+$).

(23d) 4-Bromo-2-fluoro-1-(2-methylprop-1-en-1-yl)benzene

To a solution of isopropyltriphenylphosphonium iodide (0.65 g, 1.5 mmol) in N,N-dimethylformamide (6 ml) was added slowly a solution of potassium t-butoxide (0.18 g, 1.6 mmol) in N,N-dimethylformamide (2 ml) at 0° C. with stirring, and the resulting mixture was stirred for 30 minutes. Furthermore, to the reaction mixture was added a solution of 4-bromo-2-fluorobenzaldehyde (0.20 g, 1.0 mmol) in N,N-dimethylformamide (2 ml) at the same temperature with stirring, and after raising the reaction temperature to room temperature, the resulting mixture was furthermore stirred for 1 hour. After stirring, a saturated aqueous solution of ammonium chloride (5 ml) was added to the reaction mixture to quench the reaction, and the resulting mixture was poured into water (20 ml) and extracted with ethyl acetate. The extract was washed with a saturated aqueous solution of sodium chloride and dried over sodium sulfate. After filtration, the filtrate was evaporated in vacuo, and the crude product of the title compound thus obtained was purified by chromatography on a silica gel column using a mixed solvent of ethyl acetate and hexane (0:10 to 5:95) as the eluent to afford the title compound (0.19 g) in a yield of 82% as a colourless oily product.
$^1$HNMR Spectrum (400 MHz, CDCl$_3$) δ ppm: 1.76 (s, 3H), 1.92 (s, 3H), 6.13 (s, 1H), 7.09 (t, 1H, J=8.2 Hz), 7.19-7.24 (m, 2H). IR Spectrum (liquid film): 1403, 1483, 1562, 1599 cm$^{-1}$. Mass Spectrum (EI$^+$) m/z: 228 (M$^+$).

(23e) 3-Fluoro-4-isobutylbenzoic acid

To a solution of 4-bromo-2-fluoro-1-(2-methylprop-1-en-1-yl)benzene (0.19 g, 0.81 mmol) that was obtained in Example 23 (23d) in tetrahydrofuran (4 ml) was added dropwise a 1.6 M solution of n-butyllithium in hexane (0.62 ml, 0.97 mmol) at −78° C. with stirring, and the resulting mixture was stirred at the same temperature for 1 hour while bubbling carbon dioxide into the solution. After stirring, a 1N aqueous sodium hydroxide solution (2 ml) was added to the reaction mixture to quench the reaction, and the resulting aqueous layer was washed with ether, acidified with a 10M aqueous hydrochloric acid solution and extracted with ethyl acetate again. The extract was washed with a saturated aqueous solution of sodium chloride and dried over sodium sulfate. After filtration, the filtrate was evaporated in vacuo. Subsequently, to a solution of the residue obtained in ethanol (3 ml) was added 10% palladium on carbon (30 mg), and the resulting mixture was stirred at room temperature for 1 hour under a hydrogen atmosphere. After stirring, the reaction mixture was filtered with Celite, and the filtrate was evaporated in vacuo to afford the title compound (0.12 g) in a yield of 77% as a white crystalline solid.
$^1$HNMR Spectrum (400 MHz, CDCl$_3$) δ ppm: 0.93 (t, 6H, J=6.6 Hz), 1.88-2.00 (m, 1H), 2.58 (d, 2H, J=7.4 Hz), 7.25 (t, 1H, J=7.8 Hz), 7.73 (dd, 1H, J=7.8 Hz, 1.6 Hz), 7.81 (dd, 1H, J=10.2 Hz, 1.6 Hz).

(23f) {5-[5-(3-Fluoro-4-isobutylphenyl)-1,2,4-oxadiazol-3-yl]pyridin-2-yl}methanol The crude product of the title compound was synthesized by conducting the reaction similar to that mentioned in Example 12 (12a) using 3-fluoro-4-isobutylbenzoic acid (0.12 g, 0.63 mmol) that was obtained in Example 23 (23e), 1-hydroxybenzotriazole (89 mg, 0.66 mmol), 1-ethyl-3-(3-dimethylaminopropyl)carbodiimide hydrochloride (0.13 g, 0.66 mmol), 6-({[t-butyl(dimethyl)silyl]oxy}methyl)-N'-hydroxypyridine-3-carboximidamide (0.17 g, 0.60 mmol) that was obtained in Example 23 (23c), and 1.0 M solution of tetrabutylammoniumfluoride in tetrahydrofuran (1.2 mL, 1.2 mmol). Subsequently, the crude product of the title compound thus obtained was purified by chromatography on a silica gel column using a mixed solvent of ethyl acetate and hexane (2:3 to 1:1) as the eluent to afford the title compound (0.16 g) in a yield of 80% as a white crystalline solid.
$^1$HNMR Spectrum (400 MHz, CDCl$_3$) δ ppm: 0.96 (d, 6H, J=6.6 Hz), 1.62 (bs, 1H), 1.91-2.04 (m, 1H), 2.62 (d, 2H, J=8.2 Hz), 4.87 (s, 2H), 7.36 (t, 1H, J=7.8 Hz), 7.43 (d, 1H, J=8.2 Hz), 7.87 (dd, 1H, J=10.2 Hz, 1.6 Hz), 7.93 (dd, 1H, J=7.8 Hz, 1.6 Hz), 8.44 (dd, 1H, J=8.2 Hz, 2.0 Hz), 9.34 (d, 1H, J=1.6 Hz). IR Spectrum (KBr): 1030, 1128, 1394, 1500, 1560, 1594, 1612, 3170 cm$^{-1}$. Mass Spectrum (FAB$^+$) m/z: 328 ((M+H)$^+$).

(23g) Methyl 1-({5-[5-(3-fluoro-4-isobutylphenyl)-1,2,4-oxadiazol-3-yl]pyridin-2-yl}methyl)azetidine-3-carboxylate {5-[5-(3-Fluoro-4-isobutylphenyl)-1,2,4-oxadiazol-3-yl]pyridin-2-yl}methanol (0.16 g, 0.47 mmol) that was obtained in Example 23 (23H), carbon tetrabromide (0.23 g, 0.71 mmol), and triphenylphosphine (0.19 g, 0.71 mmol) were dissolved in dichloromethane (6 ml) at 0° C. and stirred at the same temperature for 10 minutes. After stirring, the reaction mixture was evaporated in vacuo, and the residue obtained was purified by chromatography on a silica gel column using a mixed solvent of ethyl acetate and hexane (1:6) to afford the reaction intermediate. Subsequently, to a solution of the reaction intermediate obtained in dichloromethane (7 ml) were added successively methyl 3-azetidinecarboxylate hydrochloride (0.11 g, 0.71 mmol) and N,N-diisopropylethylamine (0.25 ml, 1.4 mmol) with stirring, and the resulting mixture was stirred at room temperature for 13 hours. After stirring, a saturated aqueous solution of sodium hydrogencarbonate (2 ml) was added to the reaction mixture to quench the reaction, and the resulting mixture was poured into water (20 ml) and extracted with ethyl acetate. The extract was washed with a saturated aqueous solution of sodium chloride and dried over sodium sulfate. After filtration, the filtrate was evaporated in vacuo, and the crude product of the title compound thus obtained was purified by chromatography on a silica gel column using a mixed solvent of ethyl acetate and hexane (1:12) as the eluent to afford the title compound (0.12 g) in a yield of 59% as a white crystalline solid.
$^1$HNMR Spectrum (400 MHz, CDCl$_3$) δ ppm: 0.96 (d, 6H, J=6.6 Hz), 1.90-2.04 (m, 1H), 2.62 (d, 2H, J=7.0 Hz), 3.35-3.46 (m, 1H), 3.48 (t, 2H, J=7.2 Hz), 3.66 (t, 2H, J=7.4 Hz), 3.73 (s, 3H), 3.87 (s, 2H), 7.35 (t, 1H, J=8.2 Hz), 7.48 (d, 1H, J=7.4 Hz), 7.86 (dd, 1H, J=10.0 Hz, 1.6 Hz), 7.93 (dd, 1H, J=7.8 Hz, 1.6 Hz), 8.39 (dd, 1H, J=8.2 Hz, 2.1 Hz), 9.30 (d, 1H, J=1.2 Hz). IR Spectrum (KBr): 1218, 1340, 1373, 1398, 1500, 1559, 1729 cm$^{-1}$. Mass Spectrum (FAB$^+$) m/z: 425 ((M+H)$^+$).

(23h) 1-({5-[5-(3-Fluoro-4-isobutylphenyl)-1,2,4-oxadiazol-3-yl]pyridin-2-yl}methyl)azetidine-3-carboxylic acid The title compound (90 mg) was synthesized in a yield of 81% as a white crystalline solid using methyl 1-({5-[5-(3-fluoro-4-isobutylphenyl)-1,2,4-oxadiazol-3-yl]pyridin-2-yl}methyl)azetidine-3-carboxylate (0.12 g, 0.27 mmol) that was obtained in Example 23 (23g) and a 1 N aqueous solution of sodium hydroxide (0.81 mL, 0.81 mmol) by conducting the reaction similar to that mentioned in Example 3 (3e).
$^1$HNMR Spectrum (400 MHz, CD$_3$CO$_2$D) δ ppm: 0.97 (d, 6H, J=6.6 Hz), 1.93-2.05 (m, 1H), 2.65 (d, 2H, J=7.0 Hz), 3.83-3.94 (m, 1H), 4.48-4.57 (m, 2H), 4.60-4.71 (m, 2H), 4.82 (s, 2H), 7.47 (t, 1H, J=7.8 Hz), 7.77 (d, 1H, J=8.2 Hz), 7.92 (d, 1H, J=9.8 Hz), 7.99 (d, 1H, J=7.8 Hz), 8.60 (d, 1H, J=8.2 Hz), 9.34 (s, 1H). IR Spectrum (KBr): 1129, 1344, 1367, 1399, 1500, 1602, 1627, 2128, 2958 cm$^{-1}$. Mass Spectrum (FAB$^+$) m/z: 411 ((M+H)$^+$).

Example 24

1-({5-[5-(3-Chloro-4-isobutylphenyl)-1,2,4-oxadiazol-3-yl]-6-methylpyridin-2-yl}methyl)azetidine-3-carboxylic acid

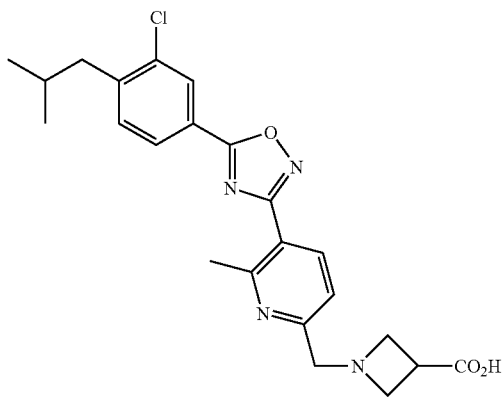

(24a) 2-(Methylthio)-6-{[(triisopropylsilyl)oxy]methyl}nicotinonitrile

To a solution of 6-formyl-2-(methylthio)nicotinonitrile (1.0 g, 5.6 mmol) in methanol (10 ml) was slowly added sodium borohydride at 0° C. with stirring, and the resulting mixture was stirred at the same temperature for 10 minutes. After evaporating the solvent in vacuo, the residue obtained was diluted with ethyl acetate, poured into water (20 ml) and extracted with ethyl acetate. The extract was washed with a saturated aqueous solution of sodium chloride and dried over magnesium sulfate. After filtration, the filtrate was evaporated in vacuo. Subsequently, to a solution of the residue obtained and imidazole (0.76 g, 11 mmol) in N,N-dimethylformamide (6 ml) was added triisopropylsilyl chloride (1.3 ml, 6.2 mmol) with stirring, and the resulting mixture was stirred at room temperature for 2 hours. After stirring, the reaction mixture was poured into water (20 ml) and extracted with ether. The extract was washed with a saturated aqueous solution of sodium chloride and dried over magnesium sulfate. After filtration, the filtrate was evaporated in vacuo, and the crude product of the title compound thus obtained was purified by chromatography on a silica gel column using a mixed solvent of ethyl acetate and hexane (0:10 to 3:97) as the eluent to afford the title compound (1.7 g) in a yield of 91% as a colourless oily product.

$^1$HNMR Spectrum (400 MHz, CDCl$_3$) δ ppm: 1.10 (d, 18H, J=6.6 Hz), 1.18-1.25 (m, 3H), 2.60 (s, 3H), 4.89 (s, 2H), 7.34 (d, 1H, J=7.8 Hz), 7.80 (d, 1H, J=7.8 Hz). IR Spectrum (KBr): 1372, 1423, 1552, 1573, 2220 cm$^{-1}$. Mass Spectrum (FAB$^+$) m/z: 337 ((M+H)$^+$).

(24b) 2-(Methylsulfonyl)-6-{[(triisopropylsilyl)oxy]methyl}nicotinonitrile

To a solution of 2-(methylthio)-6-{[(triisopropylsilyl)oxy]methyl}nicotinonitrile (1.5 g, 4.5 mmol) that was obtained in Example 24 (24a) in ethanol (10 ml) was added m-chlorobenzoic acid (2.3 g, 14 mmol) at 0° C. with stirring, and after raising the reaction temperature to room temperature, the resulting mixture was stirred for 3 hours and then evaporated in vacuo. Subsequently, to a solution of the residue obtained in ether (20 ml) was added a saturated aqueous solution of potassium carbonate (10 ml) with stirring, and the resulting mixture was stirred for 1 hour. After stirring, the reaction mixture was poured into water (20 ml) and extracted with ether. The extract was washed with a saturated aqueous solution of sodium chloride and dried over magnesium sulfate. After filtration, the filtrate was evaporated in vacuo, and the crude product of the title compound thus obtained was purified by chromatography on a silica gel column using a mixed solvent of ethyl acetate and hexane (2:8 to 3:7) as the eluent to afford the title compound (1.7 g) in a yield of 100% as a white crystalline solid.

$^1$HNMR Spectrum (400 MHz, CDCl$_3$) δ ppm: 1.12 (d, 18H, J=6.8 Hz), 1.19-1.28 (m, 3H), 3.36 (s, 3H), 5.02 (s, 2H), 7.99 (d, 1H, J=7.8 Hz), 8.26 (d, 1H, J=7.8 Hz). IR Spectrum (KBr): 1317, 1384, 1463, 1585, 2237 cm$^{-1}$. Mass Spectrum (FAB$^+$) m/z: 369 ((M+H)$^+$).

(24c) 2-Methyl-6-{[(triisopropylsilyl)oxy]methyl}nicotinonitrile

To a solution of 2-(methylsulfonyl)-6-{[(triisopropylsilyl)oxy]methyl}nicotinonitrile (0.80 g, 2.2 mmol) that was obtained in Example 24 (24b) in ether (10 ml) was added a 3.0 M solution of methylmagnesium bromide in ether (1.5 ml, 4.4 mmol) at −78° C. with stirring, and the resulting mixture was stirred at the same temperature for 1 hour. After stirring, a saturated aqueous solution of ammonium chloride (1 ml) was added to the reaction mixture to quench the reaction, and the resulting mixture was poured into water (20 ml) and extracted with ether. The extract was washed with a saturated aqueous solution of sodium chloride and dried over magnesium sulfate. After filtration, the filtrate was evaporated in vacuo, and the crude product of the title compound thus obtained was purified by chromatography on a silica gel column using a mixed solvent of ethyl acetate and hexane (0:10 to 1:9) as the eluent to afford the title compound (0.64 g) in a yield of 95% as a white crystalline solid.

$^1$HNMR Spectrum (400 MHz, CDCl$_3$) δ ppm: 1.09 (d, 18H, J=6.6 Hz), 1.18-1.26 (m, 3H), 2.74 (s, 3H), 4.92 (s, 2H), 7.55 (d, 1H, J=7.8 Hz), 7.92 (d, 1H, J=7.8 Hz). IR Spectrum (KBr): 1128, 1410, 1463, 1567, 1590, 2227 cm$^{-1}$. Mass Spectrum (FAB$^+$) m/z: 305 ((M+H)$^+$).

(24d) N'-Hydroxy-2-methyl-6-{[(triisopropylsilyl)oxy]methyl}pyridine-3-carboximidamide The crude product of the title compound was synthesized by conducting the reaction similar to that mentioned in Example 1 (1d) using 2-methyl-6-{[(triisopropylsilyl)oxy]methyl}nicotinonitrile (0.63 g, 2.1 mmol) that was obtained in Example 24 (24c) and a 40% aqueous solution of hydroxylamine (0.5 mL). Subsequently, the crude product of the title compound thus obtained was purified by recrystallization from a mixed solvent of ethyl acetate and hexane (1:9) to afford the title compound (0.61 g) in a yield of 86% as a white crystalline solid.

$^1$HNMR Spectrum (400 MHz, CDCl$_3$) δ ppm: 1.09 (d, 18H, J=6.8 Hz), 1.15-1.26 (m, 3H), 2.63 (s, 3H), 4.79 (brs, 2H), 4.92 (s, 2H), 7.18 (br, 1H), 7.46 (d, 1H, J=7.8 Hz), 7.72 (d, 1H, J=7.8 Hz). IR Spectrum (KBr): 1124, 1462, 1579, 1597, 1644, 3050, 3337, 3449 cm$^{-1}$. Mass Spectrum (FAB$^+$) m/z: 338 ((M+H)$^+$).

(24e) (4-Bromo-2-chlorophenyl)methanol

To a solution of 4-bromo-2-chlorobenzoic acid (3.1 g, 13.2 mmol) in tetrahydrofuran (30 ml) was added a 1.0 M solution of borane-tetrahydrofuran complex in tetrahydrofuran (13.8 ml, 13.8 mmol) at 0° C. with stirring, and the resulting mixture was stirred at the same temperature for 20 minutes, and after raising the reaction temperature to room temperature, the reaction mixture was furthermore stirred for 4 hours. After stirring, water (10 ml) was added to the reaction mixture to quench the reaction, and the resulting mixture was poured into a saturated aqueous solution of sodium hydrogencarbonate (50 ml) and extracted with ethyl acetate. The extract was washed with a saturated aqueous solution of sodium chloride and dried over sodium sulfate. After filtration, the filtrate was evaporated in vacuo, and the crude product of the title compound thus obtained was purified by chromatography on a silica gel column using a mixed solvent of ethyl acetate and hexane (1:9 to 7:3) as the eluent to afford the title compound (2.8 g) in a yield of 97% as a white crystalline solid.

$^1$HNMR Spectrum (400 MHz, CDCl$_3$) δ ppm: 7.51 (d, 1H, J=2.0 Hz), 7.40 (dd, 1H, J=8.2 Hz, 2.0 Hz), 7.36 (d, 1H, J=8.2 Hz), 4.73 (d, 2H, J=6.3 Hz), 1.90 (t, 1H, J=6.3 Hz). IR Spectrum (KBr): 1036, 1063, 1385, 1469, 1561, 1586, 3239 cm$^{-1}$. Mass Spectrum (EI$^+$) m/z: 220 (M$^+$).

(24f) 4-Bromo-2-chlorobenzaldehyde

To a solution of (4-bromo-2-chlorophenyl)methanol (2.8 g, 12.8 mmol) that was obtained in Example 24 (24e) in dichloromethane (50 ml) was added pyridinium dichromate (7.2 g, 19.2 mmol) with stirring, and the resulting mixture was stirred at room temperature for 1 hour. After stirring, ether (250 ml) was added to the reaction mixture under stirring, and the resulting mixture was filtered with Celite. The filtrate was evaporated in vacuo, and the crude product of the title compound thus obtained was purified by chromatography on a silica gel column using a mixed solvent of ethyl acetate and hexane (1:20) as the eluent to afford the title compound (2.0 g, yield: 70%) as a white crystalline solid.

$^1$HNMR Spectrum (400 MHz, CDCl$_3$) δ ppm: 7.55 (dd, 1H, J=8.2 Hz, 1.6 Hz), 7.66 (d, 1H, J=1.6 Hz), 7.79 (d, 1H, J=8.2 Hz), 10.42 (s, 1H). IR Spectrum (KBr): 1201, 1374, 1577, 1693 cm$^{-1}$. Mass Spectrum (EI$^+$) m/z: 218 (M$^+$).

(24g) 4-Bromo-2-chloro-1-(2-methylprop-1-en-1-yl) benzene

The crude product of the title compound was synthesized by conducting the similar reaction to that mentioned in Example 23 (23d) using isopropyltriphenylphosphonium iodide (5.4 g, 12.6 mmol), potassium t-butoxide (1.5 g, 13.5 mmol) and 4-bromo-2-chlorobenzaldehyde (2.0 g, 9.0 mmol) that was obtained in Example 24 (24f). Subsequently, the crude product of the title compound thus obtained was purified by chromatography on a silica gel column using a mixed solvent of ethyl acetate and hexane (0:10 to 6:94) as the eluent to afford the title compound (2.1 g) in a yield of 94% as a colourless oily product.

$^1$HNMR Spectrum (400 MHz, CDCl$_3$) δ ppm: 1.74 (s, 3H), 1.93 (s, 3H), 6.20 (s, 1H), 7.10 (d, 2H, J=8.2 Hz), 7.33 (dd, 1H, J=8.2 Hz, 2.0 Hz), 7.53 (d, 1H, J=2.0 Hz). IR Spectrum (thin film): 1045, 1083, 1373, 1468, 1579 cm$^{-1}$. Mass Spectrum (EI$^+$) m/z: 244 (M$^+$).

(24h) 3-Chloro-4-isobutylbenzoic acid

The title compound (1.5 g) was synthesized in a yield of 99% as a white crystalline solid by conducting the reaction similar to that mentioned in Example 23 (23e) using 4-bromo-2-chloro-1-(2-methylprop-1-en-1-yl)benzene (2.1 g, 8.5 mmol) that was obtained in Example 24 (24g), 1.6 M solution of n-butyllithium in hexane (5.6 mL), and 5% platinum on carbon (200 mg).

$^1$HNMR Spectrum (400 MHz, CDCl$_3$) δ ppm: 0.95 (d, 6H, J=6.6 Hz), 1.96-2.08 (m, 1H), 2.68 (d, 2H, J=7.4 Hz), 7.28 (d, 1H, J=7.8 Hz), 7.90 (d, 1H, J=7.0 Hz), 8.08 (s, 1H). Mass Spectrum (FAB$^+$) m/z: 212 (M$^+$).

(24i) {5-[5-(3-Chloro-4-isobutylphenyl)-1,2,4-oxadiazol-3-yl]-6-methylpyridin-2-yl}methanol The crude product of the title compound was synthesized by conducting the similar reaction to that mentioned in Example 12 (12a) using 3-chloro-4-isobutylbenzoic acid (0.11 g, 0.50 mmol) that was obtained in Example 24 (24h), 1-hydroxybenzotriazole (72 mg, 0.53 mmol), 1-ethyl-3-(3-dimethylaminopropyl)carbodiimide hydrochloride (0.10 g, 0.53 mmol), N'-hydroxy-2-methyl-6-{[(triisopropylsilyl) oxy]methyl}pyridine-3-carboximidamide (0.16 g, 0.48 mmol) that was obtained in Example 24 (24d), and a 1.0 M solution of tetrabutylammonium fluoride in tetrahydrofuran (0.96 ml, 0.96 mmol). Subsequently, the crude product of the tile compound thus obtained was purified by chromatography on a silica gel column using a mixed solvent of ethyl acetate and hexane (1:1) as the eluent to afford the title compound (0.15 g) in a yield of 89% as a crystalline white solid.

$^1$HNMR Spectrum (400 MHz, CDCl$_3$) δ ppm: 0.97 (d, 6H, J=6.8 Hz), 2.00-2.09 (m, 1H), 2.71 (d, 2H, J=7.3 Hz), 2.95 (s, 3H), 3.87 (t, 1H, J=4.9 Hz), 4.81 (d, 2H, J=4.9 Hz), 7.24 (d, 1H, J=7.8 Hz), 7.38 (d, 1H, J=7.8 Hz), 8.01 (dd, 1H, J=7.8 Hz, 1.5 Hz), 8.21 (d, 1H, J=1.5 Hz), 8.39 (d, 1H, J=7.8 Hz). IR Spectrum (KBr): 1332, 1407, 1454, 1591, 3238 cm$^{-1}$. Mass Spectrum (FAB$^+$) m/z: 358 ((M+H)$^+$).

(24j) Methyl 1-({5-[5-(3-chloro-4-isobutylphenyl)-1,2,4-oxadiazol-3-yl]-6-methylpyridin-2-yl}methyl) azetidine-3-carboxylate The crude product of the title compound was synthesized by conducting the similar reaction to that mentioned in Example 23 (23g) using {5-[5-(3-chloro-4-isobutylphenyl)-1,2,4-oxadiazol-3-yl]-6-methylpyridin-2-yl}methanol (0.15 g, 0.42 mmol) that was obtained in Example 24 (24i), carbon tetrabromide (0.22 g, 0.67 mmol), triphenylphosphine (0.18 g, 0.67 mmol), methyl 3-azetidinecarboxylate hydrochloride (96 mg, 0.63 mmol), and N,N-diisopropylethylamine (0.22 ml, 1.3 mmol). Subsequently, the crude product of the title compound thus obtained was purified by chromatography on a silica gel column using a mixed solvent of ethyl acetate and hexane (1:1 to 2:1 or 3:1) as the eluent to afford the title compound (0.11 g) in a yield of 58% as a pale yellowish oily product.

$^1$HNMR Spectrum (400 MHz, CDCl$_3$) δ ppm: 0.97 (d, 6H, J=6.6 Hz), 1.98-2.10 (m, 1H), 2.70 (d, 2H, J=7.4 Hz), 2.91 (s, 3H), 3.34-3.45 (m, 1H), 3.47 (t, 2H, J=7.2 Hz), 3.66 (t, 2H, J=7.6 Hz), 3.73 (s, 3H), 3.83 (s, 2H), 7.32 (d, 1H, J=7.8 Hz), 7.37 (d, 1H, J=7.8 Hz), 8.01 (dd, 1H, J=7.8 Hz, 1.9 Hz), 8.21

(d, 1H, J=1.6 Hz), 8.34 (d, 1H, J=7.8 Hz). IR Spectrum (KBr): 1203, 1332, 1405, 1438, 1450, 1589, 1735, 2957 cm$^{-1}$. Mass Spectrum (FAB$^+$) m/z: 455 ((M+H)$^+$).

(24k) 1-({5-[5-(3-Chloro-4-isobutylphenyl)-1,2,4-oxadiazol-3-yl]-6-methylpyridin-2-yl}methyl)azetidine-3-carboxylic acid The title compound (76 mg) was synthesized in a yield of 72% as a white crystalline solid by conducting the reaction similar to that mentioned in Example 3 (3e) using methyl 1-({5-[5-(3-chloro-4-isobutylphenyl)-1,2,4-oxadiazol-3-yl]-6-methylpyridin-2-yl}methyl)azetidine-3-carboxylate (0.11 g, 0.24 mmol) that was obtained in Example 24 (24j) and a 1 N aqueous solution of sodium hydroxide (0.72 mL, 0.72 mmol).

$^1$HNMR Spectrum (400 MHz, CD$_3$CO$_2$D) δ ppm: 0.98 (d, 6H, J=6.6 Hz), 2.00-2.09 (m, 1H), 2.75 (d, 2H, J=7.0 Hz), 2.93 (s, 3H), 3.83-3.94 (m, 1H), 4.46-4.58 (m, 2H), 4.61-4.71 (m, 2H), 4.77 (s, 2H), 7.49 (d, 1H, J=7.8 Hz), 7.55 (d, 1H, J=7.8 Hz), 8.08 (d, 1H, J=6.6 Hz), 8.23 (s, 1H), 8.53 (d, 1H, J=7.8 Hz). IR Spectrum (KBr): 1335, 1385, 1568, 1589, 1611, 3412, 3480 cm$^{-1}$. Mass Spectrum (FAB$^+$) m/z: 441 ((M+H)$^+$).

Example 25

1-({5-[5-(3-Chloro-4-isobutylphenyl)-1,2,4-oxadiazol-3-yl]-6-ethylpyridin-2-yl}methyl)azetidine-3-carboxylic acid

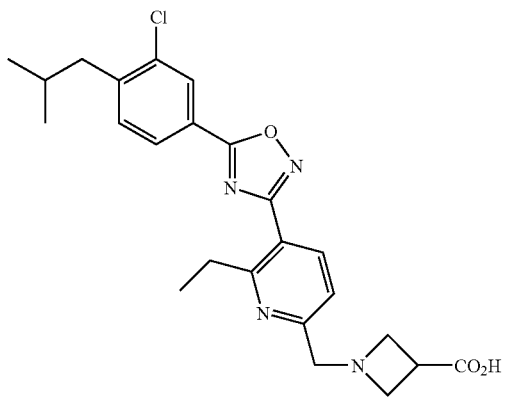

(25a) 2-Ethyl-6-{[(triisopropylsilyl)oxy]methyl}nicotinonitrile

The crude product of the title compound was synthesized by conducting the similar reaction to that mentioned in Example 24 (24c) using 2-(methylsulfonyl)-6-{[(triisopropylsilyl)oxy]methyl}nicotinonitrile (0.78 g, 2.1 mmol) that was obtained in Example 24 (24b) and a 3.0 M solution of ethylmagnesium bromide in ether (1.4 ml, 4.2 mmol). Subsequently, the crude product of the title compound thus obtained was purified by chromatography on a silica gel column using a mixed solvent of ethyl acetate and hexane (0:10 to 1:9) as the eluent to afford the title compound (0.65 g) in a yield of 97% as a white crystalline solid.

$^1$HNMR Spectrum (400 MHz, CDCl$_3$) δ ppm: 1.09 (d, 18H, J=6.8 Hz), 1.16-1.25 (m, 3H), 1.34 (t, 3H, J=7.4 Hz), 3.02 (q, 2H, J=7.4 Hz), 4.94 (s, 2H), 7.55 (d, 1H, J=7.8 Hz), 7.92 (d, 1H, J=7.8 Hz). IR Spectrum (KBr): 1125, 1409, 1464, 1564, 1587, 2227 cm$^{-1}$. Mass Spectrum (FAB$^+$) m/z: 319 ((M+H)$^+$).

(25b) 2-Ethyl-N'-hydroxy-6-{[(triisopropylsilyl)oxy]methyl}pyridine-3-carboximidamide The crude product of the title compound was synthesized by conducting the reaction similar to that mentioned in Example 1 (1d) using 2-ethyl-6-{[(triisopropylsilyl)oxy]methyl}nicotinonitrile (0.75 g, 2.4 mmol) that was obtained in Example 25 (25a) and a 40% aqueous solution of hydroxylamine (0.5 mL). Subsequently, the crude product of the title compound thus obtained was purified by chromatography on a silica gel column using a mixed solvent of ethyl acetate and hexane (3:7 to 1:1) as the eluent to afford the title compound (0.80 g) in a yield of 95% as a white crystalline solid.

$^1$HNMR Spectrum (400 MHz, CDCl$_3$) δ ppm: 1.10 (d, 18H, J=6.8 Hz), 1.16-1.24 (m, 3H), 1.28 (t, 3H, J=7.4 Hz), 2.93 (q, 2H, J=7.4 Hz), 4.80 (brs, 2H), 4.93 (s, 2H), 7.45 (d, 1H, J=7.8 Hz), 7.69 (d, 1H, J=7.8 Hz), 8.08 (br, 1H). IR Spectrum (KBr): 1120, 1385, 1404, 1462, 1573, 1596, 1637, 3161, 3282, 3362 cm$^{-1}$. Mass Spectrum (FAB$^+$) m/z: 352 ((M+H)$^+$).

(25c) {5-[5-(3-Chloro-4-isobutylphenyl)-1,2,4-oxadiazol-3-yl]-6-ethylpyridin-2-yl}methanol The crude product of the title compound was synthesized by conducting the similar reaction to that mentioned in Example 12 (12a) using 3-chloro-4-isobutylbenzoic acid (0.10 g, 0.48 mmol) that was obtained in Example 24 (24h), 1-hydroxybenzotriazole (69 mg, 0.51 mmol), 1-ethyl-3-(3-dimethylaminopropyl)carbodiimide hydrochloride (97 mg, 0.51 mmol), 2-ethyl-N'-hydroxy-6-{[(triisopropylsilyl)oxy]methyl}pyridine-3-carboximidamide (0.16 g, 0.46 mmol) that was obtained in Example 25 (25b), and a 1.0 M solution of tetrabutylammonium fluoride in tetrahydrofuran (0.92 ml, 0.92 mmol). Subsequently, the crude product of the title compound thus obtained was purified by chromatography on a silica gel column using a mixed solvent of ethyl acetate and hexane (1:2) as the eluent to afford the title compound (0.15 g) in a yield of 89% as a white crystalline solid.

$^1$HNMR Spectrum (400 MHz, CDCl$_3$) δ ppm: 0.97 (d, 6H, J=6.8 Hz), 1.38 (t, 3H, J=7.3 Hz), 2.00-2.10 (m, 1H), 2.71 (d, 2H, J=7.3 Hz), 3.29 (q, 2H, J=7.3 Hz), 4.09 (t, 1H, J=4.7 Hz), 4.82 (d, 2H, J=4.7 Hz), 7.21 (d, 1H, J=8.3 Hz), 7.38 (d, 1H, J=7.8 Hz), 8.01 (dd, 1H, J=7.8 Hz, 1.5 Hz), 8.21 (d, 1H, J=1.5 Hz), 8.34 (d, 1H, J=8.3 Hz). IR Spectrum (KBr): 1324, 1442, 1451, 1567, 1587, 3286, 3366 cm$^{-1}$. Mass Spectrum (FAB$^+$) m/z: 372 ((M+H)$^+$).

(25d) Methyl 1-({5-[5-(3-chloro-4-isobutylphenyl)-1,2,4-oxadiazol-3-yl]-6-ethylpyridin-2-yl}methyl)azetidine-3-carboxylate The crude product of the title compound was synthesized by conducting the similar reaction to that mentioned in Example 23 (23g) using {5-[5-(3-chloro-4-isobutylphenyl)-1,2,4-oxadiazol-3-yl]-6-ethylpyridin-2-yl}methanol (0.15 g, 0.40 mmol) that was obtained in Example 25 (25c), carbon tetrabromide (0.27 g, 0.80 mmol), triphenylphosphine (0.21 g, 0.80 mmol), methyl 3-azetidinecarboxylate hydrochloride (91 mg, 0.60 mmol) and N,N-diisopropylethylamine (0.21 ml, 1.2 mmol). Subsequently, the crude product of the title compound thus obtained was purified by chromatography on a silica gel column using a mixed solvent of ethyl acetate and hexane (1:1 to 2:1 or 3:1) as the eluent to afford the title compound (0.16 g) in a yield of 83% as a pale yellowish oily product.

$^1$HNMR Spectrum (400 MHz, CDCl$_3$) δ ppm 0.97 (d, 6H, J=6.6 Hz), 1.26 (t, 3H, J=7.4 Hz), 1.99-2.10 (m, 1H), 2.71 (d, 2H, J=7.0 Hz), 3.24 (q, 2H, J=7.4 Hz), 3.35-3.46 (m, 1H), 3.49 (t, 2H, J=7.2 Hz), 3.67 (t, 2H, J=7.8 Hz), 3.73 (s, 3H), 3.84 (s, 2H), 7.30 (d, 1H, J=7.8 Hz), 7.37 (d, 1H, J=8.2 Hz), 8.00 (dd, 1H, J=8.2 Hz, 1.6 Hz), 8.20 (d, 1H, J=1.6 Hz), 8.28 (d, 1H, J=7.8 Hz). IR Spectrum (KBr): 1179, 1203, 1405, 1449, 1589, 1740 cm$^{-1}$. Mass Spectrum (FAB$^+$) m/z: 469 ((M+H)$^+$).

(25e) 1-({5-[5-(3-Chloro-4-isobutylphenyl)-1,2,4-oxadiazol-3-yl]-6-ethylpyridin-2-yl}methyl)azetidine-3-carboxylic acid The title compound (0.10 g) was synthesized in a yield of 71% as a white crystalline solid by conducting the reaction similar to that mentioned in Example 3 (3e) using methyl 1-({5-[5-(3-chloro-4-isobutylphenyl)-1,2,4-oxadiazol-3-yl]-6-ethylpyridin-2-yl}methyl)azetidine-3-carboxylate (0.15 g, 0.32 mmol) that was obtained in Example 25 (25d) and a 1 N aqueous solution of sodium hydroxide (0.96 mL, 0.96 mmol).

$^1$HNMR Spectrum (400 MHz, CD$_3$CO$_2$D) δ ppm 0.98 (d, 6H, J=6.3 Hz), 1.37 (t, 3H, J=7.2 Hz), 1.95-2.09 (m, 1H), 2.74 (d, 2H, J=7.0 Hz), 3.29 (q, 2H, J=7.2 Hz), 3.87-3.97 (m, 1H), 4.47-4.60 (m, 2H), 4.67-4.78 (m, 2H), 4.79 (s, 2H), 7.49 (d, 1H, J=7.8 Hz), 7.51 (d, 1H, J=7.4), 8.08 (d, 1H, J=7.4 Hz), 8.23 (s, 1H), 8.47 (d, 1H, J=7.8 Hz). IR Spectrum (KBr): 1337, 1389, 1397, 1589, 1611, 3432 cm$^{-1}$. Mass Spectrum (FAB$^+$) m/z: 455 ((M+H)$^+$).

Example 26

1-({5-[5-(3-Chloro-4-isobutylphenyl)-1,2,4-oxadiazol-3-yl]pyridin-2-yl}methyl)azetidine-3-carboxylic acid

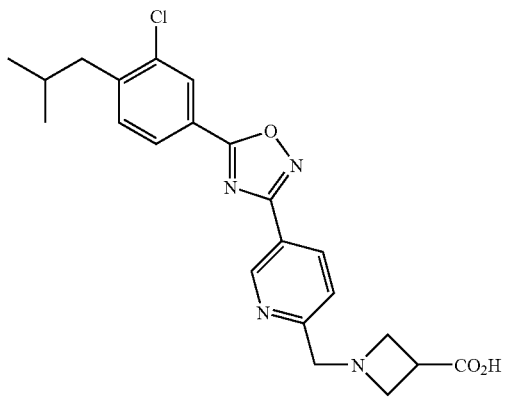

(26a) {5-[5-(3-Chloro-4-isobutylphenyl)-1,2,4-oxadiazol-3-yl]pyridin-2-yl}methanol The crude product of the title compound was synthesized by conducting the similar reaction to that mentioned in Example 12 (12a) using 3-chloro-4-isobutylbenzoic acid (0.13 g, 0.61 mmol) that was obtained in Example 24 (24h), 1-hydroxybenzotriazole (86 mg, 0.64 mmol), 1-ethyl-3-(3-dimethylaminopropyl)carbodiimide hydrochloride (0.12 g, 0.64 mmol), 6-({[t-butyl(dimethyl)silyl]oxy}methyl)-N'-hydroxypyridine-3-carboximidamide (0.16 g, 0.58 mmol) that was obtained in Example 23 (23c), and a 1.0 M solution of tetrabutylammonium fluoride in tetrahydrofuran (1.2 ml, 1.2 mmol). Subsequently, the crude product of the title compound thus obtained was purified by chromatography on a silica gel column using a mixed solvent of ethyl acetate and hexane (2:3 to 1:1) as the eluent to afford the title compound (0.19 g) in a yield of 94% as a white crystalline solid.

$^1$HNMR Spectrum (400 MHz, CDCl$_3$) δ ppm: 0.98 (d, 6H, J=6.6 Hz), 1.99-2.10 (m, 1H), 2.71 (d, 2H, J=7.4 Hz), 3.62 (bs, 1H), 4.87 (s, 2H), 7.39 (d, 1H, J=7.8 Hz), 7.44 (d, 1H, J=8.2 Hz), 8.03 (dd, 1H, J=7.8 Hz, 1.6 Hz), 8.23 (d, 1H, J=1.6 Hz), 8.44 (dd, 1H, J=8.2 Hz, 2.2 Hz), 9.34 (d, 1H, J=1.2 Hz). IR Spectrum (KBr): 1336, 1393, 1411, 1488, 1607, 3213, 3353, 3436 cm$^{-1}$. Mass Spectrum (FAB$^+$) m/z: 344 ((M+H)$^+$).

(26b) Methyl 1-({5-[5-(3-chloro-4-isobutylphenyl)-1,2,4-oxadiazol-3-yl]pyridin-2-yl}methyl)azetidine-3-carboxylate The crude product of the title compound was synthesized by conducting the reaction similar to that mentioned in Example 23 (23g) using {5-[5-(3-chloro-4-isobutylphenyl)-1,2,4-oxadiazol-3-yl]pyridin-2-yl}methanol (0.18 g, 0.54 mmol) that was obtained in Example 26 (26a), carbon tetrabromide (0.36 g, 1.1 mmol), triphenylphosphine (0.28 g, 1.1 mmol), methyl 3-azetidinecarboxylate hydrochloride (0.12 g, 0.81 mmol), and N,N-diisopropylethylamine (0.28 mL, 1.6 mmol). Subsequently, the crude product of the title compound thus obtained was purified by chromatography on a silica gel column using a mixed solvent of ethyl acetate and hexane (2:1 to 3:1) as the eluent to afford the title compound (0.15 g) in a yield of 61% as a white crystalline solid.

$^1$HNMR Spectrum (400 MHz, CDCl$_3$) δ ppm: 0.97 (d, 6H, J=6.7 Hz), 1.98-2.08 (m, 1H), 2.70 (d, 2H, J=7.0 Hz), 3.33-3.46 (m, 1H), 3.47 (t, 2H, J=7.0 Hz), 3.65 (t, 2H, J=7.6), 3.72 (s, 3H), 3.86 (s, 2H), 7.35 (d, 1H, J=7.8 Hz), 7.46 (d, 1H, J=8.2 Hz), 7.99 (dd, 1H, J=7.8 Hz, 1.6 Hz), 8.19 (d, 1H, J=1.6 Hz), 8.36 (dd, 1H, J=8.2 Hz, 2.0 Hz), 9.28 (d, 1H, J=2.0 Hz). IR Spectrum (KBr): 1207, 1339, 1352, 1389, 1486, 1605, 1738 cm$^{-1}$. Mass Spectrum (FAB$^+$) m/z: 441 ((M+H)$^+$).

(26c) 1-({5-[(3-Chloro-4-isobutylphenyl)-1,2,4-oxadiazol-3-yl]pyridin-2-yl}methyl)azetidine-3-carboxylic acid The title compound (0.12 g) was synthesized in a yield of 90% as a white crystalline solid by conducting the reaction similar to that mentioned in Example 3 (3e) using methyl 1-({5-[5-(3-chloro-4-isobutylphenyl)-1,2,4-oxadiazol-3-yl]pyridin-2-yl}methyl)azetidine-3-carboxylate (0.14 g, 0.32 mmol) that was obtained in Example 26 (26b) and a 1 N aqueous solution of sodium hydroxide (0.96 mL, 0.96 mmol).

$^1$HNMR Spectrum (400 MHz, CD$_3$CO$_2$D) δ ppm: 0.98 (d, 6H, J=6.6 Hz), 1.94-2.07 (m, 1H), 2.75 (d, 2H, J=7.0 Hz), 3.83-3.94 (m, 1H), 4.49-4.60 (m, 2H), 4.60-4.70 (m, 2H), 4.83 (s, 2H), 7.50 (d, 1H, J=7.8 Hz), 7.78 (d, 1H, J=7.4 Hz), 8.09 (d, 1H, J=7.8 Hz), 8.25 (s, 1H), 8.60 (d, 1H, J=7.4 Hz), 9.35 (s, 1H). IR Spectrum (KBr): 1368, 1403, 1569, 1587, 1605, 3431 cm$^{-1}$. Mass Spectrum (FAB$^+$) m/z: 427 ((M+H)$^+$).

Example 27

1-({5-[5-(4-Isobutyl-3-methylphenyl)-1,2,4-oxadiazol-3-yl]-6-methylpyridin-2-yl}methyl)azetidine-3-carboxylic acid 1/2 oxalate

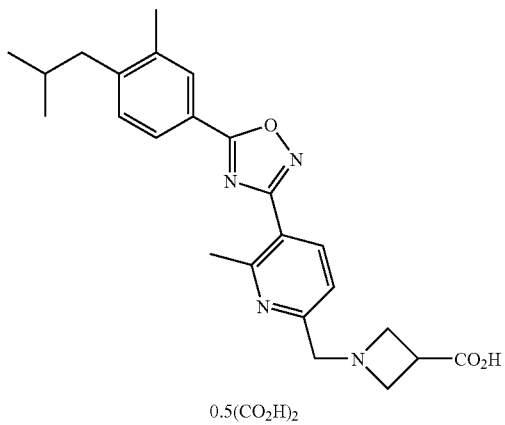

0.5(CO₂H)₂

(27a) (4-Bromo-2-methylphenyl)methanol

The crude product of the title compound was synthesized by conducting the similar reaction to that mentioned in Example 24 (24e) using 4-bromo-2-methylbenzoic acid (4.0 g, 19 mmol) and a 1.0 M solution of borane-tetrahydrofuran complex in tetrahydrofuran (20 ml, 20 mmol). Subsequently, the crude product of the title compound thus obtained was purified by chromatography on a silica gel column using a mixed solvent of ethyl acetate and hexane (1:19 to 3:2) as the eluent to afford the title compound (3.7 g) in a yield of 99% as a colourless oily product.
$^1$HNMR Spectrum (400 MHz, CDCl$_3$) δ ppm: 1.60 (t, 1H, J=5.5 Hz), 2.32 (s, 3H), 4.65 (d, 2H, J=5.5 Hz), 7.23 (d, 1H, J=8.6 Hz), 7.32-7.36 (m, 2H). IR Spectrum (thin film): 1006, 1040, 1396, 1454, 1483, 1594, 3328 cm$^{-1}$. Mass Spectrum (EI$^+$) m/z: 200 (M$^+$).

(27b) 4-Bromo-2-methylbenzaldehyde

The crude product of the title compound was synthesized by conducting the reaction similar to that mentioned in Example 24 (24f) using (4-bromo-2-methylphenyl)methanol (3.7 g, 19 mmol) that was obtained in Example 27 (27a) and pyridinium dichromate (11g, 28 mmol). Subsequently, the crude product of the title compound thus obtained was purified by chromatography on a silica gel column using a mixed solvent of ethyl acetate and hexane (1:19 to 1:4) as the eluent to afford the title compound (2.4 g) in a yield of 64% as a colourless oily product.
$^1$HNMR Spectrum (400 MHz, CDCl$_3$) δ ppm: 2.65 (s, 3H), 7.45 (s, 1H), 7.51 (dd, 1H, J=8.2 Hz, 1.6 Hz), 7.66 (d, 1H, J=8.2 Hz), 10.25 (s, 1H). IR Spectrum (KBr): 1288, 1301, 1588, 1686 cm$^{-1}$. Mass Spectrum (EI$^+$) m/z: 198 (M$^+$).

(27c) 4-Bromo-2-methyl-1-(2-methylprop-1-en-1-yl)benzene

The crude product of the title compound was synthesized by conducting the reaction similar to that mentioned in Example 23 (23d) using isopropyltriphenylphosphonium iodide (7.2 g, 17 mmol), potassium t-butoxide (2.0 g, 18 mmol), and 4-bromo-2-methylbenzaldehyde (2.4 g, 12 mmol) that was obtained in Example 27 (27b). Subsequently, the crude product of the title compound thus obtained was purified by chromatography on a silica gel column using a mixed solvent of ethyl acetate and hexane (0:10 to 6:94) as the eluent to afford the title compound (2.2 g) in a yield of 84% as a colourless oily product.
$^1$HNMR Spectrum (400 MHz, CDCl$_3$) δ ppm: 1.67 (d, 3H, J=1.2 Hz), 1.89 (d, 3H, J=1.6 Hz), 2.19 (s, 3H), 6.09 (s, 1H), 6.95 (d, 1H, J=8.2 Hz), 7.23 (dd, 1H, J=8.2 Hz, 2.0 Hz), 7.28 (d, 1H, J=2.0 Hz). IR Spectrum (thin film): 1444, 1478, 1587 cm$^{-1}$. Mass Spectrum (EI$^+$) m/z: 224 (M$^+$).

(27d) 4-Isobutyl-3-methylbenzoic acid

The title compound (1.4 g) was synthesized in a yield of 95% as a white crystalline solid by conducting the reaction similar to that mentioned in Example 23 (23e) using 4-bromo-2-methyl-1-(2-methylprop-1-en-1-yl)benzene (2.2 g, 9.8 mmol) that was obtained in Example 27 (27c), 1.6 M solution of n-butyllithium in hexane (6.5 mL, 10 mmol), and 10% palladium on carbon (200 mg).
$^1$HNMR Spectrum (400 MHz, CDCl$_3$) δ ppm: 0.94 (d, 6H, J=6.3 Hz), 1.84-1.96 (m, 1H), 2.36 (s, 3H), 2.54 (d, 2H, J=7.0 Hz), 7.19 (d, 1H, J=7.8 Hz), 7.84 (d, 1H, J=7.8 Hz), 7.88 (s, 1H).

(27e) {5-[5-(4-Isobutyl-3-methylphenyl)-1,2,4-oxadiazol-3-yl]-6-methyl pyridin-2-yl}methanol The crude product of the title compound was synthesized by conducting the similar reaction to that mentioned in Example 12 (12a) using 4-isobutyl-3-methylbenzoic acid (96 mg, 0.50 mmol) that was obtained in Example 27 (27d), 1-hydroxybenzotriazole (72 mg, 0.53 mmol), 1-ethyl-3-(3-dimethylaminopropyl)carbodiimide hydrochloride (0.10 g, 0.53 mmol), N'-hydroxy-2-methyl-6-{[(triisopropylsilyl)oxy]methyl}pyridine-3-carboximidamide (0.16 g, 0.48 mmol) that was obtained in Example 24 (24d) and a 1.0 M solution of tetrabutylammonium fluoride in tetrahydrofuran (0.96 ml, 0.96 mmol). Subsequently, the crude product of the title compound thus obtained was purified by chromatography on a silica gel column using a mixed solvent of ethyl acetate and hexane (1:2) as the eluent to afford the title compound (0.15 g) in a yield of 91% as a white crystalline solid.
$^1$HNMR Spectrum (400 MHz, CDCl$_3$) δ ppm: 0.96 (d, 6H, J=6.6 Hz), 1.87-1.98 (m, 1H), 2.42 (s, 3H), 2.57 (d, 2H, J=7.0 Hz), 2.95 (s, 3H), 3.92 (bs, 1H), 4.81 (s, 2H), 7.24 (d, 1H, J=8.2 Hz), 7.28 (d, 1H, J=8.2 Hz), 7.95 (dd, 1H, J=7.8 Hz, 1.6 Hz), 7.99 (s, 1H), 8.39 (d, 1H, J=8.2 Hz). IR Spectrum (KBr): 1334, 1445, 1460, 1557, 3204, 3445 cm$^{-1}$. Mass Spectrum (FAB$^+$) m/z: 338 ((M+H)$^+$).

(27f) Methyl 1-({5-[5-(4-isobutyl-3-methylphenyl)-1,2,4-oxadiazol-3-yl]-6-methylpyridin-2-yl}methyl)azetidine-3-carboxylate The crude product of the title compound was synthesized by conducting the similar reaction to that mentioned in Example 23 (23g) using {5-[5-(4-isobutyl-3-methylphenyl)-1,2,4-oxadiazol-3-yl]-6-methylpyridin-2-yl}methanol (0.14 g, 0.43 mmol) that was obtained in Example 27 (27e), carbon tetrabromide (0.29 g, 0.86 mmol), triphenylphosphine (0.23 g, 0.86 mmol), methyl 3-azetidinecarboxylate hydrochloride (98 mg, 0.65 mmol), and N,N-diisopropylethylamine (0.22 ml, 1.3 mmol). Subsequently, the crude product of the title compound thus obtained was purified by chromatography on a silica gel column using a mixed solvent of ethyl acetate and hexane (2:1 to 3:1) as the eluent to afford the title compound (0.12 g) in a yield of 66% as a colourless oily product.

$^1$HNMR Spectrum (400 MHz, CDCl$_3$) δ ppm: 0.96 (d, 6H, J=6.6 Hz), 1.88-1.97 (m, 1H), 2.41 (s, 3H), 2.57 (d, 2H, J=7.4 Hz), 2.91 (s, 3H), 3.36-3.44 (m, 1H), 3.47 (t, 2H, J=7.4 Hz), 3.65 (t, 2H, J=7.2 Hz), 3.73 (s, 3H), 3.83 (s, 2H), 7.27 (d, 1H, J=7.8 Hz), 7.31 (d, 1H, J=7.8 Hz), 7.95 (dd, 1H, J=7.8 Hz, 1.8 Hz), 7.99 (s, 1H), 8.33 (d, 1H, J=8.2 Hz). IR Spectrum (liquid film): 1176, 1202, 1336, 1561, 1592, 1739 cm$^{-1}$. Mass Spectrum (FAB$^+$) m/z: 435 ((M+H)$^+$).

(27g) 1-({5-[5-(4-Isobutyl-3-methylphenyl)-1,2,4-oxadiazol-3-yl]-6-methylpyridin-2-yl}methyl)azetidine-3-carboxylic acid 1/2 oxalate The title compound (0.10 g) was synthesized in a yield of 78% as a white crystalline solid by conducting the similar reaction to that mentioned in Example 21 (21d) using methyl 1-({5-[5-(4-isobutyl-3-methylphenyl)-1,2,4-oxadiazol-3-yl]-6-methylpyridin-2-yl}methyl)azetidine-3-carboxylate (0.12 g, 0.28 mmol) that was obtained in Example 27 (27f), a 1N aqueous solution of sodium hydroxide (0.84 ml, 0.84 mmol), acetic acid (48 µl, 0.84 mmol), and oxalic acid (13 mg, 0.14 mmol).

$^1$HNMR Spectrum (400 MHz, CD$_3$CO$_2$D) δ ppm: 0.97 (d, 6H, J=6.6 Hz), 1.88-1.99 (m, 1H), 2.43 (s, 3H), 2.61 (d, 2H, J=7.4 Hz), 2.93 (s, 3H), 3.84-3.96 (m, 1H), 4.46-4.56 (m, 2H), 4.62-4.74 (m, 2H), 4.77 (s, 2H), 7.35 (d, 1H, J=8.2 Hz), 7.55 (d, 1H, J=8.2 Hz), 7.99 (d, 1H, J=7.4 Hz), 8.03 (s, 1H), 8.53 (d, 1H, J=8.2 Hz). IR Spectrum (KBr): 1337, 1382, 1565, 1588, 1618, 3410 cm$^{-1}$. Mass Spectrum (FAB$^+$) m/z: 421 ((M+H)$^+$).

Example 28

1-({5-[5-(4-Isobutyl-3-methylphenyl)-1,2,4-oxadiazol-3-yl]pyridin-2-yl}methyl)azetidine-3-carboxylic acid 1/2 oxalate

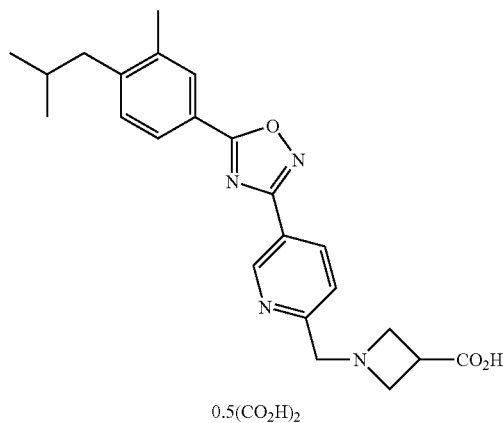

0.5(CO$_2$H)$_2$ (28a) {5-[5-(4-Isobutyl-3-methylphenyl)-1,2,4-oxadiazol-3-yl]pyridin-2-yl}methanol The crude product of the title compound was synthesized by conducting the similar reaction to that mentioned in Example 12 (12a) using 4-isobutyl-3-methylbenzoic acid (0.12 g, 0.61 mmol) that was obtained in Example 27 (27d), 1-hydroxybenzotriazole (86 mg, 0.64 mmol), 1-ethyl-3-(3-dimethylaminopropyl)carbodiimide hydrochloride (0.12 g, 0.64 mmol), 6-({[t-butyl(dimethyl)silyl]oxy}methyl)-N'-hydroxypyridine-3-carboximidamide (0.16 g, 0.58 mmol) that was obtained in Example 23 (23c), and tetrabutylammonium fluoride (a 1.0 M solution in tetrahydrofuran, 1.2 ml, 1.2 mmol). Subsequently, the crude product of the title compound thus obtained was purified by chromatography on a silica gel column using a mixed solvent of ethyl acetate and hexane (2:3 to 1:1) as the eluent to afford the title compound (0.19 g) in a yield of 99% as a white crystalline solid.

$^1$HNMR Spectrum (400 MHz, CDCl$_3$) δ ppm: 0.97 (d, 6H, J=6.6 Hz), 1.65 (bs, 1H), 1.84-1.97 (m, 1H), 2.42 (s, 3H), 2.58 (d, 2H, J=7.0 Hz), 4.87 (s, 2H), 7.28 (d, 1H, J=8.2 Hz), 7.42 (d, 1H, J=8.2 Hz), 7.96 (dd, 1H, J=7.8 Hz, 1.6 Hz), 8.00 (s, 1H), 8.44 (dd, 1H, J=8.2 Hz, 2.4 Hz), 9.35 (d, 1H, J=2.4 Hz). IR Spectrum (KBr): 1066, 1394, 1559, 1612, 3203 cm$^{-1}$. Mass Spectrum (FAB$^+$) m/z: 324 ((M+H)$^+$).

(28b) Methyl 1-({5-[5-(4-isobutyl-3-methylphenyl)-1,2,4-oxadiazol-3-yl]pyridin-2-yl}methyl)azetidine-3-carboxylate The crude product of the title compound was synthesized by conducting the similar reaction to that mentioned in Example 23 (23g) using {5-[5-(4-isobutyl-3-methylphenyl)-1,2,4-oxadiazol-3-yl]pyridin-2-yl}methanol (0.19 g, 0.58 mmol) that was obtained in Example 28 (28a), carbon tetrabromide (0.39 g, 1.2 mmol), triphenylphosphine (0.30 g, 1.2 mmol), methyl 3-azetidinecarboxylate hydrochloride (0.13 mg, 0.87 mmol), and N,N-diisopropylethylamine (0.30 ml, 1.7 mmol). Subsequently, the crude product of the title compound thus obtained was purified by chromatography on a silica gel column using a mixed solvent of ethyl acetate and hexane (1:1 to 2:1 or 3:1) as the eluent to afford the title compound (0.15 g) in a yield of 60% as a white crystalline solid.

$^1$HNMR Spectrum (400 MHz, CDCl$_3$) δ ppm: 0.96 (d, 6H, J=6.7 Hz), 1.86-1.97 (m, 1H), 2.41 (s, 3H), 2.57 (d, 2H, J=7.4 Hz), 3.34-3.44 (m, 1H), 3.47 (t, 2H, J=7.2 Hz), 3.64 (t, 2H, J=7.6), 3.72 (s, 3H), 3.85 (s, 2H), 7.25 (d, 1H, J=7.8 Hz), 7.45 (d, 1H, J=8.2 Hz), 7.93 (d, 1H, J=7.8 Hz), 7.97 (s, 1H), 8.37 (dd, 1H, J=8.2 Hz, 2.0 Hz), 9.28 (d, 1H, J=2.0 Hz). IR Spectrum (KBr): 1191, 1208, 1224, 1388, 1732 cm$^{-1}$. Mass Spectrum (FAB$^+$) m/z: 421 ((M+H)$^+$).

(28c) 1-({5-[5-(4-Isobutyl-3-methylphenyl)-1,2,4-oxadiazol-3-yl]pyridin-2-yl}methyl)azetidine-3-carboxylic acid 1/2 oxalate The title compound (0.13 g) was synthesized in a yield of 83% as a white crystalline solid by conducting the reaction similar to that mentioned in Example 21 (21d) using methyl 1-({5-[5-(4-isobutyl-3-methylphenyl)-1,2,4-oxadiazol-3-yl]pyridin-2-yl}methyl)azetidine-3-carboxylate (0.14 g, 0.34 mmol) that was obtained in Example 28 (28b), a 1 N aqueous solution of sodium hydroxide (11.0 mL, 1.0 mmol), acetic acid (58 µL, 1.0 mmol), and oxalic acid (15 mg, 0.17 mmol).

$^1$HNMR Spectrum (400 MHz, CD$_3$CO$_2$D) δ ppm: 0.98 (d, 6H, J=6.6 Hz), 1.88-2.01 (m, 1H), 2.44 (s, 3H), 2.61 (d, 2H, J=7.4 Hz), 3.84-3.95 (m, 1H), 4.28-4.60 (m, 2H), 4.60-4.72 (m, 2H), 4.82 (s, 2H), 7.35 (d, 1H, J=7.8 Hz), 7.78 (d, 1H, J=7.8 Hz), 8.00 (d, 1H, J=7.8 Hz), 8.04 (s, 1H), 8.60 (d, 1H, J=7.8 Hz), 9.34 (s, 1H). IR Spectrum (KBr): 1343, 1366, 1398, 1591, 1606, 3431 cm$^{-1}$. Mass Spectrum (FAB$^+$) m/z: 407 ((M+H)$^+$).

Example 29

1-({6-Ethyl-5-[5-(4-isobutyl-3-methylphenyl)-1,2,4-oxadiazol-3-yl]pyridin-2-yl}methyl)azetidine-3-carboxylic acid

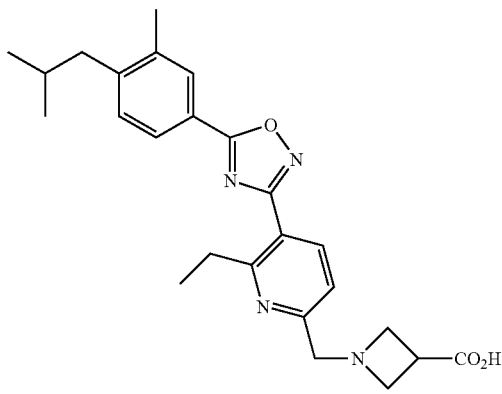

(29a) {6-Ethyl-5-[5-(4-isobutyl-3-methylphenyl)-1,2,4-oxadiazol-3-yl]pyridin-2-yl}methanol The crude product of the title compound was synthesized by conducting the similar reaction to that mentioned in Example 12 (12a) using 4-isobutyl-3-methylbenzoic acid (92 mg, 0.48 mmol) that was obtained in Example 27 (27d), 1-hydroxybenzotriazole (69 mg, 0.51 mmol), 1-ethyl-3-(3-dimethylaminopropyl)carbodiimide hydrochloride (97 mg, 0.51 mmol), 2-ethyl-N'-hydroxy-6-{[(triisopropylsilyl)oxy]methyl}pyridine-3-carboximidamide (0.16 g, 0.46 mmol) that was obtained in Example 25 (25b), and a 1.0 M solution of tetrabutylammonium fluoride in tetrahydrofuran (0.92 ml, 0.92 mmol). Subsequently, the crude product of the title compound thus obtained was purified by chromatography on a silica gel column using a mixed solvent of ethyl acetate and hexane (1:3) as the eluent to afford the title compound (0.15 g) in a yield of 93% as a white crystalline solid.
$^1$HNMR Spectrum (400 MHz, CDCl$_3$) δ ppm: 0.96 (d, 6H, J=6.3 Hz), 1.37 (t, 3H, J=7.4 Hz), 1.85-1.98 (m, 1H), 2.41 (s, 3H), 2.57 (d, 2H, J=7.0 Hz), 3.29 (q, 2H, J=7.4 Hz), 4.14 (bs, 1H), 4.82 (s, 2H), 7.21 (d, 1H, J=8.2 Hz), 7.28 (d, 1H, J=7.8 Hz), 7.95 (dd, 1H, J=7.8 Hz, 1.6 Hz), 7.99 (s, 1H), 8.34 (d, 1H, J=8.2 Hz). IR Spectrum (KBr): 1071, 1322, 1342, 1454, 1556, 1591, 3266, 3342 cm$^{-1}$. Mass Spectrum (FAB$^+$) m/z: 352 ((M+H)$^+$).

(29b) Methyl 1-({6-ethyl-5-[5-(4-isobutyl-3-methylphenyl)-1,2,4-oxadiazol-3-yl]pyridin-2-yl}methyl)azetidine-3-carboxylate The crude product of the title compound was synthesized by conducting the similar reaction to that mentioned in Example 23 (23g) using {6-ethyl-5-[5-(4-isobutyl-3-methylphenyl)-1,2,4-oxadiazol-3-yl]pyridin-2-yl}methanol (0.15 g, 0.42 mmol) that was obtained in Example 29 (29a), carbon tetrabromide (0.28 g, 0.84 mmol), triphenylphosphine (0.22 g, 0.84 mmol), methyl 3-azetidinecarboxylate hydrochloride (96 mg, 0.63 mmol), and N,N-diisopropylethylamine (0.22 ml, 1.3 mmol). Subsequently, the crude product of the title compound thus obtained was purified by chromatography on a silica gel column using a mixed solvent of ethyl acetate and hexane (1:1 to 2:1) as the eluent to afford the title compound (0.13 g) in a yield of 71% as a colourless oily product.
$^1$HNMR Spectrum (400 MHz, CDCl$_3$) δ ppm: 0.96 (d, 6H, J=6.3 Hz), 1.33 (t, 3H, J=7.4 Hz), 1.87-1.97 (m, 1H), 2.41 (s, 3H), 2.57 (d, 2H, J=7.0 Hz), 3.24 (q, 2H, J=7.4 Hz), 3.33-3.44 (m, 1H), 3.49 (t, 2H, J=7.2 Hz), 3.67 (t, 2H, J=7.6), 3.73 (s, 3H), 3.84 (s, 2H), 7.27 (d, 1H, J=8.2 Hz), 7.29 (d, 1H, J=7.8 Hz), 7.95 (d, 1H, J=7.8 Hz), 7.99 (s, 1H), 8.27 (d, 1H, J=8.2 Hz). IR Spectrum (liquid film): 1176, 1202, 1340, 1560, 1591, 1739 cm$^{-1}$. Mass Spectrum (FAB$^+$) m/z: 449 ((M+H)$^+$).

(29c) 1-({6-Ethyl-5-[5-(4-isobutyl-3-methylphenyl)-1,2,4-oxadiazol-3-yl]pyridin-2-yl}methyl)azetidine-3-carboxylic acid The title compound (0.10 g) was synthesized in a yield of 82% as a white crystalline solid by conducting the reaction similar to that mentioned in Example 3 (3e) using methyl 1-({6-ethyl-5-[5-(4-isobutyl-3-methylphenyl)-1,2,4-oxadiazol-3-yl]pyridin-2-yl}methyl)azetidine-3-carboxylate (0.13 g, 0.29 mmol) that was obtained in Example 29 (29b) and a 1 N aqueous solution of sodium hydroxide (0.87 mL, 0.87 mmol).
$^1$HNMR Spectrum (400 MHz, CD$_3$CO$_2$D) δ ppm: 0.97 (d, 6H, J=6.6 Hz), 1.36 (t, 3H, J=7.4 Hz), 1.89-2.00 (m, 1H), 2.43 (s, 3H), 2.61 (d, 2H, J=7.4 Hz), 3.29 (q, 2H, J=7.4 Hz), 3.84-3.95 (m, 1H), 4.47-4.61 (m, 2H), 4.61-4.73 (m, 2H), 4.78 (s, 2H), 7.35 (d, 1H, J=7.8 Hz), 7.49 (d, 1H, J=7.8 Hz), 7.98 (d, 1H, J=7.8 Hz), 8.02 (s, 1H), 8.47 (d, 1H, J=8.2 Hz). IR Spectrum (KBr): 1327, 1338, 1400, 1563, 1590, 1617, 3451 cm$^{-1}$. Mass Spectrum (FAB$^+$) m/z: 435 ((M+H)$^+$).

Example 30

1-({6-Ethyl-5-[5-(3-fluoro-4-isobutylphenyl)-1,2,4-oxadiazol-3-yl]pyridin-2-yl}methyl)azetidine-3-carboxylic acid

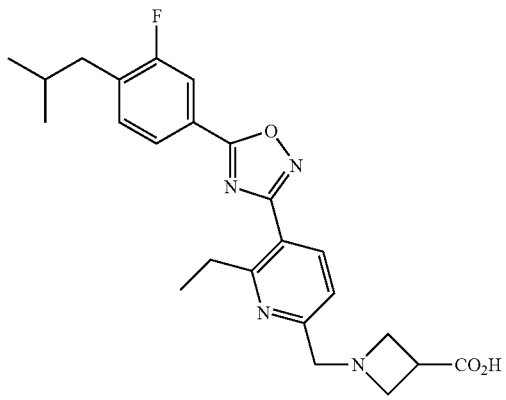

(30a) {6-Ethyl-5-[5-(3-fluoro-4-isobutylphenyl)-1,2,4-oxadiazol-3-yl]pyridin-2-yl}methanol The crude product of the title compound was synthesized by conducting the similar reaction to that mentioned in Example 12 (12a) using 3-fluoro-4-isobutylbenzoic acid (0.11 g, 0.54 mmol) that was obtained in Example 23 (23e), 1-hydroxybenzotriazole (86 mg, 0.56 mmol), 1-ethyl-3-(3-dimethylaminopropyl)carbodiimide hydrochloride (0.11 g, 0.56 mmol), 2-ethyl-N'-hydroxy-6-{[(triisopropylsilyl)oxy]methyl}pyridine-3-carboximidamide (0.18 g, 0.51 mmol) that was obtained in Example 25 (25b), and a 1.0 M solution of tetrabutylammonium fluoride in tetrahydrofuran (1.0 ml, 1.0 mmol). Subsequently, the crude product of the title compound thus obtained was purified by chromatography on a silica gel column using a mixed solvent of ethyl acetate and hexane (2:8 to 4:6) as the eluent to afford the title compound (0.13 g) in a yield of 74% as a white crystalline solid.

$^1$HNMR Spectrum (400 MHz, CDCl$_3$) δ ppm: 0.96 (d, 6H, J=6.7 Hz), 1.37 (t, 3H, J=7.4 Hz), 1.91-2.03 (m, 1H), 2.61 (d, 2H, J=7.0 Hz), 3.28 (q, 2H, J=7.4 Hz), 4.09 (br, 1H), 4.80 (s, 2H), 7.19 (d, 1H, J=7.8 Hz), 7.31-7.36 (m, 1H), 7.81-7.91 (m, 2H), 8.32 (d, 1H, J=7.8 Hz). IR Spectrum (KBr): 762, 899, 1078, 1427, 1453, 1509, 1568, 1593, 2957, 3294 cm$^{-1}$. Mass Spectrum (FAB$^+$) m/z: 356 ((M+H)$^+$).

(30b) Methyl 1-({6-ethyl-5-[5-(3-fluoro-4-isobutylphenyl)-1,2,4-oxadiazol-3-yl]pyridin-2-yl}methyl)azetidine-3-carboxylate The crude product of the title compound was synthesized by conducting the similar reaction to that mentioned in Example 23 (23g) using {6-ethyl-5-[5-(3-fluoro-4-isobutylphenyl)-1,2,4-oxadiazol-3-yl]pyridin-2-yl}methanol (0.13 g, 0.38 mmol) that was obtained in Example 30 (30a), carbon tetrabromide (0.25 g, 0.75 mmol), triphenylphosphine (0.20 g, 0.75 mmol), methyl 3-azetidinecarboxylate hydrochloride (78 mg, 0.51 mmol), and N,N-diisopropylethylamine (0.15 ml, 0.86 mmol). Subsequently, the crude product of the title compound thus obtained was purified by chromatography on a silica gel column using a mixed solvent of ethyl acetate and hexane (3:7 to 7:3) as the eluent to afford the title compound (0.11 g) in a yield of 69% as a pale yellow oily product.

$^1$HNMR Spectrum (400 MHz, CDCl$_3$) δ ppm: 0.96 (d, 6H, J=6.6 Hz), 1.33 (t, 3H, J=7.4 Hz), 1.92-2.03 (m, 1H), 2.61 (d, 2H, J=7.0 Hz), 3.24 (q, 2H, J=7.4 Hz), 3.35-3.45 (m, 1H), 3.49 (t, 2H, J=7.8 Hz), 3.67 (t, 2H, J=7.8 Hz), 3.73 (s, 3H), 3.84 (s, 2H), 7.28-7.37 (m, 2H), 7.83-7.93 (m, 2H), 8.27 (d, 1H, J=8.2 Hz). IR Spectrum (liquid film): 1203, 1342, 1562, 1590, 1739, 2958 cm$^{-1}$. Mass Spectrum (FAB$^+$) m/z: 453 ((M+H)$^+$).

(30c) 1-({6-Ethyl-5-[5-(3-fluoro-4-isobutylphenyl)-1,2,4-oxadiazol-3-yl]pyridin-2-yl}methyl)azetidine-3-carboxylic acid The title compound (90 mg) was synthesized in a yield of 87% as a white crystalline solid by conducting the reaction similar to that mentioned in Example 3 (3e) using methyl 1-({6-ethyl-5-[5-(3-fluoro-4-isobutylphenyl)-1,2,4-oxadiazol-3-yl]pyridin-2-yl}methyl)azetidine-3-carboxylate (0.11 g, 0.24 mmol) that was obtained in Example 30 (30b) and a 1 N aqueous solution of sodium hydroxide (0.71 mL, 0.71 mmol).

$^1$HNMR Spectrum (400 MHz, CD$_3$CO$_2$D) δ ppm: 0.97 (d, 6H, J=6.6 Hz), 1.37 (t, 3H, J=7.5 Hz), 1.92-2.04 (m, 1H), 2.65 (d, 2H, J=7.3 Hz), 3.29 (q, 2H, J=7.5 Hz), 3.86-3.97 (m, 1H), 4.45-4.77 (m, 4H), 4.79 (s, 2H), 7.43-7.53 (m, 2H), 7.87-8.00 (m, 2H), 8.47 (d, 1H, J=8.1 Hz). IR Spectrum (KBr): 760, 900, 1103, 1342, 1402, 1508, 1561, 1592, 2873, 2963, 3438 cm$^{-1}$. Mass Spectrum (FAB$^+$) m/z: 439 ((M+H)$^+$).

The present invention will hereinafter be described in more detail by way of the Test Examples and Formulation Examples below, but the scope of the present invention should not be limited to these examples.

Test Example 1

Assessment of Antiarthritic Activity of the Compounds

The inhibitory activity of a medicinal composition comprising a compound of the present invention is investigated using adjuvant-induced arthritic rats, which exhibit symptoms similar to those of human arthritis, using the rate of inhibition of swelling of the right hind paw (adjuvant injected side) as indicator.

Lewis rats aged 8 weeks are used for the study.

(1) Preparation of Adjuvant

Heat-killed dried *Mycobacterium butyricum* are ground on an agate mortar and then suspended in dry-sterilized liquid paraffin to make a 2 mg/ml suspension. The resulting suspended solution is then sonicated and used as adjuvant.

(2) Preparation of Test Compounds

The test compounds are dissolved or suspended in 0.5% tragacantha solution.

(3) Induction of Adjuvant-induced Arthritis

Arthritis is induced by intradermal injection of the adjuvant prepared in (1) described above (0.05 ml) into the foot pad of the right hindlimb of rats in the drug-treated group and in the control group. Rats that are not treated with adjuvant are separately used as normal control group.

(4) Administration of the Compound

The test compounds prepared in (2) described above are orally administered to rats of the compound-treated group at a volume of 5 ml/kg once daily from the injection day of the adjuvant (day 0) for 18 successive days. To rats in the control groups 0.5% tragacantha solution alone is similarly administered.

(5) Calculation of Inhibition Rate of Swollen Foot Volume by the Test Compound

On the 11th and 18th days after drug administration is started, the right foot volume of each rat is measured by customized apparatus for determination of the volume. The average swelling volume of each group is thus calculated.

Percent inhibition of swelling of the injected foot of treated animals as compared with that of the control animals is calculated according to the following equation:

Inhibition rate of swollen foot volume (%)={1−[(swollen foot volume of animals treated with a compound)−(foot volume of normal control animals)]/[(swollen foot volume of control animals)−(foot volume of normal control animals)]}×100

Test Example 2

Determination of Inhibitory Activities of the Compound Against Host-Versus-graft Reaction (HvGR) in the Rat (1) Two strains of rats [Lewis rats (male, 6 weeks of age, Charles River Japan Inc.) and WKAH/Hkm rats (male, 7 weeks of age, Japan SLC Inc.)] were used. Five rats (host) per group were used.

(2) Induction of HvGR

Spleen cells were isolated from the spleens of WKAH/Hkm rats or Lewis rats and floated in RPMI1640 medium (Life Technologies Inc.) at a concentration of 1×10$^8$ cells/ml. A 0.1-ml aliquot of the medium containing the free-floating spleen cells (1×10$^7$ cells) of WKAH/Hkm rats or Lewis rats was then intradermally injected into the bilateral foot pads of the hindlimbs of both sides of Lewis rats.

(3) Administration of Test Compound

The test compound was suspended in 0.5% tragacantha solution. The suspended solution of a compound of the present invention (5 ml/kg of body weight of the rat) was orally administered to rats of the drug-treated group (the Lewis rats in which spleen cells of WKAH/Hkm rats were injected and the test compound was administered) once daily for 4 successive days starting on the day of the spleen cell injection. Furthermore, tragacantha solution (0.5%) instead of the test substance was orally administered to rats in the "same strain group" (Lewis rats injected with spleen cells of Lewis rats) and the control group (Lewis rats injected with spleen cells of WKAH/Hkm rats and not treated with the test compound).

(4) Determination of Inhibitory Activity Against HvGR

The average weight of the popliteal lymph nodes of the same strain rats was subtracted from the individual weights of the popliteal lymph nodes of individual rats ("weight of the popliteal lymph nodes after HvGR-induction"). The inhibitory activity of a compound was calculated from the "weight of the popliteal lymph nodes after HvGR induction" of individual rats in the drug-treated group versus the average "weight of the popliteal lymph nodes after HvGR induction" in the control group. The results are summarized in Table 5 shown below.

TABLE 5

| Compound | Inhibition Rate (%, 1 mg/kg of administration) |
|---|---|
| Example 10 | 61.8 |
| Example 11 | 51.6 |
| Example 12 | 55.4 |
| Example 13 | 61.3 |
| Example 14 | 65.6 |
| Example 17 | 65.0 |
| Example 26 | 80.0 |
| Example 27 | 80.6 |
| Example 28 | 77.5 |
| Example 29 | 83.5 |
| Reference Compound 1 | −15.5 |
| Reference Compound 2 | −19.0 |

From the present results, the compounds of the present invention exhibited excellent inhibitory activity against HvGR.

Reference Compound 1 and Reference Compound 2 are compounds disclosed as Example 19 and Example 21 in Patent Literature 2 (International publication number WO 03/105771 pamphlet), and their chemical structures are as follows:

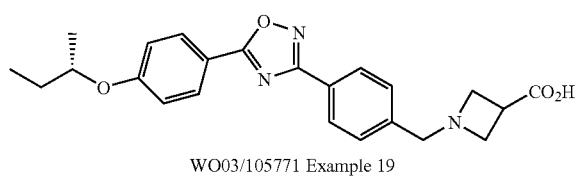

WO03/105771 Example 19

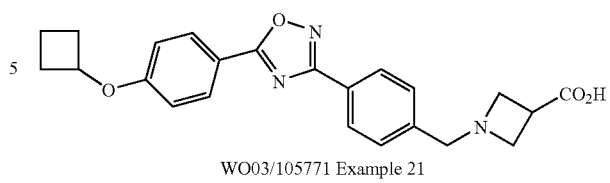

WO03/105771 Example 21

Test Example 3

Assessment of Inhibitory Activity of Compounds Against Peripheral Lymphocytes of the Rat Lewis rats (male, 5 weeks of age, Charles River Japan Inc.) are used. Five rats/group are used.

(1) Administration of Compound

The test compound is suspended in 1% tragacantha solution (vehicle). Suspended solution of the test compound is orally administered to rats at a volume of 5 ml/kg.

In control rats, vehicle instead of the suspended solution of the test compound is orally administered.

(2) Counting of Peripheral Lymphocytes

Three hours after administration of either vehicle or suspended solution of the test compound, blood is collected from the postcaval vein of the rats under ether anesthesia. Then, the collected blood is placed into a tube containing EDTA. The absolute number of lymphocytes in the blood collected is counted using a full blood count analyzer. The inhibitory activity (%) of the test compound is determined by calculation of the relative number of peripheral lymphocytes with the number of lymphocytes in the blood collected from normal rats being defined as 100%.

| (Formulation Example 1) Tablet | |
|---|---|
| A compound of the present invention | 10 mg |
| Lactose | 163 mg |
| Corn starch | 25 mg |
| Magnesium stearate | 2 mg |
| | 200 mg |

Tablets (200 mg in a tablet) are prepared by mixing powders of the above prescription in a blender, and a tableting the mixture using a tableting machine.

Advantages of the Invention

Since the compounds of the present invention exert excellent immunosuppressing activity with low toxicity, the compounds of the present invention are useful as a prophylactic or a therapeutic agent for diseases related to suppression of the immune system in mammals (particularly in humans).

The invention claimed is:
1. A compound having the formula (I) shown below,

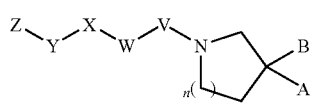

wherein
A represents a carboxyl group, a phospho group, a sulfo group, or a 1H-tetrazol-5-yl group,
B represents a hydrogen atom or a group selected from Substituent group A,
n is 0,
V represents a methylene group, which may optionally be substituted with substituent(s) selected from Substituent group A or a single bond,
W represents a 5- to 7-membered heterocyclic group, which may optionally be substituted with from 1 to 3 substituents selected from Substituent group A, in the case that V represents a methylene group which may optionally be substituted with substituent(s) selected from Substituent group A, while in the case that V represents a single bond, W represents a fused ring heterocyclic group, which may optionally be substituted with from 1 to 3 substituent(s) selected from Substituent group A,
X represents a $C_1$-$C_8$ alkylene group, which may optionally be substituted with from 1 to 5 substituents selected from Substituent group A, a $C_1$-$C_8$ alkylene group containing an oxygen atom or a sulfur atom in a carbon chain, which may optionally be substituted with from 1 to 5 substituents selected from Substituent group A, a $C_6$-$C_{10}$ arylene group, which may optionally be substituted with from 1 to 3 substituents selected from Substituent group A, a 5- to 7-membered heterocyclic group, which may optionally be substituted with from 1 to 3 substituents selected from Substituent group A, or a fused ring heterocyclic group, which may optionally be substituted with from 1 to 3 substituents selected from Substituent group A,
Y represents a $C_6$-$C_{10}$ arylene group, which may optionally be substituted with from 1 to 3 substituents selected from Substituent group A, a 5- to 7-membered heterocyclic group, which may optionally be substituted with from 1 to 3 substituents selected from Substituent group A, or a fused ring heterocyclic group, which may optionally be substituted with from 1 to 3 substituents selected from Substituent group A,
Z represents a group selected from Substituent group A, a $C_1$-$C_8$ alkyl group, which may optionally be substituted with from 1 to 5 substituents selected from Substituent group A, a $C_1$-$C_8$ alkyl group containing an oxygen atom or a sulfur atom in a carbon chain, which may optionally be substituted with from 1 to 5 substituents selected from Substituent group A, a $C_3$-$C_7$ cycloalkyl group, which may optionally be substituted with from 1 to 5 substituents selected from Substituent group A, a $C_6$-$C_{10}$ aryl group, which may optionally be substituted with from 1 to 5 substituents selected from Substituent group A, a $C_6$-$C_{10}$ aryloxy group, which may optionally be substituted with from 1 to 5 substituents selected from Substituent group A, a $C_6$-$C_{10}$ arylthio group, which may optionally be substituted with from 1 to 5 substituents selected from Substituent group A, a $C_6$-$C_{12}$ aralkyl group, which may optionally be substituted with from 1 to 5 substituents selected from Substituent group A, a $C_6$-$C_{10}$ arylcarbony group, which may optionally be substituted with from 1 to 5 substituents selected from Substituent group A, Substituent group A represents a group consisting of a halogen atom, a $C_1$-$C_6$ alkyl group, a $C_3$-$C_7$ cycloalkyl group, a $C_6$-$C_{10}$ aryl group, a $C_6$-$C_{10}$ aryloxy group, a $C_6$-$C_{12}$ aralkyl group, a halogeno $C_1$-$C_6$ alkyl group, a $C_1$-$C_6$ alkoxy group, a halogeno $C_1$-$C_6$ alkoxy group, a $C_1$-$C_6$ alkylthio group, a carboxyl group, a $C_1$-$C_6$ alkylcarboxy group, a hydroxyl group, a $C_1$-$C_6$ aliphatic acyl group, an amino group, a mono-$C_1$-$C_6$ alkylamino group, a di-$C_1$-$C_6$ alkylamino group, a $C_1$-$C_6$ aliphatic acylamino group, a cyano group, and a nitro group,
or a pharmacologically acceptable salt thereof.

2. A compound, or a pharmacologically acceptable salt thereof, according to claim 1 wherein
B represents a hydrogen atom;
A represents a carboxyl group;
V represents a methylene group, and
W is a 5- to 7-membered heterocyclic group, which may optionally be substituted with from 1 to 3 substituents selected from Substituent group A.

3. A compound, or a pharmacologically acceptable salt thereof, according to claim 2 wherein the 5- to 7-membered heterocyclic group is a thienylene, furylene, pyrrolylene, or pyridylene group.

4. A compound, or a pharmacologically acceptable salt thereof, according to claim 3 wherein W is

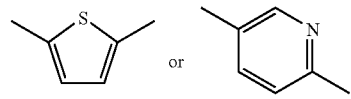

5. A compound, or a pharmacologically acceptable salt thereof, according to claim 2 wherein W represents a thienylene or pyridylene group, which may optionally be substituted with from 1 to 2 groups selected from Substituent group A.

6. A compound, or a pharmacologically acceptable salt thereof, according to claim 1 wherein V represents a single bond and W represents a fused ring heterocyclic group, which may optionally be substituted with from 1 to 3 substituents selected from Substituent group A.

7. A compound, or a pharmacologically acceptable salt thereof, according to claim 6 wherein W represents a fused ring heterocyclic group.

8. A compound, or a pharmacologically acceptable salt thereof, according to claim 7 wherein a fused ring heterocyclic group is a tetrahydrobenzofuranylene, tetrahydrobenzothienylene, or N-methyltetrahydroindolylene group.

9. A compound, or a pharmacologically acceptable salt thereof, according to claim 8 wherein a fused ring heterocyclic group has two positions available for bonding at the 2- and 4-positions.

10. A compound, or a pharmacologically acceptable salt thereof, according to claim 9 wherein a substituent at the 2-position represents a group of formula Z—Y—X.

11. A compound, or a pharmacologically acceptable salt thereof, according to claim 1 wherein
X represents a $C_1$-$C_8$ alkylene group, a $C_1$-$C_8$ alkylene group containing an oxygen atom or a sulfur atom in a carbon chain, a $C_6$-$C_{10}$ arylene group, a 5- to 7-membered heterocyclic group, or a fused ring heterocyclic group; and Y represents any one group selected from a group consisting of a phenylene group, a 5- to 7-membered heterocyclic group, which may optionally be substituted with from 1 to 3 substituents selected from Substituent group A, and a fused ring heterocyclic group, which may optionally be substituted with from 1 to 3 substituents selected from Substituent group A.

12. A compound, or a pharmacologically acceptable salt thereof, according to claim 11 wherein
X represents a 5- to 7-membered heterocyclic group, and Y represents a phenylene group, or a thienylene, pyridylene, or indolylene group which may optionally be substituted with from 1 to 3 substituents selected from Substituent group A.

13. A compound, or a pharmacologically acceptable salt thereof, according to claim 12 wherein Y represents a phenylene group or a pyridylene group.

14. A compound, or a pharmacologically acceptable salt thereof, according to claim 11 wherein Z represents a $C_6$-$C_{10}$ aryloxy group, which may optionally be substituted with from 1 to 5 substituents selected from Substituent group A.

15. A compound, or a pharmacologically acceptable salt thereof, according to claim 14 wherein Z represents a phenoxy group.

16. A compound, or a pharmacologically acceptable salt thereof, according to claim 1 wherein the formula (I) is represented by Formula (I') shown below,

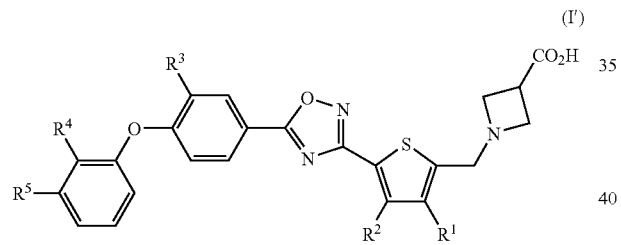

(I')

wherein
$R^1$ represents a hydrogen atom or a $C_1$-$C_6$ alkyl group,
$R^2$ represents a hydrogen atom or a $C_1$-$C_6$ alkyl group,
$R^3$ represents a hydrogen atom, a halogen atom, or a $C_1$-$C_6$ alkyl group,
$R^4$ represents a hydrogen atom, a halogen atom, a cyano group, a $C_1$-$C_6$ alkyl group, or a $C_1$-$C_6$ alkoxy group, and
$R^5$ represents a hydrogen atom or a halogen atom.

17. A compound, or a pharmacologically acceptable salt thereof, according to claim 16 wherein
$R^1$ represents a hydrogen atom
$R^2$ represents a hydrogen atom, a methyl group, or an ethyl group,
$R^3$ represents a hydrogen atom, a fluorine atom, a chlorine atom, or a methyl group
$R^4$ represents a hydrogen atom, a fluorine atom, a chlorine atom, a cyano group, a methyl group, or a methoxyl group and
$R^5$ represents a hydrogen atom or a fluorine atom.

18. A compound, or a pharmacologically acceptable salt thereof, according to claim 17 wherein $R^3$ represents a hydrogen atom or a fluorine atom and $R^4$ represents a hydrogen atom or a fluorine atom.

19. A compound, or a pharmacologically acceptable salt thereof, according to claim 1 wherein the formula (I) is represented by formula (I'') shown below,

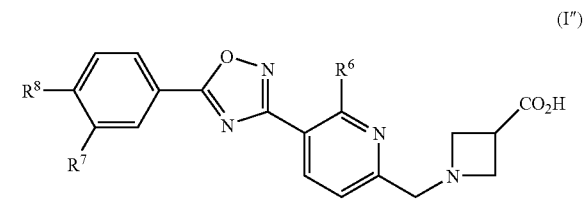

(I'')

wherein
$R^6$ represents a hydrogen atom or a $C_1$-$C_6$ alkyl group,
$R^7$ represents a hydrogen atom, a halogen atom, or a $C_1$-$C_6$ alkyl group, and
$R^8$ represents a $C_1$-$C_6$ alkyl group or a $C_1$-$C_6$ alkoxy group.

20. A compound, or a pharmacologically acceptable salt thereof, according to claim 19 wherein
$R^6$ represents a hydrogen atom, a methyl group
$R^7$ represents a hydrogen atom, a fluorine atom, a chlorine atom, or a methyl group, and
$R^8$ represents a n-propyl group, a n-butyl group, or an isobutyl group.

21. A compound, or a pharmacologically acceptable salt thereof, according to claim 1 wherein said compound is selected from the group consisting of:
1-[(4-{5-[4-Phenyl-5-(trifluoromethyl)-2-thienyl]-1,2,4-oxadiazol-3-yl}-2-furyl)methyl]azetidine-3-carboxylic acid,
1-[(4-Ethyl-5-{5-[3-fluoro-4-(3-fluorophenoxy)phenyl]-1,2,4-oxadiazol-3-yl}-2-thienyl)methyl]azetidine-3-carboxylic acid,
1-[(4-Ethyl-5-{5-[4-(2-methoxyphenoxy)phenyl]-1,2,4-oxadiazol-3-yl}-2-thienyl)methyl]azetidine-3-carboxylic acid,
1-[(5-{5-[3-Chloro-4-(3-fluorophenoxy)phenyl]-1,2,4-oxadiazol-3-yl}-4-ethyl-2-thienyl)methyl]azetidine-3-carboxylic acid,
1-[(4-Ethyl-5-{5-[4-(2-methoxyphenoxy)phenyl]-1,2,4-oxadiazol-3-yl}-2-thienyl)methyl]azetidine-3-carboxylic acid,
1-({5-[5-(4-Isobutylphenyl)-1,2,4-oxadiazol-3-yl]-2-furyl}methyl)azetidine-3-carboxylic acid,
1-({5-[5-(4-Cyclohexylphenyl)-1,2,4-oxadiazol-3-yl]-2-furyl}methyl)azetidine-3-carboxylic acid,
1-(2-{5-[4-Phenyl-5-(trifluoromethyl)-2-thienyl]-1,2,4-oxadiazol-3-yl}-4,5,6,7-tetrahydro-1-benzofuran-4-yl)azetidine-3-carboxylic acid,
1-({5-[5-(4-Phenoxyphenyl)-1,2,4-oxadiazol-3-yl]-2-thienyl}methyl)azetidine-3-carboxylic acid,
1-({4-[5-(4-Benzoylphenyl)-1,2,4-oxadiazol-3-yl]-2-thienyl}methyl)azetidine-3-carboxylic acid,
1-({4-[5-(4-Benzylphenyl)-1,2,4-oxadiazol-3-yl]-2-thienyl}methyl)azetidine-3-carboxylic acid,
1-({4-[5-(1-Isobutyl-1H-indol-5-yl)-1,2,4-oxadiazol-3-yl]-2-thienyl}methyl)azetidine-3-carboxylic acid,
1-({6-[5-(4-Isobutylphenyl)-1,2,4-oxadiazol-3-yl]pyridin-3-yl}methyl)azetidine-3-carboxylic acid, and
1-({5-[5-(4-Isobutylphenyl)-1,2,4-oxadiazol-3-yl]pyridin-2-yl}methyl)azetidine-3-carboxylic acid.

22. A compound, or a pharmacologically acceptable salt thereof, according to claim 1 wherein said compound is selected from the group consisting of:

1-({5-[5-(4-Phenoxyphenyl)-1,2,4-oxadiazol-3-yl]-2-thienyl}methyl)azetidine-3-carboxylic acid,
1-[(4-Ethyl-5-{5-[3-fluoro-4-(3-fluorophenoxy)phenyl]-1,2,4-oxadiazol-3-yl}-2-thienyl)methyl]azetidine-3-carboxylic acid,
1-[(4-Ethyl-5-{5-[4-(2-methoxyphenoxy)phenyl]-1,2,4-oxadiazol-3-yl}-2-thienyl)methyl]azetidine-3-carboxylic acid,
1-[(5-{5-[3-Chloro-4-(3-fluorophenoxy)phenyl]-1,2,4-oxadiazol-3-yl}-4-ethyl-2-thienyl)methyl]azetidine-3-carboxylic acid,
1-[(4-Ethyl-5-{5-[4-(2-methoxyphenoxy)phenyl]-1,2,4-oxadiazol-3-yl}-2-thienyl)methyl]azetidine-3-carboxylic acid,
1-[(5-{5-[4-(2,3-Difluorophenoxy)phenyl]-1,2,4-oxadiazol-3-yl}-4-ethyl-2-thienyl)methyl]azetidine-3-carboxylic acid,
1-[(4-Ethyl-5-{5-[3-fluoro-4-(2-fluorophenoxy)phenyl]-1,2,4-oxadiazol-3-yl}-2-thienyl)methyl]azetidine-3-carboxylic acid,
1-[(5-{5-[4-(2,3-Difluorophenoxy)-3-fluorophenyl]-1,2,4-oxadiazol-3-yl}-4-ethyl-2-thienyl)methyl]azetidine-3-carboxylic acid,
1-[(5-{5-[3-Chloro-4-(2-fluorophenoxy)phenyl]-1,2,4-oxadiazol-3-yl}-4-ethyl-2-thienyl)methyl]azetidine-3-carboxylic acid,
1-[(5-{5-[3-Chloro-4-(2,3-difluorophenoxy)phenyl]-1,2,4-oxadiazol-3-yl}-4-ethyl-2-thienyl)methyl]azetidine-3-carboxylic acid,
1-[(5-{(5-[4-(2-Chlorophenoxy)phenyl]-1,2,4-oxadiazol-3-yl}-4-ethyl-2-thienyl)methyl]azetidine-3-carboxylic acid,
1-[(5-{5-[4-(2-Chlorophenoxy)-3-fluorophenyl]-1,2,4-oxadiazol-3-yl}-4-ethyl-2-thienyl)methyl]azetidine-3-carboxylic acid,
1-({3-Methyl-5-[5-(4-phenoxyphenyl)-1,2,4-oxadiazol-3-yl]-2-thienyl}methyl)azetidine-3-carboxylic acid and
1-({3-Ethyl-5-[5-(4-phenoxyphenyl)-1,2,4-oxadiazol-3-yl]-2-thienyl}methyl)azetidine-3-carboxylic acid.

23. A compound, or a pharmacologically acceptable salt thereof, according to claim 1 wherein said compound is selected from the group consisting of:
1-({5-[5-(4-Isobutyl-3-methylphenyl)-1,2,4-oxadiazol-3-yl]pyridin-2-yl}methyl)azetidine-3-carboxylic acid,
1-({5-[5-(3-Fluoro-4-isobutylphenyl)-1,2,4-oxadiazol-3-yl]pyridin-2-yl}methyl)azetidine-3-carboxylic acid,
1-({5-[5-(3-Chloro-4-isobutylphenyl)-1,2,4-oxadiazol-3-yl]pyridin-2-yl}methyl)azetidine-3-carboxylic acid,
1-({5-[5-(4-Isobutyl-3-methylphenyl)-1,2,4-oxadiazol-3-yl]-6-methylpyridin-2-yl}methyl)azetidine-3-carboxylic acid,
1-({5-[5-(3-Fluoro-4-propylphenyl)-1,2,4-oxadiazol-3-yl]-6-methylpyridin-2-yl}methyl)azetidine-3-carboxylic acid,
1-({5-[5-(4-Butyl-3-fluorophenyl)-1,2,4-oxadiazol-3-yl]-6-methylpyridin-2-yl}methyl)azetidine-3-carboxylic acid,
1-({5-[5-(3-Fluoro-4-isobutylphenyl)-1,2,4-oxadiazol-3-yl]-6-methylpyridin-2-yl}methyl)azetidine-3-carboxylic acid,
1-({5-[5-(3-Chloro-4-isobutylphenyl)-1,2,4-oxadiazol-3-yl]-6-methylpyridin-2-yl}methyl)azetidine-3-carboxylic acid,
1-({6-Ethyl-5-[5-(4-isobutyl-3-methylphenyl)-1,2,4-oxadiazol-3-yl]pyridin-2-yl}methyl)azetidine-3-carboxylic acid,
1-({6-Ethyl-5-[5-(3-fluoro-4-propylphenyl)-1,2,4-oxadiazol-3-yl]pyridin-2-yl}methyl)azetidine-3-carboxylic acid,
1-({5-[5-(4-Butyl-3-fluorophenyl)-1,2,4-oxadiazol-3-yl]-6-ethylpyridin-2-yl}methyl)azetidine-3-carboxylic acid,
1-({6-Ethyl-5-[5-(3-fluoro-4-isobutylphenyl)-1,2,4-oxadiazol-3-yl]pyridin-2-yl}methyl)azetidine-3-carboxylic acid and
1-({5-[5-(3-Chloro-4-isobutylphenyl)-1,2,4-oxadiazol-3-yl]-6-ethylpyridin-2-yl}methyl)azetidine-3-carboxylic acid.

24. A compound, or a pharmacologically acceptable salt thereof, according to claim 1 wherein said compound is selected from the group consisting of:
1-({4-Methyl-5-[5-(4-phenoxyphenyl)-1,2,4-oxadiazol-3-yl]-2-thienyl}methyl)azetidine-3-carboxylic acid,
1-({5-[5-(3-Fluoro-4-phenoxyphenyl)-1,2,4-oxadiazol-3-yl]-4-methyl-2-thienyl}methyl)azetidine-3-carboxylic acid,
1-({4-Ethyl-5-[5-(4-phenoxyphenyl)-1,2,4-oxadiazol-3-yl]-2-thienyl}methyl)azetidine-3-carboxylic acid,
1-[(4-Ethyl-5-{5-[4-(3-fluorophenoxy)phenyl]-1,2,4-oxadiazol-3-yl}-2-thienyl)methyl]azetidine-3-carboxylic acid,
1-({4-Ethyl-5-[5-(3-fluoro-4-phenoxyphenyl)-1,2,4-oxadiazol-3-yl]-2-thienyl}methyl)azetidine-3-carboxylic acid, and
1-[(4-Ethyl-5-{5-[4-(2-fluorophenoxy)phenyl]-1,2,4-oxadiazol-3-yl}-2-thienyl)methyl]azetidine-3-carboxylic acid.

25. A medicinal composition comprising a pharmacologically effective amount of a compound or pharmacologically acceptable salt thereof according to claim 1 in a pharmacologically acceptable carrier.

26. A medicinal composition, according to claim 25 wherein
B represents a hydrogen atom;
A represents a carboxyl group;
n represents 0; and
V represents a methylene group, and
W is a 5- to 7-membered heterocyclic group, which may optionally be substituted with from 1 to 3 substituents selected from Substituent group A.

27. A medicinal composition, according to claim 26 wherein the 5- to 7-membered heterocyclic group is a thienylene, furylene, pyrrolylene, or pyridylene group.

28. A medicinal composition, according to claim 27 wherein
X represents a $C_1$-$C_8$ alkylene group, a $C_1$-$C_8$ alkylene group containing an oxygen atom or a sulfur atom in a carbon chain, a $C_6$-$C_{10}$ arylene group, a 5- to 7-membered heterocyclic group, or a fused ring heterocyclic group; and
Y represents any one group selected from a group consisting of a phenylene group, a 5- to 7-membered heterocyclic group, which may optionally be substituted with from 1 to 3 substituents selected from Substituent group A, and a fused ring heterocyclic group, which may optionally be substituted with from 1 to 3 substituents selected from Substituent group A.

29. A medicinal composition, according to claim 25 wherein said compound is selected from the group consisting of:
1-[(4-{5-[4-Phenyl-5-(trifluoromethyl)-2-thienyl]-1,2,4-oxadiazol-3-yl}-2-furyl)methyl]azetidine-3-carboxylic acid, 1-[(4-Ethyl-5-{5-[3-fluoro-4-(3-fluorophenoxy)phenyl]-1,2,4-oxadiazol-3-yl}-2-thienyl)methyl]azetidine-3-carboxylic acid,
1-[(4-Ethyl-5-{5-[4-(2-methoxyphenoxy)phenyl]-1,2,4-oxadiazol-3-yl}-2-thienyl)methyl]azetidine-3-carboxylic acid,
1-[(5-{5-[3-Chloro-4-(3-fluorophenoxy)phenyl]-1,2,4-oxadiazol-3-yl}-4-ethyl-2-thienyl)methyl]azetidine-3-carboxylic acid,
1-[(4-Ethyl-5-{5-[4-(2-methoxyphenoxy)phenyl]-1,2,4-oxadiazol-3-yl}-2-thienyl)methyl]azetidine-3-carboxylic acid,
1-({5-[5-(4-Isobutylphenyl)-1,2,4-oxadiazol-3-yl]-2-furyl}methyl)azetidine-3-carboxylic acid,
1-({5-[(5-(4-Cyclohexylphenyl)-1,2,4-oxadiazol-3-yl]-2-furyl}methyl)azetidine-3-carboxylic acid,
1-(2-{5-[4-Phenyl-5-(trifluoromethyl)-2-thienyl]-1,2,4-oxadiazol-3-yl}-4,5,6,7-tetrahydro-1-benzofuran-4-yl)azetidine-3-carboxylic acid,
1-({5-[5-(4-Phenoxyphenyl)-1,2,4-oxadiazol-3-yl]-2-thienyl}methyl)azetidine-3-carboxylic acid,
1-({4-[5-(4-Benzoylphenyl)-1,2,4-oxadiazol-3-yl]-2-thienyl}methyl)azetidine-3-carboxylic acid,
1-({4-[5-(4-Benzylphenyl)-1,2,4-oxadiazol-3-yl]-2-thienyl}methyl)azetidine-3-carboxylic acid,
1-({4-[5-(1-Isobutyl-1H-indol-5-yl)-1,2,4-oxadiazol-3-yl]-2-thienyl}methyl)azetidine-3-carboxylic acid,
1-({6-[5-(4-Isobutylphenyl)-1,2,4-oxadiazol-3-yl]pyridin-3-yl}methyl)azetidine-3-carboxylic acid, and
1-({5-[5-(4-Isobutylphenyl)-1,2,4-oxadiazol-3-yl]pyridin-2-yl}methyl)azetidine-3-carboxylic acid.

30. A medicinal composition, according to claim 25 wherein said compound is selected from the group consisting of:
1-({5-[5-(4-Phenoxyphenyl)-1,2,4-oxadiazol-3-yl]-2-thienyl}methyl)azetidine-3-carboxylic acid,
1-[(4-Ethyl-5-{5-[3-fluoro-4-(3-fluorophenoxy)phenyl]-1,2,4-oxadiazol-3-yl}-2-thienyl)methyl]azetidine-3-carboxylic acid,
1-[(4-Ethyl-5-{5-[4-(2-methoxyphenoxy)phenyl]-1,2,4-oxadiazol-3-yl}-2-thienyl)methyl]azetidine-3-carboxylic acid,
1-[(5-{5-[3-Chloro-4-(3-fluorophenoxy)phenyl]-1,2,4-oxadiazol-3-yl}-4-ethyl-2-thienyl)methyl]azetidine-3-carboxylic acid,
1-[(4-Ethyl-5-{5-[4-(2-methoxyphenoxy)phenyl]-1,2,4-oxadiazol-3-yl}-2-thienyl)methyl]azetidine-3-carboxylic acid,
1-[(5-{5-[4-(2,3-Difluorophenoxy)phenyl]-1,2,4-oxadiazol-3-yl}-4-ethyl-2-thienyl)methyl]azetidine-3-carboxylic acid,
1-[(4-Ethyl-5-{5-[3-fluoro-4-(2-fluorophenoxy)phenyl]-1,2,4-oxadiazol-3-yl}-2-thienyl)methyl]azetidine-3-carboxylic acid,
1-[(5-{5-[4-(2,3-Difluorophenoxy)-3-fluorophenyl]-1,2,4-oxadiazol-3-yl}-4-ethyl-2-thienyl)methyl]azetidine-3-carboxylic acid,
1-[(5-{5-[3-Chloro-4-(2-fluorophenoxy)phenyl]-1,2,4-oxadiazol-3-yl}-4-ethyl-2-thienyl)methyl]azetidine-3-carboxylic acid,
1-[(5-{5-[3-Chloro-4-(2,3-difluorophenoxy)phenyl]-1,2,4-oxadiazol-3-yl}-4-ethyl-2-thienyl)methyl]azetidine-3-carboxylic acid,
1-[(5-{5-[4-(2-Chlorophenoxy)phenyl]-1,2,4-oxadiazol-3-yl}-4-ethyl-2-thienyl)methyl]azetidine-3-carboxylic acid,
1-[(5-{5-[4-(2-Chlorophenoxy)-3-fluorophenyl]-1,2,4-oxadiazol-3-yl}-4-ethyl-2-thienyl)methyl]azetidine-3-carboxylic acid,
1-({3-Methyl-5-[5-(4-phenoxyphenyl)-1,2,4-oxadiazol-3-yl]-2-thienyl}methyl)azetidine-3-carboxylic acid and
1-({3-Ethyl-5-[5-(4-phenoxyphenyl)-1,2,4-oxadiazol-3-yl]-2-thienyl}methyl)azetidine-3-carboxylic acid.

31. A medicinal composition, according to claim 25 wherein said compound is selected from the group consisting of:
1-({5-[5-(4-Isobutyl-3-methylphenyl)-1,2,4-oxadiazol-3-yl]pyridin-2-yl}methyl)azetidine-3-carboxylic acid,
1-({5-[5-(3-Fluoro-4-isobutylphenyl)-1,2,4-oxadiazol-3-yl]pyridin-2-yl}methyl)azetidine-3-carboxylic acid,
1-({5-[5-(3-Chloro-4-isobutylphenyl)-1,2,4-oxadiazol-3-yl]pyridin-2-yl}methyl)azetidine-3-carboxylic acid,
1-({5-[5-(4-Isobutyl-3-methylphenyl)-1,2,4-oxadiazol-3-yl]-6-methylpyridin-2-yl}methyl)azetidine-3-carboxylic acid,
1-({5-[5-(3-Fluoro-4-propylphenyl)-1,2,4-oxadiazol-3-yl]-6-methylpyridin-2-yl}methyl)azetidine-3-carboxylic acid,
1-({5-[5-(4-Butyl-3-fluorophenyl)-1,2,4-oxadiazol-3-yl]-6-methylpyridin-2-yl}methyl)azetidine-3-carboxylic acid,
1-({5-[5-(3-Fluoro-4-isobutylphenyl)-1,2,4-oxadiazol-3-yl]-6-methylpyridin-2-yl}methyl)azetidine-3-carboxylic acid,
1-({5-[5-(3-Chloro-4-isobutylphenyl)-1,2,4-oxadiazol-3-yl]-6-methylpyridin-2-yl}methyl)azetidine-3-carboxylic acid,
1-({6-Ethyl-5-[5-(4-isobutyl-3-methylphenyl)-1,2,4-oxadiazol-3-yl]pyridin-2-yl}methyl)azetidine-3-carboxylic acid,
1-({6-Ethyl-5-[5-(3-fluoro-4-propylphenyl)-1,2,4-oxadiazol-3-yl]pyridin-2-yl}methyl)azetidine-3-carboxylic acid,
1-({5-[5-(4-Butyl-3-fluorophenyl)-1,2,4-oxadiazol-3-yl]-6-ethylpyridin-2-yl}methyl)azetidine-3-carboxylic acid,
1-({6-Ethyl-5-[5-(3-fluoro-4-isobutylphenyl)-1,2,4-oxadiazol-3-yl]pyridin-2-yl}methyl)azetidine-3-carboxylic acid and
1-({5-[5-(3-Chloro-4-isobutylphenyl)-1,2,4-oxadiazol-3-yl]-6-ethylpyridin-2-yl}methyl)azetidine-3-carboxylic acid.

32. A medicinal composition, according to claim 25 wherein said compound is selected from the group consisting of:
1-({4-Methyl-5-[5-(4-phenoxyphenyl)-1,2,4-oxadiazol-3-yl]-2-thienyl}methyl)azetidine-3-carboxylic acid,
1-({5-[5-(3-Fluoro-4-phenoxyphenyl)-1,2,4-oxadiazol-3-yl]-4-methyl-2-thienyl}methyl)azetidine-3-carboxylic acid,
1-({4-Ethyl-5-[5-(4-phenoxyphenyl)-1,2,4-oxadiazol-3-yl]-2-thienyl}methyl)azetidine-3-carboxylic acid,
1-[(4-Ethyl-5-{5-[4-(3-fluorophenoxy)phenyl]-1,2,4-oxadiazol-3-yl}-2-thienyl)methyl]azetidine-3-carboxylic acid,
1-({4-Ethyl-5-[5-(3-fluoro-4-phenoxyphenyl)-1,2,4-oxadiazol-3-yl]-2-thienyl}methyl)azetidine-3-carboxylic acid, and
1-[(4-Ethyl-5-{5-[4-(2-fluorophenoxy)phenyl]-1,2,4-oxadiazol-3-yl}-2-thienyl)methyl]azetidine-3-carboxylic acid.

* * * * *